(12) United States Patent
Victors et al.

(10) Patent No.: US 11,715,551 B2
(45) Date of Patent: Aug. 1, 2023

(54) SYSTEMS AND METHODS FOR EVALUATING QUERY PERTURBATIONS

(71) Applicant: Recursion Pharmaceuticals, Inc., Salt Lake City, UT (US)

(72) Inventors: Mason Victors, Salt Lake City, UT (US); Berton Earnshaw, Salt Lake City, UT (US); Renat Khaliullin, Salt Lake City, UT (US); Blake Borgeson, Salt Lake City, UT (US); Peter McLean, Salt Lake City, UT (US); Nathan Lazar, Salt Lake City, UT (US); Katie-Rose Skelly, Salt Lake City, UT (US)

(73) Assignee: Recursion Pharmaceuticals, Inc.

( * ) Notice: Subject to any disclaimer, the term of this patent is extended or adjusted under 35 U.S.C. 154(b) by 528 days.

(21) Appl. No.: 16/905,162

(22) Filed: Jun. 18, 2020

(65) Prior Publication Data

US 2020/0402628 A1    Dec. 24, 2020

Related U.S. Application Data

(60) Provisional application No. 62/863,700, filed on Jun. 19, 2019, provisional application No. 62/863,711, (Continued)

(51) Int. Cl.
*G16H 20/10* (2018.01)
*G16H 10/40* (2018.01)

(52) U.S. Cl.
CPC ............. *G16H 20/10* (2018.01); *G16H 10/40* (2018.01)

(58) Field of Classification Search
None
See application file for complete search history.

(56) References Cited

U.S. PATENT DOCUMENTS 10,146,914 B1    12/2018  Victors et al.
10,769,501 B1 *   9/2020  Ando ..................... G06V 20/70

FOREIGN PATENT DOCUMENTS

WO         0202740 A2    1/2002
WO      2020018519 A1    1/2020

OTHER PUBLICATIONS

PCT/US20/38500, International Search Report and Written Opinion, dated Aug. 28, 2020,, 8 pgs.
(Continued)

*Primary Examiner* — Alan Torrico-Lopez

(57) ABSTRACT

Methods and systems for evaluating a query perturbation, in a cell based assay representing a test state, are provided. Control data points having dimensions representing measurements of different features across control cell aliquots are obtained. Test data points having dimensions representing measurements of different features across test cell aliquots are obtained. A composite test vector is computed between measures of central tendency across the control data points and measures of central tendency across the test data points. Query perturbation data points having dimensions representing measurements of different features across perturbation cell aliquots are obtained. A composite query perturbation vector is computed between measures of central tendency across the control data points and measures of central tendency across the plurality of query perturbation data points.

21 Claims, 58 Drawing Sheets

Related U.S. Application Data filed on Jun. 19, 2019, provisional application No. 62/863,414, filed on Jun. 19, 2019, provisional application No. 62/863,696, filed on Jun. 19, 2019.

(56) References Cited

OTHER PUBLICATIONS

Litichevskiy, et al., "A Library of Phosphoproteomic and Chromatin Signatures for Characterizing Cellular Responses to Drug Perturbations", Cell Syst; Publication [online] Apr. 25, 2018 [retrieved Aug. 5, 2020]. Retrieved from the Internet <URL:https://www.ncbi.nlm.nih.gov/pmc/articles/PMC5951639/;, Apr. 25, 2018, pp. 1-25.

* cited by examiner

| Feature measurements database 220 |
|---|
| Query perturbation 1 data set 222-1 |
|    Control perturbation data 224-1 |
|       Context 1; Control perturbation 1; Characteristic 1; Instance 1  226-1-1-1-1-1 |
|       ⋮ |
|       Context M; Control perturbation S; Characteristic N; Instance O  226-1-M-S-N-O |
|    Test perturbation data 228-1 |
|       Context 1; Test perturbation 1; Characteristic 1; Instance 1  230-1-1-1-1-1 |
|       ⋮ |
|       Context M; Test perturbation P; Characteristic N; Instance Q  230-1-M-P-N-Q |
|    Query perturbation data 232-1 |
|       Context 1; Test perturbation 1; Characteristic 1; Instance 1  234-1-1-1-1-1 |
|       ⋮ |
|       Context M; Test perturbation P; Characteristic N; Instance V  234-1-M-P-N-V |
| ⋮ |
| Query perturbation R data set 232-R |

Fig. 2B

| Query perturbation data points database 270 |
| --- |
| Query perturbation 1 data points 272-1 |
| Control data points 274-1 |
| Context 1; Control perturbation 1 276-1-1-1 |
| ⋮ |
| Context M; Control perturbation S 276-1-M-S |
| Test data points 278-1 |
| Context 1; Test perturbation 1 280-1-1-1 |
| |
| Context M; Test perturbation P 280-1-M-P |
| Query data points 282-1 |
| Context 1; Test perturbation 1 284-1-1-1 |
| ⋮ |
| Context M; Test perturbation P 284-1-M-P |
| ⋮ |
| Query perturbation R data points 272-R |

Fig. 2C

Composite vectors database 286

Query perturbation 1 composite vectors 288-1

Composite test vectors 290-1

Context 1 292-1-1

⋮

Context M 292-1-M

Composite query vectors 294-1

Context 1 296-1-1

⋮

Context M 296-1-M

Query perturbation R composite vectors 288-R

4002 Obtain, for each respective control perturbation in a set of control perturbations, a corresponding control data point, thereby obtaining a plurality of control data points, wherein each corresponding control data point comprises a plurality of dimensions, each dimension in the plurality of dimensions representing a measure of central tendency of a different feature, in a plurality of features across a corresponding plurality of control aliquots of cells in corresponding wells, in the plurality of wells, representing the respective control perturbation

4004 The set of control perturbations consists of a plurality of control siRNA that do not directly affect expression of a gene associated with the test state

4006 The plurality of control siRNA consists of between 10 and 50 different control siRNA

4008 The measure of central tendency of the different feature across the corresponding plurality of control aliquots of the cells representing the respective control perturbation is an arithmetic mean, weighted mean, midrange, midhinge, trimean, Winsorized mean, median, or mode of the different feature across between two and twenty control aliquots of the cells representing the respective control perturbation in between two and twenty corresponding wells in the plurality of wells

4010 Each feature in the plurality of features represents a color, texture, or size of the cell or an enumerated portion of the cell

4012 The obtaining includes imaging a corresponding well in the plurality of wells to form a corresponding two-dimensional pixelated image having a corresponding plurality of native pixel values and wherein a different feature in the plurality of features of the obtaining arises as a result of a convolution or a series convolutions and pooling operators run against native pixel values in the corresponding plurality of native pixel values of the corresponding two-dimensional pixelated image

4014 The respective plurality of control aliquots of the cells is exposed to the respective control perturbation for at least one hour prior to obtaining the measurement of each feature in the plurality of features across the plurality of control aliquots

Fig. 4A 4002 continued...

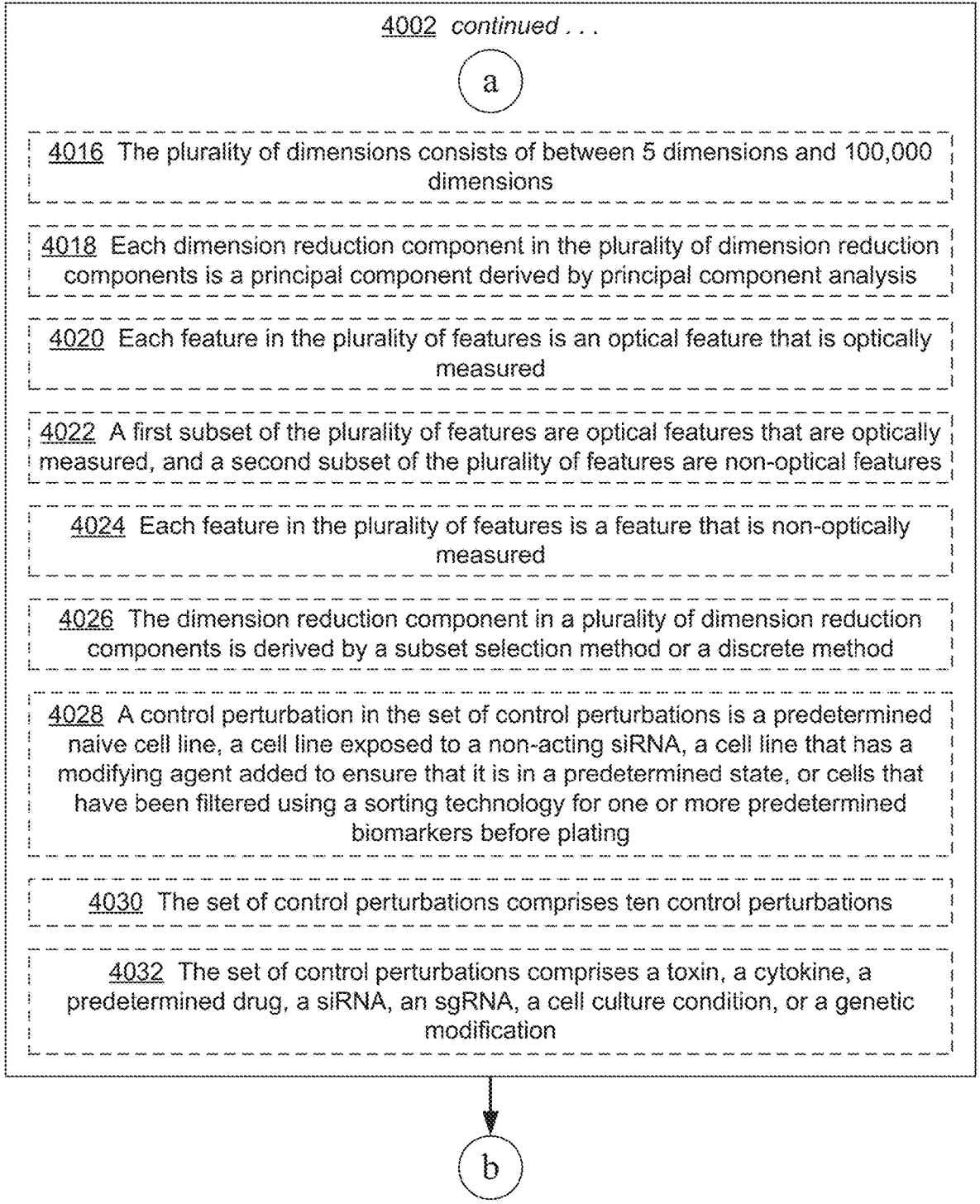

4016 The plurality of dimensions consists of between 5 dimensions and 100,000 dimensions 4018 Each dimension reduction component in the plurality of dimension reduction components is a principal component derived by principal component analysis 4020 Each feature in the plurality of features is an optical feature that is optically measured 4022 A first subset of the plurality of features are optical features that are optically measured, and a second subset of the plurality of features are non-optical features 4024 Each feature in the plurality of features is a feature that is non-optically measured 4026 The dimension reduction component in a plurality of dimension reduction components is derived by a subset selection method or a discrete method 4028 A control perturbation in the set of control perturbations is a predetermined naive cell line, a cell line exposed to a non-acting siRNA, a cell line that has a modifying agent added to ensure that it is in a predetermined state, or cells that have been filtered using a sorting technology for one or more predetermined biomarkers before plating 4030 The set of control perturbations comprises ten control perturbations 4032 The set of control perturbations comprises a toxin, a cytokine, a predetermined drug, a siRNA, an sgRNA, a cell culture condition, or a genetic modification

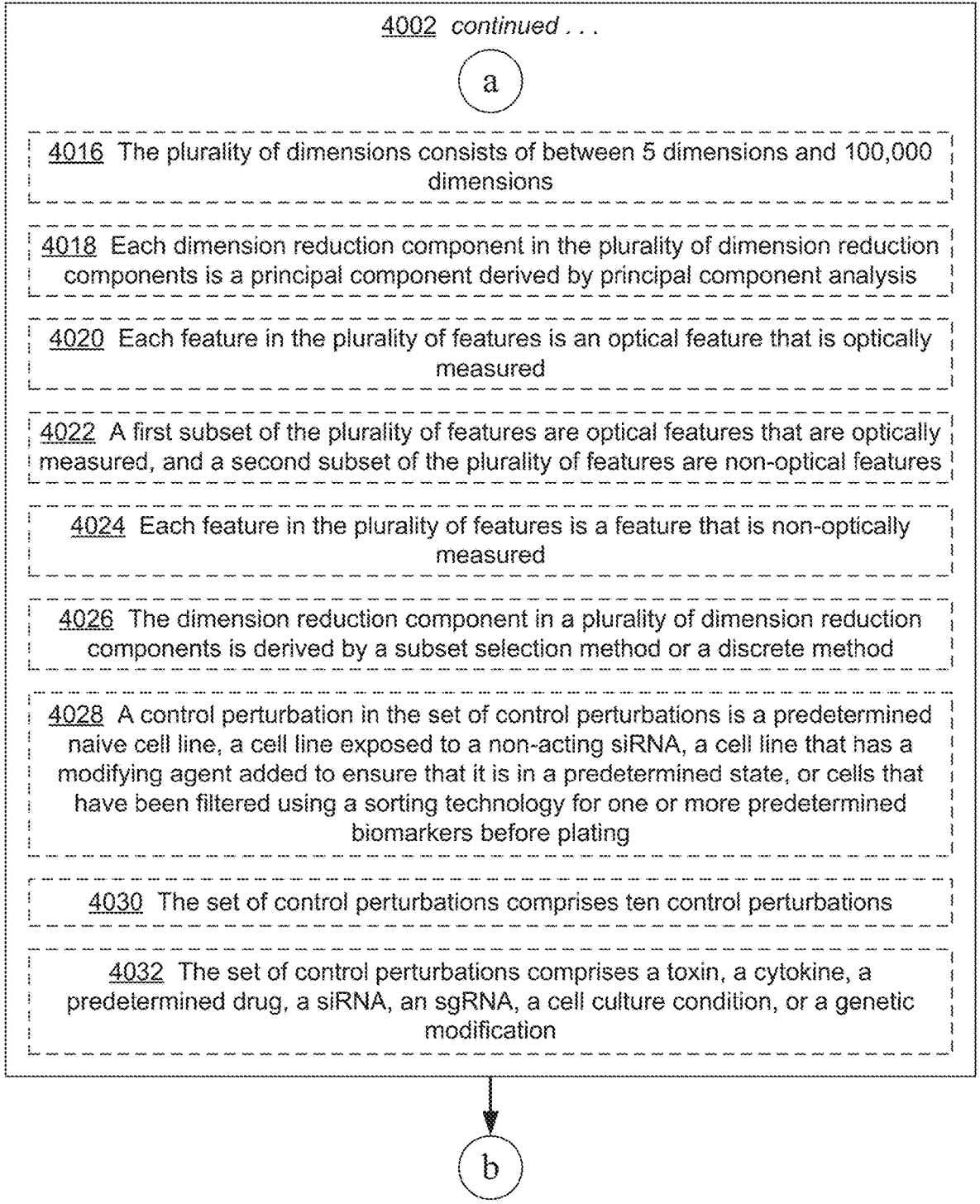

Fig. 4B

4034 Obtain, for each respective test perturbation in a set of one or more test perturbations, a corresponding test data point, thereby obtaining a plurality of test data points, wherein each corresponding test data point comprises the plurality of dimensions, each dimension in the plurality of dimensions comprising a measurement of central tendency of a different feature, in the plurality of features, determined across a corresponding plurality of test aliquots of the cells representing the respective test perturbation in corresponding wells in the plurality of wells 4036 The set of test perturbations consists of a plurality of target siRNA that directly affect expression of a gene associated with the test state 4038 The plurality of target siRNA consists of between 4 and 12 different target siRNA 4040 The measure of central tendency of the different feature across the corresponding plurality of test aliquots of the cells representing the respective test perturbation is an arithmetic mean, weighted mean, midrange, midhinge, trimean, Winsorized mean, median, or mode of the different feature across between two and twenty test aliquots of the cells upon exposure representing the respective test perturbation in between two and twenty corresponding wells in the plurality of wells 4042 The plurality of test aliquots of the cells is exposed to the respective test perturbation or at least one hour, two hours, three hours, one day, two days, three days, four days, or five days prior to obtaining the measurement of each feature in the plurality of features across the plurality of test aliquots 4044 The set of test perturbations comprises ten test perturbations 4046 The set test perturbations comprises a toxin, a cytokine, a predetermined drug, a siRNA, an sgRNA, a cell culture condition, or a genetic modification other than a control perturbation

Fig. 4C

4048 Compute a composite test vector, the composite test vector between (i) a first point defined by a respective measure of central tendency across the plurality of control data points for each dimension in the plurality of dimensions and (ii) a second point defined by a respective measure of central tendency across the plurality of test data points for each dimension in the plurality of dimensions 4050 Obtain a plurality of query perturbation data points, wherein each corresponding query perturbation data point comprises the plurality of dimensions, each dimension in the plurality of dimensions comprising a measure of central tendency of a different feature, in the plurality of features, determined across a plurality of instances of query perturbation aliquots of the cells representing a respective test perturbation, in the plurality of test perturbations, and a first amount of the query perturbation in a corresponding subset of the plurality of wells 4052 The measure of central tendency of the different feature across the corresponding plurality of query perturbation aliquots of the cells jointly representing the respective test perturbation and the query perturbation is an arithmetic mean, weighted mean, midrange, midhinge, trimean, Winsorized mean, median, or mode of the different feature across between two and twenty query perturbation aliquots of the cells jointly representing the respective test perturbation and the query perturbation in between two and twenty corresponding wells in the plurality of wells 4054 The plurality of query perturbation aliquots of the cells is exposed to the respective test perturbation and the query perturbation for at least one hour, two hours, three hours, one day, two days, three days, four days, or five days prior to obtaining the measurement of each feature in the plurality of features across the plurality of query perturbation aliquots 4056 The corresponding plurality of query perturbation aliquots of the cells is jointly exposed to the respective test perturbation and the query perturbation for at least one hour prior, two hours, three hours, one day, two days, three days, four days, or five days prior to obtaining the measurement of the plurality of features in the obtaining 4058 The plurality of query perturbations includes at least 1000 query perturbations

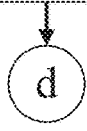 Fig. 4D

4112 Repeat the obtaining (4050), computing (4060), computing (4062), and computing (4064) for each respective amount of the query perturbation in a plurality of respective amounts of the query perturbation, where each respective amount of the query perturbation in the plurality of respective amounts of the query perturbation is expressed as a corresponding concentration of the query perturbation in the corresponding subset of the plurality of wells, thereby obtaining an on target score and an off target score at each concentration in a plurality of concentrations for the query perturbation, the evaluating (4066) includes plotting the query perturbation at each respective concentration in the plurality of concentrations on a two-dimensional plot using the on target score for the query perturbation at the respective concentration as a coordinate in a first dimension of the two-dimensional plot and the respective concentration as a coordinate in a second dimension of the two-dimensional plot thereby obtaining an on target curve for the query perturbation, and the evaluating (4066) further includes plotting the query perturbation at each respective concentration in the plurality of concentrations on the two-dimensional plot using the off target score for the query perturbation at the respective concentration as a coordinate in the first dimension of the two-dimensional plot and the respective concentration as a coordinate in the second dimension of the two-dimensional plot thereby obtaining an off target curve for the query perturbation

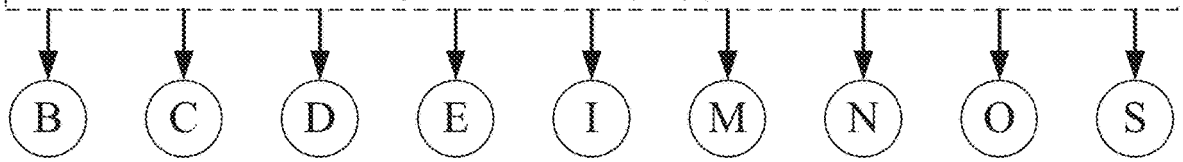

Fig. 4O

4114 Use the on target curve and the off target curve to quantify a therapeutic window for the query perturbation, where the therapeutic window is determined by an area of a closed two-dimensional shape bounded by (i) an amplitude of the on target curve between a first position on the on target curve that represents a maximum on target score in the on target curve and a second position that represents an intersection of the on target curve and the off target curve, (ii) a third position on the off target curve that represents a maximum off target score in the off target curve and the second point, and (iii) a line drawn between the first position and the third position 4116 The area is weighted by a closest distance between the second position and the line drawn between the first position and the third position 4118 The area is weighted by the concentration of the query perturbation at the second position

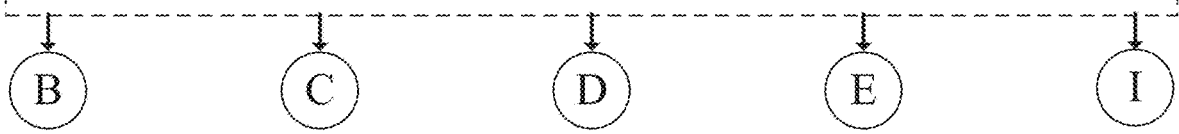

Fig. 4P

4120 Use the on target curve and the off target curve to quantify a rescue quality for the query perturbation, wherein the rescue quality is determined by integrating a difference between (a) the amplitude of the first position and (b) the maximum on target score at each respective concentration in the plurality of concentrations, where the maximum on target score at each respective concentration in the plurality of concentrations is the largest on target score from among the on target curve and the off target curve at the respective concentration

Fig. 4Q

4122 Use the on target curve and the off target curve to quantify a rescue quality for the query perturbation, wherein the rescue quality is calculated as:

$$\int_{i=[a]}^{[b]} \max(\text{phenotype}(c_i), \text{side}(c_i)) * \frac{\log(c_i * \text{weight})}{c_i}$$

where $c_i$ is an $i^{th}$ concentration of the compound in the plurality of concentrations for the compound, $i$ is an index to each concentration of the compound in the plurality of concentrations, [a] is one of a lowest and a highest concentration of the compound in the plurality of concentrations, [b] is the other of the lowest and the highest concentration of the compound in the plurality of concentrations, phenotype($c_i$) is the on target score for the compound at concentration $c_i$ in the phenotype curve, side($c_i$) is the on target score for the compound at concentration $c_i$ in the side effect curve, and weight is a numerical weight

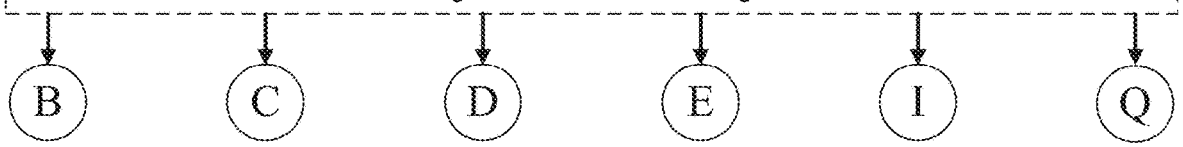

Fig. 4R

4124 Compute a plurality of test vectors, where each respective test vector in the plurality of test vectors is between (i) the first point and (ii) a second point defined by a respective test data point in the set of test data points for each dimension in the plurality of dimensions 4126 Compute a plurality of control state vectors, where each respective control state vector in the plurality of control state vectors is between (i) the first point and (ii) a third point defined by a respective control data point in the set of control data points for each dimension in the plurality of dimensions

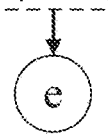

Fig. 4S

4142 Compute a normalized tightness of the plurality of test state data points

4144 the normalized tightness is computed by a procedure that includes:

for each respective test vector in the plurality of test vectors, computing a test state similarly metric between (i) the respective test vector and (ii) a distribution metric of the plurality of test vectors with the respective test vector removed from the plurality of test vectors, thereby obtaining a plurality of test state similarity metrics for the plurality of test vectors, each test state similarity metric in the plurality of test state similarity metrics uniquely corresponding to a test perturbation in the set of test perturbations, and computing a complementary distribution, by a process comprising:

(a) for each respective control state vector in the plurality of control state vectors, computing a respective control similarity metric between (i) the respective control vector and (ii) a distribution metric of the plurality of control vectors with the respective control vector removed from the plurality of control vectors, thereby obtaining the plurality of control similarity metrics, each control similarity metric in the plurality of control similarity metrics uniquely corresponding to a control perturbation in the set of control perturbations, and (b) computing the complementary distribution as a distribution metric of the plurality of control similarity metrics; and determining a first measure of central tendency of the angle between (i) each respective test state similarity metric in the plurality of test state similarity metrics to (ii) the complementary distribution across the plurality of test state similarity metrics, and normalizing the first measure of central tendency of the angle by a second measure of central tendency of the angle between (i) each control similarity metric in the plurality of control similarity metrics to (ii) the complementary distribution across the plurality of control similarity metrics, wherein the normalized first measure of central tendency represents the normalized tightness of the plurality of test state data points

4146 The distribution metric of the plurality of test vectors with the respective test vector removed from the plurality of test vectors is a measure of central tendency of each corresponding dimension in the plurality of dimensions across the plurality of test vectors other than the respective test vector 4148 The measure of central tendency of each corresponding dimension in the plurality of dimensions across the plurality of test vectors other than the respective test vector is an arithmetic mean, weighted mean, midrange, midhinge, trimean, Winsorized mean, median, or mode of the corresponding dimension across the plurality of test vectors 4150 The respective test state similarly metric between (i) the respective test vector and (ii) the distribution metric of the plurality of test vectors with the respective test vector removed from the plurality of test vectors is computed as a distance between corresponding dimensions of the test vector and the distribution metric of the plurality of test vectors with the respective test vector removed from the plurality of test vectors 4152 The distance is an angular distance computed as:

$$\frac{\sum_{i}^{n} A_i B_i}{\sqrt{\sum_{i=1}^{n} A_i^2} \sqrt{\sum_{i=1}^{n} B_i^2}}$$

where, $A_i$ is a dimension $i$ in the respective test vector, $B_i$ is the distribution metric of corresponding dimension $i$ in the plurality of dimensions across the plurality of test vectors other than the respective test vector, and $n$ is the number of dimensions in respective test vector (h)

4154 The distribution metric of the plurality of control vectors with the respective control vector removed from the plurality of control vectors is a measure of central tendency of each corresponding dimension in the plurality of dimensions across the plurality of control vectors other than the respective control vector 4156 The measure of central tendency of each corresponding dimension in the plurality of dimensions across the plurality of control vectors other than the respective control vector is an arithmetic mean, weighted mean, midrange, midhinge, trimean, Winsorized mean, median, or mode of the corresponding dimension across the plurality of control vectors 4158 The respective control similarly metric between (i) the respective control vector and (ii) the distribution metric of the plurality of control vectors with the respective control vector removed from the plurality of control vectors is computed as a distance between corresponding dimensions of the control vector and the distribution metric of the plurality of control vectors with the respective control vector removed from the plurality of control vectors 4160 The distance is an angular distance computed as:

$$\frac{\sum_{i}^{n} A_i B_i}{\sqrt{\sum_{i=1}^{n} A_i^2} \sqrt{\sum_{i=1}^{n} B_i^2}}$$

where, $A_i$ is a dimension $i$ in the respective control vector, $B_i$ is the distribution metric of corresponding dimension $i$ in the plurality of dimensions across the plurality of control vectors other than the respective control vector, and $n$ is the number of dimensions in respective control vector (B) (C) (D) (E) (I)

4176 Plotting each respective test vector in the plurality of test vector on a two-dimensional plot using the on target score for the respective test vector as a coordinate in a first dimension of the two-dimensional plot and the off target score for the respective test vector as a coordinate in a second dimension of the two-dimensional plot, thereby obtaining a plurality of test state data points 4178 Plotting each respective control vector in the plurality of control vector on the two-dimensional plot using the on target score for the respective control vector as a coordinate in the first dimension and the off target score for the respective control vector as a coordinate in the second dimension, thereby obtaining a plurality of control data points 4180 Computing the assay quality as a normalized distance between the plurality of test state data points and the plurality of control data points 4182 Determining a test state quality by computing a normalized tightness of the plurality of test state data points 4184 Using the rescue quality for the query perturbation, the assay quality, and the test state quality to calculate an overall quality 4186 The overall quality is computed as:

$$(\text{rescue quality for the compound}) * \exp^{(\text{assay quality} - 1)} * \frac{1}{1 + \exp^{(1 - \text{phenotype quality})}}$$

4188 The normalized tightness is computed by a procedure that includes:

for each respective test vector in the plurality of test vectors, computing a test state similarly metric between (i) the respective test vector and (ii) a distribution metric of the plurality of test vectors with the respective test vector removed from the plurality of test vectors, thereby obtaining a plurality of test state similarity metrics for the plurality of test vectors, each test state similarity metric in the plurality of test state similarity metrics uniquely corresponding to a test perturbation in the set of test perturbations, and computing a null distribution, by a process including:

(a) for each respective control vector in the plurality of control vectors, computing a respective control similarity metric between (i) the respective control vector and (ii) a distribution metric of the plurality of control vectors with the respective control vector removed from the plurality of control vectors, thereby obtaining the plurality of control similarity metrics, each control similarity metric in the plurality of control similarity metrics uniquely corresponding to a control perturbation in the set of control perturbations, and (b) computing the null distribution as a distribution metric of the plurality of control similarity metrics; and determining a first measure of central tendency of the angle between (i) each respective test state similarity metric in the plurality of test state similarity metrics to (ii) the null distribution across the plurality of test state similarity metrics, and normalizing the first measure of central tendency of the angle by a second measure of central tendency of the angle between (i) each control similarity metric in the plurality of control similarity metrics to (ii) the null distribution across the plurality of control similarity metrics, wherein the normalize first measure of central tendency represents the normalized tightness of the plurality of test state data points

Fig. 4Z

4190 Eliminate one or more query perturbations from the plurality of query perturbations using an elimination criterion that is based, at least in part, on the on target score of each query perturbation in the plurality of query perturbations 4192 The elimination criterion is:

E= uudx- K×uuudx, where, each respective query perturbation in the plurality of query perturbations that has an on target score of less than E is eliminated from the plurality of query perturbations, uudx = is a measure of central tendency of the on target score across the plurality of query perturbations, uuudx = is a standard deviation of the on target score across the plurality of query perturbations, K = is a weight, and for each respective query perturbation remaining in the plurality of query perturbations, the obtaining (4050), computing (4060), computing (4062), and computing (4064) is repeated for each respective amount of the respective query perturbation in a plurality of respective amounts of the respective query perturbation, where each respective amount of the respective query perturbation is expressed as a corresponding concentration of the respective query perturbation in the corresponding subset of the plurality of wells, thereby obtaining an on target score and an off target score at each concentration in a plurality of concentrations for the respective query perturbation

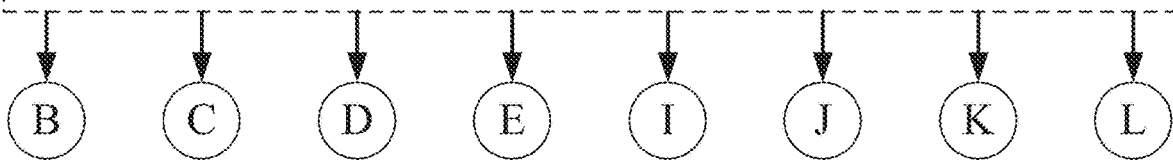

Fig. 4AA

4194 Fit the on target curve to a first sigmoidal function

4196 The first sigmoidal function has the form:

$$\left(c + \frac{(d-c)}{\left(1 + \left(\left(\frac{x}{EC_{50}}\right)\right)^b\right)}\right) + \left(c + \frac{(d-c)}{\left(1 + \left(\left(\frac{x}{EC_{50}}\right)\right)^b\right)}\right),$$

where:

$c$ = a minimum on target score computed for the query perturbation, $d$ = a maximum on target score computed for the query perturbation, $EC_{50}$ = a concentration of the query perturbation that represents half of its on target effect, $x$ = a concentration of the query perturbation in the plurality of concentrations, and $b$ = a hill slope of the on target curve

4198 Fit the off target curve to a second sigmoidal function

4200 The second sigmoidal function has the form:

$$\left(c' + \frac{(d'-c')}{\left(1 + \left(\left(\frac{x}{EC_{50}'}\right)\right)^b\right)}\right) + \left(c' + \frac{(d'-c')}{\left(1 + \left(\left(\frac{x}{EC_{50}'}\right)\right)^b\right)}\right),$$

where:

$c$ = a minimum off target score computed for the query perturbation, $d$ = a maximum off target score computed for the query perturbation, $EC_{50}$ = a concentration of the query perturbation that represents half of its on target effect, $x$ = a concentration of the query perturbation in the plurality of concentrations, and $b$ = a hill slope of the off target curve

4204 The corresponding plurality of control aliquots of the cells of the obtaining (4002) consists of cells of a single cell type, the corresponding plurality of test aliquots of the cells of the obtaining (4034) consists of cells of the single cell type, and the plurality of instances of query perturbation aliquots of the cells jointly representing the respective test perturbation and the query perturbation of the obtaining (4050) consists of cells of the single cell type

---

4206 The corresponding plurality of control aliquots of the cells of each instance of the obtaining (4002) consists of cells of a single cell type, the corresponding plurality of test aliquots of the cells of each instance of the obtaining (4034) consists of cells of the single cell type, and the plurality of instances of query perturbation aliquots of the cells jointly representing the respective test perturbation and the query perturbation of each instance of the obtaining (4050) consists of cells of the single cell type

---

4208 The corresponding wells in the plurality of wells for the plurality of control aliquots of the cells of the obtaining (4002) includes a first plurality of wells, wherein each well in the first plurality of wells comprises an aliquot of a different type of cells in a corresponding plurality of cell types, the corresponding wells in the plurality of wells for the plurality of test aliquots of the cells of the obtaining (4034) includes a second plurality of wells, wherein each well in the second plurality of wells comprises an aliquot of a different type of cells in the corresponding plurality of cell types, and the corresponding wells in the plurality of wells for the plurality of query perturbation aliquots of the cells of the obtaining (4050) includes a third plurality of wells, wherein each well in the third plurality of wells comprises an aliquot of a different type of cells in the corresponding plurality of cell types

4210 The plurality of cells types includes at least three cell types

4212 The corresponding wells in the plurality of wells for the plurality of control aliquots of the cells in each instance of the obtaining (4002) includes a corresponding first plurality of wells, wherein each well in the corresponding first plurality of wells comprises an aliquot of a different type of cells in a corresponding plurality of cell types, the corresponding wells in the plurality of wells for the plurality of test aliquots of the cells of each instance of the obtaining (4034) includes a corresponding second plurality of wells, wherein each well in the corresponding second plurality of wells comprises an aliquot of a different type of cells in the corresponding plurality of cell types, and the corresponding wells in the plurality of wells for the plurality of query perturbation aliquots of the cells of each instance of the obtaining (4050) includes a corresponding third plurality of wells, wherein each well in the corresponding third plurality of wells comprises an aliquot of a different type of cells in the corresponding plurality of cell types 4214 The plurality of cells types includes at least three cell types

Fig. 4AD

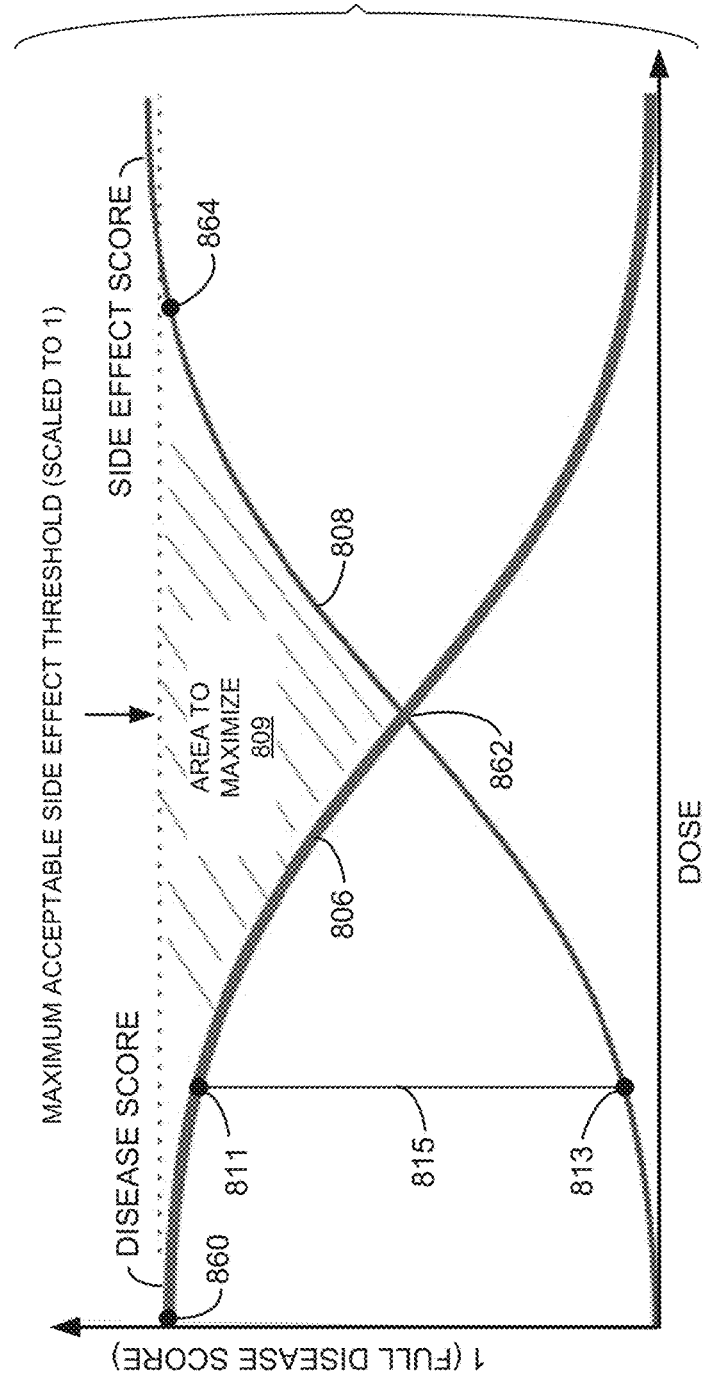
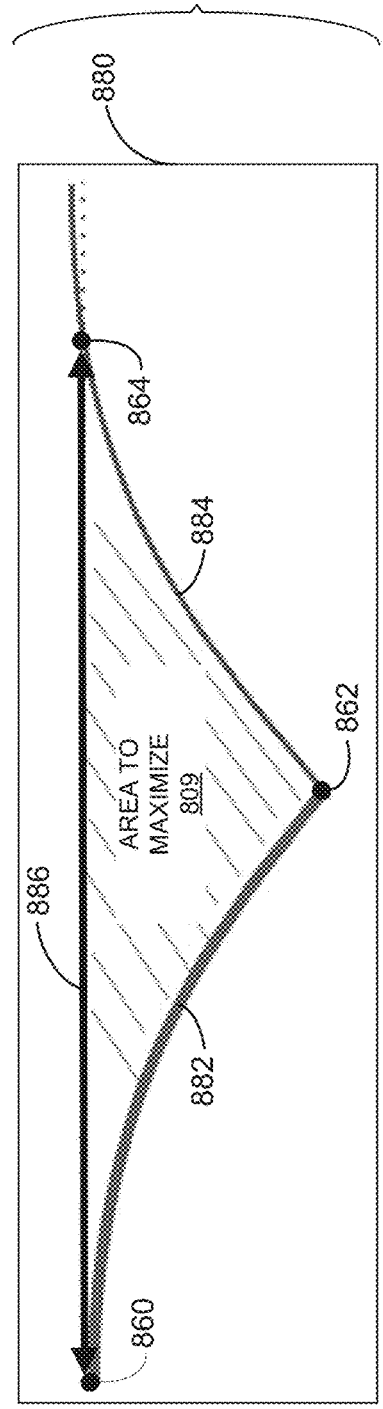

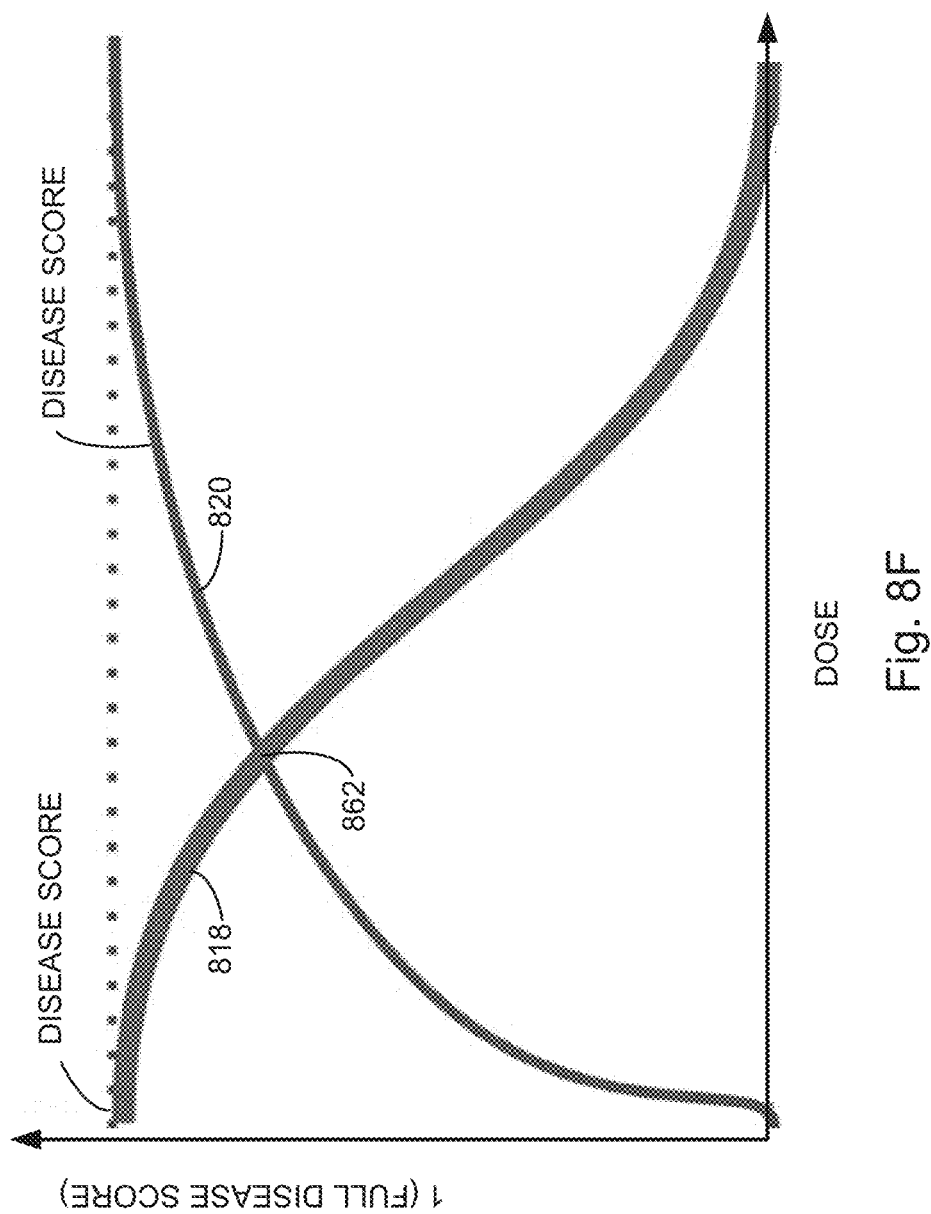

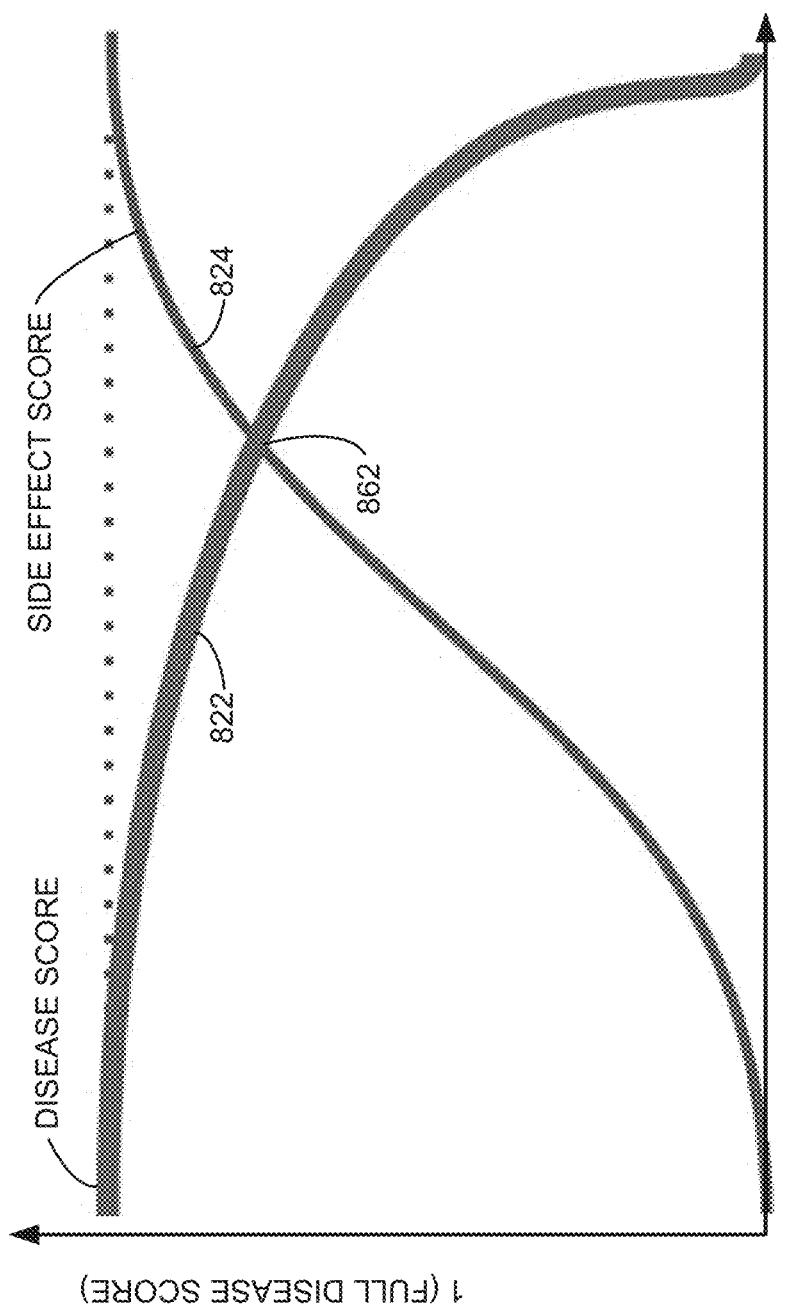

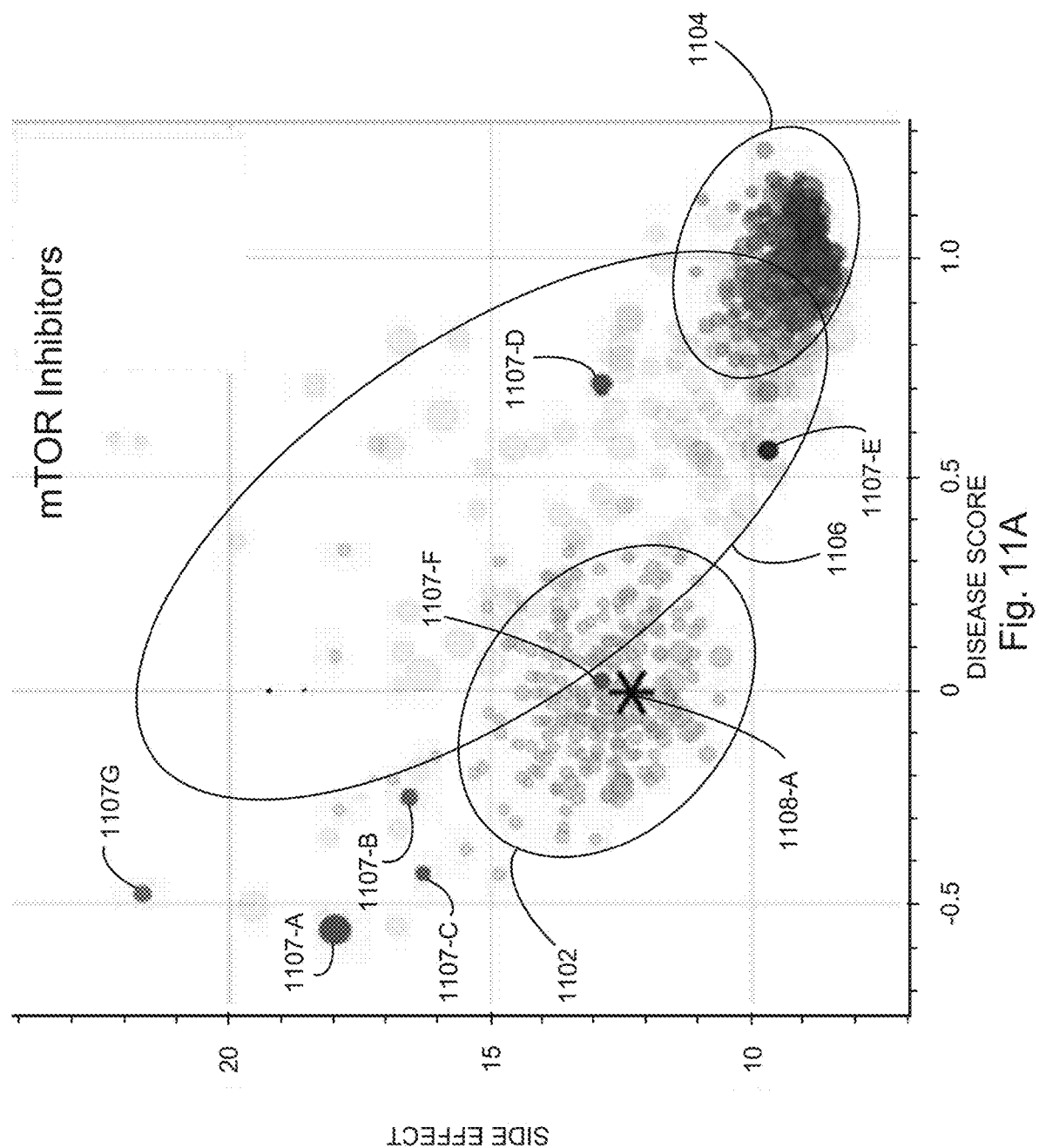

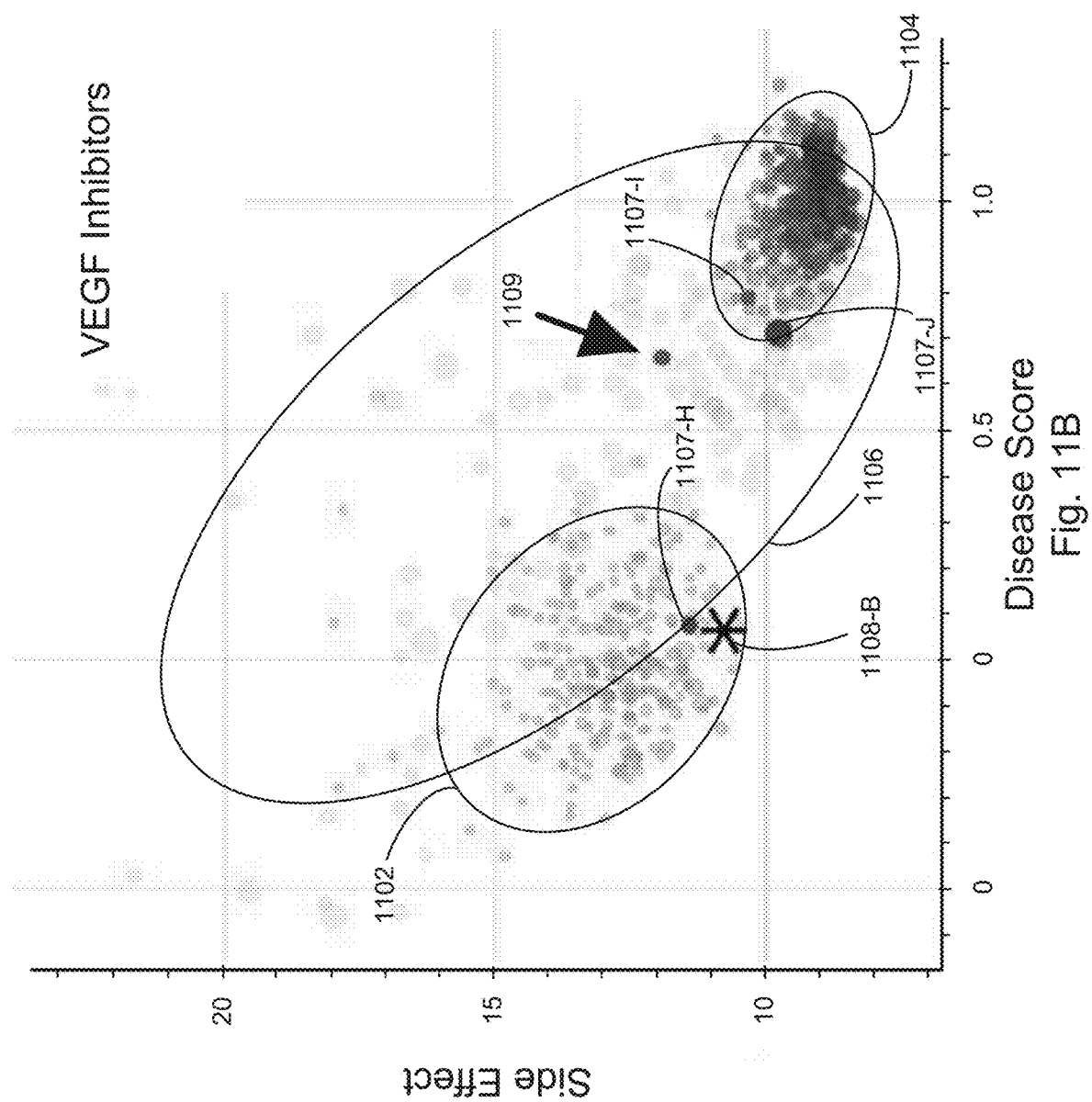

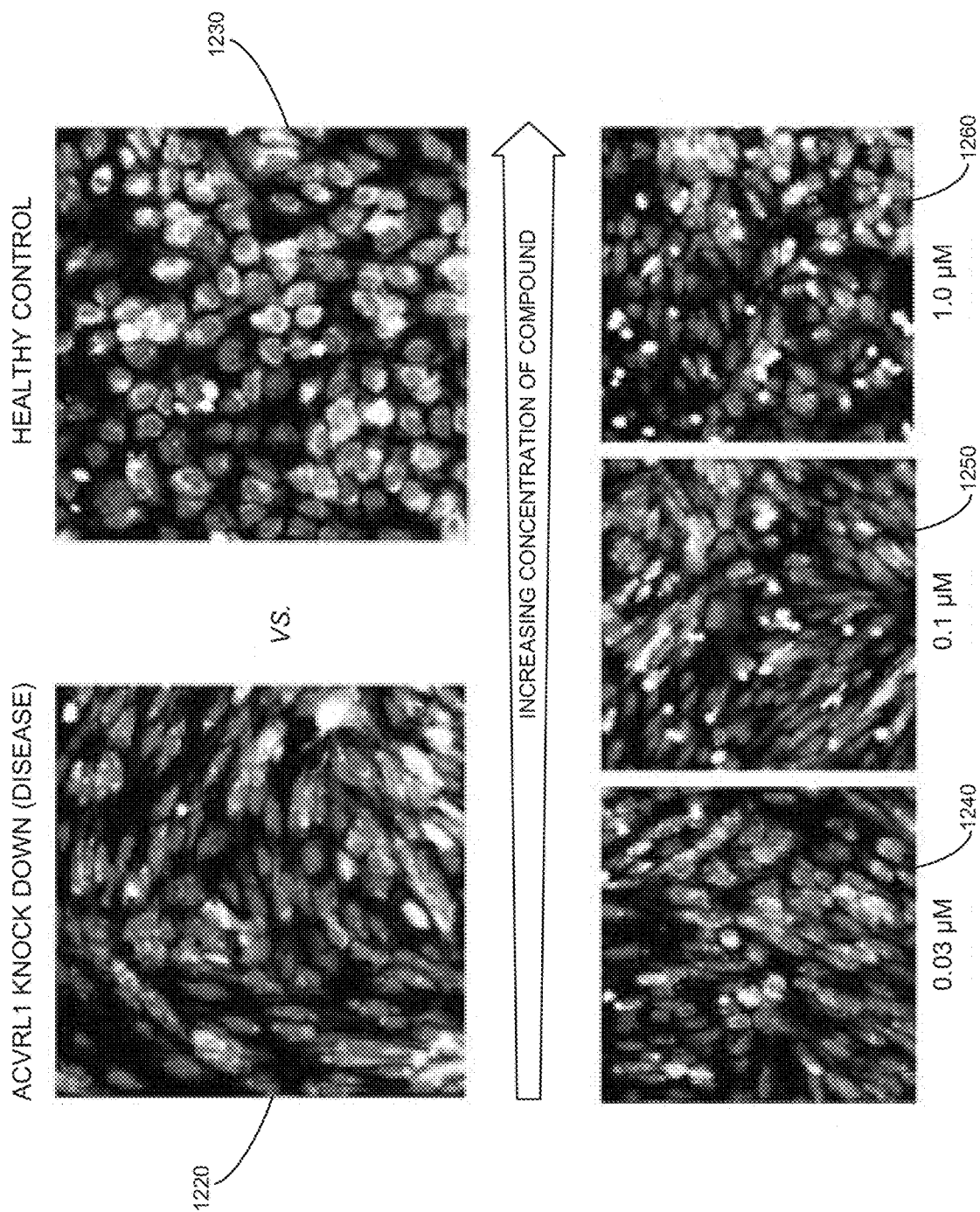

SYSTEMS AND METHODS FOR EVALUATING QUERY PERTURBATIONS

CROSS-REFERENCE TO RELATED APPLICATIONS

This application claims priority to the provisional patent application, Ser. No. 62/863,414, entitled "SYSTEMS AND METHODS FOR EVALUATING QUERY PERTURBATIONS," by Mason Victors et al., with filing date Jun. 19, 2019, which is herein incorporated by reference in its entirety.

This application also claims priority to the provisional patent application, Ser. No. 62/863,696, entitled "METHODS AND SYSTEMS FOR PREDICTING COMPOUND LIABILITIES," by Berton Earnshaw, with filing date Jun. 19, 2019, which is herein incorporated by reference in its entirety.

This application also claims priority to the provisional patent application, Ser. No. 62/863,700, entitled "SYSTEMS AND METHODS FOR COMBINING MULTIDIMENSIONAL PHENOMIC DATA WITH OTHER SOURCES OF BIOLOGICAL DATA FOR DRUG DISCOVERY," by Berton Earnshaw, with filing date Jun. 19, 2019, which is herein incorporated by reference in its entirety.

This application also claims priority to the provisional patent application, Ser. No. 62/863,711, entitled "SYSTEMS AND METHODS FOR IDENTIFYING MECHANISM OF ACTION AND POLYPHARMACOLOGY," by Berton Earnshaw, with filing date Jun. 19, 2019, which is herein incorporated by reference in its entirety.

This application is related to U.S. patent application Ser. No. 15/910,822 filed on Mar. 2, 2018, entitled "Systems and Methods for Evaluating Whether Perturbations Discriminate on Target Effect" by Mason Victors et al., and assigned to the assignee of the present application.

This application is related to PCT Patent Application No. PCT/US2019/019846 filed on Feb. 27, 2019, entitled "Systems and Methods for Discriminating Effects on Targets" by Mason Victors et al., and assigned to the assignee of the present application.

This application is related to PCT Patent Application No. PCT/US2020/022048 filed on Mar. 11, 2020, entitled "Process Control in Cell Based Assays" by Mason Victors et al., and assigned to the assignee of the present application.

TECHNICAL FIELD

The present disclosure relates generally to systems and methods for high throughput compound library screening.

BACKGROUND

High throughput screening (HTS) is a process used in pharmaceutical drug discovery to test large compound libraries containing thousands to millions of compounds for various biological effects. HTS typically uses robotics, such as liquid handlers and automated imaging devices, to conduct biochemical, genetic, and/or phenotypical assays, on large compound libraries in multiwell plates (also referred to as microwell plates), e.g., 96-well, 384-well, 1536-well, or 3456-well plates. In this fashion, promising compounds that provide a desired biochemical, genetic, or phenotypic effect can be quickly identified from the large compound libraries, for further testing and development towards the goal of discovering a new pharmaceutical agent for disease treatment. For a review of basic HTS methodologies see, for example, Wildey et al., 2017, "Chapter Five—High-Throughput Screening," Annual Reports in Medicinal Chemistry, Academic Press, 50:149-95, which is hereby incorporated by reference.

Conventional HTS methodologies rely on disease-specific biological assays that measure candidate drug effects on specific identified biological targets. This requires a substantial understanding of the disease and the corresponding etiology prior to the design and implementation of a drug discovery strategy for a particular disease. Swinney and Xia, 2014, Future Med. Chem. 6(9):987-1002. Thus, it is difficult to design effective screening methodologies for diseases for which the etiology is poorly understood. However, even when the etiology of a disease is well understood, a target-specific assay developed based on these understandings is not capable of capturing complex polypharmacological effects (see, Reddy and Zhang, 2014, "Polypharmacology: drug discovery for the future," Expert Rev. Clin. Pharmacol. 6(1): doi:10.1586/ecp.12.74, which is hereby incorporated by reference) or effects mediated through an unknown target. Moreover, there is a significant cost in capital, labor, and time to develop an assay that is specific to a particular molecular target.

Finally, because conventional HTS methodologies are target-specific, it is difficult to determine whether a candidate therapeutic agent—which might demonstrate a desired effect on the pre-identified target—will also generate unwanted off-target effects in the screening assay. Thus, conventionally, further assays are required to test for the presence of such off-target effects after identifying a candidate therapeutic agent in the initial high-throughput screen.

SUMMARY

Given the above background, methods and systems for screening compound libraries in a target-agnostic fashion are needed in the art. Such methods and systems would overcome the requirement to develop a different target-based assay for each disease, improving the speed and reducing the cost of drug discovery. Such methods and systems would also improve screening methodologies by facilitating identification of candidate therapeutics with effects that are mediated through any molecular target, including previously unidentified targets. Further, methods and systems that allow for the identification polypharmacological effects in a high throughput screening environment are also needed in the art. Such methods and systems would improve screening methodologies by facilitating identification of candidate therapeutics with effects that are mediated through multiple molecular targets, which would not be identified through the use of any number of target-specific assays. Finally, methods and systems for identifying both on-target and off-target effects in a single high-throughput screening assay are also needed in the art. Such methods and systems would overcome the requirement of running separate screens for on-target and off-target effects, improving the speed and reducing the cost of drug discovery.

The present disclosure addresses, among others, the need for systems and methods that facilitate intelligent screening of compound libraries without a molecular understanding of the disease and the corresponding etiology. Further, the systems and methods described herein facilitate identification of compounds that rescue cellular disease phenotype without causing high levels of off-target effects. The methods and systems described herein are also useful for identifying therapeutic concentration windows for such compounds, where on-target drug effects are high and off-target effects are low. In this fashion, the methods and systems described herein for screening compounds in a compound library speeds-up and reduces the cost of pharmaceutical drug discovery.

The methods and systems disclosed herein leverage automated biology and machine learning. In some embodiments, the methods and systems use of microscopy to measure large numbers of changes (e.g., sub-cellular and cell population changes) caused by perturbations and application of machine learning to discover high-dimensional phenotypes across many disease models. High-throughput drug screens according to these and other methods described herein can uncover promising drug candidates that rescue complex disease signatures. This unique approach allows rapid modeling and screening of potential treatments for hundreds of traditionally refractory diseases, making it ideally suited to tackle urgent unmet medical needs, e.g., such as the treatment of patients with poorly understood, polypharmacologically challenging, and/or rare diseases.

For instance, there are approximately 6,000 rare diseases affecting an estimated 25 million people in the United States. Rare diseases disproportionately affect children, and many children with rare genetic diseases do not live to see their 5th birthday. Therapeutic development for these diseases has been slow, and less than 5% of rare diseases have an FDA-approved treatment. This is due in part to the conventional requirement of HTS that the etiology of the disease be well understood in order to design a target-specific assay for screening. The disclosed methods and systems overcome this requirement, facilitating screening of therapies for diseases, such as rare diseases, for which the etiology is not well understood.

The present disclosure, however, is not limited to methods and systems for screening therapeutics for rare diseases or even diseases for which the etiology is poorly understood. As described above, the methods and systems disclosed herein improve conventional screening methodologies, for instance, by facilitating identification of candidate therapies with effects acting through unidentified molecular targets and/or having polypharmacological effects, and by facilitating evaluation of on-target and off-target effects from a single assay.

In one aspect, the disclosure provides methods, systems, and computable readable media for screening a set of compounds by considering on-target and off-target effects of the compounds. In some embodiments, the screening includes obtaining results from a cell-based assay performed in one or more multiwell plates. The results include feature measurements from a plurality of control states representing wild-type phenotypes, a plurality of test states representing disease-state phenotypes, and a plurality of query states in which the effects of compounds on the disease-state phenotypes are tested. Control data points are obtained that each include a plurality of dimensions, where each dimension represents either (i) a measure of central tendency of a measurement of a different feature across a plurality of control instances of a cell context or (ii) a measure of central tendency of a different dimension reduction component determined using measurements of the features across the plurality of control instances of the cell context. test data points are obtained that each include a plurality of dimensions, where each dimension represents either (i) a measure of central tendency of a measurement of a different feature across a plurality of test instances of a perturbed cell context or (ii) a measure of central tendency of a different dimension reduction component determined using measurements of the features across the plurality of test instances of the perturbed cell context. Query data points are obtained that each include a plurality of dimensions, where each dimension represents either (i) a measure of central tendency of a measurement of a different feature across a plurality of query instances of a perturbed cell context exposed to a compound or (ii) a measure of central tendency of a different dimension reduction component determined using measurements of the features across the plurality of query instances of the perturbed cell context exposed to the compound. A composite test vector is computed between (i) a first point defined by a respective measure of central tendency across the plurality of control data points for each dimension and (ii) a second point defined by a respective measure of central tendency across the plurality of test data points for each dimension. A query composite test vector is computed between (i) the first point and (ii) a respective measure of central tendency across the plurality of query perturbation data points for each dimension. An on-target score is computed for the perturbed cell context exposed to a compound as a projection of the query perturbation vector onto the composite test vector, and an off-target score is computed for the perturbed cell context exposed to the compound as a rejection of the query perturbation vector against the composite test vector. The on-target score and/or off-target score for the perturbed cell context exposed to the compound is then evaluated. In some embodiments, on-target and off-target scores of perturbed cell contexts exposed to multiple compounds and/or multiple concentrations of a compound are evaluated by plotting the scores in a coordinate system that is defined in part by the feature measurements of the control cell contexts.

BRIEF DESCRIPTION OF THE DRAWINGS

FIGS. 2A, 2B, 2C, and 2D collectively illustrate an example system/device for screening one or more compounds based on on-target and off-target effects when exposed to one or more perturbed cell contexts, in accordance with various embodiments of the present disclosure.

FIGS. 8A, 8B, 8C, 8D, 8E, 8F, and 8G illustrate example response scoring plots independently fitting dose-response on-target scores and dose-response off-target scores for a perturbed cell context exposed to a compound to a sigmoid curve, in accordance with various embodiments of the present disclosure.

FIGS. 11A, 11B, and 11C show examples of inhibitors of mTOR, VEGF, and EGFR/Her2 that rescue a high-dimensional phenotype associated with NF2 deficiency, in accordance with various embodiments of the present disclosure.

FIGS. 12A, 12B, 12C, 12D, and 12E illustrate example results from screens of VEGFR inhibitors to identify drug candidates for the treatment of HHT, using an ACVRL1 knock down model, in accordance with various embodiments of the present disclosure.

Like reference numerals refer to corresponding parts throughout the several views of the drawings.

DETAILED DESCRIPTION

Figure 1:
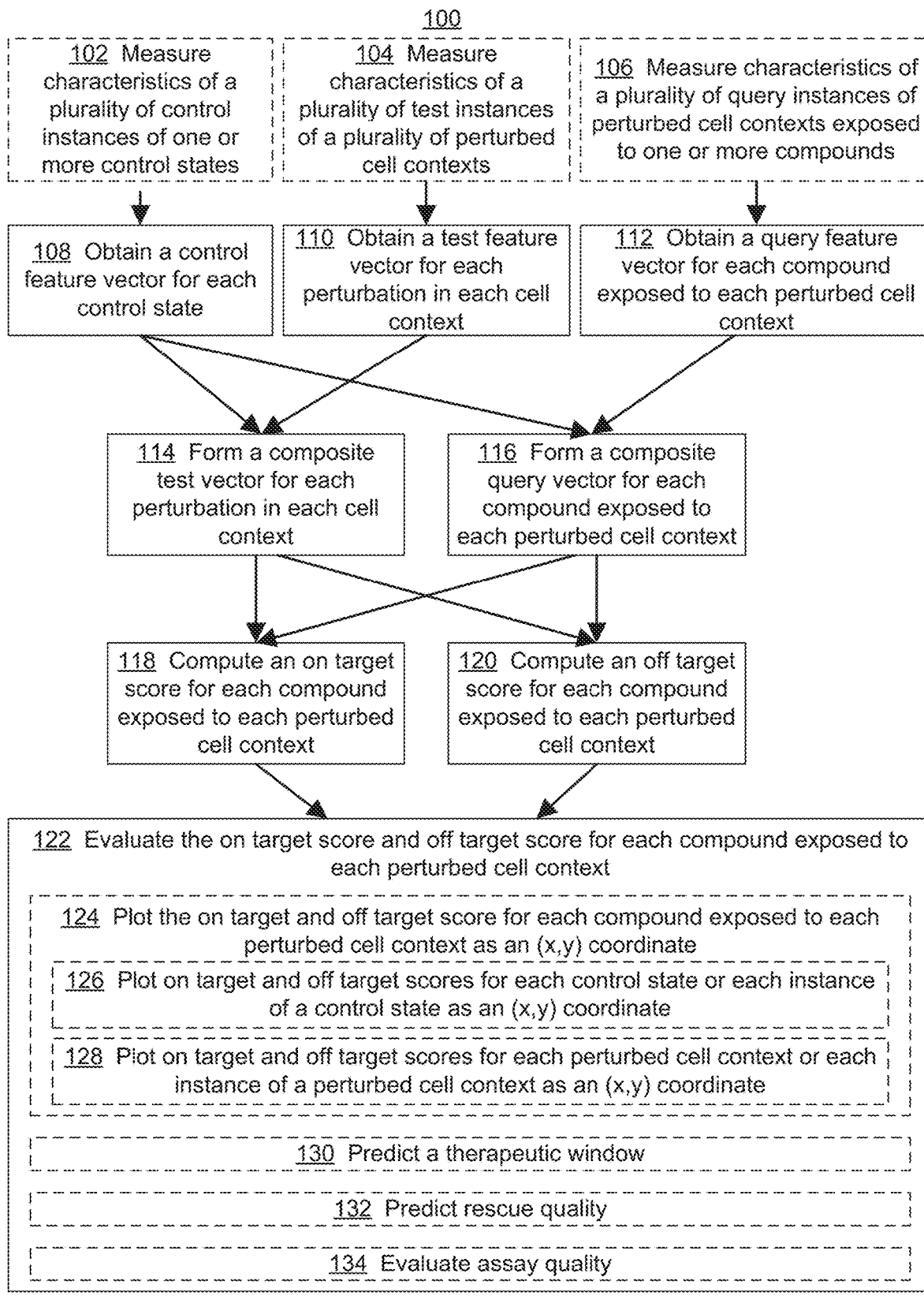
FIG. 1 illustrates an exemplary workflow for screening one or more compounds based on on-target and off-target effects when exposed to one or more perturbed cell contexts, in accordance with various embodiments of the present disclosure.

Reference will now be made in detail to various embodiments of the subject matter, examples of which are illustrated in the accompanying drawings. While various embodiments are discussed herein, it will be understood that they are not intended to limit to these embodiments. On the contrary, the presented embodiments are intended to cover alternatives, modifications and equivalents, which may be included within the spirit and scope the various embodiments as defined by the appended claims. Furthermore, in this Description of Embodiments, numerous specific details are set forth in order to provide a thorough understanding of embodiments of the present subject matter. However, embodiments may be practiced without these specific details. In other instances, well known methods, procedures, components, and circuits have not been described in detail as not to unnecessarily obscure aspects of the described embodiments.

Overview of Discussion

Conventional high throughput screening methodologies are inefficient because they cannot readily identify candidate drugs that act through an unknown molecular target and/or have complex pharmacologic properties. As a result, the discovery of effective therapeutic agents for treatment of disease is unnecessarily slow, expensive, and inefficient. This is particularly true for diseases with poorly understood etiologies, for which target-based assays are either limited in their effectiveness or cannot be designed at all. Thus, effective treatments for many diseases represent an urgent area of great unmet medical need, while therapies for other diseases are unnecessarily expensive due to the excessive cost of drug discovery, in terms of both capital and labor. Advantageously, the present disclosure addresses these needs by provide drug discovery screening platforms that are quickly adaptable for use in screening compound libraries against nearly any disease state, regardless of whether a target-specific assay has been developed. Moreover, the drug discovery platforms described herein are readily able to measure polypharmacological effects and identify therapeutic candidates acting through unknown molecular targets. The screening platform described herein leverages the design of high-dimensional structural phenotypes across hundreds of disease models in massively parallel high-throughput drug screens.

For example, as described in the Examples, analysis of studies using this platform to identify compound candidates for treatment of A-T, SMA, and NF2 highlight the potential of the disclosed screening platform to rapidly uncover highly translatable drug candidates in a fraction of the time and cost of traditional drug screening. Significantly, the methods described herein facilitate drug screening without having a predetermined target hypothesis. This is particularly valuable for finding drugs that affect novel targets or that work through complex polypharmacology. For example, as reported in Example 1, a strong disease phenotype ameliorative class effect displayed by glucocorticoids for the treatment of A-T was identified, as well as their previously unreported dichotomous grouping in terms of phenotypic side-effect profiles. The screening platform specifically identified betamethasone and dexamethasone as hits, both of which have been validated independently in human trials. However, the screening method also uncovered the ability of mometasone, which harbored a more attractive side-effect profile than betamethasome and dexamethasone, to better rescue ATM deficiency in an orthogonal disease-relevant assay.

Similarly, as described in Example 2, the screening platform disclosed herein quickly identified HDAC inhibitors among other drug classes as potential treatments of SMA, including one specific HDAC inhibitor that has already progressed to clinical trials for the disease.

Finally, as described in Example 3, the screening platform disclosed herein identified the three major drug classes (mTOR, VEGF, and EGFR/Her2 inhibitors) that have known efficacy for the treatment of cancer syndromes caused by NF2 deficiency. Of note, the screening platform specifically identified the therapeutic effects of AZD2014 and sunitinib, both of which are being evaluated in advanced clinical trials for NF2 associated pathologies. Together, these data demonstrate the ability of the unique approach of the disclosed screening platform to rapidly uncover highly translatable drug candidates as well as differentiate them with remarkable sensitivity.

Accordingly, in some embodiments, the present disclosure provides a method for screening one or more compounds based on on-target and off-target effects when exposed to one or more perturbed cell contexts. The screening method is based on correlations between features determined from characteristic measurements of (i) a cell context, (ii) a perturbation of the cell context, and (iii) the perturbation of the cell context exposed to one or more compounds, e.g., as applied across a compound library, as described in detail below. The various features used in these analyses can either be a measurement (e.g., average measurements) of a particular characteristics of a given condition or an algebraic combination of measurements of a plurality of characteristics of the given condition, e.g., as identified by deep learning analysis. Multidimensional vectors constructed from these features are used to compute on-target scores and off-target scores for each compound screened. In some embodiments, the on-target scores are based upon the projection of a first multidimensional vector constructed from features determined from instances of a perturbation of a cell context exposed to a compound on a second multidimensional vector constructed from features determined from instances of the perturbation of the cell context when not exposed to the compound, e.g., relative to a center of a multidimensional space defined during the screening process. In some embodiments, the off-target scores are based upon the rejection of the first multidimensional vector constructed from features determined from instances of the perturbation of the cell context exposed to the compound on the second multidimensional vector constructed from feature determined from instances of the perturbation of the cell context when not exposed to the compound, e.g., relative to a center of a multidimensional space defined during the screening process.

Notation and Nomenclature

Some portions of the detailed descriptions which follow are presented in terms of procedures, logic blocks, processes, modules and other symbolic representations of operations on data bits within a computer memory. These descriptions and representations are the means used by those skilled in the data processing arts to most effectively convey the substance of their work to others skilled in the art. In the present application, a procedure, logic block, process, module, or the like, is conceived to be one or more self-consistent procedures or instructions leading to a desired result. The procedures are those requiring physical manipulations of physical quantities. Usually, although not necessarily, these quantities take the form of electrical or magnetic signals capable of being stored, transferred, combined, compared, and otherwise manipulated in an electronic device/component.

It should be borne in mind, however, that all of these and similar terms are to be associated with the appropriate physical quantities and are merely convenient labels applied to these quantities. Unless specifically stated otherwise as apparent from the following discussions, it is appreciated that throughout the description of embodiments, discussions utilizing terms such as "accessing," "computing adding," "calculating," "coloring." "deriving," "determining," "displaying," "eliminating," "embedding," "evaluating," "exposing," "expressing," "filtering," "finding," "fitting," "graphing," "imaging," "measuring," "measuring a central tendency," "normalizing," "obtaining," "outputting," "plotting," "providing," "quantifying," "reducing," "removing," "representing," "shading," "sizing," "sorting," "using," or the like, refer to the actions and processes of an electronic device or component such as: a processor, a controller, a computer system, a memory, or the like, or a combination thereof. The electronic device or component(s) manipulates and transforms data represented as physical (electronic and/or magnetic) quantities within the registers and memories into other data similarly represented as physical quantities within memories or registers or other such information storage, transmission, processing, or display components.

Embodiments described herein may be discussed in the general context of computer/processor executable instructions residing on some form of non-transitory computer/processor readable storage medium, such as program modules or logic, executed by one or more computers, processors, or other devices. Generally, program modules include routines, programs, objects, components, data structures, etc., that perform particular tasks or implement particular abstract data types. The functionality of the program modules may be combined or distributed as desired in various embodiments.

In the figures, a single block may be described as performing a function or functions; however, in actual practice, the function or functions performed by that block may be performed in a single component or across multiple components, and/or may be performed using hardware, using software, or using a combination of hardware and software. To clearly illustrate this interchangeability of hardware and software, various illustrative components, blocks, modules, circuits, and steps have been described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure. Also, the example hardware described herein may include components other than those shown, including well-known components.

The techniques described herein may be implemented in hardware, or a combination of hardware with firmware and/or software, unless specifically described as being implemented in a specific manner. Any features described as modules or components may also be implemented together in an integrated logic device or separately as discrete but interoperable logic devices. If implemented in software, the techniques may be realized at least in part by a non-transitory computer/processor-readable storage medium comprising computer/processor-readable instructions that, when executed, cause a processor and/or other components of a computer or electronic device to perform one or more of the methods described herein. The non-transitory computer/processor-readable data storage medium may form part of a computer program product, which may include packaging materials.

The non-transitory processor readable storage medium (also referred to as a non-transitory computer readable storage medium) may comprise random access memory (RAM) such as synchronous dynamic random access memory (SDRAM), read only memory (ROM), non-volatile random access memory (NVRAM), electrically erasable programmable read-only memory (EEPROM), FLASH memory, compact discs, digital versatile discs, optical storage media, magnetic storage media, hard disk drives, other known storage media, and the like. The techniques additionally, or alternatively, may be realized at least in part by a processor-readable communication medium that carries or communicates code in the form of instructions or data structures and that can be accessed, read, and/or executed by a computer or other processor.

The various illustrative logical blocks, modules, circuits and instructions described in connection with the embodiments disclosed herein may be executed by one or more processors, such as host processor(s) or core(s) thereof, digital signal processors (DSPs), general purpose microprocessors, application specific integrated circuits (ASICs), application specific instruction set processors (ASIPs), field programmable gate arrays (FPGAs), graphics processing unit (GPU), microcontrollers, or other equivalent integrated or discrete logic circuitry. The term "processor" or the term "controller" as used herein may refer to any of the foregoing structures or any other structure suitable for implementation of the techniques described herein. In addition, in some aspects, the functionality described herein may be provided within dedicated software modules or hardware modules configured as described herein. Also, the techniques, or aspects thereof, may be fully implemented in one or more circuits or logic elements. A general purpose processor may be a microprocessor, but in the alternative, the processor may be any conventional processor, controller, microcontroller, or state machine. A processor may also be implemented as a combination of computing devices, e.g., a plurality of microprocessors, one or more microprocessors in conjunction with an ASIC or DSP, or any other such configuration or suitable combination of processors.

Definitions

It will also be understood that, although the terms first, second, etc. may be used herein to describe various elements, these elements should not be limited by these terms. These terms are only used to distinguish one element from another. For example, a first cell context could be termed a second cell context, and, similarly, a second cell context could be termed a first cell context, without departing from the scope of the present disclosure. The first cell context and the second cell context are both cell contexts, but they are not the same cell context.

The terminology used in the present disclosure is for the purpose of describing particular embodiments only and is not intended to be limiting of what is described. As used in the detailed description and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

As used herein, the term "cell context" or "cellular context" refers to an experimental condition including an aliquot of cells of one or more cell types and a chemical environment, a culture medium and optionally a test perturbation, exclusive of a query perturbation, e.g., that does not include a compound being screened. That is, control states and test states constitute cell contexts, while query perturbation states constitute cell contexts that are exposed to a query perturbation. In some embodiments, a cell context includes a genetic or epigenetic modification, e.g., a genetic modification introduced by site-specific means, such as crispr, or epigenetic modification, such as introduction of a control siRNA.

As used herein, the term "control perturbation" refers to a change in a cell context that does not cause a cellular phenotype representative of a diseased cell phenotype. In some embodiments, a control perturbation is used to control for background noise and/or unintended effects of a test perturbation. For instance, where one or more siRNA that knocks down expression of a targeted gene is used as a test perturbation, one or more siRNAs that do not knock down expression of the target gene may be used as a control perturbation, e.g., to account for any non-targeted effects of using the siRNA as a test perturbation.

As used herein, the term "control instance," "control state", or simply "control" refers to an experimental condition that is not perturbed to simulate a disease state and lacks a query perturbation (e.g., that is not treated with a candidate therapeutic agent and/or physical treatment) whose therapeutic effects are being screened. That is, a control state is any state that is representative of a biological state that is achieved when a compound rescues a corresponding perturbed cell context. In some embodiments, a control state refers to an aliquot of cells of one or more cell types in a particular chemical environment (e.g., culture medium), e.g., a single 'healthy' cell context. In some embodiments, a control state refers to average features of an aliquot of cells of one or more cell types in a plurality of chemical environments (e.g., culture mediums), e.g., an average of a plurality of 'healthy' cell contexts, each of which is tested separately in their own wells. In some embodiments, the "control" state is sampled through any context that is believed to be a "good control"—i.e., a context that incorporates as many or all of the same technical and biological effects and biases without obscuring the effect of the intended biological perturbation. For some experiments, this means a specific set of reagents is used over which random samples are drawn in order to mimic non-specific, random biological artifacts of the experimental approach. For example, in a case where the perturbed cell context includes exposure of cells to an siRNA that knocks-down expression of a particular gene, a control state may include one or more cell contexts in which the cells are exposed to siRNAs that do not knock-down the expression of the particular gene, e.g., siRNA with one or more nucleotide changes relative to the siRNA capable of knocking-down expression of the particular gene. In other embodiments, a control state includes naive, untreated cells (e.g., which are not treated with a perturbing siRNA or a control siRNA), as a control for the technical and biological effects and biases of the experimental approach. In some embodiments, at the intersection of all these different types of "healthy" control contexts, is the notion that a population of replicates and/or different test perturbations are sampled to create a distribution of vectors that describes the state of cells in the experiment absent the query perturbation.

As used herein, the term "test perturbation" refers to a change in a cell context causing a perturbed cellular phenotype, e.g., representative of a diseased cell. In some embodiments, a test perturbation includes a reagent that is exposed to, and acts upon, an aliquot of cells, e.g., an siRNA or CRISPR treatment that knocks-down expression of a gene in the cell, a compound that perturbs a cellular process (e.g., inhibits a cellular signaling pathway, inhibits a metabolic pathway, inhibits a cellular checkpoint, etc.), a toxin, a CRISPR reagent, a signaling molecule, a pathogen, a signaling molecule, or a biologic (e.g., an antibody or enzyme). In some embodiments, a test perturbation includes a physical change to the cell context, e.g., a temperature change and/or a change in the surrounding chemical environment (e.g., a change in the nutrient composition of a cell culture medium in which a cell context is growing).

As used herein, the term "perturbed cell context," "test perturbation state," or simply a "test state" refers to an experimental condition (e.g., cell context) that is perturbed to simulate a disease state and lacks or significantly lacks a compound whose therapeutic effects are being screened. In some embodiments, the composition of a test state differs from the composition of a corresponding control state only by the inclusion of a test perturbation. In other embodiments, where a corresponding control state includes a control perturbation, the composition of a test state differs from the composition of the control state based on the targeted effects of the test perturbation which are not caused by the control perturbation.

As used herein, the term "query perturbation" refers to a candidate therapy being screened for efficacy against a test perturbation. In some embodiments, a query perturbation includes a compound or a combination of compounds, e.g., one or more possible therapeutic agents. As used herein, the term "compound" encompasses both "small molecule" chemical compounds and biologic therapeutic agents. In some embodiments, a query perturbation includes a physical treatment, e.g., including a temperature treatment, a radiation treatment, and/or a change in the surrounding chemical environment (e.g., a change in the nutrient composition of a cell culture medium in which a cell context is growing). Non-limiting examples of query perturbations include siRNA, gene therapies, heat-shock, a chemical compound, a biologic, cell therapies, and combinations thereof. In some embodiments, a query perturbation includes both a compound (e.g., small molecule or biologic), or a combination of compounds, and a physical treatment.

As used herein, the term "query perturbation state" refers to an experimental condition that is perturbed to simulate a disease state and is exposed to a query perturbation. Generally, the composition of a query perturbation state differs from a corresponding test state only by the exposure to the query perturbation, e.g., the addition of a candidate drug. Accordingly, a query perturbation aliquot of cells representing a respective test perturbation refers to a physical sample of the test perturbation state that is exposed to the query perturbation. In some embodiments, the query perturbation state also differs from a corresponding test state by the inclusion of a substance required to deliver the query perturbation, e.g., a solvent such as DMSO. However, in some embodiments, any such substance required for the delivery of the query perturbation is also included in the test state, e.g., when DMSO is used as a solvent for a candidate drug, DMSO is also added (in the absence of the candidate drug) to the test state.

Methods and Systems for Compound Screening

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

Referring to FIG. 1, the present disclosure provides a method 100 for screening one or more therapies (also referred to herein as query perturbations), e.g., chemical compounds, based on the on-target and off-target effects when one or more perturbed cell contexts are exposed to the query perturbations. In some embodiments, method 100 includes obtaining (108) control feature vectors (e.g., control data points 274 of FIG. 2C) for control states, e.g., cell contexts representative of a 'healthy' phenotype. The control feature vector is constructed from features derived from measurements of characteristics of the control state, where the features of the vector include, e.g., a direct measurement of a particular characteristic of the control state, a dimension-reduced component of such measurements, and/or a complex feature (e.g., an algorithmic combination of multiple measurements) determined by deep learning. In some embodiments, each dimension of the vector represents a measure of central tendency of a different feature derived from characteristics measured across a plurality of instances of the control state (e.g., replicates and/or instances of related control cell contexts). In some embodiments, the method also includes measuring (102) the characteristics of a plurality of control instances (e.g., replicates or separate instances of related control cell contexts) of one or more control states, to generate control perturbation data 224, which are used to construct the control feature vector 276.

Method 100 also includes obtaining (110) test feature vectors (e.g., test data points 278) for test perturbation states, e.g., perturbed cell contexts representative of a 'diseased phenotype.' The test feature vector is constructed from features derived from measurements of characteristics of the test state (e.g., the perturbed cell context in the absence of a query perturbation). In some embodiments, each dimension of the vector represents a measure of central tendency of a different feature derived from characteristics measured across a plurality of instances of the test state (e.g., replicates and/or instances of related perturbed cell contexts). In some embodiments, the method also includes measuring (104) the characteristics of a plurality of test instances (e.g., replicates or separate instances of related test cell contexts) of one or more test states, to generate test perturbation data 228, which are used to construct the test feature vector 280.

Method 100 also includes obtaining (112) query feature vectors (e.g., query data points 282) for query perturbation states, e.g., perturbed cell contexts that are exposed to a possible therapy, e.g., a chemical compound. The query feature vector is constructed from features derived from measurements of characteristics of the query state (e.g., the perturbed cell context that has been exposed to a query perturbation). In some embodiments, each dimension of the vector represents a measure of central tendency of a different feature derived from characteristics measured across a plurality of instances of the query state (e.g., replicates and/or instances of related perturbed cell contexts exposed to a query perturbation). In some embodiments, the method also includes measuring (106) the characteristics of a plurality of query instances (e.g., replicates or separate instances of related test cell contexts exposed to a query perturbation) of one or more test states, to generate query perturbation data 232, which are used to construct the query feature vector 284.

Figure 5:
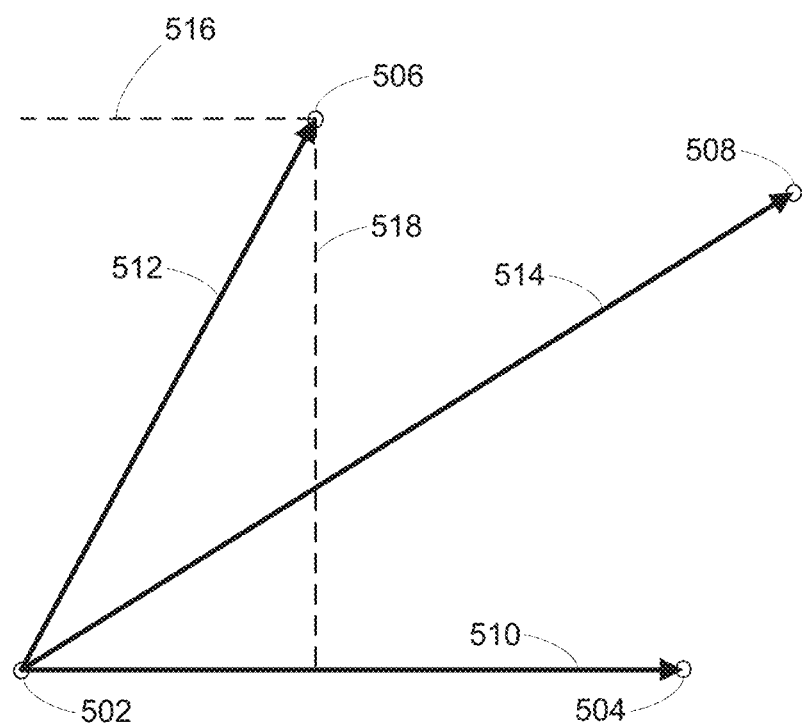
FIG. 5 illustrates determination of off-target and on-target scores based on the relationship between a composite test vector and a composite query vector computed from feature measurements of a cell context, a perturbation of the cell context, and the perturbation of the cell context exposed to a compound, in accordance with various embodiments of the present disclosure.

Method 100 then includes forming (114) a composite test vector (e.g., composite test vector 292 in FIG. 2D; vector 510 between points 502 and 504 as illustrated in FIG. 5) for each perturbation in each cell context, based on differences between the value of each dimension of the control feature vector 276 and the value of each dimension of the test feature vector 280 for corresponding control states and test states. The method also includes forming (116) a composite query vector (e.g., composite query vector 296 in FIG. 2D; vector 512 between points 502 and 506 as illustrated in FIG. 5) for each compound exposed to each perturbed cell context, based on the differences between the value of each dimension of the control feature vector 276 and the value of each dimension of the query feature vector 284 for corresponding control states and query states. Other vectors, such as vector 514 between points 502 and 508 may also be calculated from the vector data.

Method 100 then includes computing (118) an on-target score for each compound exposed to each query state, e.g., by taking the projection of the composite query vector 284 on the composite test vector 280 (e.g., projection 516 in FIG. 5). The method also includes computing (120) an off-target score for each compound exposed to each query state, e.g., by taking the rejection of the composite query vector 284 on the composite test vector 280 (e.g., rejection 518 in FIG. 5). In some embodiments, different on-target and/or off-target scores are generated for a particular query perturbation by comparing (e.g., projecting and/or rejecting) a composite query vector with a different test vectors, e.g., generated for a sub-disease context or for a known efficacy and/or side-effect. For example, by projecting a composite query vector constructed for a perturbation being screened onto a composite query vector constructed for a compound with a known clinical effect, and/or vice-a-versa, a prediction about the clinical effect of the perturbation being screened can be made. For example, where the projection of the composite query vector constructed for a perturbation being screened is equal to the magnitude of the composite query vector constructed for a compound with a known clinical effect, it can be predicted that the perturbation being screened will have at least as efficacious effect on the disease state as the compound with the known clinical effect. Similarly, by rejecting a composite query vector constructed for a perturbation being screened onto a composite query vector constructed for a compound with a known side-effect, and/or vice-a-versa, a prediction about the off-target clinical effects of the perturbation being screened can be made. For example, where the magnitude of the resulting rejection is small, it can be predicted that the perturbation being screened will have a similar off-target clinical profile as the known compound. In contrast, as the magnitude of the resulting rejection becomes larger, it can be predicted that the off-target clinical profile of the perturbation being screened will significantly differ from that of the known compound, e.g., in the magnitude of the effect and/or type of effect. For a summary of vector mathematics including projections and rejections of multi-dimensional vectors, see, Vector Analysis, Louis Brand, Dover Publications, Inc. (2006), the content of which are expressly incorporated herein by reference in its entirety, for all purposes.

Method 100 then includes evaluating (122) the on-target score and off-target score for each compound exposed to each query perturbation. In some embodiments, the evaluating includes plotting (124) the on-target score and off-target score for each compound in the disease model context as an (x,y) coordinate (e.g., illustrated as purple triangles in FIG. 6 and purple circles in FIG. 7A). In some embodiments, the evaluating also includes plotting (126) on-target and off-target scores for each control state (e.g., representative of a 'healthy state') for each instance of a control state as an (x,y) coordinate (e.g., as illustrated as green squares in FIG. 6 and green circles in FIG. 7A-7C). In some embodiments, the evaluating also includes plotting (128) on-target and off-target scores for each test state (e.g., representative of a 'diseased state') or each instance of a test state as an (x,y) coordinate (e.g., as illustrated as red circles in FIG. 6 and red circles in FIG. 7A-7C).

In this fashion, the ability of a therapy (e.g., a compound) to address a disease phenotype is visualized as the proximity of a point representing the on-target and off-target effects of the compound to points representing control states and points representing diseased states. That is, the closer the point representing the query state is to the points representative of the control state, the greater the effect the compound had rescuing the diseased phenotype, and vice-a-versa. Similarly, the off-target effects the compound had on the cell contexts are visualized as the height (y-value) of the point relative to the height of the points representing control states. That is, the higher the point on the y-axis, the greater the effect the query perturbation had on phenotypes of the cells unrelated to the disease phenotypes, e.g., side-effects.

Figure 8A:
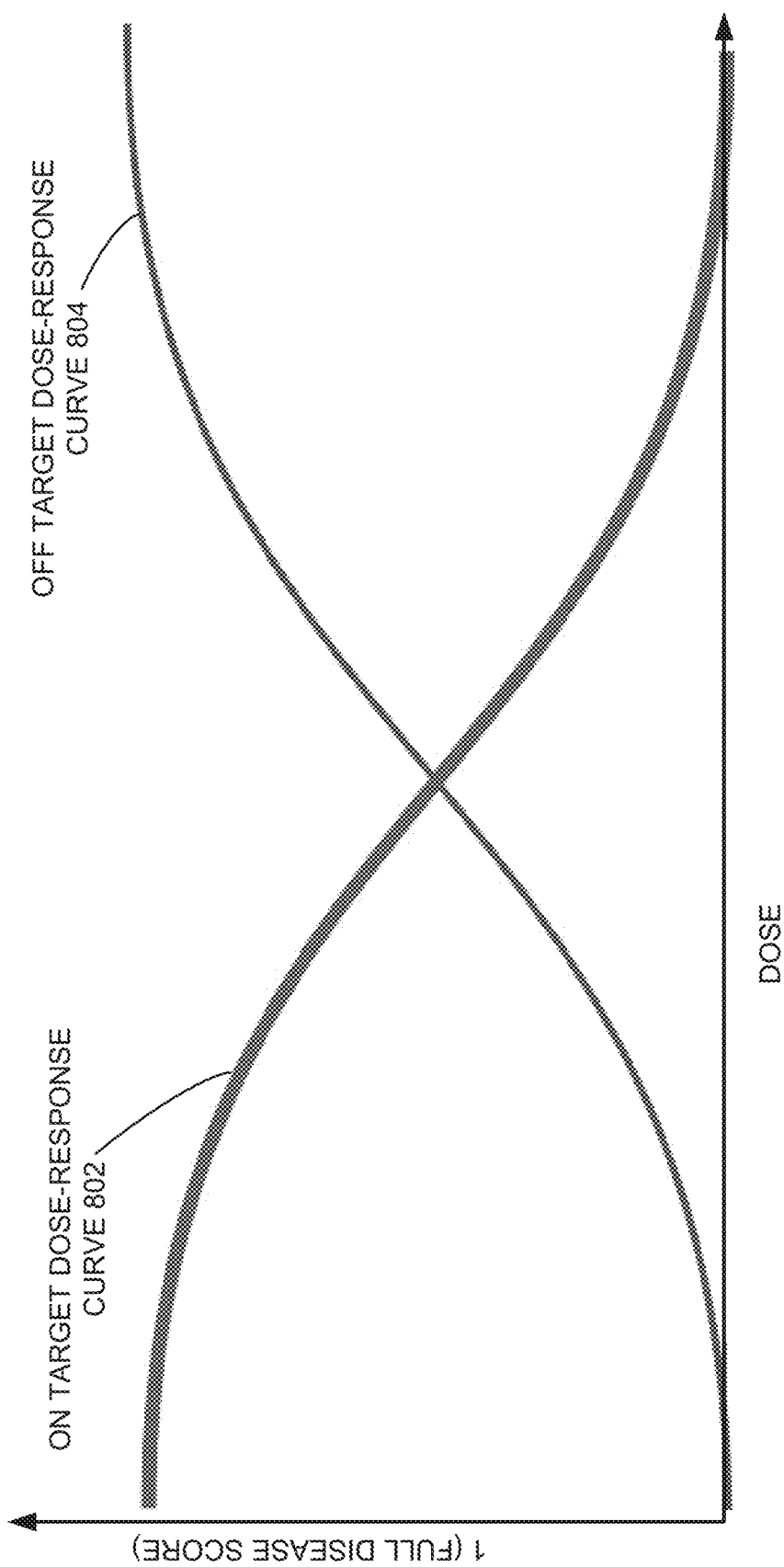

In some embodiments, the evaluating includes predicting (130) a therapeutic window for a compound, for instance, by plotting the on-target and off-target scores for perturbed cell contexts exposed to increasing concentrations of a compound (i.e., query states having increased concentrations of a compound). For example, as illustrated in FIGS. 8B and 8C, dose-response curves can be used to find therapeutic windows in which a compound provides a large on-target effect (e.g., shifting points away from disease phenotypes and towards healthy phenotypes) with a relatively small off-target effect (e.g., avoiding concentrations at which the off-target effect pushes the point away from the healthy phenotypes). Similarly, as shown in FIG. 8, on-target and off-target scores can be plotted separately and regions identified that maximize on-target effects while minimizing off-target effects. For example, in some embodiments, the region evaluated is an area defined by the upper boundaries of the on-target ('disease') score and off-target ('side effect') score, e.g., area 809 as illustrated in FIG. 8B. In some embodiments, the region evaluated is a difference between the on-target ('disease') score and off-target ('side effect') score at a single point, e.g., difference 815 between points 811 and 813 as illustrated in FIG. 8B. In yet other embodiments, the region evaluated is an algebraic combination of various areas formed by and differences between on-target ('disease') score and off-target ('side effect') score plots.

In some embodiments, the evaluating includes predicting (132) a rescue quality, e.g., as described below with respect to steps 4120 and 4122 of method 4000. In some embodiments, the evaluating includes evaluating (134) assay quality, e.g., as described below with respect to steps 4124 and others of method 4000.

In some embodiments, the imaging data can be combined with bioassay datasets, to further enhance the evaluation of candidate drugs. For example, in some embodiments, bioassay toxicity data can be used to identify candidate drugs that may have toxic off-target effects. Similarly, in some embodiments, absorption, distribution, metabolism, and excretion (ADME) data can be used to evaluate the potential bioavailability of candidate drugs. In some embodiments, cell fate data can be used to identify the effect of a candidate drug on the growth of a target cell. In some embodiments, pathway and/or mechanistic data can be used to evaluate the mechanism of action of a candidate drug. Non-limiting examples of bioassays useful for collecting these types of data are shown in Table 1.

TABLE 1

Example assays for producing bioassay data to supplement phenomic imaging data.

| Type of Assay | Example Assay |
| --- | --- |
| Toxicity Assays | |
| Mitochondrial toxicity | Glu/Gal assay |
| Genomic toxicity | DNA damage γH2Aχ assay |
| | AMES II assay |
| | Micro-nuclearity assay |
| Drug-induced liver injury | 3D spheroid assay |
| | Hepatocyte viability assay |
| Cardiac toxicity | hERG assay |
| | 3D cardiomyocyte model |
| | COX assay |
| Neuro-toxicity | 3D neuro model |
| Kidney toxicity | 3D kidney model |
| ADME Assays | |
| Drug-drug interactions | Cyp450 inhibition and induction assay |
| Biodistribution | Blood-Brain Barrier (BBB) assay |
| | Epithelian permeability assay |
| Transporter interactions | PGP assay |
| | PSAP assay |
| Plasma protein interactions | Serum shift assay |
| Cell Fate Assays | |
| Cell cycle (G1, S, G2) assays | |
| Quiescence (G0) assays | |
| Mitotic index | |
| Multinuclearity | |
| Apoptosis | Cleaved caspase 3 assay |
| | Nuclear morphology |
| Cell viability | Cell count |
| | CellTiter-Glo |
| | WST-8 assay |
| Pathway/Mechanistic Assays | |
| Immunofluorescence/pathway markers | |
| Transcriptomics | |
| Synthetic interaction assays | |

A detailed description of a system 250 for screening one or more compounds based on on-target and off-target effects when exposed to one or more perturbed cell contexts is described in conjunction with FIGS. 2A, 2B, 2C, and 2D. As such, FIGS. 2A, 2B, 2C, and 2D collectively illustrate the topology of a system, in accordance with an embodiment of the present disclosure. In the topology, there are modules for screening compounds for on-target effects and off-target effects useful for identifying therapeutic candidate compounds and beneficial therapeutic ranges and specific concentrations for using those compounds, e.g., based on the relationships between multidimensional vectors formed from a plurality of features of control states, test states, and query states. Generation of the various multidimensional vectors, comparison of the geometric properties of the multidimensional vectors, and identification of candidate compounds based on the geometric relationships is performed as described in further detail below by system 250 of FIG. 2A.

Figure 2A:
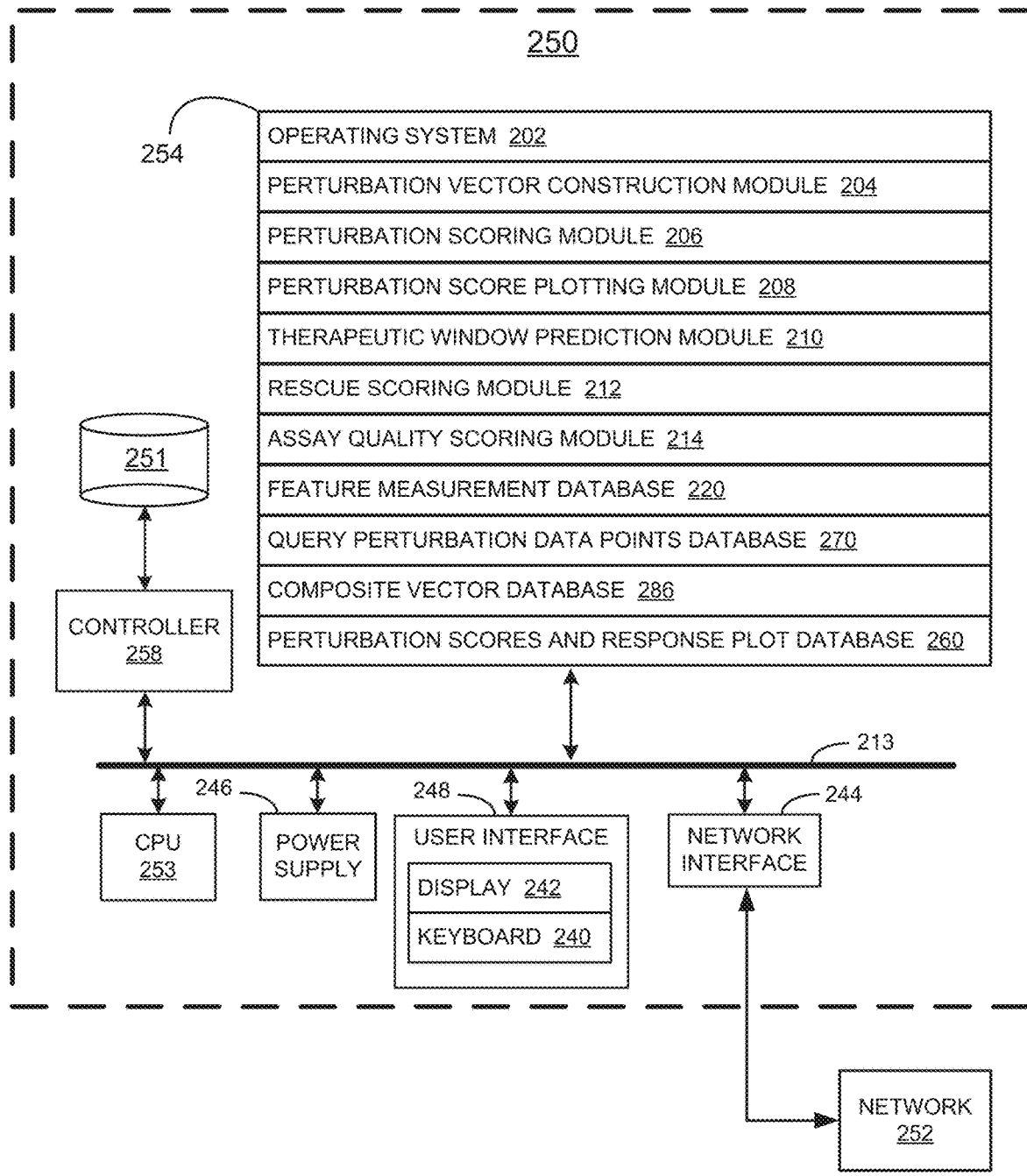

Referring to FIG. 2A, in typical embodiments, system 250 comprises one or more computers. For purposes of illustration in FIG. 2A, system 250 is represented as a single computer that includes all of the functionality for screening one or more compounds based on on-target and off-target effects when exposed to one or more perturbed cell contexts. However, the disclosure is not so limited. In some embodiments, the functionality for screening one or more compounds based on on-target and off-target effects when exposed to one or more perturbed cell contexts is spread across any number of networked computers and/or resides on each of several networked computers and/or is hosted on one or more virtual machines at a remote location accessible across the communications network 252. One of skill in the art will appreciate that any of a wide array of different computing topologies are used for the application and all such topologies are within the scope of the present disclosure.

With the foregoing in mind, an example system 250 for screening one or more compounds based on on-target and off-target effects when exposed to one or more perturbed cell contexts includes one or more processing units (CPU's) 253, a network or other communications interface 244, a memory 254 (e.g., random access memory), one or more magnetic disk storage and/or persistent devices 251 optionally accessed by one or more controllers 258, one or more communication busses 213 for interconnecting the aforementioned components, a user interface 248, the user interface 248 including a display 242 and input 240 (e.g., keyboard, keypad, touch screen), and a power supply 246 for powering the aforementioned components. Display 242 or other similar display may be utilized for plotting results and/or displaying plotted information as an interactive graphical user interface. In some embodiments, data in memory 254 is seamlessly shared with non-volatile memory 251 using known computing techniques such as caching. In some embodiments, memory 254 and/or memory 251 includes mass storage that is remotely located with respect to the central processing unit(s) 253. In other words, some data stored in memory 254 and/or memory 251 may in fact be hosted on computers that are external to the system 250 but that can be electronically accessed by the system 250 over an Internet, intranet, or other form of network or electronic cable (illustrated as element 252 in FIG. 2A) using network interface 244.

In some embodiments, the memory 254 of the system 250 for screening one or more compounds based on on-target and off-target effects when exposed to one or more perturbed cell contexts stores:

an operating system 202 that includes procedures for handling various basic system services;

a perturbation vector constructions module 204, e.g., for generating control feature vectors/control data points (108; 4002), test feature vectors/test data points (110; 4034), and query feature vectors/query perturbation data points (112; 4050) and/or computing a composite test vector (114; 4048, e.g., vector 510 in FIG. 5) and a composite query vector (116, 4060, e.g., vector 512 in FIG. 5) and/or computing a control vector (4070; 4076) and/or computing a test vector (4082; 4088 (FIG. 4J));

a perturbation scoring module 206, for computing e.g., on-target scores for a query perturbation (118; 4062, e.g., on-target score 516 in FIG. 5), off-target scores for a query perturbation (120; 4064, e.g., off-target score 518 in FIG. 5), on-target scores for a control vector or control perturbation (4072; 4078), off-target scores for a control vector or control perturbation (4074; 4080), on-target scores for a test vector or test perturbation (4084; 4090 (FIG. 4J)), off-target scores for a control vector or control perturbation (4086; 4092 (FIG. 4J))

a perturbation score plotting module 208, for plotting on-target scores and off-target scores as (x,y) coordinates, e.g., of query perturbations (124; 4068, e.g., illustrated as blue and purple circles in FIGS. 7A and 7B, and purple triangles in FIG. 6), control perturbations (4074; 4080, e.g., illustrated as green squares in FIG. 6 and green shaded circles in FIGS. 7A and 7B), and test perturbations (4086; 4093, e.g., illustrated as red circles in FIGS. 6, 7A, and 7B) and/or separately as a function of query compound concentration (4112, e.g., illustrated as on-target dose-response curves 802, 806, 810, 814, 818, and 822 and off-target dose-response curves 804, 808, 812, 816, 820, and 824 in FIGS. 8A, 8B, 8C, 8D, 8E, 8F, and 8G, respectively);

a therapeutic window prediction module 210, e.g., for quantifying a therapeutic window for a query compound (FIG. 4P; 4114; 4116; and 4118);

a rescue scoring module 212, e.g., for quantifying a rescue quality for a query compound (4120; 4122);

an assay quality scoring module 214, e.g., for computing a normalized tightness of test state data points (4142; 4182) and/or for computing an overall quality of the assay (4184);

a feature measurement database 220 (illustrated in more detail in FIG. 2B), e.g., for storing compound perturbation data sets 222 including control characteristic measurements 226 for control perturbation data sets 224, test characteristic measurements 230 for test perturbation data sets 228, and query characterization measurements 234 for query perturbation data sets 232 a query perturbation data point database 270 (illustrated in more detail in FIG. 2C), e.g., for storing data points (e.g., as multidimensional vectors) 272 for query compounds, including control data points 274, test data points 278, and query data points 282 (all of FIG. 2C) and a composite vector database 286 (illustrated in more detail in FIG. 2D), e.g., for storing query perturbation composite vectors 288, including composite test vectors 290 and composite query vectors 294 (all of FIG. 2D); and a perturbation score and response plot database 260, e.g., for storing on-target and off-target scores and plots of on-target and off-target scores.

In some embodiments, modules 204, 206, 208, 210, 212, and/or 214 are accessible within any browser (phone, tablet, laptop/desktop). In some embodiments modules 204, 206, 208, 210, 212, and/or 214 run on native device frameworks, and are available for download onto the system 250 running an operating system 202 such as Android or iOS.

In some implementations, one or more of the above identified data elements or modules of the system 250 for screening one or more compounds based on on-target and off-target effects when exposed to one or more perturbed cell contexts are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 254 and/or 251 optionally stores a subset of the modules and data structures identified above. Furthermore, in some embodiments the memory 254 and/or 251 stores additional modules and data structures not described above.

In some embodiments, system 250 for screening one or more compounds based on on-target and off-target effects when exposed to one or more perturbed cell contexts is a smart phone (e.g., an iPHONE), laptop, tablet computer, desktop computer, or other form of electronic device. In some embodiments, the system 250 is not mobile. In some embodiments, the system 250 is a mobile device which may be human portable (e.g., worn by a human, carried in a human hand, carried in a pocket of a human's clothing, carried by a human in a backpack, etc.).

Figure 3:
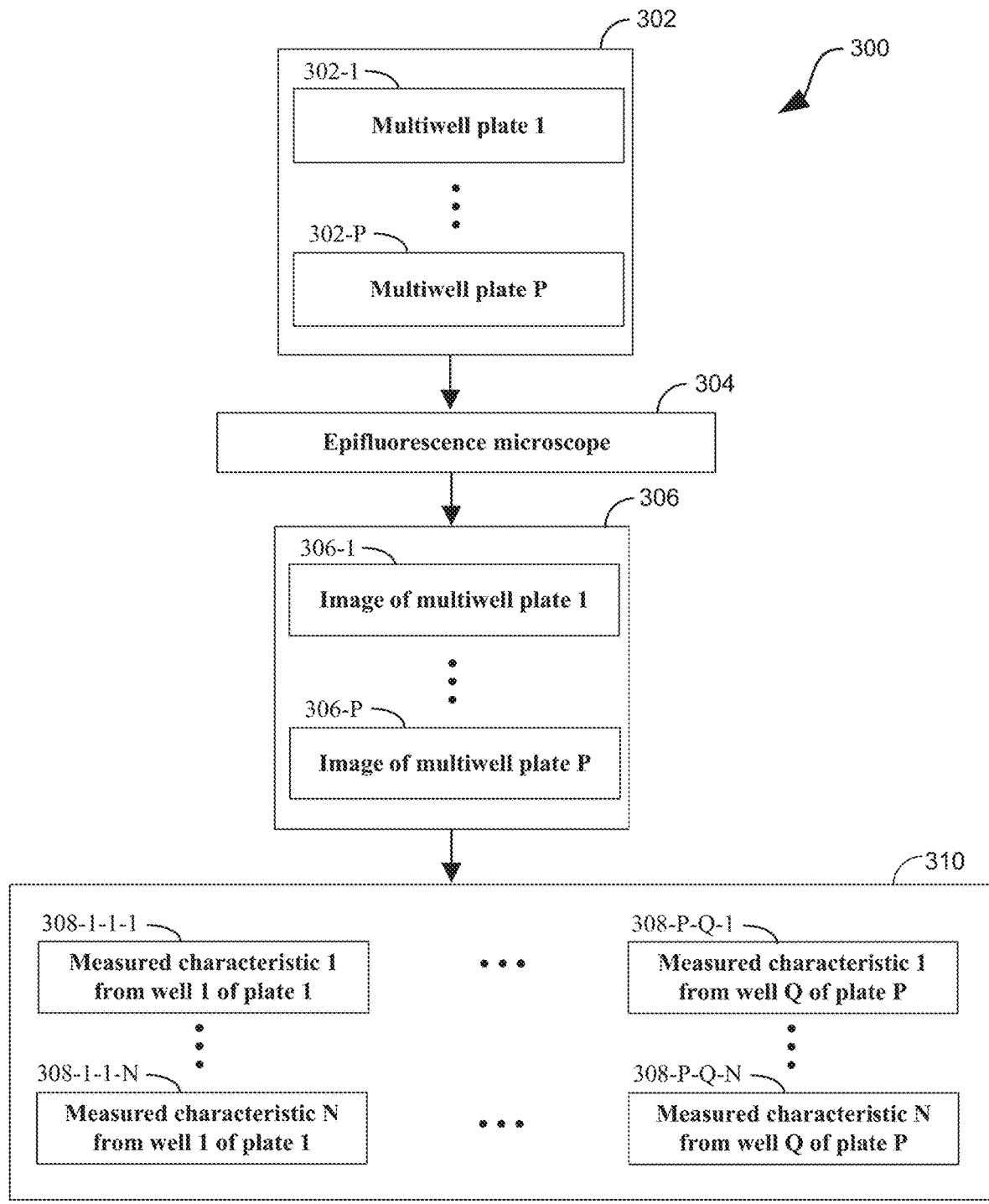
FIG. 3 illustrates an example workflow for acquiring measurements of different features for screening one or more compounds based on on-target and off-target effects when exposed to one or more perturbed cell contexts, in accordance with various embodiments of the present disclosure.

FIG. 3 illustrates an example workflow 300 for acquiring measurements of different features for screening one or more compounds based on on-target and off-target effects when exposed to one or more perturbed cell contexts, in accordance with various embodiments of the present disclosure. In some embodiments, the present disclosure relies upon the acquisition of a data set 222 that includes measurements of a plurality of characteristics 308 (e.g., control characteristic measurements 226, test characteristic measurements 230, and query characteristic measurements 234) for control states (e.g., 'normal' cell contexts), test perturbation states (e.g., "disease" cell contexts not exposed to a therapeutic candidate compound), and query perturbation states (e.g., "disease" cell contexts exposed to a therapeutic candidate compound) for one or more therapeutic candidate compounds, in one or more replicates, in one or more cell contexts, at one or more concentrations. As an example, each candidate compound i in a plurality of M compounds is introduced into wells of a multiwell plate 302 (e.g., 302-1 . . . 302-P) at each of k concentrations for each of I perturbed cell contexts in j instances (where the query perturbation is represented by a single cell context perturbed in a single fashion, an instance is the same as a replicate; where the query perturbation is represented by one or more cell context perturbed in related fashions (e.g., each of which may be performed in replicates), an instance represents a single experimental condition within a set of different experimental conditions that collectively represent the query state), resulting in X wells containing compound i, where $X=(j)*(k)*(l)$. N characteristics are then measured from each well $\{1 \ldots Q\}$ of each multiwell plate $(1 \ldots P)$, resulting in $N*A*X*$ query characteristic measurements for the candidate compounds. Additionally, $C=(m)*(n)$ control characteristic measurements and $T=(o)*(l)$ test characteristic measurements are made, where m instances of no compound are measured across n control states and o instances of no compound are measured across the l perturbed cell contexts, keeping in mind that each instance may represent a replicate or may represent a single experimental condition in a plurality of experimental conditions that collectively represent the control state or the test state. A plurality of multiwell plates 302 may be utilized. The characteristic measurements are then used to generate the features that make up the multi-dimensional data points.

As described in detail herein, in some embodiments, control states correspond to unperturbed cell contexts, e.g., the same cell contexts as used for the query characterization measurements and test query measurements without the perturbation (e.g., not exposed to an siRNA that knocks down gene expression in the test and query assays). In other embodiments, control states correspond to other contexts that are representative of a 'healthy' phenotype but may be exposed to one or more control perturbations (e.g., substances, mutations, or physical condition), e.g., an off-target siRNA molecule, for example to account for background variability or noise. In some embodiments, a control state characteristic measurements corresponding to test and query states are taken from a plurality of different control contexts, e.g., to account for variability and/or background noise. For example, in some embodiments, a control context is established from multiple instances of cell contexts exposed to different off-target siRNA molecules.

In some embodiments, referring to FIG. 3, these characteristic measurements are acquired by capturing images 306 (e.g., 306-1 . . . 306-P) of the multiwell plates 302 using, for example, epifluorescence microscopy 304. The images 306 are then used as a basis for obtaining the measurements of the N different characteristic measurements from each of the wells in the multiwell plates, thereby forming dataset 310 (e.g., data set 222). Data set 310 is then used to generate features and, in turn, multidimensional control data points, test data points, and query data points which are subsequently used to generate composite test vectors, query perturbation vectors, etc.

Now that details of a system 250 for screening one or more compounds based on on-target and off-target effects when exposed to one or more perturbed cell contexts have been disclosed, details regarding a flow chart of processes and features of the system, in accordance with an embodiment of the present disclosure, are disclosed with reference to FIGS. 4A through 4AD. In some embodiments, such processes and features of the system are carried out by perturbation vector construction module 204, perturbation scoring module 206, perturbation score plotting module 208, therapeutic window prediction module 210, rescue scoring module 212, and/or assay quality scoring module 214, as illustrated in FIG. 2A.

Referring to method 4000 and FIGS. 4A-4AD, the systems described herein (e.g., system 250) includes instructions for performing a method (e.g., methods 100 and/or 4000 and/or portions thereof) for screening one or more compounds based on on-target and off-target effects when exposed to one or more perturbed cell contexts, e.g., evaluating query perturbations in a cell-based assay representing a test state. In some embodiments, the cell based assays are performed in a plurality wells across one or more multiwell plates.

With reference now to FIGS. 1, 2A-2D and 4A-4AD, all or portions of some embodiments described herein are composed of computer-readable and computer-executable instructions that reside, for example, in computer-usable/computer-readable storage media of a computer system. That is, FIGS. 2A-2D illustrate one example of a type of computer (computer system 250) that can be used in accordance with or to implement various embodiments which are discussed herein. It is appreciated that computer system 250 of FIG. 2A is only an example and that embodiments as described herein can operate on or within a number of different computer systems including, but not limited to, general purpose computer systems, networked computer systems, embedded computer systems, server devices, client devices, various intermediate devices/nodes, stand alone computer systems, media centers, handheld computer systems, multi-media devices, portable computers/devices, and the like. Computer system 250 of FIG. 2A is well adapted to utilize native or peripheral tangible computer-readable storage media such as, for example, memory/storage 251 and/or 254).

The following discussion sets forth in detail the operation of some example methods of operation of embodiments. With reference to FIGS. 1 and 4A-4AD, flow diagrams 100 and 4000 each illustrates example procedures which may be used by various embodiments. Flow diagram 100 and 4000 include some procedures that, in various embodiments, are carried out by a processor (e.g., CPU 253) under the control of computer-readable and computer-executable instructions. In this fashion, procedures described herein and in conjunction with flow diagram 100 and/or 4000 are or may be implemented using a computer, in various embodiments. The computer-readable and computer-executable instructions can reside in any computer readable storage media, such as, for example, in data storage features such as memory/storage 251 and/or 254 (of FIG. 2A) or the like. The computer-readable and computer-executable instructions, which reside on computer readable storage media, are used to control or operate in conjunction with, for example, one or some combination of processor (e.g., CPU 253) or other similar processor(s). Although specific procedures are disclosed in flow diagrams 100 and/or 4000, such procedures are examples. That is, embodiments are well suited to performing various other procedures or variations of the procedures recited in flow diagrams 100 and/or 4000. Likewise, in some embodiments, the procedures in flow diagrams 100 and/or 4000 may be performed in an order different than presented and/or not all of the procedures described in one or more of these flow diagrams may be performed. It is further appreciated that procedures described inflow diagrams 100 and/or 4000 may be implemented in hardware, or a combination of hardware and firmware, or a combination of hardware.

Control States

Turning now to FIG. 4A, method 4000 includes obtaining (4002), for each respective control perturbation in a set of control perturbations, a corresponding control data point, thereby obtaining a plurality of control data points, where each corresponding control data point comprises a plurality of dimensions (e.g., control data point 276 includes a plurality of dimensions based on control perturbation measurements 226). In some embodiments, each dimension in the plurality of dimensions represents a measure of central tendency of a different feature derived from measurement of one or more characteristic, in the plurality of features, across a corresponding plurality of control aliquots of cells in corresponding wells, in the plurality of wells, representing the respective control perturbation, e.g., upon exposure of the corresponding plurality of control state aliquots of the cells to a respective control perturbation or to no perturbation at all. For example, each of T dimensions of data point 276-1-1-1 corresponds to a measure of central tendency of a different feature derived from characteristic measurements 226-1-1-1-$i$-$j$, where i=1–N characteristics and j=1–O instances of control perturbation 1 in context 1. In some embodiments, each dimension in the plurality of dimension includes a measure of central tendency of a respective dimension reduction component determined using the plurality of features across the corresponding plurality of control aliquots of the cells. For example, each of U dimensions of data point 276-1-1-1 corresponds to a measure of central tendency of a different dimension reduction component calculated based on the plurality of features that are derived from measurements 226-1-1-1-$i$-$j$, where i=1–N features and j=1–O instances of control perturbation 1 in context 1.

In some embodiments, the underlying data (e.g., previously collected control characteristic measurements) are obtained and control data points (e.g., control feature vectors) are constructed therefrom, e.g., by combining data received for individual characteristic measurements. In some embodiments, characteristic measurements are collected directly by the system (e.g., system 250), e.g., the system includes instructions for processing images acquired of microwell/multiwell plates. In some embodiments, the vectors and/or underlying data for the vectors is obtained from a remote source, e.g., over network 252 via network interface 244.

Generally, the "control" state is sampled through anything that is believed to be a "good control," e.g., conditions that incorporate as many or all of the same technical and biological effects and biases as a test or query state without obscuring the effect of the intended biological perturbation. For some experiments, this means a specific set of reagents is used over which random samples are drawn in order to mimic non-specific, random biological artifacts of the experimental approach. In others, naive, untreated cells are used because that is what best controls for the technical and biological effects and biases of the experimental approach. In yet others, a parental cell line, or cells treated with a specific buffering agent, etc., are used. At the intersection of all these different types of "healthy," is the notion that a population of replicates and/or perturbations is repeatedly sampled to create a distribution of vectors that describes the state of cells in the experiment absent the query perturbation.

In some embodiments, the set of control perturbations (e.g., control perturbations 1 through S represented in FIGS. 2A, 2B, and 2C) includes (4004) a plurality of control siRNA that do not directly affect expression of a gene associated with the test state. For instance, in some embodiments, a perturbation being tested partially disrupts the expression of a gene or a function of a gene product and a corresponding control perturbation includes one or more siRNA that does not disrupt expression of the gene. In a particular embodiment, a perturbation being tested includes siRNA-mediated knock-down of a target gene expression in a background cell context, e.g., with one or more siRNA having a sequence targeting the gene, and a corresponding control state includes the background cell context exposed to one or more siRNA that does not target the gene, for instance, one or more 'control' siRNA that includes one or more nucleotide changes relative to the siRNA targeting the gene used for the test and/or query perturbation. In this fashion, a control siRNA is used to control for background effects, e.g., effects other than the intended gene expression knockdown, caused by the inclusion of a target siRNA used to create a test and/or query perturbation.

In some embodiments, in addition to not targeting the gene targeted in the test and/or query perturbation, a control siRNA also does not target any other gene in the genome of the organism. In some embodiments, e.g., where the siRNA used in the test and/or query perturbation partially targets a second gene (e.g., unintentionally) within the genome of the organism (e.g., with lower affinity or sequence identity than the target gene), a control siRNA is designed to maintain partial targeting of the second gene with the genome, but not the gene targeted to establish the perturbation being tested. In some embodiments, a control siRNA targets a gene in the genome of the organism that is different from the gene targeted in the test and/or query perturbation, e.g., a gene that is not associated with a disease phenotype of interest.

In some embodiments, each instance of the control state includes a single control siRNA and only one control siRNA is used across all instances of the corresponding control state. In some embodiments, each instance of the control state includes a single control siRNA, but different control siRNA are used across the instances of the corresponding control state, e.g., such that the control state samples various instances of a single control siRNA. In some embodiments, each instance of the control state includes a plurality of control siRNA. For instance, in some embodiments, all instances of a control state include the same plurality of control siRNA. In other embodiments, different instances of a control state include different pluralities of control siRNA.

In some embodiments, the plurality of control siRNA includes at least 10 different control siRNA, e.g., which are included together in instances of a control perturbation, included in different combinations across a set of instances of a control perturbation, or included individually in separate instances of a control perturbation. In some embodiments, the plurality of control siRNA includes at least 3, 5, 10, 15, 20, 25, 30, 35, 40, 45, 50, 75, 100, 250, or more control siRNA. In one embodiment, the plurality of control siRNA includes from 10 to 100 different control siRNA. In one embodiment, the plurality of control siRNA includes (4006) from 10 to 50 control siRNA.

In some embodiments, the measure of central tendency of the different feature derived from characteristics measured across the corresponding plurality of control aliquots of the cells representing the respective control perturbation is an arithmetic mean, weighted mean, midrange, midhinge, trimean, geometric mean, geometric median, Winsorized mean, median, or mode of the value for the different features determined for each of the plurality of control aliquots of the cells representing the respective control perturbation. In some embodiments, the measure of central tendency of the different feature across the corresponding plurality of control aliquots of the cells representing the respective control perturbation is an arithmetic mean, weighted mean, midrange, midhinge, trimean, geometric mean, geometric median, Winsorized mean, median, or mode of the value for the different feature determined for between two and twenty control aliquots of the cells representing the respective control perturbation in between two and twenty corresponding wells in the plurality of wells (4008).

In some embodiments, each feature is derived from a combination of measurable characteristics selected from a color, texture, and size of the cell context, or an enumerated portion of the cell context (4010). In some embodiments, obtaining the corresponding control data point includes imaging a corresponding well in the plurality of wells to form a corresponding two-dimensional pixelated image having a corresponding plurality of native pixel values and where a different feature in the plurality of features arises as a result of a convolution or a series convolutions and pooling operators run against native pixel values in the corresponding plurality of native pixel values of the corresponding two-dimensional pixelated image (4012). That is, in some embodiments, the plurality of features includes latent features of an image of the respective well in the multiwell plate.

In some embodiments, each feature in the plurality of features is derived from a characteristic that is optically measured (4020). In some embodiments, a first subset of the plurality of features are derived from characteristics that are optically measured, and a second subset of the plurality of features are derived from characteristics that are non-optically measured (4022). In some embodiments, each feature in the plurality of features is derived from a characteristic that is non-optically measured (4024). The skilled artisan will know of other characteristic measurements suitable for use in the present methods, for example, as described in detail below.

In some embodiments, the respective plurality of control aliquots of the cells is exposed to the respective control perturbation for at least one hour prior to obtaining the measurement of each characteristic used to derive the plurality of features across the plurality of control aliquots (4014). For instance, in some embodiments, a control state includes an aliquot of a cellular context (e.g., a particular wild type or mutant cell line or mixture of wild type or mutant cell lines) that is exposed to a control perturbation, e.g., a control siRNA and/or a buffer, used to control for background effects. In some embodiments, the control aliquots of the cells are exposed to a control perturbation for at least 15 minutes, 30 minutes, one hour, two hours, three hours, four hours, six hours, twelve hours, one day, two days, or longer prior to obtaining the measurements of each characteristic.

With reference to FIG. 4B, in some embodiments, the plurality of dimensions (e.g., representative of the number of different features determined from the characteristic measurements) includes between 5 dimensions and 100,000 dimensions (4016). In some embodiments, the plurality of dimensions includes at least 5, 10, 25, 50, 100, 250, 500, 1000, 2500, 5000, 10,000, 25,000, 50,000, 100,000, 250,000, 500,000, 1,000,000, or more dimensions.

In some embodiments, each feature in the plurality of features is a dimension reduction component that is a principal component derived by principal component analysis (4018). In some embodiments, each dimension reduction component is derived by a subset selection method or a discrete method (4026). The skilled artisan will know of various dimension reduction techniques suitable for reducing the number of dimensions in a control data point (e.g., a control feature vector), as described in more detail below.

In some embodiments, a control perturbation in the set of control perturbations is a predetermined naive cell line, a cell line exposed to a non-acting siRNA, a cell line that has a modifying agent added to ensure that it is in a predetermined state, or cells that have been filtered using a sorting technology for one or more predetermined biomarkers before plating (4028). In some embodiments, the set of control perturbations comprises a toxin, a CRISPR reagent, a signaling molecule, a cytokine, a predetermined drug, a siRNA, an sgRNA, a cell culture condition, or a genetic modification (4032). Non-limiting examples of control cell contexts suitable for use in the methods provided herein are described in detail below. In some embodiments, the set of control perturbations includes at least ten control perturbations (4030). In other embodiments, the set of control perturbations is at least 3, 4, 5, 6, 7, 8, 9, 10, 15, 20, 25, 30, 40, 50, or more control perturbations.

Test States

With reference to FIG. 4C, in some embodiments, method 4000 also includes obtaining (4034), for each respective test perturbation in a set of one or more test perturbations, a corresponding test data point, thereby obtaining a plurality of test data points, where each corresponding test data point includes the plurality of dimensions (e.g., test data point 280 includes a plurality of dimensions (e.g., the same number of dimensions as control data point 226) based on test perturbation measurements 230). In some embodiments, each dimension in the plurality of dimensions includes a measurement of central tendency of a different feature, in the plurality of features, across a corresponding plurality of test aliquots of the cells representing the respective test perturbation in corresponding wells in the plurality of wells, e.g., upon exposure of the corresponding plurality of test aliquots of the cells to the respective test perturbation. For example, each of T dimensions of data point 280-1-1-1 corresponds to a measure of central tendency of a different feature derived from characteristic measurements 230-1-1-1-$i$-$j$, where $i=1$-N features and $j=1$-Q instances of test perturbation 1 in context 1. In some embodiments, each dimension in the plurality of dimension includes a measure of central tendency of a respective dimension reduction component determined using the plurality of features across the corresponding plurality of test aliquots of the cells, e.g., upon exposure of the corresponding plurality of test aliquots of the cells to the respective test perturbation. For example, each of U dimensions of data point 280-1-1-1 corresponds to a measure of central tendency of a different dimension reduction component calculated based on the plurality of features that are derived from measurements 230-1-1-1-$i$-$j$, where $i=1$-N features and $j=1$-Q instances of test perturbation 1 in context 1.

In some embodiments, the underlying data (e.g., previously collected test characteristic measurements) are obtained and test data points (e.g., perturbation test vectors) are constructed therefrom, e.g., by combining data received for individual characteristic measurements. In some embodiments, characteristic measurements are collected directly by the system (e.g., system 250), e.g., the system includes instructions for processing images acquired of microwell plates. In some embodiments, the vectors and/or underlying data for the vectors is obtained from a remote source, e.g., over network 252 via network interface 244.

In some embodiments, the set of test perturbations consists of a plurality of target siRNA that directly affect (e.g., suppress) expression of a gene associated with the test state (4036). For instance, in some embodiments, a perturbation being tested partially disrupts the expression of a gene or a function of a gene product and the set of test perturbations includes different siRNA that suppress expression of the gene (e.g., by targeting different sequences of the gene).

In some embodiments, the set of test perturbations includes a plurality of target si RNA that each directly affect expression of one of a plurality of genes corresponding to proteins in the same pathway associated with the test state, e.g., a metabolic or signaling pathway related to a disease of interest. For instance, in some embodiments, a perturbation being tested partially disrupts the function of a pathway and the set of test perturbations includes different siRNA that target genes encoding different proteins participating in the pathway. In some embodiments, multiple siRNA are used to target any one of the genes involved in the pathway (e.g., by targeting different sequences of the gene).

In some embodiments, the set of test perturbations includes a plurality of target siRNA that directly affect expression of one of a plurality of genes corresponding to proteins in different pathways associated with the test state, e.g., metabolic or signaling pathways related to a disease of interest. For instance, in some embodiments, a perturbation being tested partially disrupts the function of multiple pathways and the set of test perturbations includes different siRNA that target genes encoding different proteins participating in the various pathways. In some embodiments, multiple siRNA are used to target any one of the genes involved in the pathways (e.g., by targeting different sequences of the gene).

In some embodiments, the plurality of target siRNA consists of between 4 and 12 different target siRNA (4038). In some embodiments, the plurality of test siRNA includes at least 3, 4, 5, 6, 7, 8, 9, 10, 11, 12, 13, 14, 15, 20, 25, 30, 35, 40, 45, 50, 75, 100, 250, or more test siRNA.

In some embodiments, the set of test perturbations includes a perturbation that causes overexpression of a gene encoding a protein in a pathway associated with the test state, e.g., a metabolic or signaling pathway related to a disease of interest. For instance, in some embodiments, the perturbation includes a transgene encoding the protein of interest that is introduced into the cell context, e.g., by transient transfection, via a recombinant virus, etc. In some embodiments, the transgene includes a constitutive promoter driving expression of the protein of interest. In some embodiments, the transgene includes an inducible promoter, from which expression can be controlled through the conditions of the culture medium used in the wells. In some embodiments, the set of test perturbations include a transgene driving overexpression of a protein of interest at different levels in different test perturbations, e.g., via a dose-dependent inducible promoter element. In some embodiments, the set of test perturbations includes a plurality of perturbations that each cause overexpression of a plurality proteins in the same pathway associated with the test state, e.g., a metabolic or signaling pathway related to a disease of interest. In some embodiments, the set of test perturbations includes a plurality of perturbations that each cause overexpression of a plurality proteins in different pathways associated with the test state, e.g., a metabolic or signaling pathway related to a disease of interest.

In some embodiments, the measure of central tendency of the different feature derived from characteristics measured across the corresponding plurality of test aliquots of the cells representing the respective test perturbation is an arithmetic mean, weighted mean, midrange, midhinge, trimean, geometric mean, geometric median, Winsorized mean, median, or mode of the value for the different feature determined for each of the plurality of control aliquots. In some embodiments, the measure of central tendency of the different feature derived from characteristics measured across the corresponding plurality of test aliquots of the cells representing the respective test perturbation is an arithmetic mean, weighted mean, midrange, midhinge, trimean, geometric mean, geometric median, Winsorized mean, median, or mode of the value for the different feature determined for between two and twenty corresponding wells in the plurality of wells (4040).

In some embodiments, the plurality of test aliquots of the cells is exposed to the respective test perturbation for at least one hour, two hours, three hours, one day, two days, three days, four days, or five days prior to obtaining the measurement of each characteristic used to derive the plurality of features across the plurality of test aliquots (4042).

In some embodiments, the set of test perturbations includes at least ten test perturbations (4044). In some embodiments, the set of test perturbations includes at least 3, 4, 5, 6, 7, 8, 9, 10, 11, 12, 13, 14, 15, 20, 25, 30, 35, 40, 45, 50, 75, 100, 250, or more test perturbations.

In some embodiments, the set of test perturbations comprises a toxin, a CRISPR reagent, a signaling molecule, a cytokine, a predetermined drug, a siRNA, an sgRNA, a cell culture condition, or a genetic modification other than a control perturbation (4046).

In some embodiments, one or more genes or products of a gene listed in Table 2 are perturbed in the cells of the test state. For example, in some embodiments, the test perturbation includes one or more toxin, CRISPR reagent, signaling molecule, cytokine, predetermined drug, siRNA, sgRNA, cell culture condition, or genetic modification that affects one or more of the genes or protein encoded by a gene listed in Table 2. In some embodiments, a set of test perturbations includes a plurality of perturbations directed against a gene or product of a gene listed in Table 2. In some embodiments, a set of test perturbations includes a plurality of perturbations directed against two or more genes or products of two or more genes listed in Table 2.

TABLE 2

Example target genes for perturbation in some embodiments.
Genes

| | | | | | | | |
|---|---|---|---|---|---|---|---|
| RAD21 | PRPF4 | GMNN | IRAK3 | ZAP70 | RPGRIP1L | ZMYND10 | PEX13 |
| USP7 | TXNL4A | ARID2 | PDP1 | PLEKHM1 | BUB1 | CFAP53 | CASQ2 |
| ATP2A2 | RAD51 | APC | SMAD3 | NEK1 | CCDC88C | SFXN4 | PLA2G6 |
| CUL3 | PABPN1 | TGFBR1 | TSEN54 | TTC19 | DNAJB2 | FRAS1 | RAB28 |
| UBA1 | NRF1 | SCO1 | ANKRD11 | CACNA1F | RAI1 | PRKAR1A | SLC9A6 |
| PRPF31 | PRPF3 | COL4A1 | BBS4 | POMT1 | ETFDH | PDCD10 | OBSL1 |
| PSAP | BRAF | AHI1 | DDX11 | HNF4A | DRAM2 | LRBA | CRELD1 |
| KDM6A | MAX | EXT2 | CDK5RAP2 | NNT | ESCO2 | STIM1 | VEGFA |
| PRPF8 | SACS | NEB | PIKFYVE | AGL | SC5D | NDRG1 | TPM1 |
| EFTUD2 | BRCA2 | TSC2 | KMT2D | SCNN1A | RNASEL | OPTN | IGSF1 |
| OPA1 | DNA2 | GPR143 | SLC26A4 | THRB | ISPD | GATM | NFKB2 |
| RPS7 | TRIP11 | PDSS2 | MYO5B | LRPAP1 | ATP7B | AASS | EPM2A |
| CDC73 | USP9X | SMARCA4 | CTNS | RPS6KA3 | GJA5 | GFM1 | TTN |
| PRPF6 | SALL1 | BRCA1 | CYLD | KDM1A | EFHC1 | MSX2 | AP3B1 |
| RPS10 | SLC25A38 | LCA5 | CNNM4 | ADA | VLDLR | HFE | PIGT |
| SF3B4 | MPDZ | EVC2 | BAP1 | RASA1 | NAA10 | OAT | SMS |
| RPL11 | MCCC2 | DLG3 | FUCA1 | ACOX1 | BCKDHB | TBX19 | ANTXR1 |
| KIF11 | NGLY1 | LYST | ITGB2 | PEX1 | MYL2 | DNAH11 | XIAP |
| RPS17 | STIL | GK | GAN | RNF168 | LRRC6 | AGPAT2 | AMER1 |
| TSPAN7 | ABHD5 | NSD2 | NF1 | DPY19L2 | TAZ | LAMP2 | CFI |
| ALG11 | INPO3 | LIPA | DST | C1GALT1C1 | PHGDH | PIGL | PCBD1 |
| CTNNB1 | SMAD4 | CHD2 | FAT4 | DIAPH1 | TBC1D7 | NRL | DSP |
| BBS7 | SPAST | IFNGR1 | NF2 | MLH3 | CEP63 | ANO10 | XPC |
| NUS1 | GNPTAB | SMC1A | CEP135 | MFSD8 | TPRN | ZMYND12 | SMARCA2 |
| POLR3B | FASTKD2 | SRP72 | GYS1 | GNPTG | CEP290 | MTR | PEX2 |
| RBBP8 | CEP152 | SLC17A5 | NDUFB3 | ASNS | HOXA2 | BIN1 | MMADHC |
| SMC3 | PMM2 | CTSA | TMCO1 | MCM8 | EXOSC3 | ARFGEF2 | GCSH |
| DYRK1A | MESP2 | SMN1 | DDOST | ALDH5A1 | ASAH1 | IKBKB | EIF2B1 |
| RPS26 | ARID1A | TCTN1 | AAAS | ATP2C1 | HFM1 | DYSF | IQCB1 |
| KANSL1 | YAP1 | PEX6 | ARID1B | NEU1 | C5orf42 | PINK1 | SRCAP |
| MFN2 | SLC6A8 | KLK4 | SGSH | PHF6 | HSD3B7 | FANCG | RPGRIP1 |
| RPS19 | IARS2 | ADAM17 | DGKE | FGFR1 | F8 | CABP4 | SLC25A1 |
| VPS13B | PAFAH1B1 | AVP | GLDC | HPS4 | CRYBB2 | MTM1 | KRIT1 |
| RBM8A | FAM83H | ASPM | PKD1 | RAB3GAP2 | UROS | VPS13A | ADAMTS2 |
| TJP2 | FLNB | HCCS | UBE2A | RAB27A | PYGM | MIDI | TGIF1 |
| PTEN | DNAAF3 | FBN1 | PCCA | VCL | FAS | SDHA | PECE1 |

TABLE 2-continued

Example target genes for perturbation in some embodiments.
Genes

| | | | | | | | | |
|---|---|---|---|---|---|---|---|---|
| NIPBL | EIF2AK3 | KIAA1109 | ADAM10 | NCF1 | ARMC4 | SLC35A3 | ANTXR2 | |
| MED23 | COG8 | AIMP1 | RAB3GAP1 | PARK7 | NID1 | GPC3 | DOCK6 | |
| RPL26 | PCDH15 | ATP13A2 | NOTCH3 | FKTN | C19orf12 | ADCY1 | TCOF1 | |
| RB1 | GARS | EPG5 | CHD8 | FERMT1 | TSHR | IGLL1 | SPRED1 | |
| RPS24 | MUT | QDPR | SOX9 | CKAP2L | INPP5E | ATP2A1 | NBEAL2 | |
| CDKN2A | EXT1 | CREBBP | XPA | SMCHD1 | ACAD9 | ERCC6 | CDKN1C | |
| EP300 | TARDBP | MTMR2 | FUS | ZEB2 | SETD5 | NHEJ1 | CLN8 | |
| SMARCE1 | STK11 | GALC | PSEN2 | STX11 | SLC4A11 | CDH1 | CNGB3 | |
| MYO6 | GATA6 | HAMP | MNX1 | AP5Z1 | CDH3 | MSH6 | WDR19 | |
| MYH9 | WNK1 | AHDC1 | BCHE | SDCCAG8 | SETX | PSAT1 | SLC13A5 | |
| MSH2 | ATRX | TK2 | SLC25A20 | WDPCP | CCNO | SYNE1 | NFIX | |
| LMNA | MTFMT | MIB1 | XK | FOXP2 | CHD7 | HADH | | |
| LAMA4 | CD55 | OTOGL | NDUFA11 | SEC63 | TRAPPC9 | HNF1B | | |
| ATM | MSH3 | COG4 | SCN9A | TOPORS | TSC1 | MYCN | | |
| TP53 | GNAL | CEP164 | LDLR | SPR | EFR3B | FGD1 | | |
| HNF1A | EHMT1 | OTX2 | FBN2 | CCDC39 | SIL1 | ABCA4 | | |

With reference to FIG. 4D, in some embodiments, method 4000 also includes computing (4048) a composite test vector (e.g., composite test vector 292), the composite test vector between (i) a first point defined by a respective measure of central tendency across the plurality of control data points (e.g., control data points 276) for each dimension in the plurality of dimensions and (ii) a second point defined by a respective measure of central tendency across the plurality of test data points (e.g., test data points 280) for each dimension in the plurality of dimensions.

Figure 7A:
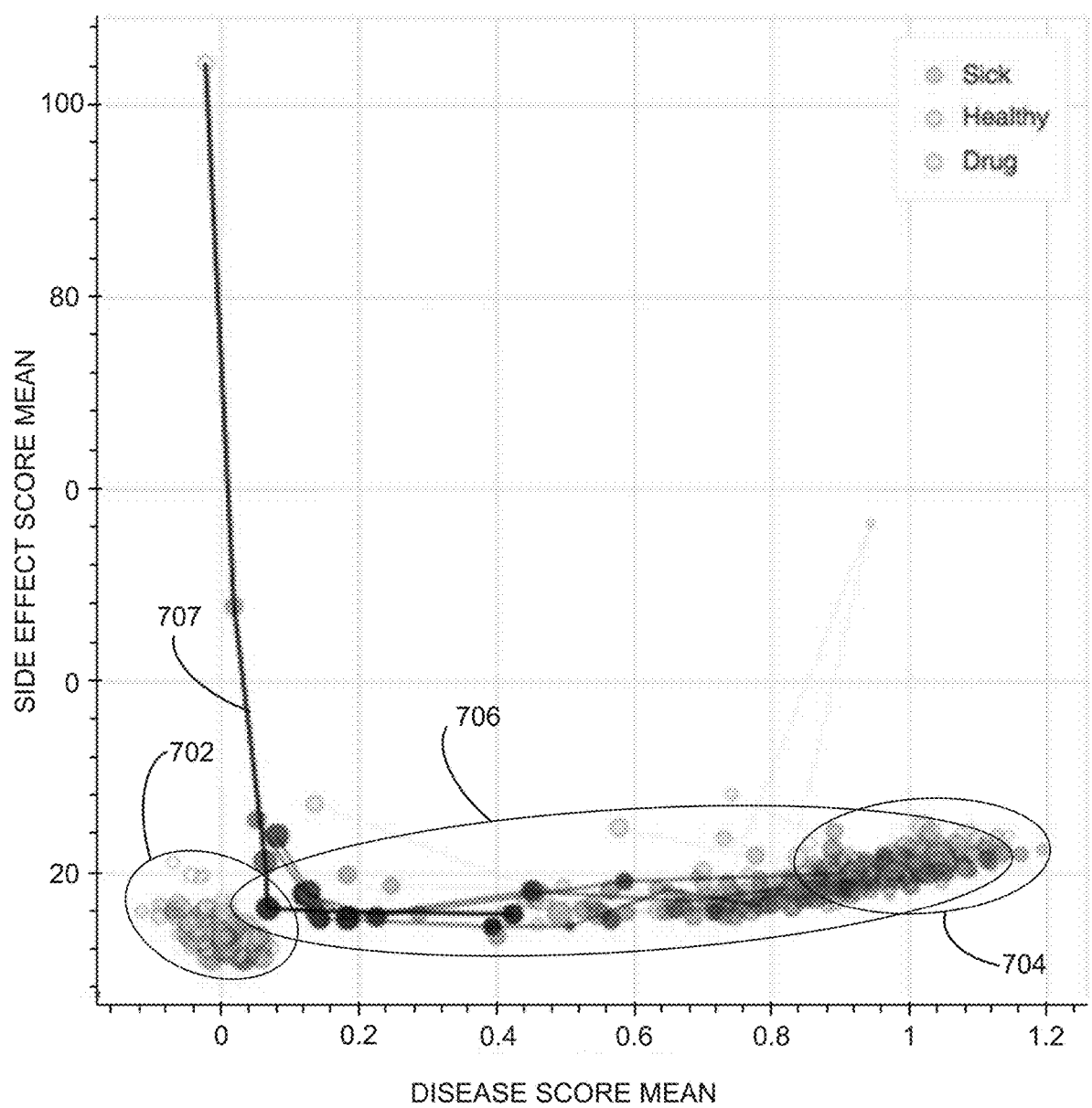
FIGS. 7A and 7B illustrate examples of dose-response curves of off-target scores as a function of on-target scores for various non-diseased/non-perturbed cell contexts (e.g., "healthy" cell contexts), perturbed cell contexts (e.g., "test" cell contexts, and perturbed cell contexts exposed to varying concentrations of various compounds (e.g., screened test cell contexts), in accordance with various embodiments of the present disclosure.
Figure 7B:
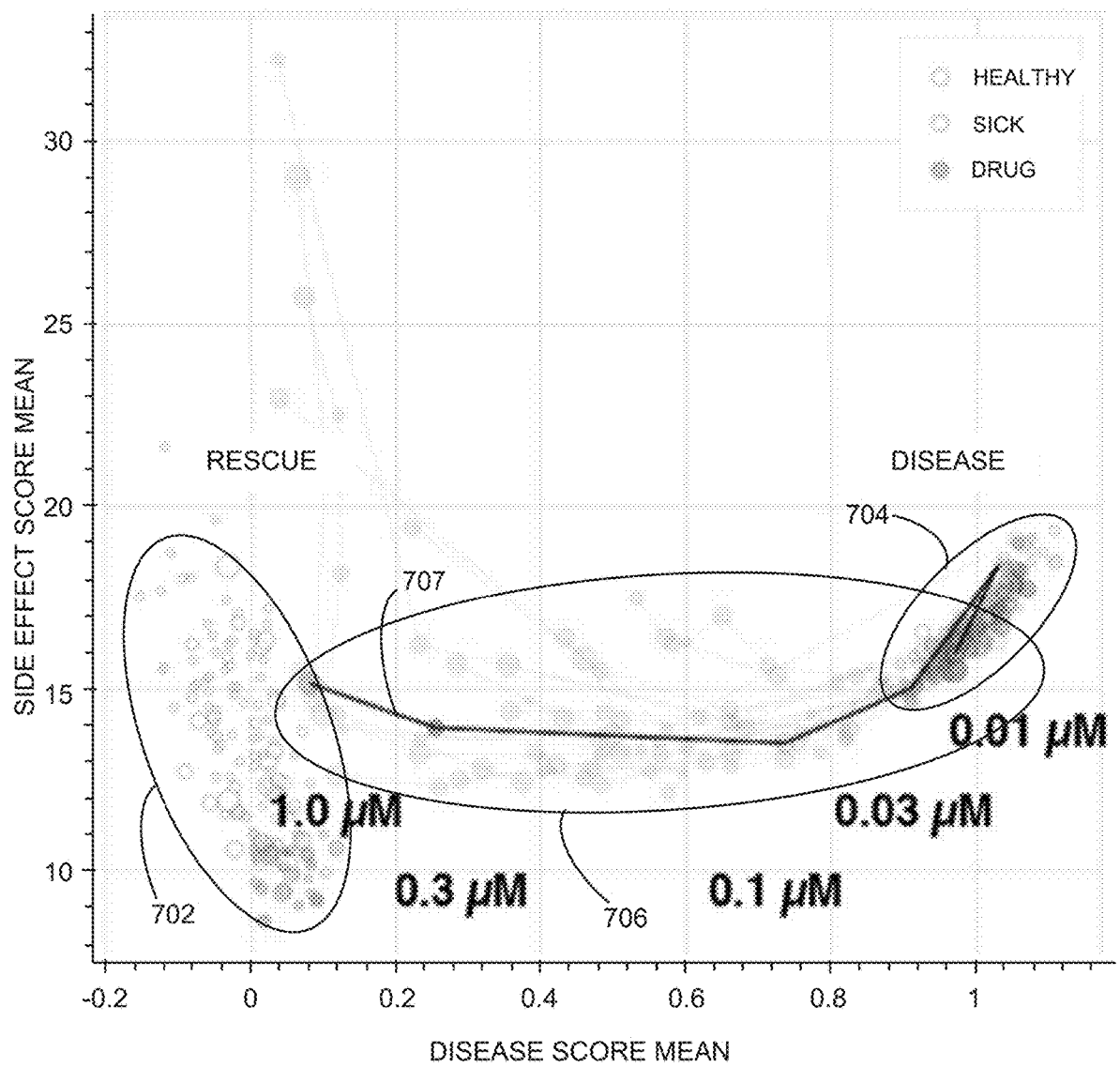
Figure 7C:
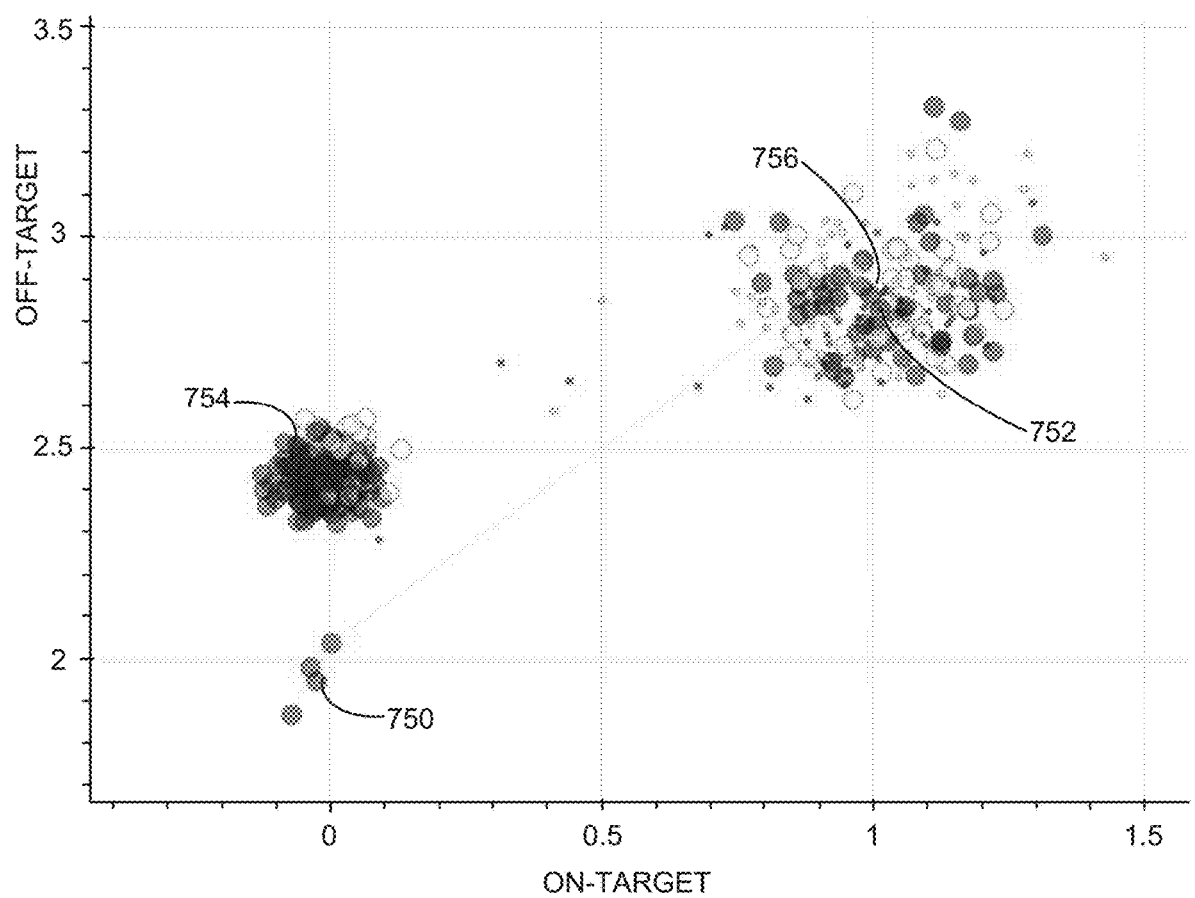
FIG. 7C illustrates an example of a dose-response curve of off-target scores as a function of on-target scores for various concentrations of a perturbing agent, as well as non-perturbed cell contexts (e.g., "healthy" cell contexts) and perturbed cell contexts (e.g., "test" cell contexts), in accordance with various embodiments of the present disclosure.

FIG. 7C illustrates a dose-response curve of off-target scores as a function of on-target scores for various concentrations of a perturbing agent (triangles), as well as non-perturbed cell contexts (e.g., "healthy" cell contexts; squares) and perturbed cell contexts (e.g., "test" cell contexts: circles).

In some embodiments, a test state is evaluated by performing a series of experiments in which the concentration of the perturbation agent (e.g., a soluble factor or siRNA) is titrated across a plurality a concentrations. The expected behavior for such an experiment is that the resulting score across the wells, from lowest concentration to greatest concentration of the perturbing agent, will form a trend from the 'healthy' cloud to the 'disease' cloud. For example, as illustrated in FIG. 7C, point 750 represents a condition containing the lowest concentration of a perturbing agent, in the titration, and is located near 'healthy' cloud 754. In contrast, point 752 represents a condition containing the highest concentration of the perturbing agent, in the titration, and is located near 'disease' cloud 756. This titration can be used to model the expected rescue of the phenotype caused by the perturbation agent.

Query States

Method 4000 also includes obtaining (4050), for each respective query perturbation in a plurality of query perturbations, a corresponding query perturbation data point, where each corresponding query perturbation data point comprises the plurality of dimensions (e.g., query data point 284 includes a plurality of dimensions based on query perturbation measurements 234). In some embodiments, each dimension in the plurality of dimensions includes a measure of central tendency of a measurement of a different feature derived from measurement of one or more characteristic, in the plurality of features, across a plurality of instances of query perturbation aliquots of the cells representing (e.g., jointly exposed to) a respective test perturbation, in the plurality of test perturbations, and a first amount of the query perturbation (e.g., candidate therapeutic molecule) in a corresponding subset of the plurality of wells. For example, each of T dimensions of data point 284-1-1-1 corresponds to a measure of central tendency of a different feature derived from characteristic measurements 234-1-1-1-i-j, where i=1-N characteristics and j=1-V instances of query perturbation 1 in context 1. In some embodiments, each dimension in the plurality of dimensions includes a measure of central tendency of a respective dimension reduction component determined using the plurality of features across the corresponding plurality of instances of query perturbation aliquots of the cells (e.g., jointly exposed to the respective test perturbation and the query perturbation) representing the respective test perturbation and the query perturbation. For example, each of U dimensions of data point 284-1-1-1 corresponds to a measure of central tendency of a different dimension reduction component calculated based on the plurality of features that are derived from measurements 234-1-1-1-i-j, where i=1-N features and j=1-V instances of query perturbation 1 in context 1.

In some embodiments, the underlying data (e.g., previously collected query characteristic measurements) are obtained and query data points (e.g., perturbation query vectors) are constructed therefrom, e.g., by combining data received for individual characteristic measurements. In some embodiments, characteristic measurements are collected directly by the system (e.g., system 250), e.g., the system includes instructions for processing images acquired of microwell/multiwell plates. In some embodiments, the vectors and/or underlying data for the vectors is obtained from a remote source, e.g., over network 252 via network interface 244.

In some embodiments, the measure of central tendency of the different feature derived from characteristics measured across the corresponding plurality of query perturbation aliquots of the cells jointly representing the respective query perturbation is an arithmetic mean, weighted mean, midrange, midhinge, trimean, geometric mean, geometric median, Winsorized mean, median, or mode of the value for different features determined for each of the plurality of query aliquots of the cells representing the respective control perturbation. In some embodiments, the measure of central tendency of the different feature derived from characteristics measured across the corresponding plurality of query perturbation aliquots of the cells jointly representing the respective query perturbation is an arithmetic mean, weighted mean, midrange, midhinge, trimean, geometric mean, geometric median, Winsorized mean, median, or mode of the value for different features determined for between two and twenty query aliquots of the cells representing the respective query perturbation in between two and twenty corresponding wells in the plurality of wells (4052).

In some embodiments, the measure of central tendency of the different feature across the corresponding plurality of query perturbation aliquots of the cells jointly representing the respective test perturbation and the query perturbation is an arithmetic mean, weighted mean, midrange, midhinge, trimean, Winsorized mean, median, or mode of the different feature across between two and twenty query perturbation aliquots of the cells jointly representing the respective test perturbation and the query perturbation in between two and twenty corresponding wells in the plurality of wells (4054).

In some embodiments, the corresponding plurality of query perturbation aliquots of the cells is jointly exposed to the respective test perturbation and the query perturbation for at least one hour prior, two hours, three hours, one day, two days, three days, four days, or five days prior to obtaining the measurement of the plurality of characteristics used to derive the plurality of features in the obtaining (4056).

In some embodiments, the plurality of query perturbations includes at least 1000 query perturbations (4058). In some embodiments, the plurality of query perturbations includes at least 10, 25, 50, 75, 100, 150, 200, 250, 300, 400, 500, 750, 1000, 1500, 2000, 3000, 4000, 5000, or more query perturbations.

Figure 4E:
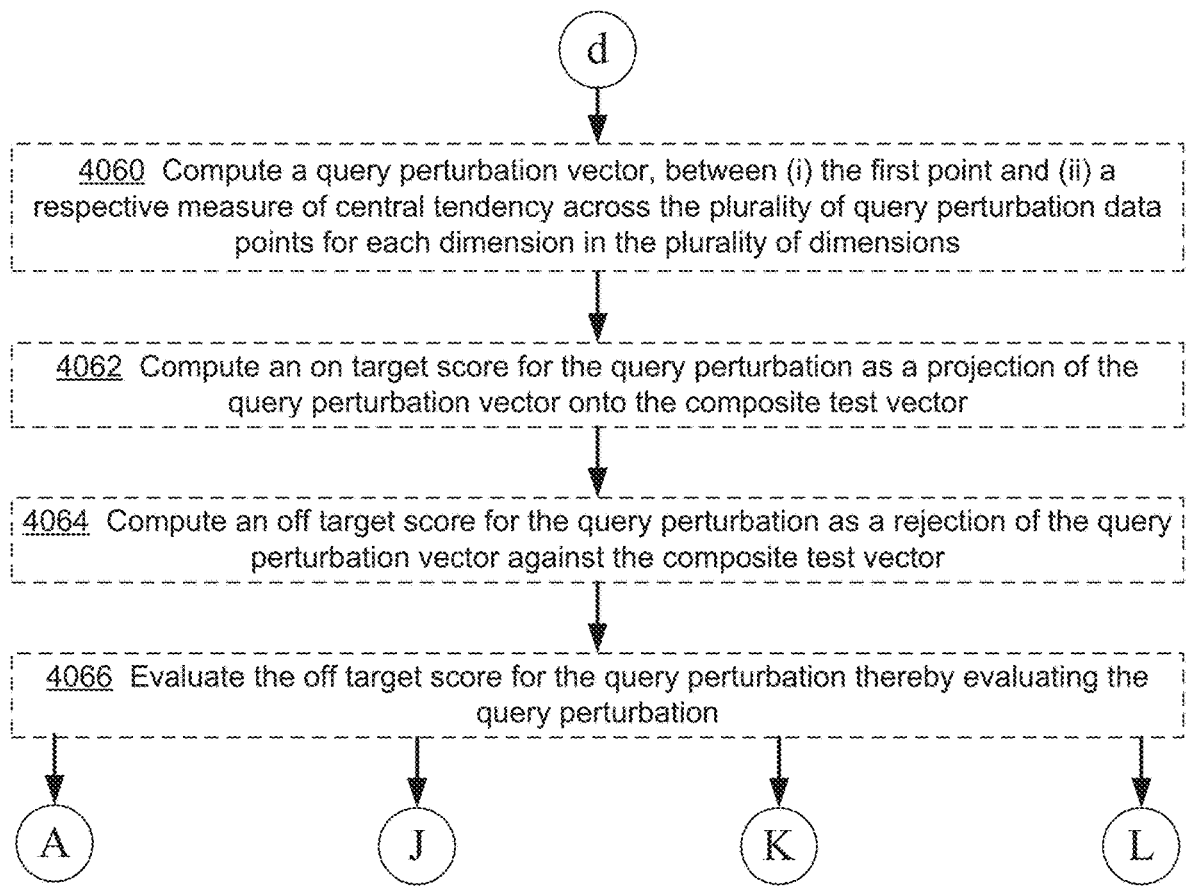
FIGS. 4A, 4B, 4C, 4D, 4E, 4F, 4G, 4I, 4I, 4J, 4K, 4L, 4M, 4N, 4O, 4P, 4Q, 4R, 4S, 4T, 4U, 4V, 4W, 4X, 4Y, 4Z, 4AA, 4AB, 4AC, and 4AD collectively provide a flow chart of processes and features for screening one or more compounds based on on-target and off-target effects when exposed to one or more perturbed cell contexts, in which optional steps are denoted by dashed boxes and/or connecting lines, in accordance with various embodiments of the present disclosure.

With reference to FIG. 4E, in some embodiments, method 4000 also includes computing (4060) a query perturbation vector (e.g., composite query vector 296), between (i) the first point (e.g., defined by a respective measure of central tendency across the plurality of control data points (e.g., control data points 276) for each dimension in the plurality of dimensions) and (ii) a respective measure of central tendency across the plurality of query perturbation data points (e.g., query data points 284) for each dimension in the plurality of dimensions. In some embodiments, the query perturbation vector, composited test vector, and/or data points may be graphed, plotted, displayed on a computer screen, or otherwise output or provided from the computer system (e.g., in a human visible format) to a human for viewing, review, evaluation, and/or decision-making purposes.

On-Target and Off-Target Scores

With continued reference to FIG. 4E, in some embodiments, method 4000 also includes computing (4062) an on-target score for the query perturbation as a projection of the query perturbation vector (e.g., composite query vector 296 or 512) onto the composite test vector (e.g., composite test vector 292 or 510), for example as shown as projection 516 in FIG. 5. In some embodiments, the on-target score is normalized, for instance, by a mean/median test score of a single corresponding perturbation (e.g., siRNA), or by the standard deviation of the control state. In some embodiments, the on-target score may be graphed, plotted, displayed on a computer screen, or otherwise output or provided from the computer system (e.g., in a human visible format) to a human for viewing, review, evaluation, and/or decision-making purposes.

Method 4000 also includes computing (4064) an off-target score for the query perturbation as a rejection of the query perturbation vector (e.g., composite query vector 296 or 512) against the composite test vector (e.g., composite test vector 292 or 510), for example as shown as rejection 518 in FIG. 5. In some embodiments, the off-target score is normalized, for instance, using the following non-limiting example equation:

$$y\_new = (y - uudy)/(\max(uudy + 5uuuhy, uuhy + 3uuuhy) - uudy) \quad \text{(Equation I)}$$

where:
y is the un-normalized off-target score;
uudy is the mean off-target score of the test perturbations;
uuhy is the mean off-target score of the control perturbations;
uuudy is the standard deviation of the off-target score of the test perturbations; and
uuuhy is the standard deviation of the off-target score of the control perturbations.

Alternatively, in some embodiments, the off-target score is normalized, for instance, using the following non-limiting example equation:

$$y\_new = (y - uudy)/2uuudy \quad \text{(Equation II)}$$

where:
y is the un-normalized off-target score;
uudy is the mean off-target score of the test perturbations; and
uuudy is the standard deviation of the off-target score of the test perturbations.

Alternatively, in some embodiments, the off-target score is normalized using a logarithm transformation. In some embodiments, the off-target score may be graphed, plotted, displayed on a computer screen, or otherwise output or provided from the computer system (e.g., in a human visible format) to a human for viewing, review, evaluation, and/or decision-making purposes.

Method 4000 includes evaluating (4066) the on-target and off-target score for the query perturbation, thereby evaluating the query perturbation, as described in detail below. The evaluation is performed by a computer system (e.g., 250) and the results of the evaluation may be graphed, plotted, displayed on a computer screen, or output or provided from the computer system (e.g., in a human visible format) to a human for viewing, review, evaluation, and/or decision-making purposes. In some embodiments, the results of the evaluation may describe a therapeutic compound for use in treating a particular condition or disease of humans and may describe one or more therapeutic concentrations (doses) at which the therapeutic compound appears to function effectively. In some embodiments, the results may characterize or quantify a rescue quality of a compound which was tested.

Figure 4F:
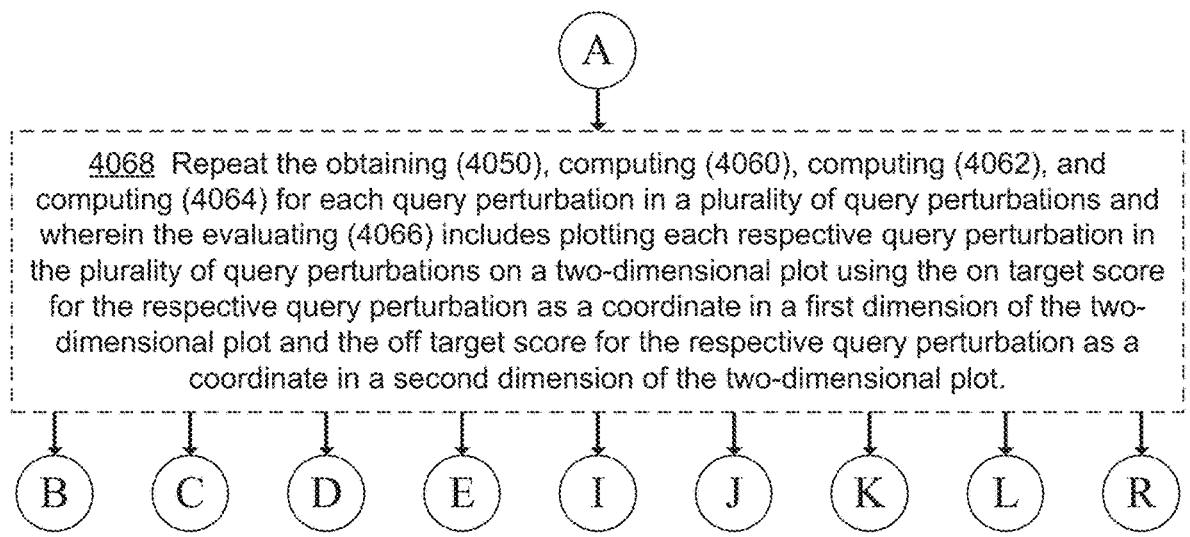

Having described the method for evaluating a single query perturbation above (e.g., screening a possible therapeutic compound at a single concentration), in some embodiments the method is repeated for a plurality of query perturbations, e.g., thereby screening a plurality of possible therapeutic compounds, and/or at a plurality of concentrations, e.g., thereby screening one or more possible therapeutic compounds in a dose-dependent fashion. For example, with reference to FIG. 4F, in some embodiments, method 4000 includes repeating (4068) the obtaining (4050), computing (4060), computing (4062), and computing (4064) for each query perturbation in a plurality of query perturbations. In some embodiments, the evaluating (4066) includes plotting each respective query perturbation in the plurality of query perturbations on a two-dimensional plot using the on-target score for the respective query perturbation as a coordinate in a first dimension of the two-dimensional plot and the off-target score for the respective query perturbation as a coordinate in a second dimension of the two-dimensional plot (e.g., as illustrated for a plurality of query perturbations shown as purple triangles in FIG. 6). The evaluations are performed by a computer system (e.g., 250) and the results of the evaluations may be graphed, plotted, displayed on a computer screen, or otherwise output or provided from the computer system (e.g., in a human visible format) to a human for viewing, review, evaluation, and/or decision-making purposes. In some embodiments, the plotted results (e.g., similar to those in FIGS. 6, 7A-7C and others plots and graphs herein) may also perform as an interactive interface or graphic user interface by presenting underlying information in response to a user selecting (such as with a cursor) a plotted point which is displayed on a display of a computer system. In some embodiments, the results of the evaluations may describe one or more therapeutic compounds for use in treating a particular condition or disease of humans and may describe one or more therapeutic concentrations (doses) at which the one or more therapeutic compounds appears to function effectively. In some embodiments, the results may characterize or quantify a rescue quality of one or more compounds which were tested.

Figure 4G:
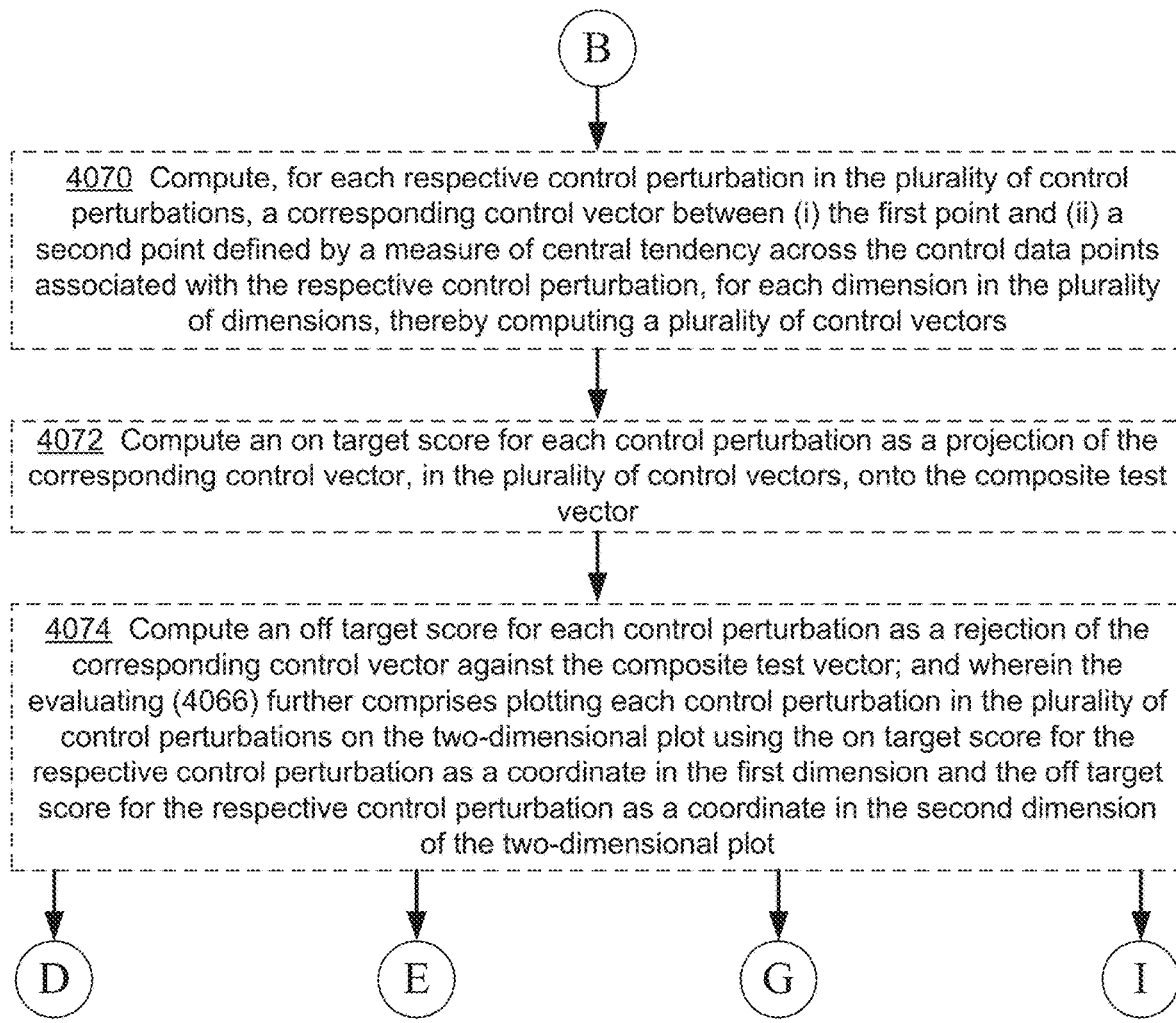

In some embodiments, e.g., in order to provide additional context to the plotted scores for the query perturbations, the projection and rejection of control perturbations (e.g., on-target and off-target effects observed in the control assays) on the composite test vector, e.g., representative of 'healthy' cell phenotypes, are plotted alongside of the query perturbations. Accordingly, with reference to FIG. 4G, in some embodiments, method 4000 includes computing (4070), for each respective control perturbation in the plurality of control perturbations, a corresponding control vector between (i) the first point, e.g., as used to compute the composite test vector and query perturbation vector and defined as by a respective measure of central tendency across the plurality of control data points for each dimension in the plurality of dimensions, and (ii) a second point defined by a measure of central tendency across the control data points associated with the respective control perturbation, for each dimension in the plurality of dimensions, thereby computing a plurality of control vectors. The method may also include computing (4072) an on-target score for each control perturbation as a projection of the corresponding control vector, in the plurality of control vectors, onto the composite test vector. The method may also include computing (4074) an off-target score for each control perturbation as a rejection of the corresponding control vector against the composite test vector. The evaluating (4066) may include plotting each control perturbation in the plurality of control perturbations on the two-dimensional plot using the on-target score for the respective control perturbation as a coordinate in the first dimension and the off-target score for the respective control perturbation as a coordinate in the second dimension of the two-dimensional plot (e.g., as illustrated for a plurality of control perturbations shown as squares in FIG. 6). In some embodiments, the projection and rejection of other reference points, e.g., truly naive/healthy cells (e.g., that are not exposed to a control perturbation), various 'reference' individual non-targeting siRNA, various targeting siRNA (to see the effect of selecting various ones), etc., are added to the plot to provide additional context to the screening conditions.

With reference again to FIG. 4E, in some embodiments, method 4000 computes (4062) an on-target score for the query perturbation as a projection of the query perturbation vector (e.g., composite query vector 296 or 512) onto the composite test vector (e.g., composite test vector 292 or 510), for example as shown as projection 516 in FIG. 5. In some embodiments, the on-target score is normalized, for instance, by a mean/median test score of a single corresponding perturbation (e.g., siRNA), or by the standard deviation of the control state.

Figure 6:
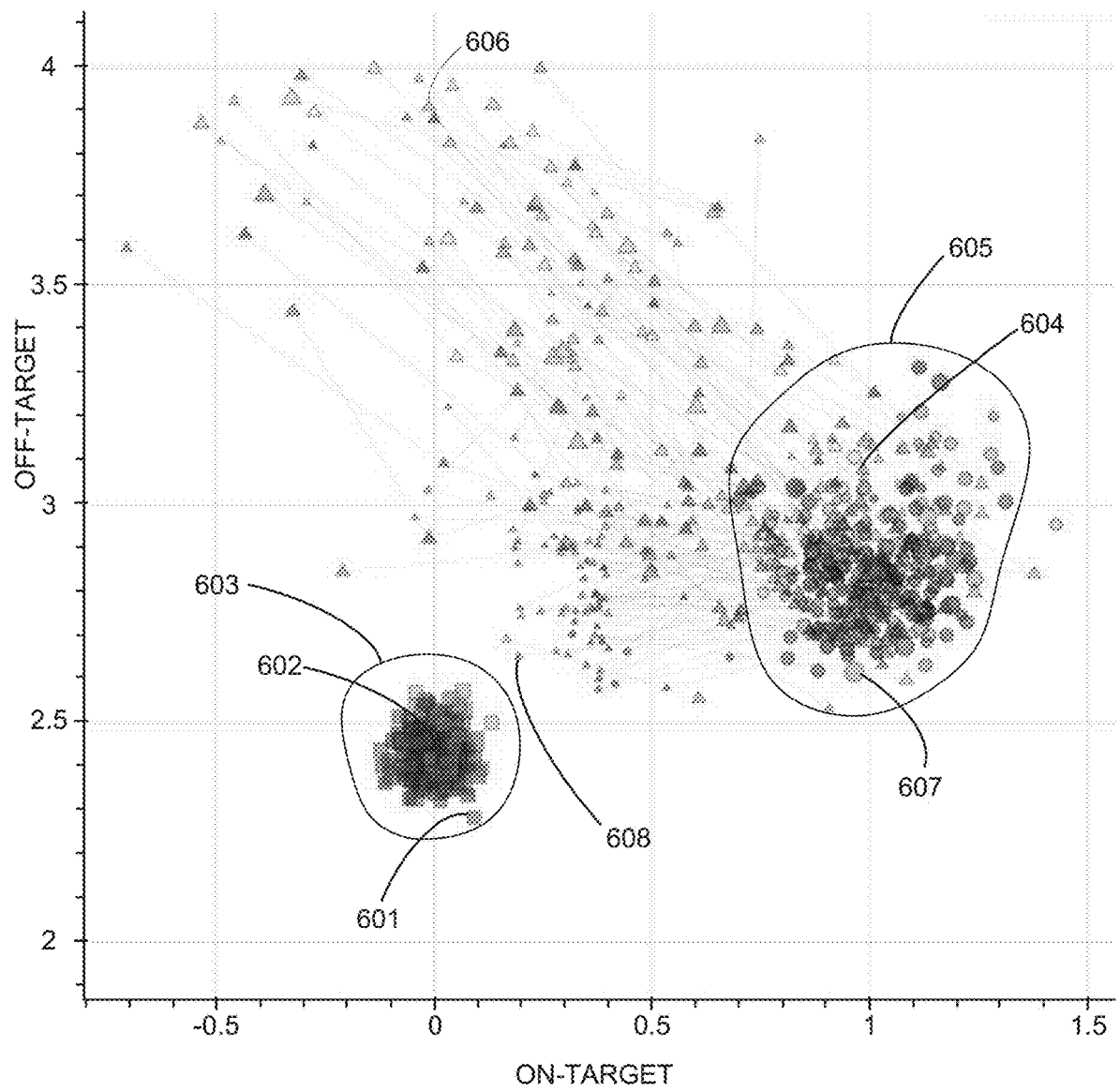
FIG. 6 illustrates an example of a plot of on-target scores as a function of off-target scores for various control cell contexts, perturbed cell contexts, and perturbed cell contexts exposed to various compounds at various concentrations, in accordance with various embodiments of the present disclosure.

Advantageously, the plotted scores for the control perturbations effectively show a 'healthy' phenotype on the plot. For example, as illustrated in FIG. 6, scores from a plurality of control perturbations are plotted as squares, such as square 601. The squares may all be shades of a particular color, such as green, in some embodiments. In FIG. 6, the plotted squares are forming a cloud of 'healthy' phenotypes around a mid-point 602, which essentially defines a baseline on-target effect score and a baseline off-target effect score representative of a healthy phenotype. Accordingly, the distance between a point corresponding to a respective query perturbation and the cloud of points representative of the control perturbations is indicative of how effectively the compound screened in the query perturbation treats the 'disease' phenotype of the perturbation. In FIG. 6, query perturbations are shown as triangles, such as triangle 604. The triangles may all be shades of a particular color, such as blue, in some embodiments. For example, the triangle shown as point 604, and representing a first query perturbation, is located within the 'disease' cloud (represented approximately by region 605), indicating that the candidate drug in the query perturbation is not rescuing the disease phenotype. The triangle shown as point 606, and representing a second query perturbation, is shifted left relative to the 'disease' cloud, having an abscissa nearly equivalent to mid-point 602 of the 'healthy' cloud (represented approximately by region 603), indicating that the candidate drug in the query perturbation rescues the disease phenotype. However, the ordinate of point 606 is twice the value of the ordinate of mid-point 602 of the 'healthy' cloud, indicating that the candidate drug causes significant off-target effects, as well. In contrast, the small triangle show as point 608, representing a third query perturbation, is located near the 'healthy cloud, indicating that the candidate drug in the query perturbation rescues the disease phenotype without causing significant off-target effects. Thus, the drug in the third query perturbation is a more promising disease therapy candidate than the drugs in the first and second query perturbations.

Figure 4H:
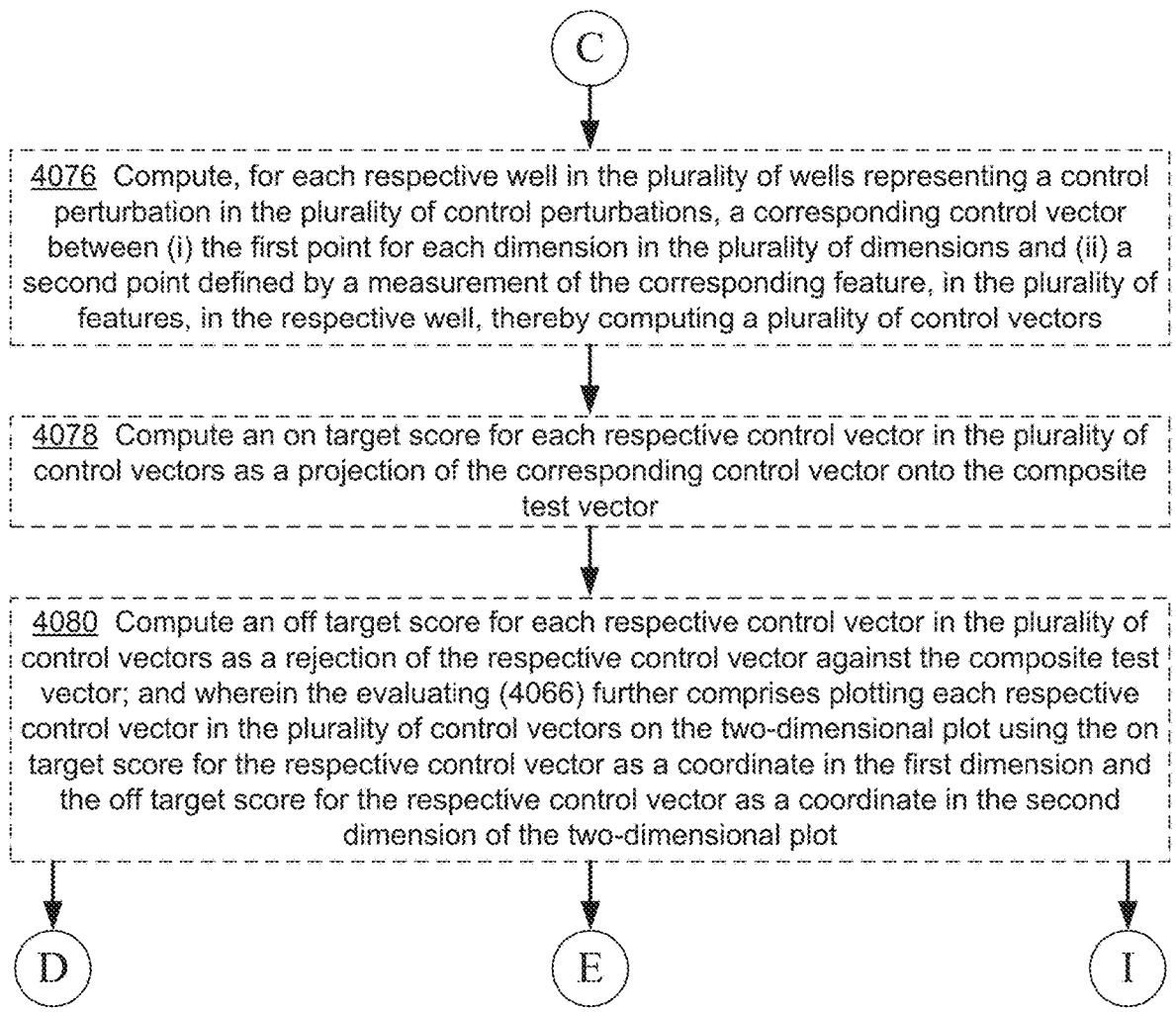

In some embodiments, on-target and off-target scores for each well of a control perturbation (e.g., each instance of an experiment corresponding to a control perturbation) are plotted to provide additional context to the plotted scores for the query perturbations. Accordingly, with reference to FIG. 4H, in some embodiments, method 4000 includes computing (4076) for each respective well in the plurality of wells representing a control perturbation in the plurality of control perturbations, a corresponding control vector between (i) the first point for each dimension in the plurality of dimensions, e.g., as used to compute the composite test vector and query perturbation vector and defined as by a respective measure of central tendency across the plurality of control data points for each dimension in the plurality of dimensions, and (ii) a second point defined by a value of the corresponding feature, in the plurality of features, determined for the respective well, thereby computing a plurality of control vectors. The method would also include computing (4078) an on-target score for each test perturbation as a projection of the corresponding test vector, in the plurality of test vectors, onto the composite test vector. The method would also include computing (4080) an off-target score for each test perturbation as a rejection of the corresponding test vector against the composite test vector. The evaluating (4066) would include plotting each test perturbation in the plurality of test perturbations on the two-dimensional plot using the on-target score for the respective test perturbation as a coordinate in the first dimension and the off-target score for the respective test perturbation as a coordinate in the second dimension of the two-dimensional plot (e.g., as illustrated for a plurality of control perturbations shown as squares in FIG. 6).

Figure 4I:
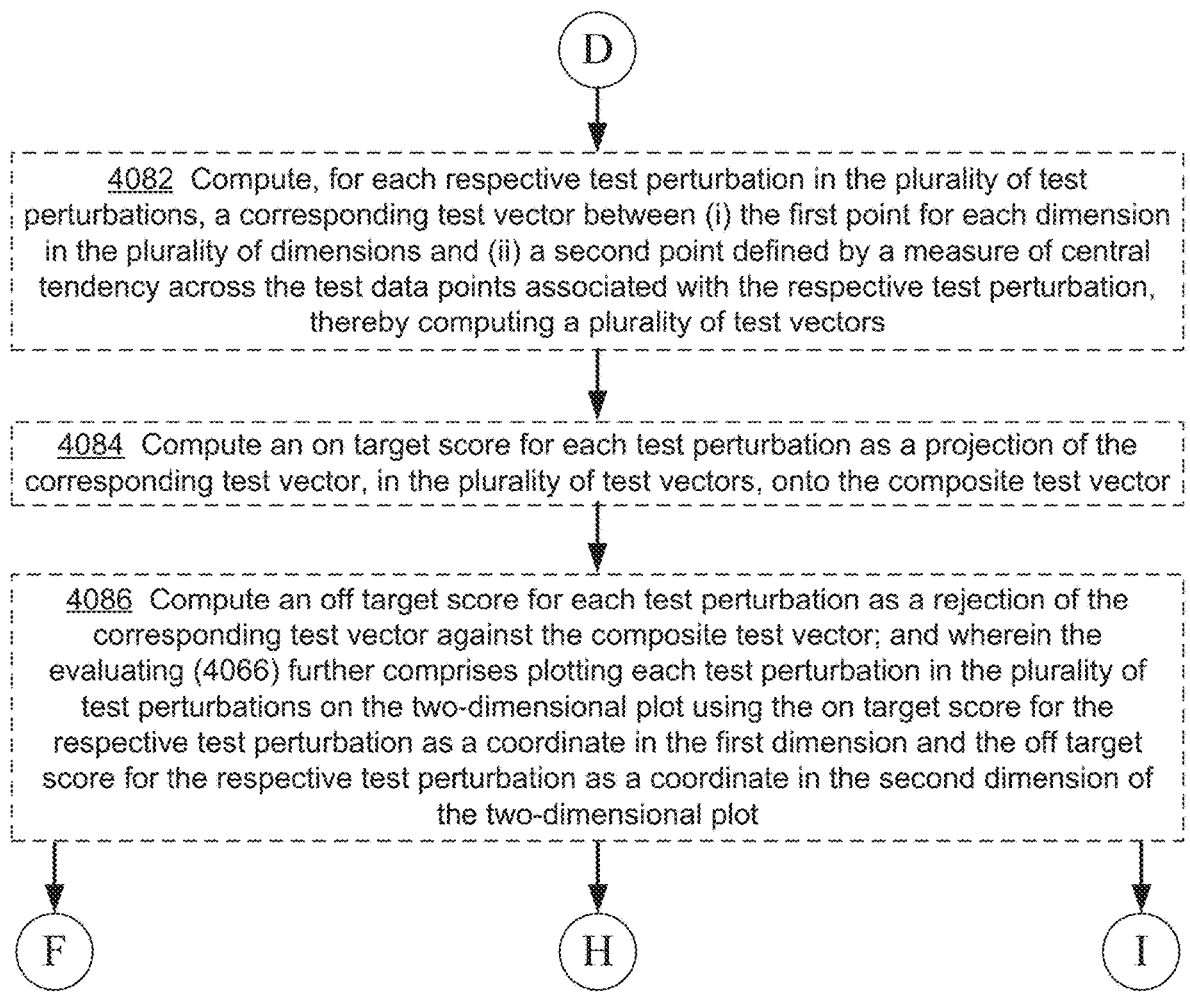
Figure 4J:
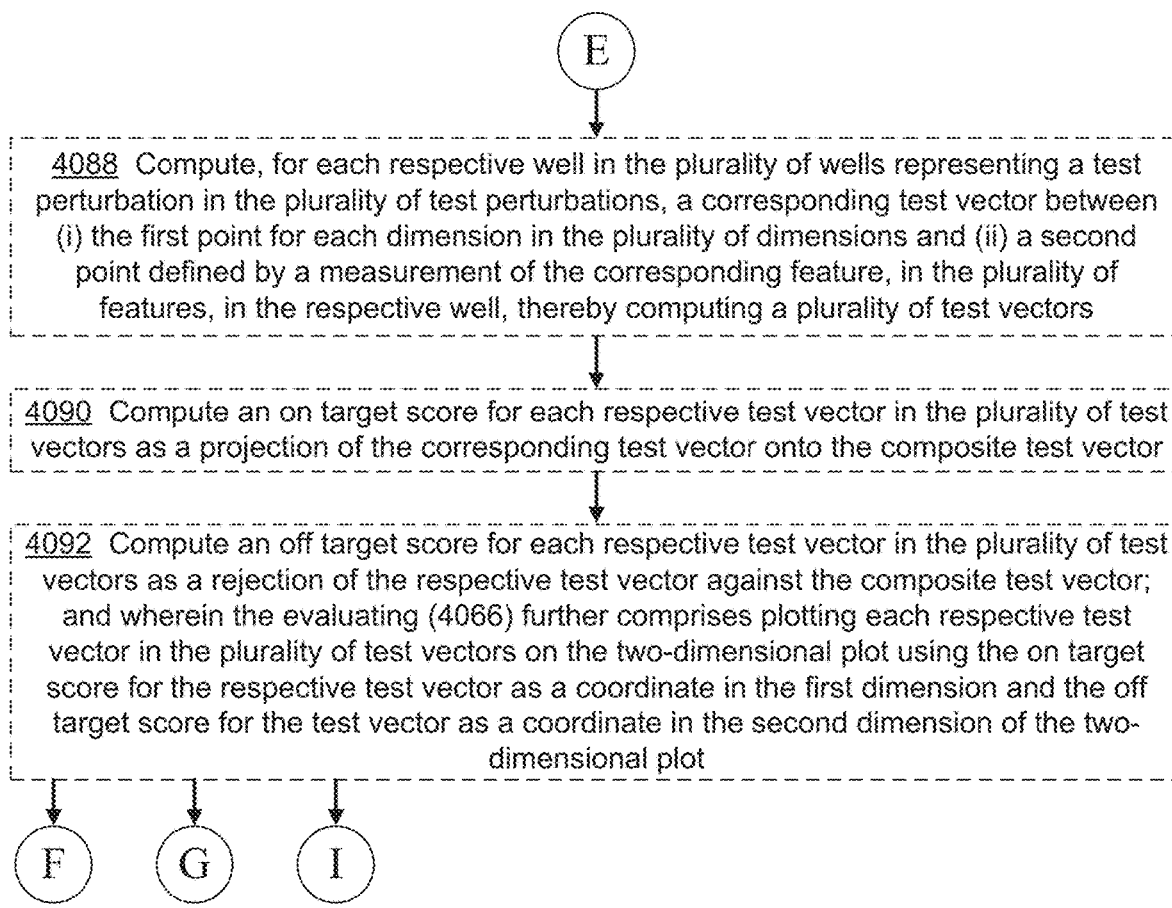

In some embodiments, e.g., in order to provide additional context to the plotted scores for the query perturbations, the projection and rejection of test perturbations (e.g., on-target and off-target effects observed in a 'disease' phenotype cell context that is not exposed to a possible therapeutic compound) on the composite test vector, e.g., representative of 'diseased' cell phenotypes, are plotted alongside of the query perturbations. Accordingly, with reference to FIG. 4I, in some embodiments, method 4000 includes computing (4082) for each respective test perturbation in the plurality of test perturbations, a corresponding test vector between (i) the first point for each dimension in the plurality of dimensions, e.g., as used to compute the composite test vector and query perturbation vector and defined as by a respective measure of central tendency across the plurality of control data points for each dimension in the plurality of dimensions, and (ii) a second point defined by a measure of central tendency across the test data points associated with the respective test perturbation. The method would also include computing (4084) an on-target score for each test perturbation as a projection of the corresponding test vector, in the plurality of test vectors, onto the composite test vector. The method would also include computing (4086) an off-target score for each test perturbation as a rejection of the corresponding test vector against the composite test vector. The evaluating (4066) would include plotting each test perturbation in the plurality of test perturbations on the two-dimensional plot using the on-target score for the respective test perturbation as a coordinate in the first dimension and the off-target score for the respective test perturbation as a coordinate in the second dimension of the two-dimensional plot (e.g., as illustrated for a plurality of test perturbations). Test perturbations may be shown as circles, such as circle 607, in FIG. 6. The circles may all be shades of a particular color, such as red, in some embodiments.

In some embodiments, on-target and off-target scores for each well of a test perturbation (e.g., each instance of an experiment corresponding to a test perturbation) are plotted to provide additional context to the plotted scores for the query perturbations. Accordingly, with reference to FIG. 4J, in some embodiments, method 4000 includes computing (4088) for each respective well in the plurality of wells representing a test perturbation in the plurality of test perturbations, a corresponding test vector between (i) the first point for each dimension in the plurality of dimensions, e.g., as used to compute the composite test vector and query perturbation vector and defined as by a respective measure of central tendency across the plurality of control data points for each dimension in the plurality of dimensions, and (ii) a second point defined by a value of the corresponding feature, in the plurality of features, determined for the respective well, thereby computing a plurality of test vectors. The method would also include computing (4090) an on-target score for each respective test vector in the plurality of test vectors as a projection of the corresponding test vector onto the composite test vector. The method would also include computing (4092) an off-target score for each respective test vector in the plurality of test vectors as a rejection of the respective test vector against the composite test vector. The evaluating (4066) would include plotting each respective test vector in the plurality of test vectors on the two-dimensional plot using the on-target score for the respective test vector as a coordinate in the first dimension and the off-target score for the test vector as a coordinate in the second dimension of the two-dimensional plot (e.g., as illustrated for a plurality of test perturbations shown as circles in FIG. 6).

Figure 4K:
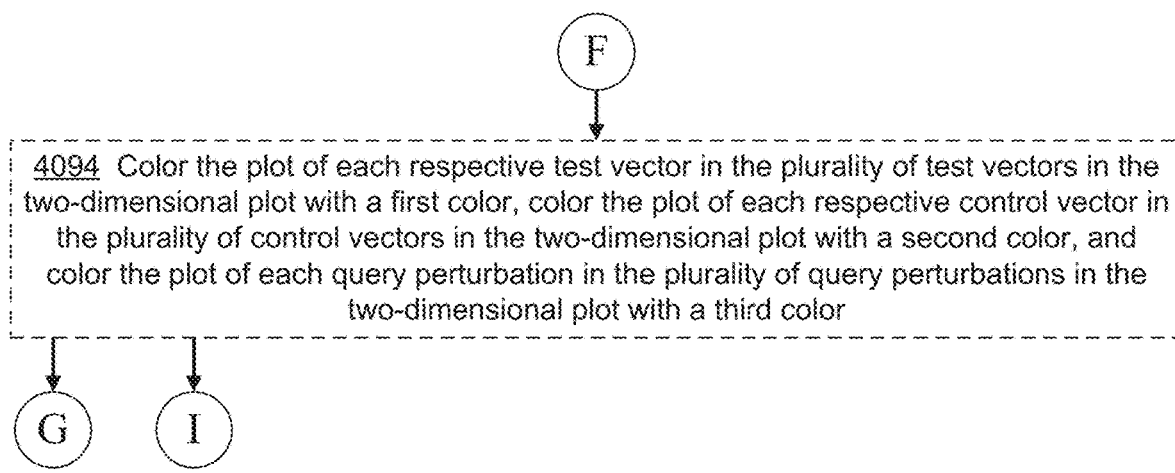

In some embodiments, the characteristics of the plotted points convey additional information about the perturbations. For example, in some embodiments, the color and/or shape of the plotted point indicates the type of sample being plotted, e.g., control, test, or query. Accordingly, with reference to FIG. 4K, in some embodiments, method 4000 includes coloring (4094) the plotted point of each respective test vector in the plurality of test vectors in the two-dimensional plot with a first color, coloring the plotted point of each respective control vector in the plurality of control vectors in the two-dimensional plot with a second color, and coloring the plotted point of each query perturbation in the plurality of query perturbations in the two-dimensional plot with a third color (e.g., as shown in FIG. 6, where test vector plots are shown as circles, control vector plots are shown as squares and query perturbation plots shown as purple triangles). Additionally or alternatively, in some embodiments, different shapes can be used for text vector plots, control vector plots, and query perturbation plots; and the different shapes may be used with or without differing colors for the different plots, and/or with or without shading (where the intensity of the shading may be proportional or inversely proportional to another feature of the plotted data).

Figure 4L:
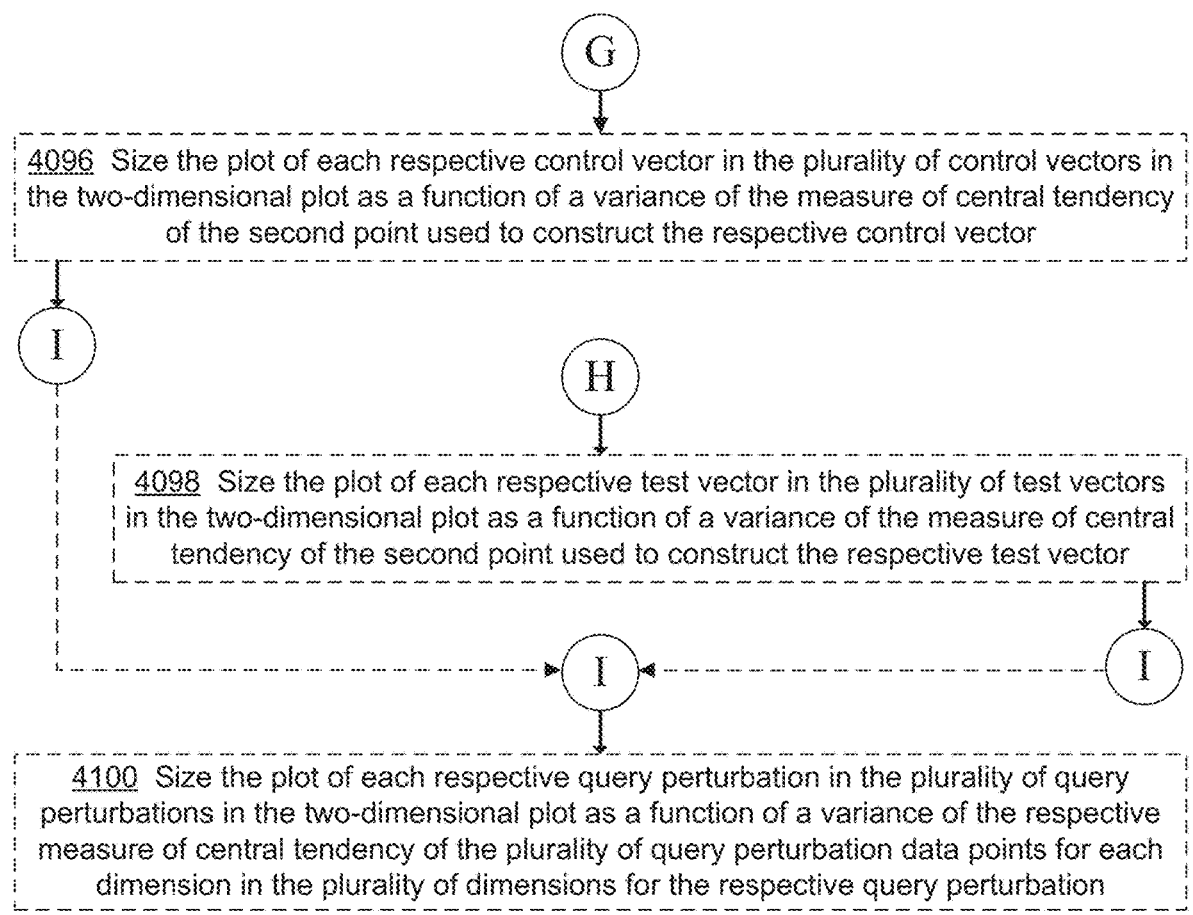

Similarly, in some embodiments, the size of the plotted point corresponds to a measure of variance in the features used to form the perturbation vector, e.g., a control vector (108), a test vector (110), or a query perturbation vector (112), as described in FIG. 1, from which the on-target and off-target scores were calculated. Accordingly, with reference to FIG. 4L, in some embodiments, method 4000 includes sizing (4096) the plotted point of each respective control vector in the plurality of control vectors in the two-dimensional plot as a function of a variance of the measure of central tendency of the second point used to construct the respective control vector. Likewise, in some embodiments, method 4000 includes sizing (4098) the plotted point of each respective test vector in the plurality of test vectors in the two-dimensional plot as a function of a variance of the measure of central tendency of the second point used to construct the respective test vector. Similarly, in some embodiments, method 4000 includes sizing (4100) the plotted point of each respective query perturbation in the plurality of query perturbations in the two-dimensional plot as a function of a variance of the respective measure of central tendency of the plurality of query perturbation data points for each dimension in the plurality of dimensions for the respective query perturbation. For instance, the plotted points corresponding to control perturbations, test perturbations, and query perturbation shown in FIG. 6 are sized based on the variance of the respective underlying features. In some embodiments, the measure of central tendency is an arithmetic mean, weighted mean, midrange, midhinge, trimean, geometric mean, geometric median, Winsorized mean, median, or mode of the variance of the respective features. Advantageously, this provides an indication of the reliability of the respective on-target and off-target scores for the plot. For example, in some embodiments, smaller points indicate smaller variances and larger points indicate larger variances.

Figure 4M:
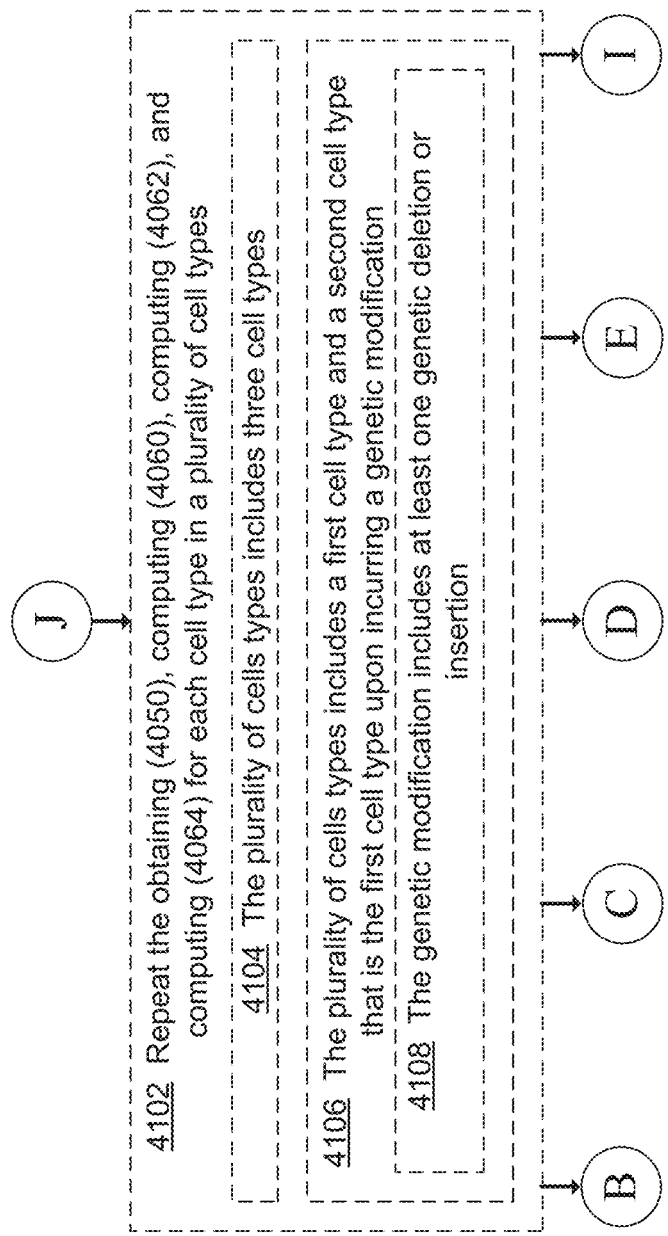

In some embodiments, each compound is screened across one or more perturbations in a plurality of cell types (cell contexts) in order to ensure that effects seen with a particular compound are not limited to a particular cell type or state of the cell, e.g., growth stage). Accordingly, with reference to FIG. 4M, in some embodiments, method 4000 includes repeating (4102) the obtaining (4050), computing (4060), computing (4062), and computing (4064) for each cell type in a plurality of cell types. In some embodiments, the plurality of cell types includes at least 3 cell types (4104). In other embodiments, the plurality of cell types includes at least 2, 3, 4, 5, 6, 7, 8, 9, 10, 15, 20, 25, 30, 40, 50, or more cell types. In some embodiments, the cell types differ by only a genetic modification, e.g., a gene deletion, insertion, or mutation. For example, in some embodiments, the plurality of cell types comprises a first cell type and a second cell type that is the first cell type upon incurring a genetic modification (4106). In some embodiments, the genetic modification includes at least one genetic deletion or insertion (4108), e.g., that causes the cell to display a 'disease' phenotype.

FIGS. 7A and 7B illustrate dose-response curves of off-target scores as a function of on-target scores for various non-diseased/non-perturbed cell contexts (e.g., "healthy" cell contexts; grouping of green circles 702), perturbed cell contexts (e.g., "test" cell contexts; grouping of red circles 704), and perturbed cell contexts exposed to varying concentrations of various compounds (e.g., screened test cell contexts; grouping of purple circles 706).

Figure 4N:
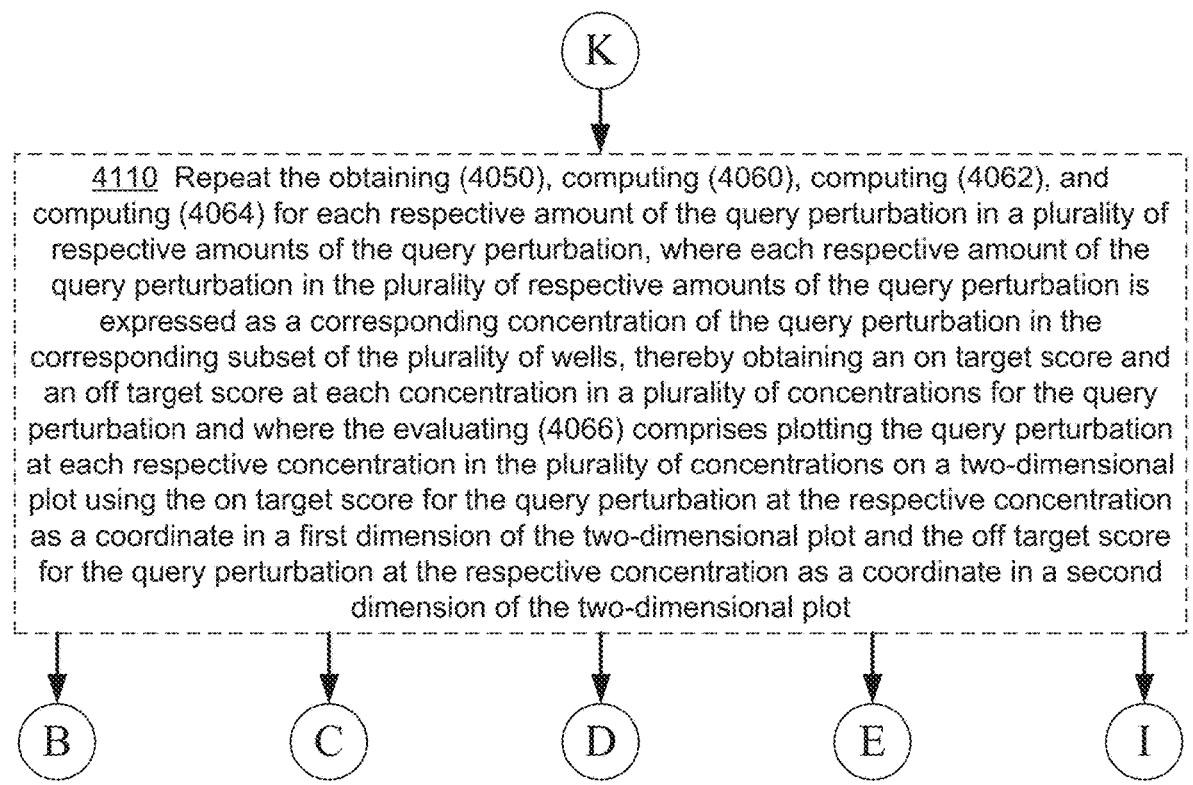

In some embodiments, each compound is screened at a plurality of concentrations, e.g., on-target and off-target scores for the compound are determined at each concentration. Accordingly, with reference to FIG. 4N, in some embodiments, method 4000 includes repeating (4110) the obtaining (4050), computing (4060), computing (4062), and computing (4064) for each respective amount of the query perturbation in a plurality of respective amounts of the query perturbation, where each respective amount of the query perturbation in the plurality of respective amounts of the query perturbation is expressed as a corresponding concentration of the query perturbation in the corresponding subset of the plurality of wells, thereby obtaining an on-target score and an off-target score at each concentration in a plurality of concentrations for the query perturbation. The evaluating (4066) would include plotting the query perturbation at each respective concentration in the plurality of concentrations on a two-dimensional plot using the on-target score for the query perturbation at the respective concentration as a coordinate in a first dimension of the two-dimensional plot and the off-target score for the query perturbation at the respective concentration as a coordinate in a second dimension of the two-dimensional plot (e.g., as illustrated as series of connected purple points 707, in FIGS. 7A and 7B). Advantageously, screening perturbations at a plurality of concentrations facilitates identification of treatments that may not be efficacious at a particular concentration, which would not be evident a priori. Screening perturbations at multiple concentrations also facilitates identification of treatments with significant off-target effects at higher concentrations, by providing information about a treatment's on-target and off-target effects across a range of concentrations. Thus, screening perturbations at a plurality of concentrations improves the identification of useful treatments.

In some embodiments, each compound is screened at a plurality of concentrations and the resulting on-target and off-target scores are plotted as independent curves, e.g., to further characterize the therapeutic qualities of a treatment. Accordingly, with reference to FIG. 4O, in some embodiments, method 4000 includes repeating (4112) the obtaining (4050), computing (4060), computing (4062), and computing (4064) for each respective amount of the query perturbation in a plurality of respective amounts of the query perturbation, where each respective amount of the query perturbation in the plurality of respective amounts of the query perturbation is expressed as a corresponding concentration of the query perturbation in the corresponding subset of the plurality of wells, thereby obtaining an on-target score and an off-target score at each concentration in a plurality of concentrations for the query perturbation. Thus, in some embodiments, the evaluating (4066) includes plotting the query perturbation at each respective concentration in the plurality of concentrations on a two-dimensional plot using the on-target score for the query perturbation at the respective concentration as a coordinate in a first dimension of the two-dimensional plot and the respective concentration as a coordinate in a second dimension of the two-dimensional plot thereby obtaining an on-target curve for the query perturbation (e.g., illustrated as modeled curves 802, 806, 810, 814, 818, and 822 in FIGS. 8A-8G). Likewise, in some embodiments, the evaluating (4066) includes plotting the query perturbation at each respective concentration in the plurality of concentrations on the two-dimensional plot using the off-target score for the query perturbation at the respective concentration as a coordinate in the first dimension of the two-dimensional plot and the respective concentration as a coordinate in the second dimension of the two-dimensional plot thereby obtaining an off-target curve for the query perturbation (e.g., illustrated as modeled curves 804, 808, 812, 816, 820, and 824 in FIGS. 8A-8G). Advantageously, plotting on-target and off-target scores as separate functions of concentration for a query perturbation facilitates identification and characterization of the therapeutic effects of a treatment, e.g., as shown by the different patterns of on-target and off-target curves illustrated in FIGS. 8A-8G.

In some embodiments, the plotted on-target and off-target scores calculated across a plurality of concentrations of a query perturbation (e.g., a compound) are fit to linear or non-linear curves. Advantageously, fitting the on-target and off-target scores to a curve allows for the quantification of areas bounded by one or more of the curves, providing information about the therapeutic effects of the query perturbation. With reference to FIG. 4AB, in some embodiments, method 4000 includes fitting (4194) the on-target curve to a first sigmoidal function. In some embodiments, method 4000 includes fitting (4198) the off-target curve to a second sigmoidal function. In some embodiments, method 4000 includes fitting the sum of the first sigmoidal function and the second sigmoidal function to allow for biphasic response of the query perturbation as a function of concentration. In some embodiments, fitting the sum of two sigmoids to allow for biphasic responses is performed as:

$$F(x)=\text{sig1}(x)+\text{sig2}(x). \tag{Equation III}$$

In some embodiments, the on target curve is constrained such that $d_1=1$ and $d_0=0$, e.g., so that the sum of the max responses is 1. That is, the sum of the max responses is positioned at the center of the disease cloud. The off target curve is constrained such that $C_1=C_2=0$, so that it needs to start out at zero side effect, that is no effect is caused when the test state is not exposed to the query perturbation.

In some embodiments, the first sigmoidal function (e.g., to which the on-target scores are fit) has (4196) the form:

$$\left(c + \frac{(d-c)}{\left(1+\left(\left(\frac{x}{EC_{50}}\right)\right)^b\right)}\right) + \left(c + \frac{(d-c)}{\left(1+\left(\left(\frac{x}{EC_{50}}\right)\right)^b\right)}\right), \quad \text{(Equation IV)}$$

where:
c=a minimum on-target score computed for the query perturbation,
d=a maximum on-target score computed for the query perturbation,
$EC_{50}$=a concentration of the query perturbation that represents half of its maximum on-target effect,
x=a concentration of the query perturbation in the plurality of concentrations, and
b=a hill slope of the on-target curve.

Similarly, in some embodiments, the second sigmoidal function (e.g., to which the off-target scores are fit) has (4200) the form:

$$\left(c' + \frac{(d'-c')}{\left(1+\left(\left(\frac{x}{EC_{50'}}\right)\right)^{b'}\right)}\right) + \left(c' + \frac{(d'-c')}{\left(1+\left(\left(\frac{x}{EC_{50'}}\right)\right)^{b'}\right)}\right), \quad \text{(Equation V)}$$

where:
c=a minimum off target score computed for the query perturbation,
d=a maximum off target score computed for the query perturbation,
$EC_{50}$=a concentration of the query perturbation that represents half of its off-target effect,
x=a concentration of the query perturbation in the plurality of concentrations, and
b=a hill slope of the off target curve.

As will be appreciated by one of skill in the art, a Hill slope describes the steepness of the curve. This variable is commonly referred to as the Hill slope, the slope factor, or the Hill coefficient. If it is positive, the curve increases as X increases. If it is negative, the curve decreases as X increases. A standard sigmoid dose-response curve, e.g., as shown above, has a Hill Slope of 1.0. When Hill slope is less than 1.0, the curve is more shallow. When the Hill slope is greater than 1.0, the curve is steeper. The Hill slope has no units.

Other sigmoidal functions, and functions approximating a sigmoidal function, known to the skilled artisan can also be used to model the on-target and off-target scores. For example, non-limiting examples of functions suitable for generating a sigmoidally-shaped curve include logistic functions, hyperbolic tangents, arctangent functions, Gompertz curves, Gudermannian functions, error functions, generalized logistic functions, smoothstep functions, and algebraic functions. For a review of these and other suitable modeling functions see, e.g., CRC Standard Curves and Surfaces with Mathematica, Third Edition, Ed. David H. von Seggern, CRC Press, the content of which is expressly incorporated herein by reference, in its entirety, for all purposes.

Quantifying Therapeutic Response

In some embodiments, sigmoidal functions modeling on-target and off-target scores across a range of concentrations for a query perturbation, e.g., as described above, are used to calculate a therapeutic response score for the query perturbation. Generally, a therapeutic response score is positively responsive to on-target scores and negatively responsive to off-target scores, such that query perturbations with higher on-target scores and lower off-target scores will have therapeutic response scores that are higher than those for compounds with lower on-target scores and higher off-target scores. FIGS. 8A-8G, described below, are offered for the purpose of illustrating the concept of a therapeutic response score. However, rather than plotting sigmoidal functions modeling on-target and off-target scores and integrating an area defined by certain boundaries within the plot, in some embodiments a therapeutic response score is determined mathematically, as a function of the on-target and off-target sigmoidal functions.

Referring to FIG. 8B and FIG. 4P, in some embodiments, method 4000 includes using (4114) the on-target curve 806 and the off-target curve 808 to quantify a therapeutic window for the query perturbation, where the therapeutic window is determined by an area 809 of a closed two-dimensional shape bounded by (i) an amplitude of the on-target curve between a first position 860 on the on-target curve that represents a maximum on-target score in the on-target curve and a second position 862 that represents an intersection of the on-target curve and the off-target curve, (ii) an amplitude of the off-target curve 808 between the second position 862 and a third position 864 on the off-target curve that represents a maximum off-target score in the off-target curve, and (iii) a line drawn between the first position and the third position, e.g., shown as area 809 in FIG. 8B. These portions of FIG. 8B are shown in isolation and in greater detail in FIG. 8C. In other words, referring to 880 of FIG. 8C, the area 809 is determined by (i) portion 882 of on-target curve 806, (ii) portion 884 of off-target curve 808, and line 886. In FIG. 8, the first position 860 has similar amplitude to the third position 864. In some embodiments the line 886 used, in part, to determine the area 809 is drawn from the first position 860 to the third position 864. In alternative embodiments, not illustrated in FIG. 8B, in the alternative, the line 886 used, in part, to define area 886 is drawn from the first position 860 with zero slope to the right until it intersects the off-target curve 808. In still further alternative embodiments, not illustrated in FIG. 8B, the line 886 used, in part, to define area 886 is drawn from the third position 860 to the left with zero slope until it intersects the on-target curve 806. These alternative embodiments are used, for example, in instances where the maximum score for the on-target and off-target curves are substantially different from each other. It will be appreciated that any number of further variations for computing are 809 are possible. For instance, in some embodiments, line 886 has zero slope and an amplitude that is the average of the amplitude of the first position 860 and the third position 864, using the coordinate system depicted in FIG. 8B. In still other embodiments, line 886 has zero slope and an amplitude that is a fixed percentage of the average of the amplitude of the first position 860 and the third position 864, using the coordinate system depicted in FIG. 8B. For instance, if the fixed percentage is 90 percent and the average of the first position 860 and the third position 864 is 100 arbitrary units, then the amplitude of line 886 is 90 arbitrary units.

In some embodiments, the therapeutic window of a query perturbation (e.g., a therapy) for a particular disease state is represented by a function of the area bounded above the two curves, such as area 809 in FIG. 8B. In some embodiments, the area corresponding to the therapeutic window is used to rank query perturbations relative to each other for addressing a particular test state, e.g., to rank which therapies may be expected to treat a corresponding disease state.

Notwithstanding the various embodiments for computing the area 809, as discussed above, in some embodiments, the area representing the therapeutic window is additionally weighted to account for the shape of the bounded area, which is affected by different effects of the query perturbations. That is, different factors are considered when determining which query perturbations are more effective at addressing a test state. These can be used to make assumptions for which therapies will be better suited for in vivo use, e.g., where the bounded area is the same for different compounds. For example, the bounded areas illustrated in FIGS. 8D-8G all have the same area X. However, the shape of the bounded area, e.g., as determined by the shape of the curves for the on-target and off-target scores, is different, providing information about the effects of the corresponding therapies. Accordingly, in some embodiments, assumptions about the shape of the area guide the ranking of query perturbations for a given test state. For example, in some embodiments, an assumption is made that therapies that rescue a phenotype (e.g., provide a beneficial therapeutic effect) at lower doses are better than therapies that rescue a phenotype at higher doses. Thus, in some embodiments, a therapeutic window (area 809) is weighted to bias scores for compounds that show effectiveness at lower doses. For example, on-target curve 818 in FIG. 8F shows effectiveness for rescuing a test state at a lower concentration of a first respective query perturbation than does on-target curve 822 in FIG. 8G for a second respective query perturbation. Thus, in some embodiments, a rescue score calculated for the query perturbation corresponding to FIG. 8F would be higher than the rescue score calculated for the query perturbation corresponding to FIG. 8G. Accordingly, in some embodiments, the area 809 (e.g., the bounded area 809 above the on-target and off-target curves) is weighted (4118) by the concentration of the query perturbation (dose) at the second position 862. Referring to FIG. 8B, consider the case where the area 809 is 110 arbitrary units squared and the concentration of the query perturbation (dose) at the second position 862 is 100 micromolar. In some such embodiments, the area 809 is weighted by multiplying $100 \times 10^{-6}$ M against 110 arbitrary units squared to arrive at a final weighted value for area 809. As will be appreciated, other forms of weighing can be performed. For instance, in some embodiments the area 809 is divided by the concentration of the query perturbation (dose) at the second position 862. Moreover, in still other embodiments, the area 809 is weighted by dividing the area by the $\log_{10}$ of the concentration of the query perturbation (dose) at the second position 862. In still other embodiments, the area 809 is weighted by multiplying the area by the $\log_{10}$ of the concentration of the query perturbation (dose) at the second position 862. Such examples serve to illustrate that there are many different ways in which the concentration of the query perturbation (dose) at the second position 862 can be used to weight area 809 and all such ways are encompassed within the scope of the present disclosure.

In some embodiments, an assumption is made that therapies that have a longer window between rescue and side effect are better than therapies having a shorter window between rescue and side effects. Thus, in some embodiments, the therapeutic window 809 is weighted to bias scores for compounds where the distance (e.g., a measure of central tendency of distance between an on-target curve and an off-target curve or a maximum distance between an on-target curve and an off-target curve at a given point) between an on-target curve calculated for a test state and a corresponding off-target curve calculated for the test state is larger. Accordingly, referring to 880 of FIG. 8C in some embodiments, the area 809 (e.g., the bounded area above the on-target and off-target curves) is weighted (4116) by a closest distance 886 between the second position 862 and the line 886 drawn between the first position 860 and the third position 864. In some embodiments, the area 809 is first computed using any of the variants discussed above prior to such weighting. Moreover, the closest distance 886 between the second position 862 and the line 886 drawn between the first position 860 and the third position 864 can be applied as a weight against the area 809 in many different ways. In some such embodiments, the area 809 representing the therapeutic window is weighted by a length of line 886. Referring to FIG. 8B, consider the case where the area 809 is 110 arbitrary units squared and the length of line 886 is 80 disease score units (y-axis units). In some such embodiments, the area 809 is weighted by multiplying 80 disease score unites against 110 arbitrary units squared to arrive at a final weighted value for area 809. As will be appreciated, other forms of weighing can be performed. For instance, in some embodiments the area 809 is divided by the length (number of disease score units) of line 886. Moreover, in still other embodiments, the area 809 is weighted by dividing the area by the $\log_{10}$ of the length of line 886. In still other embodiments, the area 809 is weighted by multiplying the area by the $\log_{10}$ of the length of line 886 (in disease score units). Such examples serve to illustrate that there are many different ways in which the concentration of the length of line 886 can be used to weight area 809 and all such ways are encompassed within the scope of the present disclosure.

Figure 8D:
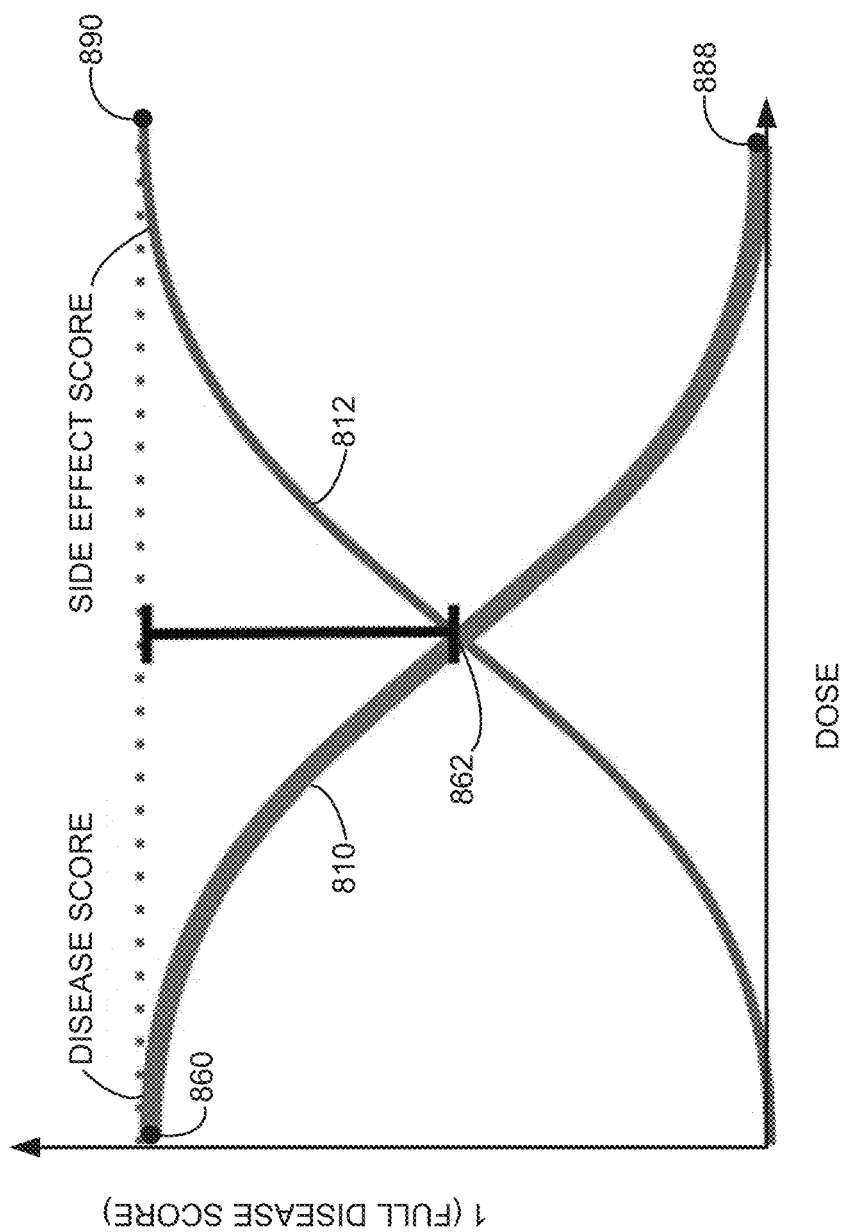
Figure 8E:
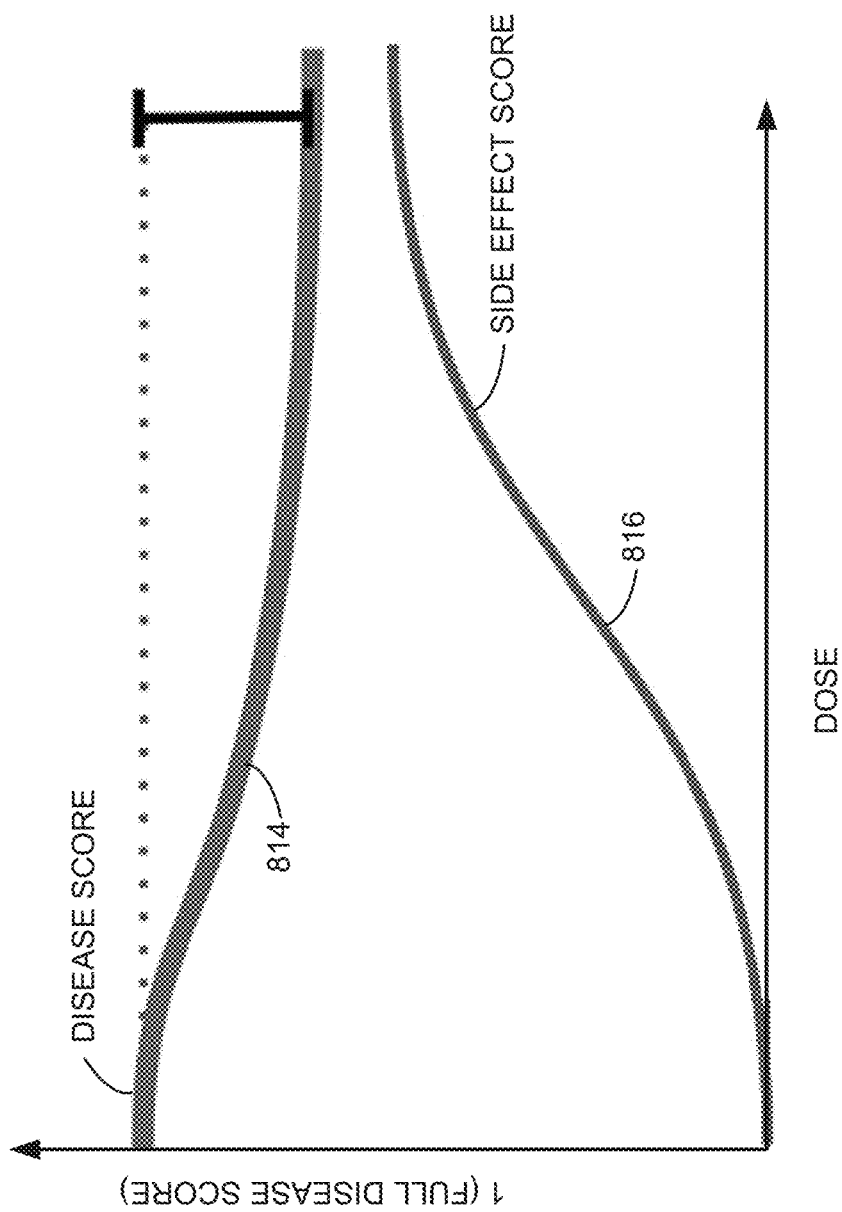

In some embodiments, an assumption is made that therapies (e.g., compounds) that provide greater rescue for a test state (e.g., provide a greater beneficial therapeutic effect) are better than therapies that provide less of a rescue effect. Accordingly, in some embodiments, a therapeutic window 809 is weighted to bias scores for compounds that show greater effectiveness. For example, on-target curve 814 in FIG. 8E plateaus at much less than complete rescue of the test state phenotype. That is, in FIG. 8E, rather than dropping down to zero at higher doses of the compound, the on-target curve plateaus at a value considerably above zero regardless of the additional amount (higher dose) of compound that is used. This is in contrast to the on-target curve 810 in FIG. 8D which drops to zero at higher concentrations (dose) of the test compounds. Thus, in some embodiments, a rescue score calculated for the query perturbation (e.g., compound) corresponding to the rescue area 809 computed using FIG. 8D is upweighted relative to the rescue score calculated for the query perturbation corresponding to the rescue area 809 computed using FIG. 8E. Such a weight can be encoded in any number of ways. For instance, in some embodiments the minimum disease score is derived from the on-target curve (e.g., the minimum y-value of the on-target curve using the coordinate system of FIG. 8) and this minimum disease score is used to weight the corresponding area 809. In the case of FIG. 8D, the minimum disease score is zero whereas in FIG. 8E the minimum disease score of the on-target curve is substantially greater than zero. Since it is desired to upweight for the lower disease score, a weight can be formulated as a fixed value minus the minimum disease score. For instance, in some embodiments, the weight is the difference between maximum disease score and the minimum disease score on the on-target curve. Thus, referring to FIG. 8D, in such embodiments, the weight would be the disease score of position 860 minus the disease score of position 888. As discussed above, such a weight can be applied against the rescue area 809 in any number of ways, thereby weighting the area. For instance, the weight can be multiplied or divided against rescue area 809, or a mathematical function of the weight, such as a logarithm of the weight can be multiplied or divided against rescue area 809.

In some embodiments, an assumption is made that therapies that provide smaller side effects (e.g., low off-target scores) are better than therapies that provide greater side effects. For example, off-target curve 816 in FIG. 8E plateaus at lower levels of off-target effects (measured in disease score units) as compared to off-target curve 812 in FIG. 8D. Thus, in some embodiments, a rescue score calculated for the query perturbation (e.g., compound) corresponding to the rescue area 809 computed using FIG. 8E would be upweighted relative to the rescue score calculated for the query perturbation corresponding to the rescue area 809 computed using FIG. 8D. Such a weight can be encoded in any number of ways. For instance, in some embodiments a maximum disease score is derived from the off-target curve (e.g., the maximum y-value of the off-target curve using the coordinate system of FIG. 8) and this maximum disease score is used to weight the corresponding area 809. In the case of FIG. 8D, the maximum disease score of the off-target curve is greater than that of corresponding off-target curve in FIG. 8E. Since it is desired to upweight for lower maximum y-value (disease units), a weight can be formulated as a fixed value minus the maximum y-value of the off-target curve. For instance, in some embodiments, the weight is the difference between maximum disease score of the on-target curve and the minimum disease score on the off-target curve. Thus, referring to FIG. 8D, in such embodiments, the weight would be the disease score of position 860 minus the disease score of position 890. In some embodiments, the weight is:

1+(disease score at position 860)−(disease score at position 890)

In still other embodiments, the weight is:

Constant+(disease score at position 860)−(disease score at position 890)

where the constant is determined on a case by case basis, e.g., for a given cell panel, compound panel, or set of test conditions. As discussed above, such weights can be applied against the rescue area 809 in any number of ways, thereby weighting the area. For instance, the weight can be multiplied or divided against rescue area 809, or a mathematical function of the weight, such as a logarithm of the weight can be multiplied or divided against rescue area 809.

With reference to FIG. 4Q, in some embodiments, method 4000 includes using (4120) the on-target curve and the off-target curve to quantify a rescue quality for the query perturbation, where the rescue quality is determined by integrating a difference between (a) the amplitude of the first position and (b) the maximum disease score at each respective concentration in the plurality of concentrations, where the maximum disease score at each respective concentration in the plurality of concentrations is the largest disease score from among the on-target curve and the off-target curve at the respective concentration. This is illustrated using in isolation and greater detail in 880 of FIG. 8C. In all concentrations to the left of point 862, the maximum disease score is found on segment 882 of on-target curve 806. Thus, for concentrations to the left of point 862, differences in disease score between line 886 and line 882 are integrated to form the first part of area 809. In all concentrations to the right of point 862, the highest disease score is found on segment 884 of off-target curve 808. Thus, for concentrations to the right of point 862, differences between line 886 and line 884 are integrated to form the second part of area 809.

In some embodiments, a therapeutic response score is calculated by integrating a relative measure of the on-target and off-target scores provided by the model sigmoidal functions at a plurality of concentrations. With reference to FIG. 4R, in some embodiments, method 4000 includes using (4122) the on-target curve and the off-target curve to quantify a rescue quality (therapeutic response score) for the query perturbation. In such embodiments the rescue quality is a measure of the quality of a query perturbation, where the rescue quality is calculated as:

$$\int_{i=[a]}^{[b]} \max(\text{phenotype}(c_i), \text{side}(c_i)) * \frac{\log(c_i * \text{weight})}{c_i} * dc \quad \text{(Equation VI)}$$

where, $c_i$ is an $i^{th}$ concentration of the compound in the plurality of concentrations for the compound, i is an index to each concentration of the compound in the plurality of concentrations,

[a] is one of a lowest and a highest concentration of the compound in the plurality of concentrations,

[b] is the other of the lowest and the highest concentration of the compound in the plurality of concentrations, phenotype ($c_i$) is the on-target score (e.g., disease score on y-axis in FIG. 8B) for the compound at concentration $c_i$ in the phenotype curve (e.g., on-target curve 806 of FIG. 8B), side ($c_i$) is the off-target score (e.g., disease score on y-axis in FIG. 8B) for the compound at concentration $c_i$ in the side effect curve (e.g., off-target curve 808 of FIG. 8B), and weight is a numerical weight.

In some embodiments, rather than taking the log of the product of the $i^{th}$ concentration of the compound and the numerical weight, the natural log or any other log base of the product is used. In some embodiments, the product of the $i^{th}$ concentration of the compound and the numerical weight represents a confidence of the Area Score, measuring the curve fit to the raw test score and side effect score. In some embodiments, a warning is given if the log of the residuals is above one standard deviation from the mean of all assays. Residuals for the test state and side effect scores are defined as the sum of the absolute residuals between the sigmoidal fits and the test state rescue and side effects data of a drug. Non-limiting examples of numerical weights include values between 100 and 100,000, e.g., 100, 250, 500, 1000, 2500, 5000, 7500, 10,000, 25,000, 50,000, 75,000, 100,000, and any value in-between. In one embodiment, the numerical weight is 7500. In some embodiments, the weight is chosen such that the rescue scores for the compounds tend to fall into a suitable distribution, such as a normal distribution. See *Statistical Reasoning*, Allyn and Bacon, Needham Heights, Mass., 1991, Chapter 7, pp. 267-299, which is hereby incorporated by reference. In some embodiments, the weight is chosen such that the rescue scores for the compounds differentiate sufficiently to rank the tested compounds.

In some embodiments the rescue quality is calculated as:

$$\sum_{i=a}^{b} \frac{e^{\left(\frac{-d^2-s^2}{\sigma^2}\right)} - e^{\left(\frac{-1}{\sigma^2}\right)}}{1 - e^{\left(\frac{-1}{\sigma^2}\right)}} \quad \text{(Equation VII)}$$

where, d is the on-target score for the perturbation at concentration i, s is the off-target score for the perturbation at concentration i, σ is a standard deviation of a Gaussian kernel, and i is an index to each concentration or a subset of concentrations of the compound in a plurality of concentrations.

In some embodiments the rescue quality is calculated as:

$$\Sigma_i 2e^{-|a_d d|^n d - a_s s^2} - 1 \quad \text{(Equation VIII)}$$

where, d is the on-target score for the perturbation at concentration i, s is the off-target score for the perturbation at concentration i, $a_d$ is a constant chosen based on measures of the spread of the disease and healthy clouds so that the quality when d=1 and s=0 is 0 and the quality at a point equidistant to the disease and healthy cloud is ½, and i is an index to each concentration or a subset of concentrations of the compound in a plurality of concentrations.

In some embodiments, assay results for one or more query perturbations are removed from the data set prior to analyzing and/or ranking the other query perturbations being screened. Such elimination allows the final ranking and plotting of the query perturbations to that remain to be filtered such that perturbations that are deemed not useful for the assay are not included. This improves the clarity of the final plots. With reference to FIG. 4AA, in some such embodiments, method 4000 eliminates (4190) one or more query perturbations from the plurality of query perturbations using an elimination criterion that is based, at least in part, on the on target score of each query perturbation in the plurality of query perturbations. In some such embodiments, the elimination criterion (4192) is:

$$E = uudx - K^* uuudx, \quad \text{(Equation IX)}$$

where:

each respective query perturbation in the plurality of query perturbations that has an on target score of less than E is eliminated from the plurality of query perturbations, uudx=is a measure of central tendency of the on target score across the plurality of query perturbations, uuudx=is a standard deviation of the on target score across the plurality of query perturbations, and K=is a weight.

That is, those perturbations that were K standard deviations below the average score for the perturbations are eliminated. For instance, if K is "1", then those perturbations that are more than 1 standard deviation below the average score for the perturbations are eliminated. If K is "2", then those perturbations that are more than 2 standard deviations below the average score for the perturbations are eliminated. For each respective query perturbation remaining in the plurality of query perturbations, the obtaining (4050), computing (4060), computing (4062), and computing (4064) is repeated for each respective amount of the respective query perturbation in a plurality of respective amounts of the respective query perturbation. Each respective amount of the respective query perturbation is expressed as a corresponding concentration of the respective query perturbation in the corresponding subset of the plurality of wells, thereby obtaining an on target score and an off target score at each concentration in a plurality of concentrations for the respective query perturbation. In some embodiments, the weight (K) is 3. In other embodiments, the weight K is 1, 2, 3, 4, 5, 6, 7, 8, 9, 10, or more. In some embodiments, a minimum and/or maximum number of query perturbations are required to progress. Accordingly, in some embodiments, a shift of the threshold is shifted if the desired minimum or maximum specifications are violated, e.g., to allow for the method to proceed.

FIG. 6 illustrates an example plot of on-target and off-target effects of screened compounds, created according to the methods described here. The plot displays information on the impact of each drug in terms of both its ability to rescue morphological defects associated with knockdown of a disease-associated gene, as well as the magnitude of non-specific effects (e.g., side effects and toxicity) induced by treatment. The data are displayed relative to vehicle-treated knockdowns (Disease), shown as green squares and negative controls (Control), shown as red circles. Drug responses are displayed as purple triangles. The disease score (depicted along the x-axis) measures the similarity between the loss-of-function disease signature under investigation and the signature of each treatment. The side effect score (depicted on the y-axis) measures the remaining effects of a treatment that are separate from the disease signature. A drug corresponding to a query perturbation with a disease score and an off-target score closer to the center of the cloud of 'healthy' controls is more likely to successfully rescue the disease signature without providing side-effects relative to other drugs. The size of the markers in each data plot reflect the confidence in the disease score (the larger the marker, the more confidence in the disease score). FIGS. 7A and 7B illustrate examples of similar plots which may be generated with assays performed with increasing concentrations of the candidate drug, as shown by the connected purple points 707.

Assay Quality

In some embodiments, one or more metric relating to the quality of the screening assay is determined, e.g., to evaluate the performance of the screening methodology used and inform on the confidence of query perturbations (e.g., therapies) identified as promising for treatment of a particular indication, e.g., as step 134 in method 100.

Figure 4T:
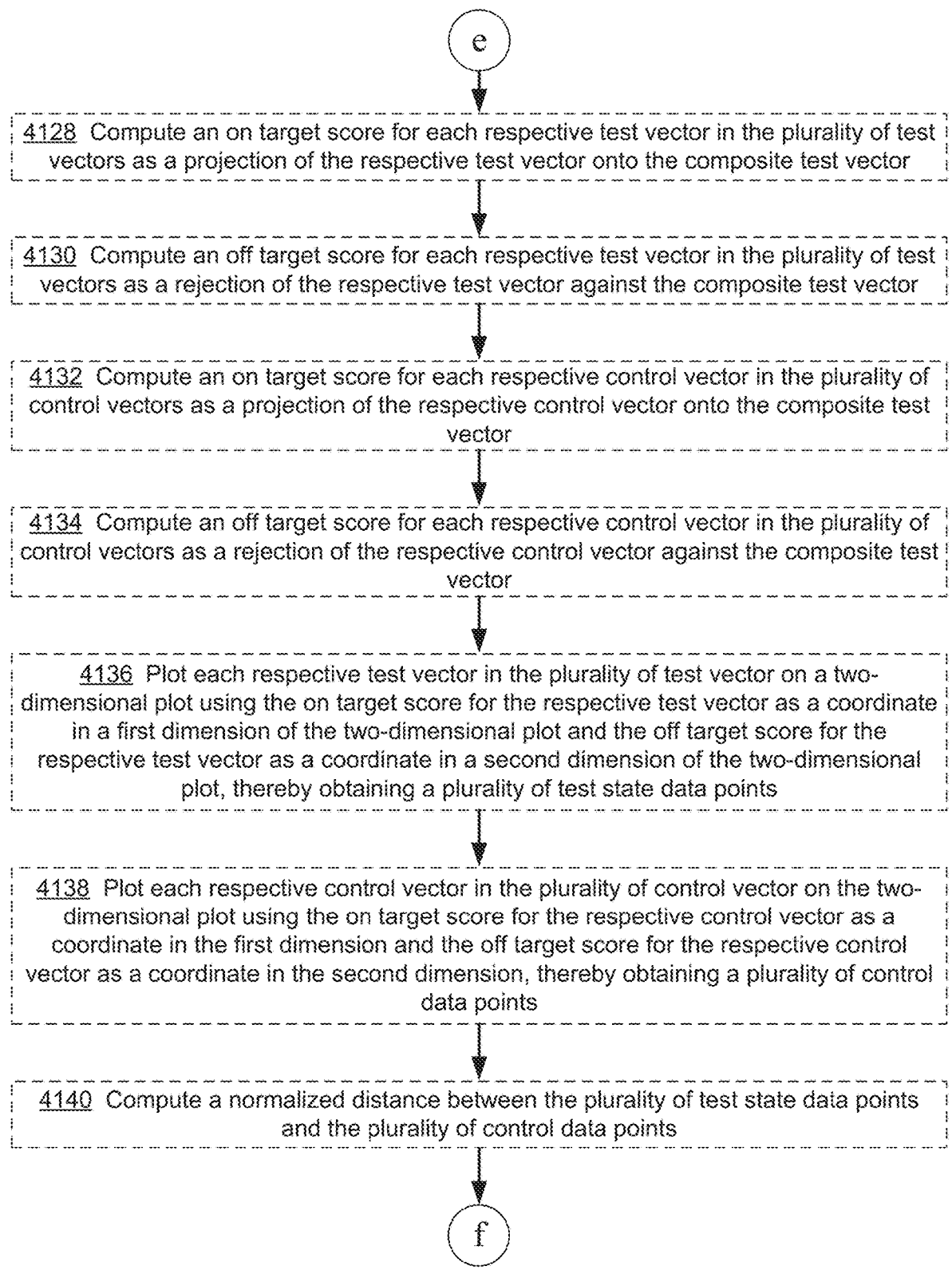

With reference to FIG. 4S, in some embodiments, method 4000 includes determining a quality of one or more test states used in the screening. In some embodiments, this includes computing (4124) a plurality of test vectors, where each respective test vector in the plurality of test vectors is between (i) the first point and (ii) a second point defined by a respective test data point in the set of test data points for each dimension in the plurality of dimensions. In some embodiments, method 4000 then includes computing (4126) a plurality of control state vectors, where each respective control state vector in the plurality of control state vectors is between (i) the first point and (ii) a third point defined by a respective control data point in the set of control data points for each dimension in the plurality of dimensions. With reference to FIG. 4T, in some embodiments, method 4000 then includes computing (4128) an on-target score for each respective test vector in the plurality of test vectors as a projection of the respective test vector onto the composite test vector. In some embodiments, method 4000 then includes computing (4130) an off-target score for each respective test vector in the plurality of test vectors as a rejection of the respective test vector against the composite test vector. In some embodiments, method 4000 then includes computing (4132) an on-target score for each respective control vector in the plurality of control vectors as a projection of the respective control vector onto the composite test vector. In some embodiments, method 4000 then includes computing (4134) an off-target score for each respective control vector in the plurality of control vectors as a rejection of the respective control vector against the composite test vector. In some embodiments, method 4000 then includes plotting (4136) each respective test vector in the plurality of test vector on a two-dimensional plot using the on-target score for the respective test vector as a coordinate in a first dimension of the two-dimensional plot and the off-target score for the respective test vector as a coordinate in a second dimension of the two-dimensional plot, thereby obtaining a plurality of test state data points. In some embodiments, method 4000 then includes plotting (4138) each respective control vector in the plurality of control vector on the two-dimensional plot using the on-target score for the respective control vector as a coordinate in the first dimension and the off-target score for the respective control vector as a coordinate in the second dimension, thereby obtaining a plurality of control data points. In some embodiments, method 4000 then includes computing (4140) a normalized distance between the plurality of test state data points and the plurality of control data points.

With reference to FIG. 4U, in some embodiments, determining the quality of one or more test states used in the screening includes computing (4142) a normalized tightness of the plurality of test state data points. In some embodiments, the normalization is made by the second moment of the second measure (angle in controls) distribution. Accordingly, with reference to FIG. 4V, in some embodiments, the normalized tightness is computed by a procedure that includes (4144), for each respective test vector in the plurality of test vectors, computing a test state similarly metric between (i) the respective test vector and (ii) a distribution metric of the plurality of test vectors with the respective test vector removed from the plurality of test vectors, thereby obtaining a plurality of test state similarity metrics for the plurality of test vectors, each test state similarity metric in the plurality of test state similarity metrics uniquely corresponding to a test perturbation in the set of test perturbations. The procedure also including computing a complementary distribution, by a sub-process that includes (a) for each respective control state vector in the plurality of control state vectors, computing a respective control similarity metric between (i) the respective control vector and (ii) a distribution metric of the plurality of control vectors with the respective control vector removed from the plurality of control vectors, thereby obtaining the plurality of control similarity metrics, each control similarity metric in the plurality of control similarity metrics uniquely corresponding to a control perturbation in the set of control perturbations, and (b) computing the complementary distribution as a distribution metric of the plurality of control similarity metrics. The procedure also including determining a first measure of central tendency of the angle between (i) each respective test state similarity metric in the plurality of test state similarity metrics to (ii) the complementary distribution across the plurality of test state similarity metrics. The procedure also including normalizing the first measure of central tendency of the angle by a second measure of central tendency of the angle between (i) each control similarity metric in the plurality of control similarity metrics to (ii) the complementary distribution across the plurality of control similarity metrics, where the normalized first measure of central tendency represents the normalized tightness of the plurality of test state data points.

In some embodiments, the distribution metric of the plurality of test vectors with the respective test vector removed from the plurality of test vectors is a measure of central tendency of each corresponding dimension in the plurality of dimensions across the plurality of test vectors other than the respective test vector (4146). In some embodiments, the measure of central tendency of each corresponding dimension in the plurality of dimensions across the plurality of test vectors other than the respective test vector is an arithmetic mean, weighted mean, midrange, midhinge, trimean, geometric mean, geometric median, Winsorized mean, median, or mode of the corresponding dimension across the plurality of test vectors (4148). In some embodiments, the respective test state similarly metric between (i) the respective test vector and (ii) the distribution metric of the plurality of test vectors with the respective test vector removed from the plurality of test vectors is computed as a distance between corresponding dimensions of the test vector and the distribution metric of the plurality of test vectors with the respective test vector removed from the plurality of test vectors (4150). In some embodiments, the distance is an angular distance computed (4152) as:

$$\frac{\sum_{i}^{n} A_i B_i}{\sqrt{\sum_{i=1}^{n} A_i^2} \sqrt{\sum_{i=1}^{n} B_i^2}} \quad \text{(Equation X)}$$

where:

$A_i$ is a dimension i in the respective test vector, $B_i$ is the distribution metric of corresponding dimension i in the plurality of dimensions across the plurality of test vectors other than the respective test vector, and n is the number of dimensions in respective test vector.

With reference to FIG. 4W, in some embodiments, the distribution metric of the plurality of control vectors with the respective control vector removed from the plurality of control vectors is a measure of central tendency of each corresponding dimension in the plurality of dimensions across the plurality of control vectors other than the respective control vector (4154). In some embodiments, the measure of central tendency of each corresponding dimension in the plurality of dimensions across the plurality of control vectors other than the respective control vector is an arithmetic mean, weighted mean, midrange, midhinge, trimean, geometric mean, geometric median, Winsorized mean, median, or mode of the corresponding dimension across the plurality of control vectors (4156). In some embodiments, the respective control similarly metric between (i) the respective control vector and (ii) the distribution metric of the plurality of control vectors with the respective control vector removed from the plurality of control vectors is computed as a distance between corresponding dimensions of the control vector and the distribution metric of the plurality of control vectors with the respective control vector removed from the plurality of control vectors (4158). In some embodiments, the distance is an angular distance computed (4160) as:

$$\frac{\sum_{i}^{n} A_i B_i}{\sqrt{\sum_{i=1}^{n} A_i^2} \sqrt{\sum_{i=1}^{n} B_i^2}} \quad \text{(Equation XI)}$$

where:

A$_i$ is a dimension i in the respective control vector,

B$_i$ is the distribution metric of corresponding dimension i in the plurality of dimensions across the plurality of control vectors other than the respective control vector, and n is the number of dimensions in respective control vector.

Figure 4X:
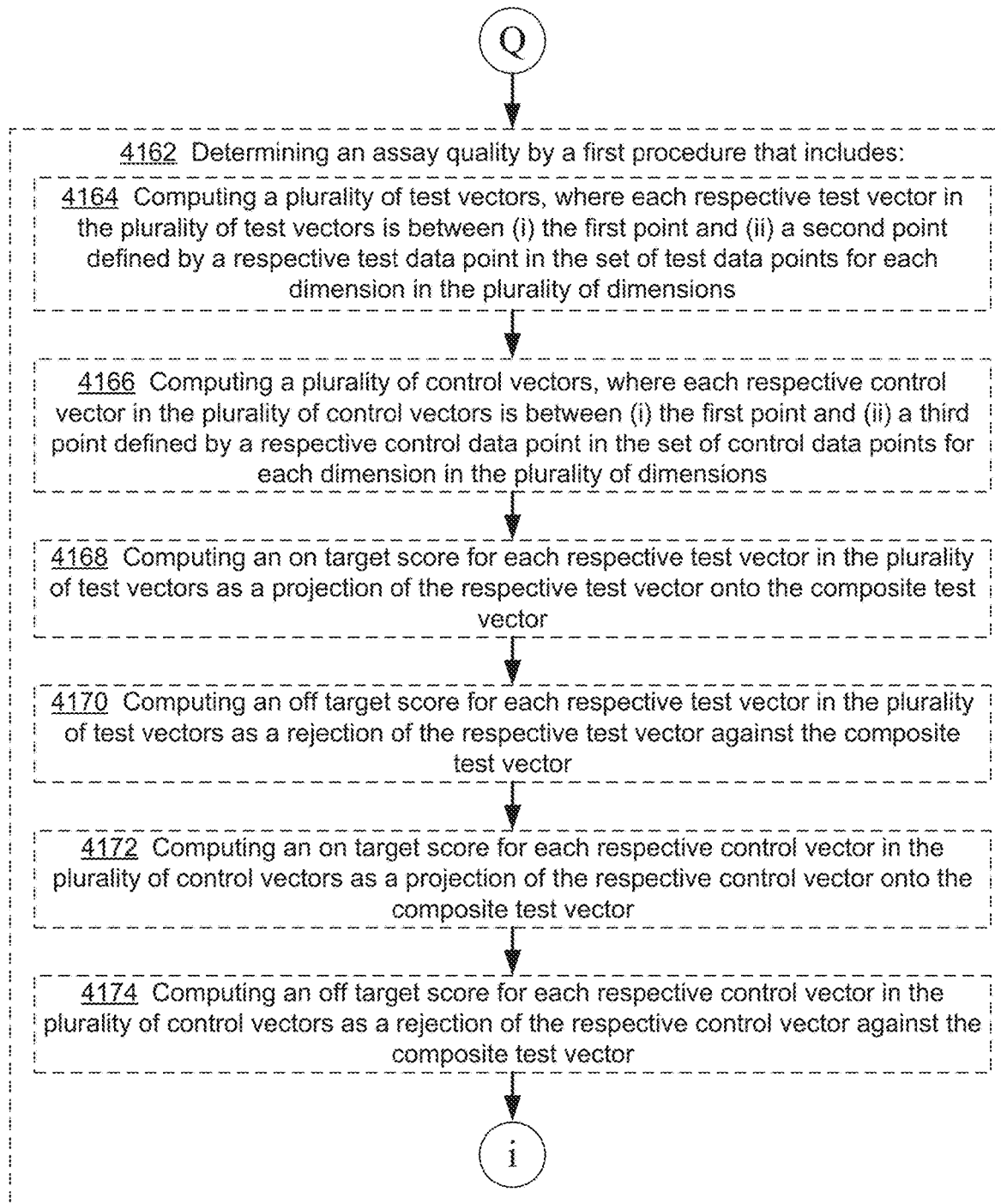

In some embodiments, the quality of one or more rescued query perturbations is determined. With reference to FIG. 4X, in some embodiments, method 4000 includes determining (4162) an overall assay quality. In some embodiments, this includes computing (4164) a plurality of test vectors, where each respective test vector in the plurality of test vectors is between (i) the first point and (ii) a second point defined by a respective test data point in the set of test data points for each dimension in the plurality of dimensions. In some embodiments, method 4000 then includes computing (4166) a plurality of control vectors, where each respective control vector in the plurality of control vectors is between (i) the first point and (ii) a third point defined by a respective control data point in the set of control data points for each dimension in the plurality of dimensions. In some embodiments, method 4000 then includes computing (4168) an on-target score for each respective test vector in the plurality of test vectors as a projection of the respective test vector onto the composite test vector. In some embodiments, method 4000 then includes computing (4170) an off-target score for each respective test vector in the plurality of test vectors as a rejection of the respective test vector against the composite test vector. In some embodiments, the method than includes computing (4172) an on-target score for each respective control vector in the plurality of control vectors as a projection of the respective control vector onto the composite test vector. In some embodiments, method 4000 then includes computing (4174) an-off target score for each respective control vector in the plurality of control vectors as a rejection of the respective control vector against the composite test vector. With reference to FIG. 4Y, in some embodiments, method 4000 then includes plotting (4176) each respective test vector in the plurality of test vector on a two-dimensional plot using the on target score for the respective test vector as a coordinate in a first dimension of the two-dimensional plot and the off target score for the respective test vector as a coordinate in a second dimension of the two-dimensional plot, thereby obtaining a plurality of test state data points. In some embodiments, method 4000 then includes plotting (4178) each respective control vector in the plurality of control vector on the two-dimensional plot using the on target score for the respective control vector as a coordinate in the first dimension and the off target score for the respective control vector as a coordinate in the second dimension, thereby obtaining a plurality of control data points. In some embodiments, method 4000 then includes computing (4180) the assay quality as a normalized distance between the plurality of test state data points and the plurality of control data points. In some embodiments, method 4000 then includes determining (4182) a test state quality by computing a normalized tightness of the plurality of test state data points. In some embodiments, method 4000 then includes using (4184) the rescue quality for the query perturbation, the assay quality, and the test state quality to calculate an overall quality.

In some embodiments, the overall quality is computed (4186) as:

$$\text{(rescue quality for the compound)} * \quad \text{(Equation XII)}$$
$$\exp^{(assay\ quality-1)} * \frac{1}{1 + \exp^{(1-phenotype\ quality)}}.$$

With reference to FIG. 4Z, in some embodiments, the normalized tightness is computed by a procedure (4188) that includes, for each respective test vector in the plurality of test vectors, computing a test state similarly metric between (i) the respective test vector and (ii) a distribution metric of the plurality of test vectors with the respective test vector removed from the plurality of test vectors, thereby obtaining a plurality of test state similarity metrics for the plurality of test vectors, each test state similarity metric in the plurality of test state similarity metrics uniquely corresponding to a test perturbation in the set of test perturbations. The procedure also includes computing a null distribution, by a sub-process that includes (a) for each respective control vector in the plurality of control vectors, computing a respective control similarity metric between (i) the respective control vector and (ii) a distribution metric of the plurality of control vectors with the respective control vector removed from the plurality of control vectors, thereby obtaining the plurality of control similarity metrics, each control similarity metric in the plurality of control similarity metrics uniquely corresponding to a control perturbation in the set of control perturbations, and (b) computing the null distribution as a distribution metric of the plurality of control similarity metrics. The procedure also includes determining a first measure of central tendency of the angle between (i) each respective test state similarity metric in the plurality of test state similarity metrics to (ii) the null distribution across the plurality of test state similarity metrics, and normalizing the first measure of central tendency of the angle by a second measure of central tendency of the angle between (i) each control similarity metric in the plurality of control similarity metrics to (ii) the null distribution across the plurality of control similarity metrics, where the normalize first measure of central tendency represents the normalized tightness of the plurality of test state data points.

In some embodiments, one or more quality metrics are determined for cell contexts used in the screening methodologies described herein. For instance, in some embodiments where a test perturbation is intended to knock down expression of a target gene, expression of the target gene in one or more instances of the test state is determined and compared to a knock down threshold expression level, to determine whether the test perturbation is achieving the desired result. Similarly, in some embodiments where a test perturbation is intended to knock down expression of a target gene, expression of the target gene in one or more instances of a corresponding control state is determined and compared to a baseline threshold expression level, to determine whether the cell context is an appropriate starting point for screening assays. Where either of these metrics fails, the assay can be redesigned to achieve the desired result. For example, when the expression of a targeted gene is not sufficiently suppressed in a test state, a different test perturbation targeting the gene of interest can be generated (e.g., a new siRNA targeting a different portion of the gene can be used in future experiments). Similarly, when a baseline level of expression of the target gene is not present in the control state, a different cell context that provides adequate expression of the gene of interest can be sought out to replace the old cell context. Methods for measuring gene expression are well known in the art and include, without limitation, quantitative PCR, hybridization, northern blotting, and mass spectroscopy.

Cell Contexts

As described above, control states, test states, and query states each refer to an experimental condition that generally includes a cell context. In some embodiments, the cell contexts used in the control states are exposed to a control perturbation, as described above. The cell contexts used in the test states and query states are perturbed (e.g., by exposure to a compound or physical condition and/or through mutation of the cellular genome), to represent a 'diseased' phenotype. Accordingly, the query states are then exposed to a query perturbation, e.g., one or more therapeutic compounds and/or physical conditions.

In some embodiments, a cell context is one or more cells that have been deposited within a well of a multiwell plate 302, such as a particular cell line, primary cells, or a co-culture system. In some embodiments, as described herein with reference to FIG. 3, at least each query perturbation (e.g., compound in a compound library) is exposed to a plurality of different perturbed cell contexts, e.g., at least two, three, four, five, six, seven, eight, nine, ten, or more perturbed cell contexts. In some embodiments, at least each query perturbation (e.g., compound in a compound library) is exposed to a single perturbed cell context (e.g., a single cell line or primary cell type).

Examples of cell types that are useful to be included in a cell context include, but are not limited to, U2OS cells, A549 cells, MCF-7 cells, 3T3 cells, HTB-9 cells, HeLa cells, HepG2 cells, HEKTE cells, SH-SY5Y cells, HUVEC cells, HMVEC cells, primary human fibroblasts, and primary human hepatocyte/3T3-J2 fibroblast co-cultures. In some embodiments cell line used as a basis for a cell context is a culture of human cells. In some embodiments, a cell line used as a basis for a cell context is any cell line set forth in Table 3 below, or a genetic modification of such a cell line. In some embodiments each cell line used as different cell context in the screening method is from the same species. In some embodiments the cell lines used for a cell context in the screening method can be from more than one species. For instance, a first cell line used as a first context is from a first species (e.g., human) and second cell line used as a second context is from a second species (e.g., monkey).

TABLE 3

Example cell types used as a basis for providing cell context in some embodiments.

| Cell Name | Tissue Type | Tissue | Phenotype | Primary |
|---|---|---|---|---|
| jb6 p+ c141 | Mouse | Skin | Adherent | no |
| jcam1.6 | Human | Lymphocyte | Suspension | no |
| jb6 rt101 | Mouse | Epithelial | Either | yes |
| jy | Human | Lymphocyte | Suspension | no |
| k562 | Human | Bone | Suspension | no |
| j82 | Human | Bladder | Adherent | no |
| ivec cells | Human | Endothelial | Adherent | no |
| jeg-3 | Human | Other | Adherent | no |
| jurkat | Human | Lymphocyte | Suspension | no |
| j5581 | Mouse | Blood | Suspension | no |
| k46 | Mouse | Lymphocyte | Suspension | no |
| j774 cells | Mouse | Macrophage | Adherent | no |
| knrk | Rat | Epithelial | Either | no |
| keratinocytes | Mouse | Keratinocyte | Adherent | yes |
| kc1 | Drosophila Melanogaster | Default | Adherent | no |
| kc18-2-40 cells | Human | Keratinocyte | Adherent | no |
| kt-3 | Human | Lymphocyte | Suspension | no |
| kmst-6 | Human | Skin | Adherent | no |
| l1210-fas | Mouse | Myoblast | Suspension | yes |
| kb | Human | Fibroblast | Adherent | no |
| keratinocytes | Human | Keratinocyte | Adherent | yes |
| kg-1 cells | Human | Bone marrow | Suspension | no |
| ks cells | Human | Skin | Adherent | yes |
| kd83 | Mouse | Blood | Suspension | no |
| l-m(tk−) | Mouse | Connective | Adherent | no |
| l8 cells | Rat | Myoblast | Adherent | yes |
| lk35.2 | Mouse | Lymphocyte | Suspension | no |
| l1210 | Mouse | Monocyte | Suspension | yes |
| lan-5 | Human | Brain | Adherent | no |
| llc-pk1 | Pig | Kidney | Adherent | no |
| lewis lung carcinoma, llc | Mouse | Lung | Either | no |
| l6e9 | Rat | Muscle | Adherent | no |
| lmh | Chicken | Liver | Adherent | no |
| l6 cells | Rat | Muscle | Adherent | no |
| lisn c4 (nih 3t3 derivative overexpressing egf) | Mouse | Fibroblast | Adherent | yes |
| lap1 | Mouse | Lymphocyte | Suspension | yes |
| lap3 | Mouse | Embryo | Adherent | no |
| l929 | Mouse | Fibroblast | Adherent | no |
| mg87 | Mouse | Fibroblast | Adherent | no |

TABLE 3-continued

Example cell types used as a basis for providing cell context in some embodiments.

| Cell Name | Tissue Type | Tissue | Phenotype | Primary |
|---|---|---|---|---|
| min6 | Mouse | Default | Either | no |
| mel | Mouse | Other | Adherent | no |
| melenoma cells | Human | Melanoma | Adherent | yes |
| mdbk | Cow | Kidney | Adherent | no |
| mkn45 gastric cancer | Human | Stomach | Adherent | yes |
| mewo | Human | Melanoma | Adherent | no |
| mda-mb-468 | Human | Breast/Mammary | Adherent | no |
| mdck | Dog | Kidney | Adherent | no |
| mf4/4 | Mouse | Macrophage | Adherent | no |
| me-180 | Human | Cervix | Adherent | yes |
| mes-sa | Human | Uterus | Adherent | no |
| mg-63 cells | Human | Bone | Adherent | no |
| mono-mac-6 cells | Human | Blood | Suspension | no |
| monocytes | Human | Blood | Suspension | yes |
| mrc-5 | Human | Lung | Adherent | yes |
| mob cells | Mouse | Osteoblast | Adherent | yes |
| msc human mesenchymal stem cell | Human | Bone marrow | Adherent | yes |
| mt-2 | Human | Lymphocyte | Adherent | yes |
| mouse embryonic fibroblasts | Mouse | Fibroblast | Adherent | yes |
| mnt1 | Human | Skin | Adherent | yes |
| ms1 | Mouse | Pancreas | Adherent | no |
| mr1 | Rat | Embryo | Adherent | no |
| mt4 | Human | Lymphocyte | Suspension | yes |
| molt4 (human acute t lymphoblastic leukaemia) | Human | Blood | Suspension | no |
| hep3b | Human | Liver | Adherent | no |
| hepatic stellate cells | Rat | Liver | Adherent | yes |
| hela 229 cells | Human | Cervix | Either | yes |
| hep2 | Human | Epithelial | Adherent | no |
| hela-cd4 | Human | Epithelial | Adherent | no |
| hct116 | Human | Colon | Adherent | no |
| hepatocytes | Mouse | Liver | Adherent | yes |
| hela s3 | Human | Cervix | Adherent | no |
| hel | Human | Lymphocyte | Suspension | yes |
| hela cells | Human | Cervix | Adherent | no |
| hela t4 | Human | Blood | Suspension | no |
| hepg2 | Human | Liver | Adherent | no |
| high 5 (bti-tn-5b1-4) | Insect | Embryo | Adherent | no |
| hit-t15 cells | Hamster | Epithelial | Adherent | no |
| hepatocytes | Rat | Liver | Adherent | yes |
| hitb5 | Human | Muscle | Adherent | yes |
| hi299 | Human | Lung | Adherent | no |
| hfff2 | Human | Foreskin | Adherent | yes |
| hib5 | Rat | Brain | Adherent | yes |
| hm-1 embryonic stem cells | Mouse | Other | Adherent | yes |
| hitb5 | Human | Muscle | Adherent | yes |
| hl-60 | Human | Lymphocyte | Suspension | no |
| hl-5 | Mouse | Heart | Adherent | no |
| hl-1 | Mouse | Heart | Adherent | no |
| glya | Hamster | Ovary | Adherent | no |
| gamma 3t3 | Mouse | Fibroblast | Adherent | no |
| gh3 | Rat | Pituitary | Adherent | no |
| granta-519 | Human | Blood | Suspension | no |
| freestyle 293 | Human | Kidney | Suspension | no |
| g401 | Human | Connective | Adherent | no |
| fto-2b (rat hepatoma) cells | Rat | Liver | Suspension | yes |
| gh4c1 | Rat | Pituitary | Adherent | yes |
| fsdc, murine dendritic cell | Mouse | Blood | Either | no |
| goto | Human | Neuroblastoma | Adherent | yes |
| gc-2spd (ts) | Mouse | Epithelial | Adherent | no |
| glomeruli | Rat | Lung | Adherent | yes |
| frt | Rat | Thyroid | Suspension | no |
| h19-7/igf-ir | Rat | Brain | Suspension | no |
| gt1 | Mouse | Brain | Adherent | no |
| griptite? 293 msr | Human | Kidney | Adherent | no |
| h441 | Human | Lung | Adherent | yes |
| h-500, leydig tumor cell | Rat | Testes | Adherent | yes |
| h4 | Human | Glial | Adherent | no |
| guinea pig endometrial stromal cells | Guinea Pig | Ovary | Adherent | yes |

TABLE 3-continued

Example cell types used as a basis for providing cell context in some embodiments.

| Cell Name | Tissue Type | Tissue | Phenotype | Primary |
|---|---|---|---|---|
| h187 | Human | Lung | Adherent | yes |
| h35 | Rat | Liver | Adherent | no |
| h-7 | Mouse | Bone marrow | Suspension | no |
| h1299 | Human | Lung | Adherent | no |
| granulosa cells | Mouse | Ovary | Either | yes |
| hbl100 cells | Human | Breast/Mammary | Adherent | no |
| h9c2 | Rat | Myoblast | Adherent | no |
| hbec-90 | Human | Brain | Adherent | no |
| has-p | Mouse | Breast/Mammary | Adherent | yes |
| hasmcs | Human | Muscle | Adherent | no |
| hc11 | Mouse | Breast/Mammary | Adherent | no |
| hacat | Human | Keratinocyte | Adherent | yes |
| hb60-5 cells | Mouse | Spleen | Adherent | no |
| h4iie | Rat | Liver | Adherent | yes |
| hca-7 | Human | Colon | Adherent | yes |
| hcd57 | Mouse | Blood | Suspension | no |
| haecs | Human | Aorta | Adherent | yes |
| rpe.40 | Hamster | Kidney | Adherent | yes |
| rcme, rabbit coronary microvessel endothelial | Rabbit | Endothelial | Adherent | yes |
| rko, rectal carcinoma cell line | Human | Colon | Adherent | no |
| ros, rat osteoblastic cell line | Rat | Osteoblast | Adherent | yes |
| rh18 | Human | Muscle | Adherent | no |
| rcho | Rat | Default | Adherent | no |
| rccd1 | Rat | Kidney | Adherent | no |
| s194 cells | Mouse | Lymphocyte | Adherent | yes |
| rin 1046-38 | Rat | Pancreas | Suspension | no |
| rw-4 | Mouse | Embryo | Adherent | yes |
| rj2.2.5 | Human | Lymphocyte | Suspension | no |
| rk13 | Rabbit | Kidney | Adherent | no |
| remc | Rat | Breast/Mammary | Adherent | no |
| sk-br-3 | Human | Breast/Mammary | Adherent | no |
| s49.1 | Mouse | Thymus | Suspension | no |
| *schizosaccharomyces pombe* | Yeast | Other | Either | yes |
| sf9 | Insect | Ovary | Suspension | no |
| sf21 | Insect | Other | Either | yes |
| sf21ae | Insect | Other | Either | yes |
| sh-sy5y | Human | Brain | Either | no |
| s2-013 | Human | Pancreas | Either | yes |
| saos-2 | Human | Bone | Adherent | no |
| siha | Human | Cervix | Adherent | no |
| scc12, human squamous cell carcinoma line (c12c20) | Human | Skin | Adherent | yes |
| shep | Human | Brain | Adherent | no |
| sk-lms-1 | Human | Other | Adherent | no |
| sk-n-sh, neuronal cells | Human | Brain | Adherent | yes |
| sk-n-as | Human | Neuroblastoma | Adherent | no |
| sknmc | Human | Brain | Adherent | no |
| sk-hep-1 cells | Human | Skin | Either | yes |
| skov3 | Human | Ovary | Adherent | no |
| sk-n-be(2) | Human | Neuroblastoma | Adherent | yes |
| smmc7721 | Human | Liver | Adherent | no |
| smooth muscle cells (aortic) rasmc (a7-r5) | Rat | Aorta | Adherent | yes |
| sl2 | Drosophila melanogaster | Default | Either | no |
| sk-ut-1 | Human | Muscle | Adherent | no |
| n2a | Mouse | Neuroblastoma | Adherent | no |
| myocytes (ventricular) | Rat | Heart | Adherent | yes |
| mtln3 | Rat | Breast/Mammary | Adherent | no |
| n1e-115 | Mouse | Brain | Adherent | no |
| mtsv1-7 | Human | Epithelial | Adherent | no |
| murine alveolar macrophages cell line mhs | Rat | Lung | Adherent | no |
| n18tg cells | Mouse | Neuroblastoma | Adherent | no |
| n13 | Mouse | Brain | Adherent | no |
| mutu group3, b-cell line | Human | Lymphocyte | Suspension | no |
| mtd-1a | Mouse | Epithelial | Adherent | yes |
| mutu i | Human | Lymphocyte | Suspension | no |
| mv1lu | Mink | Lung | Adherent | no |
| ncb20 | Mouse | Neuroblastoma | Adherent | yes |

TABLE 3-continued

Example cell types used as a basis for providing cell context in some embodiments.

| Cell Name | Tissue Type | Tissue | Phenotype | Primary |
|---|---|---|---|---|
| nb324k | Human | Kidney | Adherent | no |
| neural stem cells | Rat | Brain | Either | yes |
| neuroblastoma | Human | Brain | Adherent | yes |
| nci-h23 | Human | Lung | Adherent | no |
| nci-h460 | Human | Lung | Adherent | no |
| neurons (astrocytes) | Rat | Brain | Adherent | yes |
| neuro 2a, a murine neuroblastoma cell line | Mouse | Neuroblastoma | Adherent | no |
| nbt-ii | Rat | Bladder | Adherent | no |
| neuons (astrocytes) | Rat | Astrocyte | Adherent | yes |
| nci-h295 | Human | Kidney | Adherent | no |
| nci-h358 | Human | Lung | Adherent | no |
| neuons (hippocampal & septal) | Rat | Brain | Adherent | yes |
| neurons | Mouse | Brain | Adherent | yes |
| nhdf | Human | Fibroblast | Adh erent | no |
| neurons (post-natal/adult) | Rat | Brain | Adherent | yes |
| nhbe | Human | Lung | Adherent | yes |
| ng108-15 | Mouse | Neuroblastoma | Adherent | no |
| neurons (embryonic cortical) | Rat | Brain | Adherent | yes |
| neurons (cortical) | Mouse | Other | Adh erent | yes |
| ng 125 | Human | Neuroblastoma | Adherent | no |
| nhf3 | Human | Fibroblast | Adherent | no |
| *neurospora crassa* | Fungi | Embryo | Adherent | yes |
| neurons (superior cervical ganglia - scg) | Rat | Brain | Adherent | yes |
| neurons (ganglia) | Frog | Brain | Either | yes |
| ns20y | Mouse | Neuroblastoma | Adherent | no |
| nrk | Rat | Fibroblast | Adherent | yes |
| nmumg | Mouse | Breast/Mammary | Adherent | no |
| o23 | Hamster | Fibroblast | Adherent | no |
| nt2 | Human | Fibroblast | Adherent | no |
| nhff | Human | Foreskin | Adherent | yes |
| nih 3t3, 3t3-l1 | Mouse | Fibroblast | Adherent | no |
| ohio helas | Human | Cervix | Suspension | no |
| nih 3t6 | Mouse | Fibroblast | Adherent | no |
| nih 3t3-l1, nih 3t3 | Mouse | Embryo | Adherent | no |
| nt.2-dl | Human | Testes | Adherent | no |
| nih 3t3-l1, nih 3t3 ( ) | Mouse | Embryo | Adherent | no |
| orbital fibroblast | Human | Fibroblast | Adherent | yes |
| osteoblasts | Rat | Bone | Adherent | yes |
| p19 cells | Mouse | Embryo | Adherent | yes |
| ovcar-3 | Human | Ovary | Adherent | no |
| opaec cells | Sheep | Endothelial | Adherent | no |
| ovarian surface epithelial (ose) | Human | Ovary | Adherent | yes |
| p388d1 | Mouse | Macrophage | Adherent | yes |
| p825, mastocytoma cells | Mouse | Macrophage | Adherent | yes |
| p19c16 | Mouse | Heart | Adherent | no |
| omega e | Mouse | Embryo | Adherent | no |
| ok, derived from renal proximal tubules | Opossum | Kidney | Adherent | yes |
| p815, mastocytoma cells | Mouse | Macrophage | Adherent | yes |
| p3.653 × ag8 murine myeloma cells | Mouse | Bone marrow | Adherent | yes |
| paju, human neural crest-derived cell line | Human | Brain | Adherent | yes |
| pac-1 | Rat | Aorta | Adherent | no |
| parp−/− mouse embryonic fibroblasts | Mouse | Fibroblast | Suspension | no |
| pci-13 | Human | Skin | Adherent | no |
| pc 6 (pheochromocytoma-6) | Rat | Glial | Adherent | no |
| pancreatic islets | Rat | Pancreas | Adherent | yes |
| peripheral blood lymphocytes | Human | Blood | Either | yes |
| pc-3 | Human | Prostate | Either | no |
| pc-12 | Rat | Brain | Adherent | no |
| panc1 | Human | Pancreas | Adherent | no |
| per.c6 ® | Human | Retina | Either | no |
| pa 317 or pt67 mouse fibroblast with herpes thymidine kinase (tk) gene | Mouse | Fibroblast | Adherent | yes |

TABLE 3-continued

Example cell types used as a basis for providing cell context in some embodiments.

| Cell Name | Tissue Type | Tissue | Phenotype | Primary |
|---|---|---|---|---|
| pam212, mouse keratinocytes | Mouse | Keratinocyte | Adherent | yes |
| peripheral blood mononuclear cells (pbmc) | Human | Blood | Suspension | yes |
| qt6 | Quail | Fibroblast | Adherent | no |
| pu5-1.8 cells | Mouse | Macrophage | Suspension | no |
| primary lymphoid (oka) organ from penaeus shrimp | Shrimp | Lymphocyte | Adherent | yes |
| ps120, an nhe-deficient clone derived from ccl39 cells | Hamster | Lung | Adherent | yes |
| phoenix-eco cells | Human | Embryo | Adherent | no |
| quail embryos | Quail | Embryo | Either | yes |
| plb985 | Human | Blood | Suspension | no |
| rabbit pleural mesothelial | Rabbit | Lung | Adherent | no |
| r1 embryonic stem cell, es | Mouse | Embryo | Either | no |
| rabbit vsmc, vascular smooth muscle cells | Rabbit | Muscle | Adherent | yes |
| raec, rat aortic endothelial cells | Rat | Aorta | Adherent | yes |
| raji | Human | Lymphocyte | Suspension | no |
| rat epithelial cells | Rat | Epithelial | Adherent | yes |
| raw 264.7 cells, murine macrophage cells | Mouse | Macrophage | Adherent | yes |
| ramos | Human | Lymphocyte | Suspension | no |
| rat hepatic ito cells | Rat | Liver | Adherent | yes |
| rat adipocyte | Rat | Adipose | Adherent | yes |
| rat c5, glioma cells | Rat | Glial | Adherent | yes |
| rat-1, rat fibroblasts | Rat | Fibroblast | Adherent | yes |
| rat 2, rat fibroblasts | Rat | Fibroblast | Adherent | yes |
| rat glomerular mesangial me cells | Rat | Kidney | Adherent | yes |
| raw cells | Rat | Peritoneum | Suspension | no |
| rat-6 (r6), rat embryo fibroblast | Rat | Fibroblast | Adherent | yes |
| hmec-1 | Human | Endothelial | Adherent | yes |
| hre h9 | Rabbit | Uterus | Adherent | no |
| hmn 1 | Mouse | Neuroblastoma | Adherent | yes |
| ht-29 | Human | Colon | Adherent | no |
| hos | Human | Osteoblast | Adherent | no |
| hs68 | Human | Foreskin | Adherent | yes |
| hmcb | Human | Skin | Adherent | no |
| hs-578t | Human | Breast/Mammary | Adherent | no |
| hnscc | Human | Skin | Adherent | no |
| hpb-all | Human | Lymphocyte | Suspension | no |
| hmvec-l | Human | Lung | Adherent | no |
| hsy-eb | Human | Other | Adherent | no |
| huh 7 | Human | Liver | Adherent | no |
| htlm2 | Mouse | Breast/Mammary | Adherent | yes |
| hut 78 | Human | Skin | Suspension | no |
| ht1080 | Human | Fibroblast | Adherent | no |
| huvec, huaec | Human | Umbilicus | Adherent | yes |
| htla230 | Human | Neuroblastoma | Adherent | yes |
| hybridoma | Mouse | Spleen | Suspension | no |
| ib3-1 | Human | Lung | Adherent | no |
| ht22 | Mouse | Brain | Adherent | yes |
| human skeletal muscle | Human | Muscle | Adherent | yes |
| ht.4 | Human | Testes | Adherent | yes |
| hutu 80 | Human | Colon | Adherent | yes |
| in vivo mouse brain | Mouse | Bone | Either | yes |
| in vivo rat brain | Rat | Brain | Either | yes |
| iec-6 rie | Rat | Epithelial | Adherent | no |
| imr-32 | Human | Neuroblastoma | Adherent | no |
| ic11 | Mouse | Testes | Adherent | no |
| imr-90 | Human | Lung | Adherent | no |
| in vivo rat lung | Rat | Lung | Either | yes |
| in vivo rat liver | Rat | Liver | Either | yes |
| ins-1 | Rat | Pancreas | Adherent | no |
| in vivo rabbit eye | Rabbit | Other | Either | yes |
| in vivo mouse | Mouse | Other | Either | yes |
| imdf | Mouse | Skin | Adherent | no |
| in vivo pig | Rg | Other | Either | yes |

TABLE 3-continued

Example cell types used as a basis for providing cell context in some embodiments.

| Cell Name | Tissue Type | Tissue | Phenotype | Primary |
|---|---|---|---|---|
| caski | Human | Cervix | Adherent | no |
| cerebellar | Mouse | Brain | Adherent | yes |
| cd34+ monocytes | Human | Monocyte | Suspension | yes |
| cfk2 | Rat | Bone | Adherent | no |
| cem | Human | Blood | Suspension | no |
| catha, cath.a | Mouse | Brain | Either | no |
| ccl-16-b9 | Hamster | Lung | Adherent | no |
| ch12f3-2a | Mouse | Lymphocyte | Suspension | no |
| cf2th | Dog | Thymus | Adherent | no |
| cardiomyocytes | Human | Heart | Adherent | yes |
| cg-4 | Rat | Glial | Adherent | no |
| cell.220(b8) | Human | Default | Suspension | no |
| cardiomyocytes | Rat | Heart | Adherent | yes |
| chick embryo fibroblasts | Chicken | Embryo | Adherent | yes |
| chicken sperm | Chicken | Sperm | Adherent | yes |
| cho k1 | Hamster | Ovary | Adherent | no |
| cho 58 | Hamster | Ovary | Adherent | no |
| cho-b7 | Hamster | Ovary | Adherent | no |
| chick embryo blastodermal cells | Chicken | Embryo | Adherent | yes |
| cho -b53 | Hamster | Ovary | Adherent | yes |
| chick embryo chondrocytes | Chicken | Embryo | Adherent | yes |
| chinese hamster lung | Hamster | Lung | Adherent | no |
| cho dg44 | Hamster | Ovary | Either | no |
| cho - b53 jf7 | Hamster | Ovary | Adherent | yes |
| chicken hepatocytes | Chicken | Liver | Adherent | yes |
| cos-1 | Primate - Non Human | Kidney | Adherent | no |
| cho-lec1 | Hamster | Ovary | Adherent | yes |
| clone a | Human | Colon | Adherent | no |
| cho-lec2 | Hamster | Ovary | Adherent | no |
| colo205 | Human | Colon | Adherent | no |
| chu-2 | Human | Epithelial | Adherent | no |
| cmt-93 | Mouse | Rectum | Adherent | no |
| cho-s | Hamster | Ovary | Suspension | no |
| cho-leu c2gnt | Hamster | Ovary | Adherent | no |
| cho-trvb | Hamster | Ovary | Adherent | no |
| clone-13, mutant b lymphoblastoid | Human | Lymphocyte | Suspension | no |
| cj7 | Mouse | Embryo | Adherent | no |
| smooth muscle cells (aortic) | Rat | Muscle | Adherent | yes |
| splenocytes | Mouse | Spleen | Suspension | yes |
| smooth muscle cells (vascular) | Rat | Muscle | Adherent | yes |
| sp1 | Mouse | Breast/Mammary | Adherent | no |
| stem | Rat | Bone | Suspension | yes |
| spoc-1 | Rat | Trachael | Adherent | no |
| snb19 | Human | Brain | Adherent | no |
| splenocytes (resting b cells) | Mouse | Spleen | Suspension | yes |
| splenocytes (b cells t2) | Mouse | Spleen | Suspension | yes |
| svr | Mouse | Pancreas | Adherent | no |
| stem cells | Human | Bone marrow | Suspension | yes |
| smooth muscle cells (vascular) | Human | Muscle | Adherent | yes |
| smooth muscle cells (vascular) | Rabbit | Aorta | Adherent | yes |
| t3cho/at1a | Hamster | Ovary | Either | no |
| t-rex-cho | Hamster | Ovary | Adherent | no |
| t-rex-293 | Human | Kidney | Adherent | no |
| sw620 | Human | Colon | Adherent | no |
| t lymphocytes (t cells) | Mouse | Lymphocyte | Adherent | yes |
| t lymphocytes cytotoxic (ctl) cells | Mouse | Lymphocyte | Either | yes |
| sw480 | Human | Colon | Adherent | no |
| t lymphocytes (t cells) | Human | Lymphocyte | Adherent | yes |
| sw13 | Human | Adrenal gland/cortex | Adherent | no |
| t47d, t-47d | Human | Breast/Mammary | Adherent | no |
| t24 | Human | Bladder | Adherent | no |
| t-rex hela | Human | Cervix | Adherent | no |
| tr2 | Mouse | Brain | Adherent | no |
| tig | Human | Fibroblast | Adherent | yes |
| t98g | Human | Brain | Adherent | no |

TABLE 3-continued

Example cell types used as a basis for providing cell context in some embodiments.

| Cell Name | Tissue Type | Tissue | Phenotype | Primary |
|---|---|---|---|---|
| tsa201 | Human | Embryo | Adherent | no |
| tobacco protoplasts | Plant | Other | Suspension | yes |
| thp-1 | Human | Blood | Suspension | yes |
| tk. 1 | Mouse | Lymphocyte | Suspension | no |
| tib-90 | Mouse | Fibroblast | Adherent | no |
| ta3 | Mouse | Breast/Mammary | Adherent | no |
| tyknu cells | Human | Ovary | Adherent | no |
| u-937 | Human | Macrophage | Suspension | no |
| tgw-nu-1 | Human | Bladder | Adherent | no |
| b-lcl | Human | Blood | Suspension | no |
| b4.14 | Primate - Non Human | Kidney | Adherent | yes |
| b82 m721 | Mouse | Fibroblast | Adherent | no |
| b-tc3 | Mouse | Pancreas | Adherent | no |
| b16-f10 | Mouse | Melanoma | Adherent | no |
| b82 | Mouse | Fibroblast | Adherent | no |
| as52 | Hamster | Ovary | Adherent | no |
| b lymphocytes | Human | Blood | Suspension | yes |
| b35 | Rat | Neuroblastoma | Adherent | yes |
| b65 | Rai | Neuroblastoma | Adherent | no |
| b11 | Mouse | Spleen | Suspension | no |
| att-20 | Mouse | Pituitary | Adherent | no |
| bcl-1 | Mouse | Lymphocyte | Adherent | no |
| bac | Cow | Adrenal Gland | Adherent | yes |
| balb/c 3t3, 3t3-a31 | Mouse | Fibroblast | Adherent | no |
| be(2)-c | Human | Neuroblastoma | Adherent | no |
| bewo | Human | Other | Adherent | no |
| balb/mk | Mouse | Epithelial | Adherent | no |
| beas-2b | Human | Lung | Adherent | no |
| bewo | Human | Uterus | Adherent | yes |
| baf3, ba/f3 | Mouse | Lymphocyte | Suspension | no |
| bcec | Human | Brain | Adherent | yes |
| bc3h1 | Mouse | Brain | Adherent | yes |
| baec | Cow | Aorta | Adherent | no |
| a10 | Rat | Muscle | Adherent | no |
| a1.1 | Mouse | Lymphocyte | Adherent | yes |
| a72 | Dog | Connective | Adherent | no |
| a549 | Human | Lung | Adherent | no |
| a204 | Human | Muscle | Adherent | yes |
| a6 | Frog | Kidney | Adherent | no |
| a875 | Human | Melanoma | Adherent | yes |
| a498 | Human | Kidney | Adherent | no |
| a172 | Human | Brain | Adherent | yes |
| a-431 | Human | Skin | Adherent | no |
| a20 | Mouse | Lymphocyte | Suspension | yes |
| arpe-19 | Human | Retina | Adherent | no |
| alpha t3 | Human | Pituitary | Adherent | no |
| akr | Mouse | Spleen | Adherent | no |
| ar4-2j | Rat | Pancreas | Adherent | no |
| aortic endothelial cells | Human | Aorta | Adherent | yes |
| achn | Human | Kidney | Adherent | yes |
| adventitial fibroblasts | Human | Aorta | Adherent | yes |
| am12 | Mouse | Blood | Suspension | no |
| anterior pituitary gonadotropes | Human | Pituitary | Adherent | yes |
| ae-1 | Mouse | Spleen | Suspension | no |
| ab1 | Mouse | Embryo | Adherent | no |
| anjou 65 | Human | Default | Either | no |
| crfk | Cat | Kidney | Adherent | no |
| d.mel-2 | Insect | Embryo | Either | no |
| ct26 | Mouse | Colon | Either | yes |
| cowpea plant embryos | Fungi | Embryo | Adherent | yes |
| cos-7 | Primate - Non Human | Kidney | Adherent | no |
| crl6467 | Mouse | Liver | Adherent | no |
| cwr22rv1 | Human | Prostate | Adherent | no |
| ct60 | Hamster | Ovary | Adherent | no |
| cos-gs1 | Primate - Non Human | Kidney | Adherent | no |
| cos-m6 | Primate - Non Human | Kidney | Adherent | yes |
| cv-1 | Primate - Non Human | Kidney | Adherent | no |
| ctll-2 | Mouse | Lymphocyte | Suspension | no |
| d3 embryonic stem cells | Mouse | Embryo | Adherent | no |
| du145 | Human | Prostate | Adherent | no |
| do-11.10 | Mouse | Lymphocyte | Suspension | no |

TABLE 3-continued

Example cell types used as a basis for providing cell context in some embodiments.

| Cell Name | Tissue Type | Tissue | Phenotype | Primary |
|---|---|---|---|---|
| daudi | Human | Lymphocyte | Suspension | no |
| d10 | Mouse | Lymphocyte | Suspension | no |
| dgz | Plant | Other | Adherent | yes |
| dictyostelium | Amoeba | Other | Suspension | yes |
| dt40 | Chicken | Bursa | Suspension | no |
| *drosophila* kc | Insect | Embryo | Adherent | yes |
| df1 | Chicken | Fibroblast | Adherent | no |
| dc 2.4 cells | Mouse | Blood | Either | no |
| daoy | Human | Other | Adherent | no |
| lovo | Human | Colon | Adherent | no |
| lncap | Human | Prostate | Adherent | no |
| m21 | Human | Melanoma | Adherent | no |
| lsv5 | Human | Keratinocyte | Adherent | no |
| ltk | Mouse | Connective | Adherent | no |
| m1 | Rat | Embryo | Adherent | no |
| m3z | Human | Breast/Mammary | Adherent | no |
| m21-l | Human | Melanoma | Adherent | no |
| lymphoid cell line | Rat | Lymphocyte | Suspension | no |
| m-imcd | Mouse | Kidney | Adherent | yes |
| m12.4 | Mouse | Lymphocyte | Adherent | no |
| m21-14 | Human | Melanoma | Adherent | no |
| mat b iii | Rat | Breast/Mammary | Adherent | no |
| mda-mb-453 | Human | Breast/Mammary | Adherent | no |
| mca-rh7777 | Rat | Liver | Adherent | no |
| ma104 | Primate - Non Human | Kidney | Adherent | no |
| magi-ccr5 | Human | Epithelial | Adherent | no |
| mda-mb-231 | Human | Breast/Mammary | Adherent | no |
| mcf-10 | Human | Breast/Mammary | Adherent | no |
| mc3t3-e1 | Mouse | Osteoblast | Adherent | no |
| mc ardle 7777 | Rat | Liver | Either | yes |
| macrophages | Mouse | Peritoneum | Adherent | yes |
| mcf-7 | Human | Breast/Mammary | Adherent | no |
| macrophages | Human | Blood | Either | yes |
| maize protoplasts | Plant | Other | Adherent | no |
| umr 106-01 | Rat | Bone | Adherent | no |
| uc729-6 | Human | Lymphocyte | Either | no |
| u9737 | Human | Lymphocyte | Suspension | no |
| uok257 | Human | Kidney | Adherent | no |
| u373mg | Human | Astrocyte | Adherent | no |
| wit49 wilms tumor | Human | Lung | Either | yes |
| vero | Primate - Non Human | Kidney | Adherent | no |
| u87, u87mg | Human | Astrocyte | Adherent | no |
| umrc6 | Human | Kidney | Adherent | no |
| u251 cells | Human | Glial | Adherent | no |
| u2os | Human | Bone | Adherent | no |
| bovine chromaffin cells | Cow | Adrenal Gland | Adherent | yes |
| bowes melanoma cells | Human | Skin | Adherent | no |
| boll weevil brl-ag-3c | Insect | Other | Adherent | no |
| bm5 | Insect | Ovary | Suspension | no |
| bhk-21 | Hamster | Kidney | Either | no |
| bosc 23 | Human | Kidney | Adherent | yes |
| bms-black mexican sweet protoplasts | Default | Default | Suspension | yes |
| bfc012 | Mouse | Embryo | Adherent | no |
| bone marrow cells | Mouse | Bone marrow | Suspension | yes |
| bone marrow derived-stromal cells | Human | Bone marrow | Adherent | yes |
| bs-c-1, bsc-1 | Primate - Non Human | Kidney | Adherent | no |
| bjab | Human | Lymphocyte | Suspension | no |
| bnl cl.2 (c12) | Mouse | Liver | Adherent | no |
| btm (bovine trachael myocytes) | Cow | Muscle | Adherent | no |
| c2c12 | Mouse | Muscle | Adherent | no |
| c3a | Human | Liver | Adherent | no |
| c1.39t | Human | Fibroblast | Adherent | no |
| bt cells | Cow | Fibroblast | Adherent | no |
| bsc-40 | Primate - Non Human | Kidney | Adherent | no |
| c33 | Human | Cervix | Adherent | no |
| c1c12 | Mouse | Muscle | Adherent | no |
| c127 | Mouse | Epithelial | Adherent | no |
| bt549 | Human | Breast/Mammary | Adherent | no |
| c1r, hmy2.c1r | Human | Lymphocyte | Adherent | yes |

TABLE 3-continued

Example cell types used as a basis for providing cell context in some embodiments.

| Cell Name | Tissue Type | Tissue | Phenotype | Primary |
|---|---|---|---|---|
| c13-nj | Human | Glial | Adherent | no |
| canine gastric parietal cells | Dog | Stomach | Adherent | yes |
| calu-3 | Human | Lung | Adherent | yes |
| cak | Mouse | Fibroblast | Adherent | no |
| c57bl/6 cells | Mouse | Heart | Adherent | no |
| caco-2 cells | Human | Colon | Adherent | no |
| c3h 10t1/2 | Mouse | Fibroblast | Adherent | no |
| ca77 | Rat | Thyroid | Adherent | no |
| c6 cells | Rat | Brain | Adherent | no |
| calu-6 | Human | Lung | Adherent | no |
| capan-2 | Human | Pancreas | Adherent | no |
| c4-2 | Human | Prostate | Adherent | no |
| 143b | Human | Bone marrow | Either | no |
| 1064sk | Human | Foreskin | Adherent | yes |
| 16-9 | Human hamster hybrid cell line - transfected with two human genes | Other | Adherent | no |
| 2008 | Human | Ovary | Adherent | no |
| 208f | Rat | Fibroblast | Adherent | no |
| 293-h | Human | Kidney | Either | no |
| 293 | Human | Kidney | Either | no |
| 293 ebna | Human | Kidney | Adherent | no |
| 293t | Human | Kidney | Either | no |
| 2pk3 | Mouse | Lymphocyte | Suspension | no |
| 293-f | Human | Kidney | Either | no |
| 2780 | Human | Ovary | Adherent | no |
| 293s | Human | Kidney | Either | no |
| 2774 | Human | Ovary | Adherent | no |
| 3y1 | Rat | Fibroblast | Adherent | yes |
| 82-6 | Human | Fibroblast | Adherent | no |
| 9hte | Human | Trachael | Adherent | yes |
| 3.l2 | Mouse | Lymphocyte | Either | yes |
| 5637 | Human | Bladder | Adherent | no |
| 4t1 | Mouse | Breast/Mammary | Adherent | no |
| 3t3-f442a | Mouse | Other | Adherent | yes |
| 33.1.1 | Mouse | Lymphocyte | Suspension | no |
| 32d | Mouse | Bone marrow | Either | no |
| 4de4 | Mouse | Bone marrow | Either | yes |
| el-ts20 | Human | Breast/Mammary | Adherent | yes |
| embryonic stem cells | Mouse | Embryo | Adherent | yes |
| e. histolytica | Amoeba | Other | Suspension | yes |
| ef88 | Mouse | Fibroblast | Adherent | yes |
| el-4 | Mouse | Thymus | Suspension | no |
| ebc-1 | Human | Lung | Adherent | no |
| duck (in vivo) | Duck | Other | Suspension | yes |
| ecv | Human | Endothelial | Adherent | no |
| ecr-293 | Human | Kidney | Adherent | no |
| e14tg2a | Mouse | Embryo | Adherent | no |
| e36 | Hamster | Lung | Adherent | no |
| endothelial cells (pulmonary aorta) | Rat | Aorta | Adherent | yes |
| endothelial cells (aortic) | Pig | Aorta | Adherent | yes |
| ewing sarcoma coh cells | Human | Bone | Suspension | no |
| f9 | Mouse | Testes | Adherent | no |
| fibroblasts (cardiac) | Rat | Fibroblast | Adherent | yes |
| f442-a | Mouse | Preadiopocyte | Adherent | no |
| es-2 ovarian clear cell adenocarcinoma | Human | Ovary | Adherent | no |
| fetal neurons | Rat | Brain | Adherent | yes |
| epithelial cells (sra01/04) | Human | Epithelial | Adherent | yes |
| fibroblasts (embryo) | Rat | Fibroblast | Adherent | yes |
| fgc-4 | Rat | Liver | Adherent | yes |
| fak-/- | Mouse | Embryo | Adherent | yes |
| es-d3 | Mouse | Embryo | Adherent | no |
| epithelial cells (rte) | Rat | Trachael | Adherent | yes |
| foreskin fibroblast | Human | Foreskin | Adherent | no |
| flp-in jurkat | Human | Lymphocyte | Suspension | no |
| flp-in cho | Hamster | Ovary | Adherent | no |
| fibroblasts (neonatal dermal) | Human | Skin | Adherent | yes |

TABLE 3-continued

Example cell types used as a basis for providing cell context in some embodiments.

| Cell Name | Tissue Type | Tissue | Phenotype | Primary |
|---|---|---|---|---|
| flp-in 293 | Human | Kidney | Adherent | no |
| flp-in t-rex 293 | Human | Kidney | Adherent | no |
| flp-in cv-1 | Primate - Non Human | Kidney | Adherent | no |
| fibroblasts | Chicken | Skin | Adherent | yes |
| fibroblasts ('healthy') | Human | Fibroblast | Adherent | yes |
| fl5.12 | Mouse | Liver | Suspension | no |
| fm3a | Mouse | Breast/Mammary | Adherent | no |
| fr | Rat | Fibroblast | Adherent | no |
| nalm6 | Human | Other | Suspension | no |

As described above, in test states and query states the cell context is further perturbed, e.g., to simulate a disease phenotype. In some embodiments, the perturbation is an environmental factor applied to the cell context, e.g., that perturbs the cell relative to a reference environment (such as a growth medium that is commonly used to culture the particular cell). For example, in some embodiments, the cell context includes a component in a growth medium that significantly changes the metabolism of the one or more cells, e.g., a compound that is toxic to the one or more cells, that slows cellular metabolism, that increases cellular metabolism, that inhibits a checkpoint, that disrupts mitosis and/or meiosis, or that otherwise changes a characteristic of cellular metabolism. As other examples, the perturbation could be a shift in the osmolality, conductivity, pH, or other physical characteristic of the growth environment, or the perturbation could be addition of a pathogen (e.g., viral or microbial) or another cell type (e.g., native or engineered T-cells).

In some embodiments, the perturbation includes a mutation within the genome of the one or more cells, e.g., a human cell line in which a gene has been mutated or deleted. In some embodiments, a cell context is a cell line that has one or more documented structural variations (e.g., a documented single nucleotide polymorphism "SNP", an inversion, a deletion, an insertion, or any combination thereof). In some such embodiments, the one or more documented structural variations are homozygous variations. In some such embodiments, the one or more documented structural variations are heterozygous variations. As an example of a homozygous variation in a diploid genome, in the case of a SNP, both chromosomes contain the same allele for the SNP. As an example of a heterozygous variation in a diploid genome, in the case of the SNP, one chromosome has a first allele for the SNP and the complementary chromosome has a second allele for the SNP, where the first and second allele are different.

In some embodiments, the perturbation includes one or more nucleic acid (e.g., one or more siRNA) that are designed to suppress (e.g., knock-down or knock-out) expression of one or more genes in one or more cell types of the cell context. In some embodiments, the perturbation includes a plurality of nucleic acids (e.g., a plurality of siRNA) that are designed to suppress expression of the same gene in one or more cell types of the cell context. For example, 2, 3, 4, 5, 6, 7, 8, 9, 10, or more siRNA molecules targeting different sequences (e.g., overlapping and/or non-overlapping) of the same gene. In some embodiments, the perturbation includes one or more nucleic acid (e.g., one or more siRNA) that are designed to suppress expression of multiple genes, e.g., 2, 3, 4, 5, 6, 7, 8, 9, 10, or more genes.

In some embodiments, the plurality of genes express proteins involved in a common pathway (e.g., a metabolic or signaling pathway) in one or more cell types of the cell context. In some embodiments, the plurality of genes express proteins involved in different pathways in one or more cell types of the cell context. In some embodiments, the different pathways are partially redundant pathways for a particular biological function, e.g., different cell cycle checkpoint pathways. In some embodiments, the perturbation suppresses expression of a gene known to be associated with a disease (e.g., a checkpoint inhibitor gene associated with a cancer). In some embodiments, the perturbation suppresses expression of a gene known to be associated with a cellular phenotype (e.g., a gene that causes a metabolic phenotype in cultured cells when suppressed). In some embodiments, the perturbation suppresses expression of a gene that has not previously been associated with a disease or cellular phenotype.

In some embodiments, a cell context is perturbed by exposure to a small interfering RNA (siRNA), e.g., a double-stranded RNA molecule, 20-25 base pairs in length that interferes with the expression of a specific gene with a complementary nucleotide sequence by degrading mRNA after transcription preventing translation of the gene. An siRNA is an RNA duplex that can reduce gene expression through enzymatic cleavage of a target mRNA mediated by the RNA induced silencing complex (RISC). An siRNA has the ability to inhibit targeted genes with near specificity. See, Agrawal et al., 2003, "RNA interference: biology, mechanism, and applications," Microbiol Mol Biol Rev. 67: 657-85; and Reynolds et al., 2004, "Rational siRNA design for RNA interference," Nature Biotechnology 22, 326-330, each of which is hereby incorporated by reference. In some such embodiments, the perturbation is achieved by transfecting the siRNA into the one or more cells, DNA-vector mediated production, or viral-mediated siRNA synthesis. See, for example, Paddison et al., 2002, "Short hairpin RNAs (shRNAs) induce sequence-specific silencing in mammalian cells," Genes Dev. 16:948-958; Sui et al., 2002, A DNA vector-based RNAi technology to suppress gene expression in mammalian cells," Proc Natl Acad Sci USA 99:5515-5520; Brummelkamp et al., 2002, "A system for stable expression of short interfering RNAs in mammalian cells," Science 296:550-553; Paddison et al., 2004, "Short hairpin activated gene silencing in mammalian cells," Methods Mol Biol 265:85-100; Wong et al. 2003, "CIITAregulated plexin-A1 affects T-cell-dendritic cell interactions, Nat Immunol 2003, 4:891-898; Tomar et al., 2003, "Use of adeno-associated viral vector for delivery of small interfering RNA. Oncogene 22:5712-5715; Rubinson et al., 2003 "A lentivirus-based system to functionally silence genes in primary mammalian cells, stem cells and transgenic mice by RNA interference," Nat Genet 33:401-406; Moore et al., 2005, "Stable inhibition of hepatitis B virus proteins by small interfering RNA expressed from viral vectors," J Gene Med; and Tran et al., 2003, "Expressing functional siRNAs in mammalian cells using convergent transcription, BMC Biotechnol 3:21; each of which is hereby incorporated by reference.

In some embodiments, a cell context is perturbed by exposure to a short hairpin RNA (shRNA). See, Taxman et al., 2006, "Criteria for effective design, construction, and gene knockdown by shRNA vectors," BMC Biotechnology 6:7 (2006), which is hereby incorporated by reference. In some such embodiments, the perturbation is achieved by DNA-vector mediated production, or viral-mediated siRNA synthesis as generally discussed in the references cited above for siRNA.

In some embodiments, a cell context is perturbed by exposure to a single guide RNA (sgRNA) used in the context of palindromic repeat (e.g., CRISPR) technology. See, Sander and Young, 2014, "CRISPR-Cas systems for editing, regulating and targeting genomes," Nature Biotechnology 32, 347-355, hereby incorporated by reference, in which a catalytically-dead Cas9 (usually denoted as dCas9) protein lacking endonuclease activity to regulate genes in an RNA-guided manner. Targeting specificity is determined by complementary base-pairing of a single guide RNA (sgRNA) to the genomic loci. sgRNA is a chimeric noncoding RNA that can be subdivided into three regions: a 20 nt base-pairing sequence, a 42 nt dCas9-binding hairpin and a 40 nt terminator. In some embodiments, when designing a synthetic sgRNA, only the 20 nt base-pairing sequence is modified from the overall template. In some such embodiments, the perturbation is achieved by DNA-vector mediated production, or viral-mediated sgRNA synthesis.

In some embodiments, a cell context is perturbed by exposure to a nucleic acid construct directing over-expression of a protein. In some embodiments, the nucleic acid construct is transiently transfected into the cell context. See, Longo, P A et al., 2013, "Transient Mammalian Cell Transfection with Polyethylenimine (PEI)," Methods Enzymol. 529:227-240, hereby incorporated by reference, in which plasmid DNA is transiently transfected into mammalian cells using polyethylenimine (PEI) as a carrier molecule. In some embodiments, the nucleic acid construct is stably integrated into the genome of the cell context, e.g., in a site directed fashion. See, Lee, J S et al., 2015, "Site-specific integration in CHO cells mediated by CRISPR/Cas9 and homology-directed DNA repair pathway," Sci Rep. 5:8572, hereby incorporated by reference, in which a CRISPER/Cas9 editing system is used to integrate a 3.7 kb gene expression cassette at three different loci in CHO cells. Other systems for site-specific genome insertion are also known in the art, for example, the Cre/loxP system, the Flp/FRT system, and the phiC31/R4 integrases system.

In some embodiments, a cell context includes a tissue organoid construct. See, Boehnke K et al., "Assay Establishment and Validation of a High-Throughput Screening Platform for Three-Dimensional Patient-Derived Colon Cancer Organoid Cultures," 2016, J Biomol. Screen. 21(9): 931-41, hereby incorporated by reference, in which colon cancer patient-derived tumor cells are used to establish organoid cultures for high throughput drug discovery screening. For example, in some embodiments, corresponding control states, test states, and query states all include organoid cultures of a cell context, the cells of which are optionally exposed to a control perturbation in the control state, exposed to a test perturbation in the test state, and exposed to both the test perturbation and the query perturbation in the query state.

In some embodiments, the screening methods described herein employ a single cell context, that is a single cell type that is perturbed in the test and query states. Accordingly and with reference to FIG. 4AC, in some embodiments, the corresponding plurality of control aliquots of the cells of the obtaining (4002) has cells of a single cell type, the corresponding plurality of test aliquots of the cells of the obtaining (4034) has cells of the single cell type, and the plurality of instances of query perturbation aliquots of the cells jointly representing the respective test perturbation and the query perturbation of the obtaining (4050) has cells of the single cell type (4204). Similarly, in some embodiments, the corresponding plurality of control aliquots of the cells of each instance of the obtaining (4002) has cells of a single cell type, the corresponding plurality of test aliquots of the cells of each instance of the obtaining (4034) has cells of the single cell type, and the plurality of instances of query perturbation aliquots of the cells jointly representing the respective test perturbation and the query perturbation of each instance of the obtaining (4050) has cells of the single cell type (4206).

In some embodiments, the screening methods described herein employ a plurality of different cell contexts. In some embodiments, the different cell contexts include different cell types, e.g., cells derived from different species (e.g., human cells and monkey cells) and/or cells derived from different tissues of the same species (e.g., human liver and human kidney cells). In some embodiments, the different cell contexts include at least two cell contexts incorporating the same cell type (e.g., derived from the same tissue of the same species). In some embodiments, the different cell contexts incorporate cells of the same tissue from different organisms of the same species (e.g., kidney cells from different humans having different genomes). In some embodiments, the different cell contexts incorporate cells of the same tissue originating from the same organism of the same species, where one of the cell contexts is exposed to a first control perturbing agent and another cell context is not exposed to the control perturbing agent and/or is exposed to a second control perturbing agent. In some embodiments, the different cell contexts include multiple cell contexts incorporating the same cell type, e.g., but perturbed in different fashions. For example, in some embodiments, two cell contexts include the same cell type but are perturbed with different siRNA molecules that knock-down expression of different genes.

Accordingly, in some embodiments, the plurality of cell contexts includes two or more cell types. Similarly, in some embodiments, the plurality of cell contexts includes five or more cell types. Likewise, in some embodiments, the plurality of cell contexts includes two, three, four, five, six, seven, eight, nine, ten, or more cell types. In some embodiments, the method is performed using a single cell context.

Likewise and with continued reference to FIG. 4AC, in some embodiments, the corresponding wells in the plurality of wells for the plurality of control aliquots of the cells of the obtaining (4002) includes a first plurality of wells, where each well in the first plurality of wells includes an aliquot of a different type of cells in a corresponding plurality of cell types, the corresponding wells in the plurality of wells for the plurality of test aliquots of the cells of the obtaining (4034) includes a second plurality of wells, where each well in the second plurality of wells includes an aliquot of a different type of cells in the corresponding plurality of cell types, and the corresponding wells in the plurality of wells for the plurality of query perturbation aliquots of the cells of the obtaining (4050) includes a third plurality of wells, where each well in the third plurality of wells includes an aliquot of a different type of cells in the corresponding plurality of cell types (4208). In some embodiments, the plurality of cell types includes at least three cell types (4210).

With reference to FIG. 4AD, in some embodiments (4212), the corresponding wells in the plurality of wells for the plurality of control aliquots of the cells in each instance of the obtaining (4002) includes a corresponding first plurality of wells, wherein each well in the corresponding first plurality of wells comprises an aliquot of a different type of cells in a corresponding plurality of cell types, the corresponding wells in the plurality of wells for the plurality of test aliquots of the cells of each instance of the obtaining (4034) includes a corresponding second plurality of wells, wherein each well in the corresponding second plurality of wells comprises an aliquot of a different type of cells in the corresponding plurality of cell types, and the corresponding wells in the plurality of wells for the plurality of query perturbation aliquots of the cells of each instance of the obtaining (4050) includes a corresponding third plurality of wells, wherein each well in the corresponding third plurality of wells comprises an aliquot of a different type of cells in the corresponding plurality of cell types. In some embodiments the plurality of cells types includes at least three cell types.

In some embodiments, the screening methods described herein include a separate control cell context for each corresponding test cell context. For example, in some embodiments, a screening method that employs two respective test states contexts which include aliquots of different cell types (cells from different tissues of an organism) that are both perturbed by exposure to the same test siRNA includes different control states for each test state, e.g., that contain aliquots of the corresponding cell types that are not perturbed by the test siRNA and is optionally perturbed with control siRNA.

In some embodiments, the screening methods described herein include one or more control cell contexts that corresponds to a plurality of test cell contexts. For example, in some embodiments, a screening method that employs two respective test states contexts which include aliquots of the same respective cell type but are perturbed differently, e.g., by exposure to different test siRNA targeting the same or different genes, includes a shared control state for both test states, e.g., that contains aliquots of the respective cell type that is not perturbed by test siRNA and is optionally perturbed with control siRNA.

In some embodiments, the perturbing agent used in a test state and corresponding query state is a toxin, a CRISPR reagent, a signaling molecule, a cytokine or other signaling molecule, a pathogen, exogenous over-expression (e.g., via a transiently transfected or stably integrated expression vector such as a plasmid, adenovirus-based construct, or lentivirus-based construct), a predetermined drug, a siRNA, a sgRNA, a different cell exposure to compound time, a cell type from a different donor, or a cell culture condition, e.g., as described further below.

In some embodiments, a cell context is optimized for non-optical measurements of characteristics, e.g., via RNASeq, L1000, proteomics, toxicity assays, publicly available bioassay data, in-house generated bioassays, microarrays, or chemical toxicity assays, etc.

In some embodiments, a cell context for a test state and corresponding query state is generated by perturbing a particular cell line with a cytokine or mixture of cytokines. See Heike and Nakahata, 2002, "Ex vivo expansion of hematopoietic stem cells by cytokines," Biochim Biophys Acta 1592, 313-321, which is hereby incorporated by reference. In some embodiments the cell context includes cytokines (e.g., lymphokines, chemokines, interferons, tumor necrosis factors, etc.). In some embodiments a cell context includes lymphokines (e.g., Interleukin 2, Interleukin 3, Interleukin 4, Interleukin 5, Interleukin 6, granulocyte-macrophage colony-stimulating factor, interferon gamma, etc.). In some embodiments a cell context includes chemokines such as homeostatic chemokines (e.g., CCL14, CCL19, CCL20, CCL21, CCL25, CCL27, CXCL12, CXCL13, etc.) and/or inflammatory chemokines (e.g., CXCL-8, CCL2, CCL3, CCL4, CCL5, CCL11, CXCL10). In some embodiments a cell context includes interferons (IFN) such as a type I IFN (e.g., IFN-$\alpha$, IFN-$\beta$, IFN-$\epsilon$, IFN-$\kappa$ and IFN-$\omega$.), a type II IFN (e.g., IFN-$\gamma$), or a type III IFN. In some embodiments a cell context includes tumor necrosis factors such as TNF$\alpha$ or TNF alpha.

In some embodiments, a cell context for a test state and corresponding query state is generated by perturbing a particular cell line with a protein, such as a peptide aptamer. Peptide aptamers are combinatorial protein reagents that bind to target proteins with a high specificity and a strong affinity. By so doing, they can modulate the function of their cognate targets. In some embodiments, a peptide aptamer comprises one (or more) conformationally constrained short variable peptide domains, attached at both ends to a protein scaffold. In some embodiments, a cell context is perturbed with peptide aptamer derivatized with one or more functional moieties that can cause specific post-translational modification of their target proteins, or change the subcellular localization of the targets. See, for example, Colas et al., 2000, "Targeted modification and transportation of cellular proteins," Proc. Natl. Acad. Sci. USA. 97 (25): 13720-13725, which is hereby incorporated by reference. In some embodiments, a cell context is perturbed with a peptide that selectively affects protein-protein interactions within an entity. In some such embodiments this protein-protein interaction affects an intracellular signaling event. See, for example, Souroujon and Mochly-Rosen, 1998, "Peptide modulators of protein-protein interactions in intracellular signaling," Nature Biotechnology 16, 919-924, which is hereby incorporated by reference. In some embodiments, a cell context is perturbed with an antibody or other form of biologic.

In some embodiments, a cell context for a test state and corresponding query state is generated by perturbing a particular cell line with a nucleic acid, such as a nucleic acid aptamer. Nucleic acid aptamers are short synthetic single-stranded oligonucleotides that specifically bind to various molecular targets such as small molecules, proteins, nucleic acids, and even cells and tissues. See, Ni et al., 2011, "Nucleic acid aptamers: clinical applications and promising new horizons," Curr Med Chem 18(27), 4206, which is hereby incorporated by reference. In some instance nucleic acid aptamers are selected from a biopanning method such as SELEX (Systematic Evolution of Ligands by Exponential enrichment). See, Ellington and Szostak, 1990, "In vitro selection of RNA molecules that bind specific ligands," Nature 346(6287), 818; and Tuerk and Gold, 1990, "Systematic evolution of ligands by exponential enrichment: RNA ligands to bacteriophage T4 DNA polymerase," Science 249(4968), 505, each of which is hereby incorporated by reference. The SELEX screening method begins with a random sequence library of ssDNA or ssRNA that spans 20-100 nucleotides (nt) in length. The randomization of nucleic acid sequences provides a diversity of $4^n$, with n corresponding to the number of randomized bases. Diversities on the order of ~$10^{16}$ aptamers can typically generated and screened in the SELEX methods. Each random sequence region is flanked by constant sequences that is used for capture or priming. To overcome exonuclease degradation, aptamers can be chemically synthesized and capped with modified or inverted nucleotides to prevent terminal degradation. Modified oligonucleotides can also be incorporated within the aptamer, either during or after selection, for enhanced endonuclease stability. Some modified nucleotide triphosphates, particularly 2'-O-modified pyrimidines, can be efficiently incorporated into nucleic acid aptamer transcripts by T7 RNA polymerases. Common chemical modifications included during selection are 2'-amino pyrimidines and 2'-fluoro pyrimidines. See, Ni et al., 2011, "Nucleic acid aptamers: clinical applications and promising new horizons," Curr Med Chem 18(27), 4206, which is hereby incorporated by reference.

In some embodiments, a cell context for a test state and corresponding query state is generated by perturbing a particular cell line with a zinc finger transcription factor. In some such embodiments, the zinc finger protein transcription factor is encoded into vector that is transformed into the one or more cells, thereby causing the control of expression of one or more targeted components within the one or more cells. In some such embodiments, a sequence that is common to multiple (e.g., functionally related) components in the entity is used by a perturbation in the form of a zinc finger protein in order to control the transcription of all these components with a single perturbation in the form of a zinc finger transcription factor. In some embodiments, the perturbation in the form of a zinc finger transcription factor targets a family of related components in an entity by targeting and modulating the expression of the endogenous transcription factors that control them. See, for example, Doyon, 2008, "Heritable targeted gene disruption in zebrafish using designed zinc-finger nucleases," Nature Biotechnology 26, 702-708, which is hereby incorporated by reference.

In some embodiments, a cell context for a test state and corresponding query state is generated by introducing a mutation into the genome of a cell line, e.g., an insertion, deletion, inversion, transversion, etc. Generally, the mutation disrupts the expression or function of a target gene.

Characteristics

Each of the characteristic measurements 226, 230, and 234 used to derive the features that form the basis of elements of query perturbation data points 276, 280, and 284, or corresponding dimension reduction components thereof, is selected from a plurality of measured characteristics. In some embodiments, the one or more characteristic measurements include one or more of morphological features, expression data, genomic data, epigenomic data, epigenetic data, proteomic data, metabolomics data, toxicity data, bioassay data, etc.

In some embodiments, the corresponding set of elements of each query perturbation data points 276, 280, and 284 includes between 5 test elements and 100,000 test elements. Likewise, in some embodiments, the corresponding set of elements includes a range of elements falling within the larger range discussed above, e.g., from 100 to 100,000, from 1000 to 100,000, from 10,000 to 100,000, from 5 to 10,000, from 100 to 10,000, from 1000 to 10,000, from 5 to 1000, from 100 to 1000, and the like. Generally, the more elements included in the data points, the more information available to distinguish the on-target and off-target effects of the query perturbations. On the other hand, as the number of elements in the set increases, the computational resources required to process the data and manipulate the multidimensional vectors also increases.

In some embodiments, each characteristic used to generate the features is a characteristic that is optically measured, e.g., using fluorescent labels (e.g., cell painting) or using native imaging, as described herein and known to the skilled artisan. In some embodiments, when each characteristic is optically measured, a single image collection step (e.g., that obtains a single image or a series of images at multiple wavebands) can be used to collect image data from multiple samples, e.g., an entire multiwell plate. In some embodiments, a number of images are collected for each well in a multiwell plate. In some embodiments, multiple sub-images are collected for each well, e.g., two, three, four, five, six, or more images of different sub-sections of each well are collected. Characteristic extraction and feature generation is then performed electronically from the collected image(s), limiting the experimental time required to extract features from a large plurality of cell contexts and compounds.

In some embodiments, a first subset of the characteristics used to derived the features are optically measured (e.g., using fluorescent labels, e.g., via cell painting), and a second subset of the characteristics used to derive the features are measured non-optically. Non-limiting examples of non-optical features include gene expression levels, protein levels, single endpoint bio-assay data, metabolome data, microenvironment data, microbiome data, genome sequence and associated characteristics (e.g., epigenetic data such as methylation, 3D genome structure, chromatin accessibility, etc.), and a relationship and/or change in a particular characteristic over time, e.g., within a single sample or across a plurality of samples in a time series. Further details about these and other types of non-optical characteristics, as well as collection of data associated with these characteristics, is provided below.

In some embodiments, each characteristic is non-optically measured Further details about these and other types of non-optical features, as well as collection of data associated with these features, is provided below. Thus, in some embodiments, multiple assays are performed for each instance (e.g., replicate) of a respective cell context that is exposed to a respective compound, e.g., both a nucleic acid microarray assay and a bioassay are performed from different instances of a respective cell context exposed to a respective compound.

In some embodiments, one or more of the characteristics are determined from a non-cell-based assay. That is, in some embodiments, data collected from in vitro experiments performed in the absence of a cell is used in the construction of the multidimensional vectors described herein.

Optically-Measured Characteristics

In some embodiments, one or more of the characteristics used to derive the features represent morphological features of a cell, or an enumerated portion of a cell, upon exposure of a respective compound in the cell context. Example characteristics include, but are not limited to cell area, cell perimeter, cell aspect ratio, actin content, actin texture, cell solidity, cell extent, cell nuclear area, cell nuclear perimeter, cell nuclear aspect ratio, and algorithm-defined features (e.g., latent features). In some embodiment, example characteristics include, but are not limited to, any of the features found in Table S2 of the reference Gustafsdottir S M, et al., PLoS ONE 8(12): e80999. doi:10.1371/journal.pone.0080999 (2013), which is hereby incorporated by reference.

In some embodiments, such morphological characteristics are measured and acquired using the software program Cellprofiler. See Carpenter et al., 2006, "CellProfiler: image analysis software for identifying and quantifying cell phenotypes," Genome Biol. 7, R100 PMID: 17076895; Kamentsky et al., 2011, "Improved structure, function, and compatibility for CellProfiler: modular high-throughput image analysis software," Bioinformatics 2011/doi. PMID: 21349861 PMCID: PMC3072555; and Jones et al., 2008, CellProfiler Analyst: data exploration and analysis software for complex image-based screens, BMC Bioinformatics 9(1):482/doi: 10.1186/1471-2105-9-482. PMID: 19014601 PMCID: PMC261443, each of which is hereby incorporated by reference.

In some embodiments, one or more two-dimensional pixelated image is obtained of each well and optically-measured characteristics are derived from the pixel values of the one or more image. In some embodiments, multiple two-dimensional images are acquired of each well. In some embodiments, where each image captures a portion of the well, characteristics are measured across all images of the well.

In some embodiments, one or more three-dimensional pixelated image is obtained of each well and optically-measured characteristics are derived from the pixel values of the one or more image. For instance, in some embodiments, a plurality of two-dimensional images (e.g., confocal images) are acquired of the well at different focal lengths and the images are stacked on top of each other (z-stacking) in the respective order of the focal lengths of the images, to form a three-dimensional image.

In some embodiments, one or more four-dimensional pixelated image is obtained of each well and optically-measured characteristics are derived from the pixel values of the one or more image. For instance, in some embodiments, a plurality of two-dimensional images (e.g., confocal images) are acquired of the well at different focal lengths and the images are stacked on top of each other (z-stacking) in the respective order of the focal lengths of the images, to form a three-dimensional image, and a plurality of these three-dimensional images are collected over time to form a four-dimensional image of the well.

For a review of technological considerations of imaging platforms for high-throughput screening methods, see, Shumate and Hoffman, 2009, "Instrumental Considerations in High Content Screening," Combinatorial Chemistry & High Throughput Screening, 12(9):888-98, which is hereby incorporated by reference.

In some embodiments, the measurement of one or more characteristics is a fluorescent microscopy measurement. In some embodiments, the one or more optical emitting compounds are dyes and where the vector for a compound in the plurality of compounds includes respective measurements of characteristics used to derive features in the plurality of features for the cell context in the presence of each of at least three different dyes. In some embodiments, the one or more optical emitting compounds are dyes and data points 276, 280, and 284 include respective measurements of features in the plurality of features for the cell context in the presence of each of at least five different dyes.

Accordingly, in some embodiments, one or more characteristic is measured after exposure of the cell context to the compound and to a panel of fluorescent stains that emit at different wavelengths, such as Concanavalin A/Alexa Fluor 488 conjugate (Invitrogen, cat. no. C11252), Hoechst 33342 (Invitrogen, cat. no. H3570), SYTO 14 green fluorescent nucleic acid stain (Invitrogen, cat. no. S7576), Phalloidin/Alexa Fluor 568 conjugate (Invitrogen, cat. no. A12380), and/or MitoTracker Deep Red (Invitrogen, cat. no. M22426). In some embodiments, measured characteristics include one or more of staining intensities, textural patterns, size, and shape of the labeled cellular structures, as well as correlations between stains across channels, and adjacency relationships between cells and among intracellular structures. In some embodiments, two, three, four, five, six, seven, eight, nine, ten, or more than 10 fluorescent stains, imaged in two, three, four, five, six, seven, or eight channels, are used to measure characteristics including different cellular components and/or compartments.

In some embodiments, one or more characteristics are measured from single cells, groups of cells, and/or a field of view. In some embodiments, characteristics are measured from a compartment or a component (e.g., nucleus, endoplasmic reticulum, nucleoli, cytoplasmic RNA, F-actin cytoskeleton, Golgi, plasma membrane, mitochondria) of a single cell. In some embodiments, each channel of an imaging device used to capture images of the cells includes (i) an excitation wavelength range and (ii) a filter wavelength range in order to capture the emission of a particular dye from among the set of dyes the cell has been exposed to prior to measurement. An example of the dye that is being invoked and the type of cellular component that is measured as a characteristic for five suitable channels is provided in Table 4 below, which is adapted from Table 1 of Bray et al., 2016, "Cell Painting, a high-content image-based assay for morphological profiling using multiplexed fluorescent dyes," Nature Protocols, 11, p. 1757-74, which is hereby incorporated by reference.

TABLE 4

Example channels used for measuring characteristics

| Channel | Dye | Filter (excitation; nm) | Filter (emission; nm) | Entity component or compartment |
|---|---|---|---|---|
| 1 | Hoechst 33342 | 387/11 | 417-477 | Nucleus |
| 2 | Concanavalin A/Alexa Fluor 488 conjugate | 472/30a | 503-538a | Endoplasmic reticulum |
| 3 | SYTO 14 green fluorescent nucleic acid stain | 531/40 | 573-613 | Nucleoli, cytoplasmic RNAb |

TABLE 4-continued

Example channels used for measuring characteristics

| Channel | Dye | Filter (excitation; nm) | Filter (emission; nm) | Entity component or compartment |
|---|---|---|---|---|
| 4 | Phalloidin/Alexa Fluor 568 conjugate, wheat-germ agglutinin/Alexa Fluor 555 conjugate | 562/40 | 622-662c | F-actin cytoskeleton, Golgi, plasma membrane |
| 5 | MitoTracker Deep Red | 628/40 | 672-712 | Mitochondria |

Cell Painting and related variants of cell painting represent another form of imaging technique that holds promise. Cell painting is a morphological profiling assay that multiplexes six fluorescent dyes, imaged in five channels, to reveal eight broadly relevant cellular components or organelles. Cells are plated in multiwell plates, perturbed with the treatments to be tested, stained, fixed, and imaged on a high-throughput microscope. Next, automated image analysis software identifies individual cells and measures any number between one and tens of thousands (but most often approximately 1,000) morphological characteristics (various measures of size, shape, texture, intensity, etc. of various whole-cell and sub-cellular components) to produce a profile that is suitable for the detection of even subtle phenotypes. Profiles of cell populations treated with different experimental perturbations can be compared to suit many goals, such as identifying the phenotypic impact of chemical or genetic perturbations, grouping compounds and/or genes into functional pathways, and identifying signatures of disease. See, Bray et al., 2016, Nature Protocols 11, 1757-1774, which is hereby incorporated by reference.

In some embodiments, the measurement of a characteristic is a label-free imaging measurement of the characteristic. In some embodiments, one or more characteristic is measured by the label-free imaging technique after exposure of the cell context to a compound. Non-invasive, label free imaging techniques have emerged, fulfilling the requirements of minimal cell manipulation for cell based assays in a high content screening context. Among these label free techniques, digital holographic microscopy (Rappaz et al., 2015 Automated multi-parameter measurement of cardiomyocytes dynamics with digital holographic microscopy," Opt. Express 23, 13333-13347) provides quantitative information that is automated for end-point and time-lapse imaging using 96- and 384-well plates. See, for example, Kuhn, J. 2013, et al., "Label-free cytotoxicity screening assay by digital holographic microscopy," Assay Drug Dev. Technol. 11, 101-107; Rappaz et al., 2014 "Digital holographic microscopy: a quantitative label-free microscopy technique for phenotypic screening," Comb. Chem. High Throughput Screen 17, 80-88; and Rappaz et al., 2015 in Label-Free Biosensor Methods in Drug Discovery (ed. Fang, Y.) 307-325, Springer Science+Business Media). Light sheet fluorescence microscopy (LSFM) holds promise for the analysis of large numbers of samples, in 3D high resolution and with fast recording speed and minimal photo-induced cell damage. LSFM has gained increasing popularity in various research areas, including neuroscience, plant and developmental biology, toxicology and drug discovery, although it is not yet adapted to an automated HTS setting. See, Pampaloni et al., 2014, "Tissue-culture light sheet fluorescence microscopy (TC-LSFM) allows long-term imaging of three-dimensional cell cultures under controlled conditions," Integr. Biol. (Camb.) 6, 988-998; Swoger et al., 2014, "Imaging cellular spheroids with a single (selective) plane illumination microscope," Cold Spring Harb. Protoc., 106-113; and Pampaloni et al., 2013, "High-resolution deep imaging of live cellular spheroids with light-sheet-based fluorescence microscopy," Cell Tissue Res. 352, 161-177, all of which are hereby incorporated by reference.

In some embodiments, the measurement of one or more characteristic is a bright field measurement of the characteristic. In some embodiments, one or more characteristic is measured by bright field microscopy after exposure of the cell context to a compound. In contrast to measurements obtained by fluorescent microscopy, which requires exposing the cell context to one of more fluorescent stain, bright field microscopy does not require the use of stains, reducing phototoxicity and simplifying imaging setup. Although the lack of stains reduces the contrast provided in bright field images, as compared to fluorescent images, various techniques have been developed to improve cellular imaging in this fashion. For example, Quantitative Phase Microscopy relies on estimation of a phase map generated from images acquired at different focal lengths. See, for example, Curl C L, et al., Cytometry A 65:88-92 (2005), which is incorporated by reference herein. Similarly, a phase map can be measured using lowpass digital filtering, followed by segmentation of individual cells. See, for example, Ali R., et al., Proc. 5th IEEE International Symposium on Biomedical Imaging: From Nano to Macro, ISBI:181-84 (2008), which is incorporated by reference herein. Texture analysis, e.g., where cell contours are extracted after segmentation, can also be used in conjunction with bright field microscopy. See, for example, Korzynska A, et al., Pattern Anal Appl 10:301-19 (2007). Yet other techniques are also available to facilitate use of bright filed microscopy, including z-projection based methods. See, for example, Selinummi J., et al., PLoS One, 4(10):e7497 (2009), which is hereby incorporated by reference.

In some embodiments, the measurement of one or more characteristics is phase contrast measurement of the characteristic. In some embodiments, one or more characteristics are measured by phase contrast microscopy after exposure of the cell context to a compound. Images obtained by phase contrast or differential interference contrast (DIC) microscopy can be digitally reconstructed and quantified. See Koos, 2015, "DIC image reconstruction using an energy minimization framework to visualize optical path length distribution," Sci. Rep. 6, 30420, which is hereby incorporated by reference.

Although particular imaging techniques are specifically described herein, the methods provided herein could be performed using characteristics measured from any of a number of microscope modalities.

In some embodiments, each feature is derived from a combination of measurable characteristics selected from a color, texture, and size of the cell context, or an enumerated portion of the cell context. Example characteristic include, but are not limited to cell area, cell perimeter, cell aspect ratio, actin content, actin texture, cell solidity, cell extent, cell nuclear area, cell nuclear perimeter, and cell nuclear aspect ratio. In some embodiments, example characteristic include, but are not limited to, any of the characteristic found in Table S2 of the reference Gustafsdottir S M, et al., PLoS ONE 8(12): e80999. doi:10.1371/journal.pone.0080999 (2013), which is hereby incorporated by reference.

In some embodiments, one or more of the measured characteristic are latent characteristics, e.g., characteristics determined from a mathematical model of the data measured directly from the wells. In one embodiment, each respective instance of the plurality of instances of the cell context is imaged to form a corresponding two-dimensional pixelated image having a corresponding plurality of native pixel values and where a feature in the plurality of features comprises a result of a convolution or a series convolutions and pooling operators run against native pixel values in the plurality of native pixel values of the corresponding two-dimensional pixelated image. While this is an example of a latent characteristic that can be derived from an image, other latent characteristics and mathematical combinations of latent characteristics can also be used. A non-limiting example of the use of latent characteristics in image-based profiling of cellular structure is found in Ljosa, V., et al., J Biomol. Screen., 18(10):10.1177/1087057113503553 (2013), which is incorporated herein by reference.

Non-Optically-Measured Characteristics

In some embodiments one or more of the measured characteristic include expression data, e.g., obtained using a whole transcriptome shotgun sequencing (RNA-Seq) assay that quantifies gene expression from cells (e.g., a single cell) in counts of transcript reads mapped to gene constructs. As such, in some embodiments, RNA-Seq experiments aim at reconstructing all full-length mRNA transcripts concurrently from millions of short reads. RNA-Seq facilitates the ability to look at alternative gene spliced transcripts, post-transcriptional modifications, gene fusion, mutations/SNPs and changes in gene expression over time, or differences in gene expression in different groups or treatments. See, for example, Maher et al., 2009, "Transcriptome sequencing to detect gene fusions in cancer," Nature. 458 (7234): 97-101, which is hereby incorporated by reference. In addition to mRNA transcripts, RNA-Seq can evaluate and quantify individual members of different populations of RNA including total RNA, mRNA, miRNA, lncRNA, snoRNA, or tRNA within entities. As such, in some embodiments, one or more of the characteristics that is measured is an individual amount of a specific RNA species as determined using RNA-Seq techniques. In some embodiments, RNA-Seq experiments produce counts of component (e.g., digital counts of mRNA reads) that are affected by both biological and technical variation. In some embodiments RNA-Seq assembly is performed using the techniques disclosed in Li el al., 2008, "IsoLasso: A LASSO Regression Approach to RNA-Seq Based Transcriptome Assembly," Cell 133, 523-536 which is hereby incorporated by reference.

In some embodiments one or more of the measured characteristic are obtained using transcriptional profiling methods such an L1000 panel that measures a set of informative transcripts. In such an approach, ligation-mediated amplification (LMA) followed by capture of the amplification products on fluorescently addressed microspheres beads is extended to a multiplex reaction (e.g., a 1000-plex reaction). For instance, cells growing in 384-well plates are lysed and mRNA transcripts are captured on oligo-dT-coated plates. cDNAs are synthesized from captured transcripts and subjected to LMA using locus-specific oligonucleotides harboring a unique 24-mer barcode sequence and a 5' biotin label. The biotinylated LMA products are detected by hybridization to polystyrene microspheres (beads) of distinct fluorescent color, each coupled to an oligonucleotide complementary to a barcode, and then stained with streptavidin-phycoerythrin. In this way, each bead can be analyzed both for its color (denoting landmark identity) and fluorescence intensity of the phycoerythrin signal (denoting landmark abundance). See Subramanian et al., "A Next Generation Connectivity Map: L1000 Platform and the First 1,000,000 Profiles," Cell 171(6), 1437, which is hereby incorporated by reference. In some embodiments, between 500 and 1500 different informative transcripts are measured using this assay.

In some embodiments one or more of the measured characteristics are obtained using microarrays. A microarray (also termed a DNA chip or biochip) is a collection of microscopic nucleic acid spots attached to a solid surface that can be used to measure the expression levels of large numbers of genes simultaneously. Each nucleic acid spot contains picomoles of a specific nucleic acid sequence, known as probes (or reporters or oligos). These can be a short section of a gene or other nucleic acid element that are used to hybridize a cDNA or cRNA (also called anti-sense RNA) sample (called target) under high-stringency conditions. For instance, by way of a non-limiting example, in some embodiments, the microarrays such as the Affymetrix GeneChip microarray, a high density oligonucleotide gene expression array, is used. Each gene on an Affymetrix microarray GeneChip is typically represented by a probe set consisting of 11 different pairs of 25-bp oligos covering portions of the transcribed region of that gene. Each pair consists of a perfect match (PM) and a mismatch (MM) oligonucleotide. The PM probe exactly matches the sequence of a particular standard genotype, often one parent of a cross, while the MM differs in a single substitution in the central, $13^{th}$ base. The MM probe is designed to distinguish noise caused by non-specific hybridization from the specific hybridization signal. See, Jiang, 2008, "Methods for evaluating gene expression from Affymetrix microarray datasets," BMC Bioinformatics 9, 284, which is hereby incorporated by reference.

In some embodiments one or more of the measured characteristic are obtained using ChIP-Seq data. See, for example, Quigley and Kintner, 2017, "Rfx2 Stabilizes Foxj1 Binding at Chromatin Loops to Enable Multiciliated Cell Gene Expression," PLoS Genet 13, e1006538, which is hereby incorporated by reference. In some embodiments, ChIP-seq is used to determine how transcription factors and other chromatin-associated proteins influence phenotype-affecting mechanisms in entities (e.g., cells). Specific DNA sites in direct physical interaction with transcription factors and other proteins can be isolated by chromatin immunoprecipitation. ChIP produces a library of target DNA sites bound to a protein of interest (component) in vivo. Parallel sequence analyses are then used in conjunction with whole-genome sequence databases to analyze the interaction pattern of any protein with DNA (Johnson et al., 2007, "Genome-wide mapping of in vivo protein-DNA interactions," Science. 316: 1497-1502, which is hereby incorporated by reference) or the pattern of any epigenetic chromatin modifications. This can be applied to the set of ChIP-able proteins and modifications, such as transcription factors, polymerases and transcriptional machinery, structural proteins, protein modifications, and DNA modifications.

ChIP selectively enriches for DNA sequences bound by a particular protein (component) in living cells (entities). The ChIP process enriches specific cross-linked DNA-protein complexes using an antibody against the protein (component) of interest. Oligonucleotide adaptors are then added to the small stretches of DNA that were bound to the protein of interest to enable massively parallel sequencing. After size selection, all the resulting ChIP-DNA fragments are sequenced concurrently using a genome sequencer. A single sequencing run can scan for genome-wide associations with high resolution, meaning that binding can be located precisely on the chromosomes. Various sequencing methods can be used. In some embodiments the sequences are analyzed using cluster amplification of adapter-ligated ChIP DNA fragments on a solid flow cell substrate to create clusters of clonal copies. The resulting high density array of template clusters on the flow cell surface is sequenced by a Genome analyzing program. Each template cluster undergoes sequencing-by-synthesis in parallel using fluorescently labelled reversible terminator nucleotides. Templates are sequenced base-by-base during each read. Then, the data collection and analysis software aligns sample sequences to a known genomic sequence to identify the ChIP-DNA fragments.

In some embodiments one or more of the measured characteristics are obtained using ATAC-seq (Assay for Transposase-Accessible Chromatin using sequencing), which is a technique used in molecular biology to study chromatin accessibility. See Buenrostro et al., 2013, "Transposition of native chromatin for fast and sensitive epigenomic profiling of open chromatin, DNA-binding proteins and nucleosome position," Nature Methods 10, 1213-1218, which is hereby incorporated by reference. In some embodiments, ATAC-seq make use of the action of the transposase Tn5 on the genomic DNA of an entity. See, for example, Buenrostro et al., 2015, "ATAC-seq: A Method for Assaying Chromatin Accessibility Genome-Wide," Current Protocols in Molecular Biology: 21.29.1-21.29.9, which is hereby incorporated by reference. Transposases are enzymes catalyzing the movement of transposons to other parts in the genome. While naturally occurring transposases have a low level of activity, ATAC-seq employs a mutated hyperactive transposase. The high activity allows for highly efficient cutting of exposed DNA and simultaneous ligation of specific sequences, called adapters. Adapter-ligated DNA fragments are then isolated, amplified by PCR and used for next generation sequencing. See Buenrostro el al., 2013, "Transposition of native chromatin for fast and sensitive epigenomic profiling of open chromatin, DNA-binding proteins and nucleosome position," Nature Methods 10, 1213-1218, which is hereby incorporated by reference.

While not intending to be limited to any particular theory, transposons are believed to incorporate preferentially into genomic regions free of nucleosomes (nucleosome-free regions) or stretches of exposed DNA in general. Thus enrichment of sequences from certain loci in the genome indicates absence of DNA-binding proteins or nucleosome in the region. An ATAC-seq experiment will typically produce millions of next generation sequencing reads that can be successfully mapped on the reference genome. After elimination of duplicates, each sequencing read points to a position on the genome where one transposition (or cutting) event took place during the experiment. One can then assign a cut count for each genomic position and create a signal with base-pair resolution. This signal is used as a characteristic in some embodiments of the present disclosure. Regions of the genome where DNA was accessible during the experiment will contain significantly more sequencing reads (since that is where the transposase preferentially acts), and form peaks in the ATAC-seq signal that are detectable with peak calling tools. In some embodiments, such peaks, and their locations in the genome are used as characteristics. In some embodiments, these regions are further categorized into the various regulatory element types (e.g., promoters, enhancers, insulators, etc.) by integrating further genomic and epigenomic data such as information about histone modifications or evidence for active transcription. Inside the regions where the ATAC-seq signal is enriched, one can also observe sub-regions with depleted signal. These sub-regions, typically only a few base pairs long, are considered to be "footprints" of DNA-binding proteins. In some embodiments, such footprints, or their absence or presence thereof are used as characteristics.

In some embodiments flow cytometry methods using Luminex beads, are used to obtain values for one or more of the measured characteristics. See for example, Süsal et al., 2013, Transfus Med Hemother 40, 190-195, which is hereby incorporated by reference. For instance, the Luminex-supported single antigen bead (L-SAB) test allows for the characterization of human leukocyte antigen (HLA) antibody specificities. In such a flow cytometric method, microbeads coated with recombinant single antigen HLA molecules are employed in order to differentiate antibody reactivity in two reaction tubes against 100 different HLA class I and 100 different HLA class II alleles. An approximation of the strength of antibody reactivity is derived from the mean fluorescence intensity (MFI) and in some embodiments this serves as characteristics in the present disclosure. In addition to antibody reactivity against HLA-A, -B, -C, -DR and -DQB antigens, L-SAB is capable of detecting antibodies against HLA-DQA, -DPA, and -DPB antigens. In some embodiments, other Luminex kits are used for detection of non-HLA antibodies in order to derive values for one or more characteristics for entities in accordance with the present disclosure. For instance, in some embodiments, major histocompatibility complex class I-related chain A (MICA) and human neutrophil antibodies, and kits that utilize, instead of recombinant HLA molecules, affinity purified pooled human HLA molecules obtained from multiple cell lines (screening test to detect presence of HLA antibodies without further specification) or phenotype panels in which each bead population bears either HLA class I or HLA class II proteins of a cell lines derived from a single individual (panel reactivity, PRA-test) are used to determine value for characteristics for entities in accordance with an embodiment of the present disclosure.

In some embodiments, flow cytometry methods, such fluorescent cell barcoding, is used to obtain values for one or more of the measured characteristics. Fluorescent cell barcoding (FCB) enables high throughput, e.g., high content flow cytometry by multiplexing samples of entities prior to staining and acquisition on the cytometer. Individual cell samples (entities) are barcoded, or labeled, with unique signatures of fluorescent dyes so that they can be mixed together, stained, and analyzed as a single sample. By mixing samples prior to staining, antibody consumption is typically reduced 10 to 100-fold. In addition, data robustness is increased through the combination of control and treated samples, which minimizes pipetting error, staining variation, and the need for normalization. Finally, speed of acquisition is enhanced, enabling large profiling experiments to be run with standard cytometer hardware. See, for example, Krutzik, 2011, "Fluorescent Cell Barcoding for Multiplex Flow Cytometry," Curr Protoc Cytom Chapter 6: Unit 6.31, which is hereby incorporated by reference.

In some embodiments, metabolomics is used to obtain values for one or more of the characteristics. Metabolomics is a systematic evaluation of small molecules in order to obtain biochemical insight into disease pathways. In some embodiments, such metabolomics comprises evaluation of plasma metabolomics in diabetes (Newgard el al., 2009, "A branched-chain amino acid-related metabolic signature that differentiates obese and lean humans and contributes to insulin resistance," Cell Metab 9: 311-326, 2009) and ESRD (Wang, 2011, "RE: Metabolite profiles and the risk of developing diabetes," Nat Med 17: 448-453). In some embodiments, urine metabolomics is used to obtain values for one or more of the characteristics. Urine metabolomics offers a wider range of measurable metabolites because the kidney is responsible for concentrating a variety of metabolites and excreting them in the urine. In addition, urine metabolomics may offer direct insights into biochemical pathways linked to kidney dysfunction. See, for example, Sharma, 2013, "Metabolomics Reveals Signature of Mitochondrial Dysfunction in Diabetic Kidney Disease," J Am Soc Nephrol 24, 1901-12, which is hereby incorporated by reference.

In some embodiments, mass spectrometry is used to obtain values for one or more of the measured characteristics. For instance, in some embodiments, protein mass spectrometry is used to obtain values for one or more of the measured characteristics. In particular, in some embodiments, biochemical fractionation of native macromolecular assemblies within entities followed by tandem mass spectrometry is used to obtain values for one or more of the measured characteristics. See, for example, Wan et al., 2015, "Panorama of ancient metazoan macromolecular complexes," Nature 525, 339-344, which is hereby incorporated by reference. Tandem mass spectrometry, also known as MS/MS or MS2, involves multiple steps of mass spectrometry selection, with some form of fragmentation occurring in between the stages. In a tandem mass spectrometer, ions are formed in the ion source and separated by mass-to-charge ratio in the first stage of mass spectrometry (MS1). Ions of a particular mass-to-charge ratio (precursor ions) are selected and fragment ions (product ions) are created by collision-induced dissociation, ion-molecule reaction, photodissociation, or other process. The resulting ions are then separated and detected in a second stage of mass spectrometry (MS2). In some embodiments the detection and/or presence of such ions serve as the one or more of the measured characteristics.

In some embodiments, the characteristics that are observed for an entity or a plurality of entities are post-translational modifications that modulate activity of proteins within a cell. In some such embodiments, mass spectrometric peptide sequencing and analysis technologies are used to detect and identify such post-translational modifications. In some embodiments, isotope labeling strategies in combination with mass spectrometry are used to study the dynamics of modifications and this serves as a measured characteristic. See for example, Mann and Jensen, 2003 "Proteomic analysis of post-translational modifications," Nature Biotechnology 21, 255-261, which is hereby incorporated by reference. In some embodiments, mass spectrometry is user to determine splice variants in entities, for instance, splice variants of components within entities, and such splice variants and the detection of such splice variants serve as measured characteristics. See for example, Nilsen and Graveley, 2010, "Expansion of the eukaryotic proteome by alternative splicing, 2010, Nature 463, 457-463, which is hereby incorporated by reference.

In some embodiments, imaging cytometry is used to obtain values for one or more of the measured characteristics. Imaging flow cytometry combines the statistical power and fluorescence sensitivity of standard flow cytometry with the spatial resolution and quantitative morphology of digital microscopy. See, for example, Basiji et al., 2007, "Cellular Image Analysis and Imaging by Flow Cytometry," Clinics in Laboratory Medicine 27, 653-670, which is hereby incorporated by reference.

In some embodiments, electrophysiology is used to obtain values for one or more of the measured characteristics. See, for example, Dunlop et al., 2008, "High-throughput electrophysiology: an emerging paradigm for ion-channel screening and physiology," Nature Reviews Drug Discovery 7, 358-368, which is hereby incorporated by reference.

In some embodiments, proteomic imaging/3D imaging is used to obtain values for one or more of the measured characteristics. See for example, United States Patent Publication No. 20170276686 A1, entitled "Single Molecule Peptide Sequencing," which is hereby incorporated by reference. Such methods can be used to large-scale sequencing of single peptides in a mixture from an entity, or a plurality of entities at the single molecule level.

Assay Parameters

As described herein with reference to FIG. 3, in some embodiments, each characteristic measurement is obtained in replicate, e.g., each condition (e.g., each control state, teste state, and/or query state) is performed more than once and each characteristic measurement is obtained from each instance of the condition. In some embodiments, characteristic measurements are obtained from at least 2, 3, 4, 5, 6, 7, 8, 9, 10, 15, 20, 25, 50, 75, 100, 500, or more instances of every condition, e.g., experimental conditions are prepared in two or more replicates. In other embodiments, characteristic measurements are obtained from a single instance of each condition.

Similarly, as described herein with reference to FIG. 3, in some embodiments, each query perturbation (e.g., compound) is exposed to each cell context at a plurality of concentrations. In some embodiments, each query perturbation (e.g., compound) is exposed to each cell context using at least 2, 3, 4, 5, 6, 7, 8, 9, 10, or more concentrations. Similarly, in some embodiments, each characteristic measurement is obtained at each concentration in replicate. In other embodiments, each query perturbation (e.g., compound) is exposed to each cell context in a single instance.

With respect to the concentrations of compounds used for any particular query perturbation, the skilled artisan will know how to select a concentration for a given compound. In some embodiments, each compound will be used at the same concentrations. In some embodiments, different compounds will be used at different concentrations, e.g., based upon one or more known or expected property of the compound such as molecular weight, solubility, presence or particular functional groups, known or expected interactions, known or expected toxicity, etc. For example, in some embodiments, where a respective compound is known to be toxic to a cell type used in a particular cell context, the concentration of the compound may be adjusted, e.g., relative to the concentration used for other compounds. Generally, in the methods described herein, a compound will be used at a concentration of between 1 nM and 1 mM. In some embodiments, a compound will be used at a concentration of from 10 nM to 100 µM. In some embodiments, a compound will be used at a concentration of from 100 nM to 10 µM. However, the skilled artisan will know when a compound should be used at a concentration outside of this range.

In some embodiments, where the compounds are tested at multiple concentrations, the multiple concentrations will span at least a two-fold range on concentrations, e.g., 100 nM to 200 nM. In some embodiments, the multiple concentrations will span at least an order of magnitude, e.g., 100 nM to 1 µM. In some embodiments, the multiple concentrations will span at least two orders of magnitude, e.g., 100 nM to 10 µM. In some embodiments, the multiple concentrations will span at least three orders of magnitude, e.g., 100 nM to 100 µM.

Generally, the time over which a cell context is exposed to a compound is influenced by the particular characteristic being measured and/or the particular assay from which the characteristic data is being generated. For example, where the assay being used measures a phenomenon that occurs rapidly following exposure of the cell context to the compound, the cell context does not need to be exposed to the compound for a long period of time prior to measurement of the characteristic. Conversely, where the assay being used measures a phenomenon that occurs slowly, or after a significant delay, following exposure of the cell context to the compound, a longer incubation time should be used prior to measuring the characteristic.

In some embodiments, e.g., where latent characteristics are being extracted from a cell context, the time over which the cell context is exposed to a compound prior to measurement is determined stochastically. In some embodiments, the time over which the cell context is exposed to a compound prior to measurement is determined based on experience or trial and error with a particular assay or phenomenon. In one embodiment, exposure of the amount of the respective compound to the cell context is for at least one hour prior to obtaining the measurement. In some embodiments, the measurement is obtained by cellular imaging, e.g., using fluorescent labels (e.g., cell painting) or using native imaging, as described herein and known to the skilled artisan. In some embodiments, exposure of the amount of the respective compound to the cell context is for at least one hour prior to obtaining an image.

In some embodiments characteristic data is acquired using an automated cellular imaging system (e.g., ImageXpress Micro, Molecular Devices), where cell contexts have been arranged in multiwell plates (e.g., 384-well plates) after they have been stained with a panel of dyes that emit at different discrete wavelengths (e.g., Hoechst 33342, Alexa Fluor 594 phalloidin, etc.) and exposed to a perturbation. In some embodiments the cell contexts are imaged with an exposure that is a determined based on the marker dye used (e.g., an exposure time used to image Hoechst staining may be shorter than an exposure time used to image phalloidin staining). For each well, in some embodiments, the optimal focus is found using laser auto-focusing on a particular dye channel (e.g., the Hoechst channel). In some embodiments the automated microscope is then programmed to collect a z-stack of images (e.g., 32 images, where z=0 at the optimal focal plane, 16 images above the focal plane, 16 images below) with, e.g., 2 µm between slices.

In some embodiments each well contains several thousand cells in them, and thus each digital representation of a well captured by a camera (e.g., a single image or a composite image of multiple sub-images of the well) represents several thousand cells in each of several different wells. In some embodiments, segmentation software is used to identify individual cells in the digital images and more-over various components (e.g., cellular components) within individual cells. Once the cellular components are segmented and identified, mathematical transformations are performed on these components on order to obtain the measurements of characteristics.

Normalization

In some embodiments, the characteristic measurements, e.g., acquired from one or more multiwell plates as illustrated in FIG. 3, and/or features derived from the characteristic measurements are normalized against one or more background instances, e.g., to account for background in the characteristic measurement, which may be performed before or after construction of a multidimensional data point (276, 280, and 284). In some embodiments, the one or more background instances are cell contexts that are not exposed to any control perturbation. As such, in some embodiments, each element of a vector that represents a feature derived from a measured characteristic is determined through an independent normalization process using measurements of the same underlying characteristics from the background set (e.g., background instance). In other words, the values of a first feature that will collectively (e.g., as an average or other measure of central tendency of these value) serve as a first element in a data point are normalized in a manner that is independent of the way the values of a second feature that will serve as a second element in a data point are normalized. Such normalization generally makes use of the values for the corresponding feature from the background instances.

Accordingly, in some embodiments, a subset of the wells in the plurality of wells in each multiwell plate in the plurality of multiwell plates include an aliquot of cells of the cell context that have not been exposed to a control perturbation, a test perturbation, or a query perturbation, and the measurement of the respective characteristic from the control state, test state, and/or query state is normalized by one or more instances of the wells that contain the background state, e.g., by a mean of the characteristic measured across the background instances.

In some embodiments, the normalization of the measured characteristic is achieved using the standard deviation of the characteristic measured across the background instances by dividing the measurement of the characteristic across the plurality of instances of the control state, test state, and/or query state by a standard deviation, two standard deviations, or three standard deviations of the feature measured across the instances of the background state.

In some embodiments, the normalization of the characteristic is achieved using a measure of dispersion of the characteristic measured across the instances of the background state by dividing the measurement of the characteristic across the plurality of instances of the control state, test state, and/or query state by the measure of dispersion of the feature across the instances of the background state. In some such embodiments, this measure of dispersion is a mean deviation, a standard deviation, a variance, or some multiplication thereof (e.g., 2×mean deviation, 2×standard deviation, 2×variance, etc.).

Dimensional Reduction

In some embodiments, particularly where a large number of features are derived from measured characteristics and/or a large number of cell contexts are used, the resulting multidimensional data points used for screening query perturbations are very large, rendering the subsequent analysis computationally taxing. In order to reduce the computational burden, in some embodiments, the multidimensional data points are dimension reduced, using a statistical feature selection or feature extraction procedure known in the art, for example, principal component analysis, non-negative matrix factorization, kernel PCA, graph-based kernel PCA, UMAP, linear discriminant analysis, generalized discriminant analysis. Similarly, in some embodiments, a machine learning technique is used to reduce the number of dimensions of the multidimensional data points, e.g., a neural network, a convolutional neural network, an autoencoder, a support vector machine, a Bayesian network, or a genetic algorithm. This, in turn, reduces the computational burden of analyzing the data set by compressing the data in order to make the method more computationally efficient, e.g., by allowing the computer to apply an algorithm to the smaller dataset (the dimension-reduced data points) rather than the full dataset (the original multidimensional data points).

Principal component analysis (PCA) reduces the dimensionality of a multidimensional data point by transforming the plurality of elements (e.g., derived from measured characteristics 226, 230, and/or 234) to a new set of variables (principal components) that summarize the features of the training set. See, for example, Jolliffe, 1986, Principal Component Analysis, Springer, New York, which is hereby incorporated by reference. PCA is also described in Draghici, 2003, Data Analysis Tools for DNA Microarrays, Chapman & Hall/CRC, which is hereby incorporated by reference. Principal components (PCs) are uncorrelated and are ordered such that the kth PC has the kth largest variance among PCs across the observed data for the features. The kth PC can be interpreted as the direction that maximizes the variation of the projections of the data points such that it is orthogonal to the first k−1 PCs. The first few PCs capture most of the variation in the observed data. In contrast, the last few PCs are often assumed to capture only the residual "noise" in the observed data. As such, the principal components derived from PCA can serve as the basis of vectors that are used in accordance with the present disclosure.

Non-negative matrix factorization and non-negative matrix approximation reduce the dimensionality of a multidimensional matrix by factoring the matrix into two matrices, each of which have significantly lower dimensionality, but which provide a product having the same, or approximately the same, dimensionality as the original higher-dimensional matrix. See, for example, Lee and Seung, "Learning the parts of objects by non-negative matrix factorization, Nature, 401(6755):788-91 (1999), which is hereby incorporated by reference. See also Dhillon and Sra, "Generalized Nonnegative Matrix Approximations with Bregman Divergences," Advances in Neural Information Processing Systems 18 (NIPS 2005), which is hereby incorporated by reference.

Kernel PCA is an extension of PCA in which N elements of a vector are mapped onto a N-dimensional space using a non-trivial, arbitrary function, creating projections of the elements onto principal components lying on a lower dimensional subspace. In this fashion, kernel PCA is better equipped than PCA to reduce the dimensionality of non-linear data. See, for example, Schölkopf, "Nonlinear Component Analysis as a Kernel Eigenvalue Problem," Neural Computation, 10: 1299-1319 (198), which is hereby incorporated by reference.

Linear discriminant analysis (LDA), like PCA, reduces the dimensionality of a multidimensional vector by transforming the plurality of elements (e.g., measured elements) to a new set of variables (principal components) that summarize the features of the training set. However, unlike PCA, LDA is a supervised feature extraction method which (i) calculates between-class variance, (ii) calculates within-class variance, and then (iii) constructs a lower dimensional representation that maximizes between-class variance and minimizes within-class variance. See, for example, Tharwat, A., et al., "Linear discriminant analysis: A detailed tutorial," AI Communications, 30:169-90 (2017), which is hereby incorporated by reference.

Generalized discriminant analysis (GDA), similar to kernel PCA, maps non-linear input elements of multidimensional vectors into higher-dimensional space to provide linear properties of the elements, which can then be analyzed according to classical linear discriminant analysis. In this fashion, GDA is better equipped than LDA to reduce the dimensionality of non-linear data. See, for example, Baudat and Anouar, "Generalized Discriminant Analysis Using a Kernel Approach," Neural Comput., 12(10):2385-404 (2000).

Autoencoders are artificial neural networks used to learn efficient data codings in an unsupervised learning algorithm that applies backpropagation. Autoencoders consist of two parts, an encoder and a decoder. The encoder reads an input vector and compress it to a lower-dimensional vector, and the decoder reads the compressed vector and recreates the input vector. See, for example, Chapter 14 of Goodfellow et al., "Deep Learning," MIT Press (2016), which is hereby incorporated by reference.

Yet other dimension reductions techniques known in the art may also be applied to the methods described herein. For example, in some embodiments, a subset of features is selected for inclusion in a reduced dimension representation of a data point, while discarding other features, e.g., based on optimality criterion in linear regression. See, for example, Draper and Smith, "Applied Regression Analysis," 2d Edition, New York: John Wiley & Sons, Inc. (1981), which is hereby incorporated by reference. Similarly, in some embodiments, discrete methods, in which features are either selected or discarded, e.g., a leaps and bounds procedure, are used. See, for example, Furnival and Wilson, "Regressions by Leaps and Bounds," Technometrics, 16(4): 499-511 (1974), which is hereby incorporated by reference. Likewise, in some embodiments, linear regression by forward selection, backward elimination, or bidirectional elimination are used. See, for example, Draper and Smith, "Applied Regression Analysis," 2d Edition, New York: John Wiley & Sons, Inc. (1981). In yet other embodiments, shrinkage methods, e.g., methods that reduce/shrink the redundant or irrelevant features in a more continuous fashion are used, e.g., ridge regression, Lasso, and Derived Input Direction Methods (e.g., PCR, PLS).

Correlation Removal and Variance Standardization

In some embodiments, in the case where principal component analysis is used, each element of the multidimensional data points described herein represents a different principal component. As such, the resulting dimension-reduced vector includes principal components that are not normalized, and therefore the initial principal components which necessarily describe the greatest amount of variation have larger values then subsequent principal components. However, it is precisely these subsequent principal components that may have biological significance. Therefore, in some embodiments of the present disclosure the compounds are whitened to make all the principal components equal in value. For instance, in some embodiments, each respective principal component in the plurality of principal components is associated with a corresponding eigenvalue, and each respective principal component in the plurality of principal components is normalized by the square root of the corresponding eigenvalue prior to using the plurality of principal components to reexpress each respective vector in the plurality of vectors. In this way, the initial principal components do not overweight the comparison of vectors. More generally, any whitening transform, that is a linear transform that transforms a vector of random variables (here, the principal components) with a known covariance matrix into a set of new variables whose covariance is the identity matrix, can be used. Accordingly, there are many possible whitening procedures, including without limitation, whitening based on principal component analysis, the Cholesky matrix decomposition, and zero-phase component analysis. See, for example, Kessy A. et al., "Optimal Whitening and Decorrelation," The American Statistician, DOI: 10.1080/00031305.2016.1277159 (2018), which is hereby incorporated by reference.

EXAMPLES

Example 1—Identification of Therapies for Ataxia Telangiectasia

Ataxia telangiectasia (A-T) is a rare genetic neurodegenerative disease characterized by progressive difficulty with motor control and movement coordination (ataxia) beginning in early childhood. In addition, patients with A-T develop mucosal and cutaneous lesions due to blood vessel abnormalities (telangiectasias), increased infections due to immune dysfunction, and increased risk of lymphoma. Affected individuals often succumb to early death in the second or third decade of life due to infection or cancers.

A-T affects 1 in 40,000 individuals worldwide and is caused by mutations in the DNA-repair gene ATM, a gene expressed ubiquitously in the human body. A-T causing mutations result in impaired function of the ATM protein and defects in the DNA-damage response pathway. The disease preferentially affects cells of the cerebellum, immune system, and vasculature for unknown reasons. A-T is a devastating disease and there are currently no FDA-approved treatments that delay its progression. However, based on serendipitous findings of improvement in A-T patients' symptoms after incidental use of glucocorticoids, several human trials have been initiated to systematically evaluate their therapeutic efficacy. Betamethasone was tested in a study of 6 patients and found to improve neurological manifestations (Pignata et al. 2011). Experimenting with the route of administration of glucocorticoids, another group developed a cell-based therapeutic that involves infusion of patient-derived erythrocytes with dexamethasone. Results of a study of 22 patients with intra-erythrocyte dexamathasone demonstrated significant improvement in neurological symptoms (Magnani et al. 2014; Pignata et al. 2010). Thus, glucocorticoids currently represent one of the most advanced treatments for A-T.

Figure 9A:
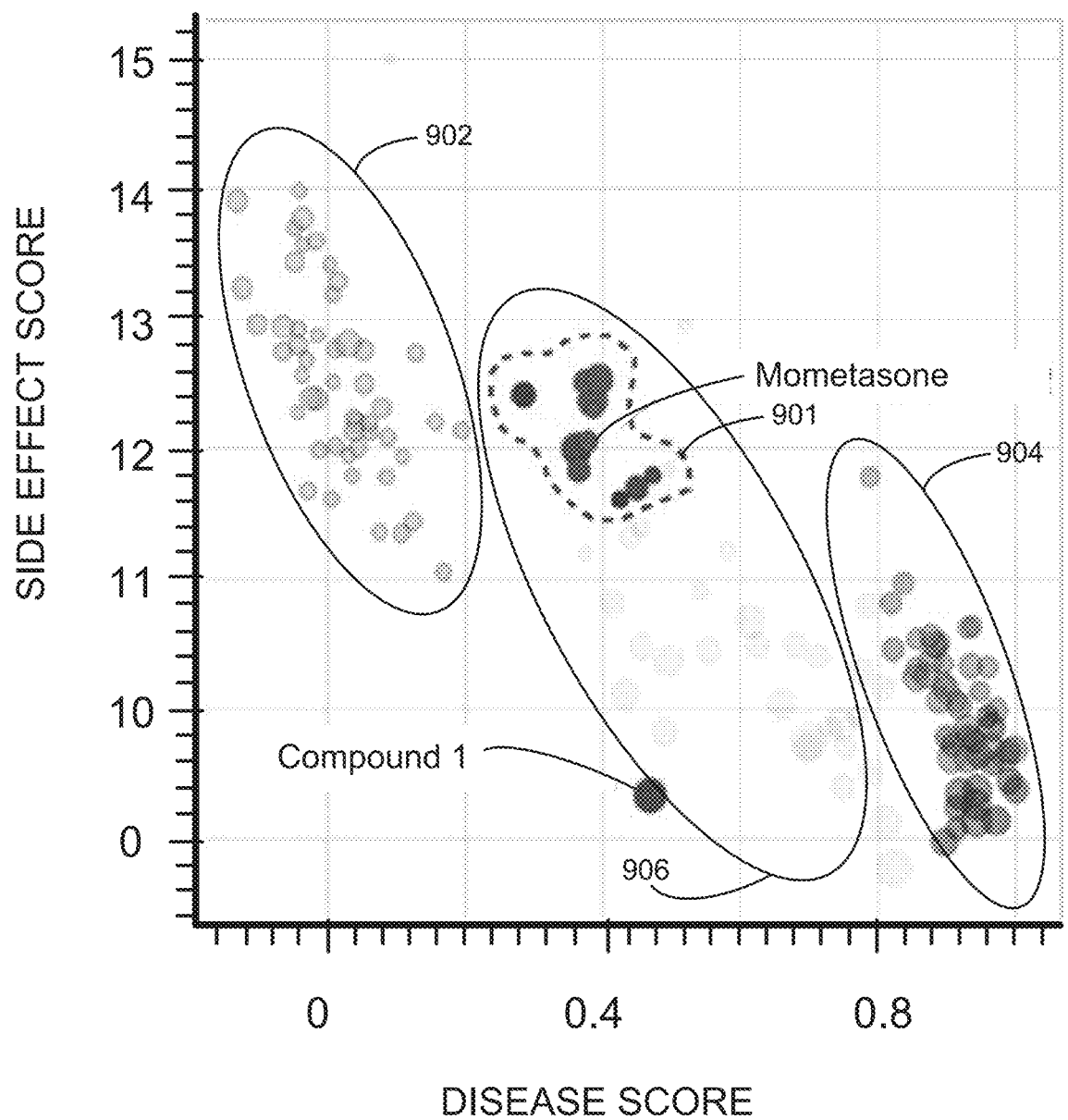
FIGS. 9A, 9B, 9C, and 9D illustrate example results from screens to identify drug candidates for A-T from a library of numerous small molecules, in accordance with various embodiments of the present disclosure.
Figure 9B:
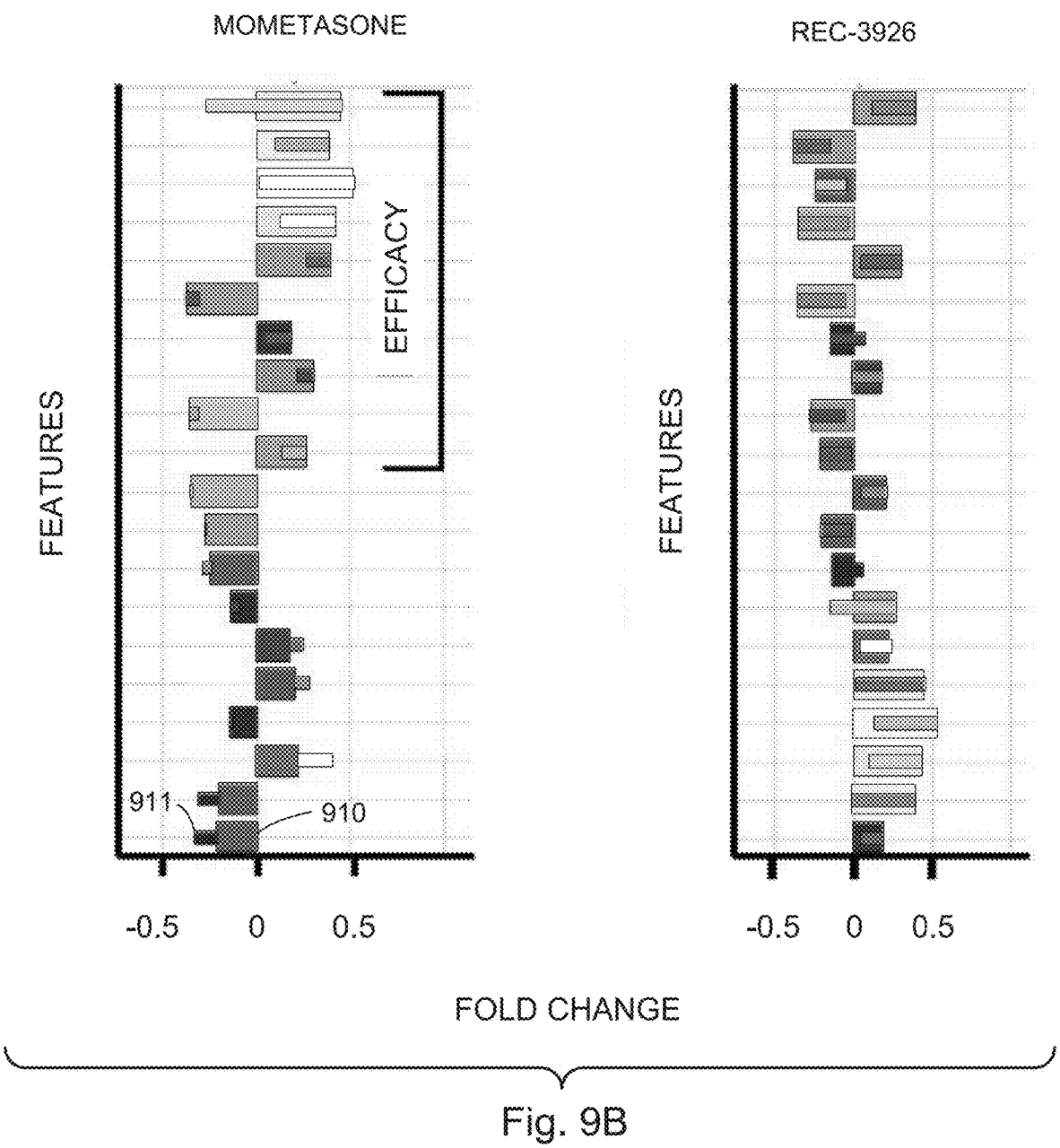
Figure 9C:
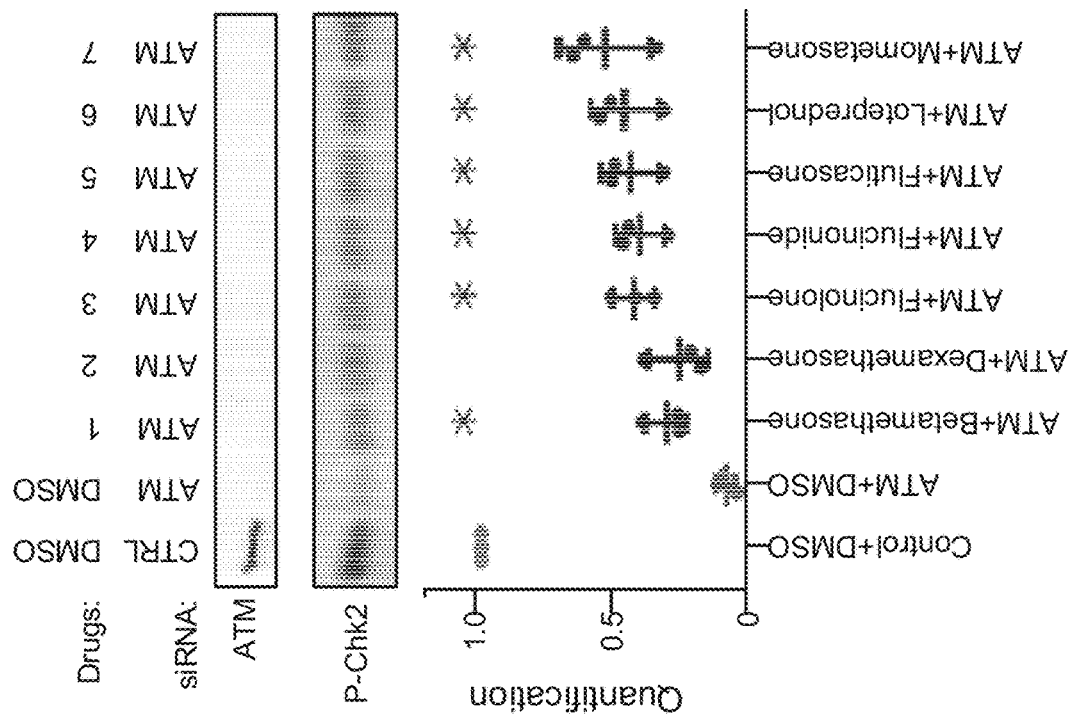
Figure 9D:
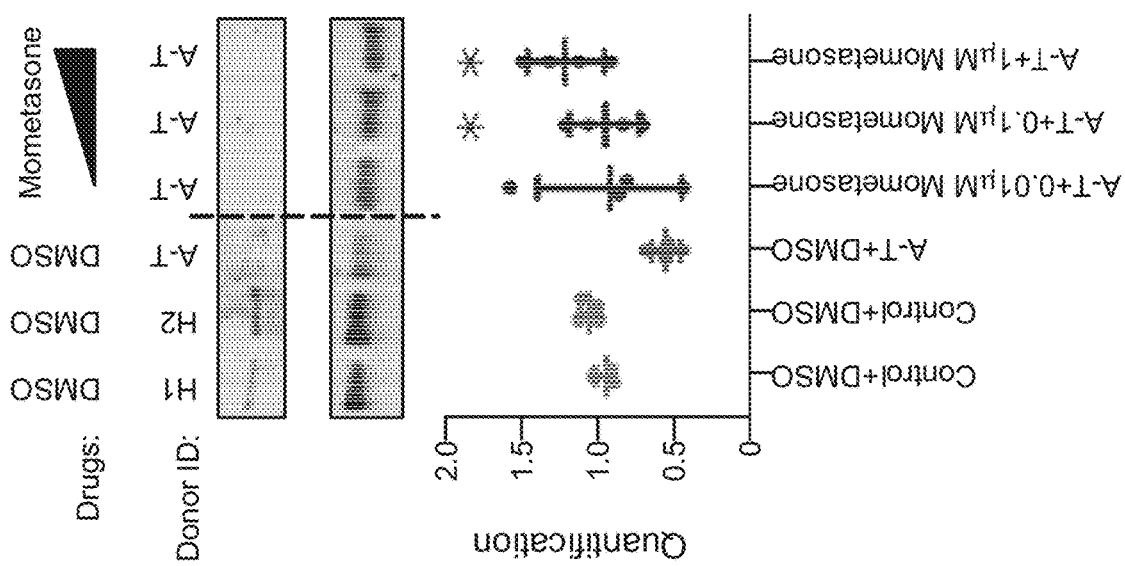

FIGS. 9A, 9B, 9C, and 9D illustrate results from screens to identify drug candidates for A-T from a library of numerous (e.g., 2000) small molecules. Hits were algorithmically selected based on effect and screened with a higher replicate count in a tertiary screen. As shown in FIG. 9A, results from a tertiary screen of the most efficacious compounds are plotted (red circles and shaded blue circles, mostly located in region 906) with respect to ATM deficient controls (green circles, and mostly located in region 904) and non-diseased controls (yellow circles, and mostly located in region 902). With respect to FIG. 9A, it is appreciated that various colors, shapes, and/or shading of the plotted items may be additionally or alternatively utilized. Glucocorticoids are identified by the dashed red polygon 901. Another highly attractive molecule based on its effect in the screen with little to no side effect profile, Compound 1, was found to act on a novel target for A-T. FIG. 9B illustrates, side-by-side, the impact of mometasone and novel the drug REC-3926 shown in FIG. 9A on the twenty most prominent phenotypic disease features. The length of the wider green bars, such as bar 910, represents changes in individual features of increasing or decreasing magnitude that best represent the ATM disease signature. The impact of each drug on individual features is overlaid in a second, narrower red shaded bar, such as bar 911. Drug class 2 rescues all of 20 features that comprise the disease signature for ATM deficiency, while mometasone rescues a subset of features (denoted by 'efficacy' bracket). The order of the features was randomized between individual plots, and individual feature labels are omitted. In some embodiments, the shade of the illustrated shape (and/or color) for a particular data point may be inversely proportional to the variance of the feature measurement. For example, in FIG. 9B, in some embodiments, the wide bars (such as bar 910) may be shaded green (as depicted) or another color, while the narrower bars (such as bar 911) may be shaded red (as depicted) or another color that is different from the wide bars; and the shade of green or red (or other selected color(s)) is inversely proportional to the variance of feature measurements. Likewise, for example, in FIG. 9A, a shade of a color such as green or red may be used to shade a symbol in a manner which is inversely proportional to the variance of the feature measurements. FIGS. 9C and 9D illustrate the effect of glucocorticoid hits on signaling pathways associated with ATM deficiency as assayed by Western Blot. siRNA transfected A549 cells (FIG. 9C) and primary fibroblasts from a patient with AT (FIG. 9D) were treated with $H_2O_2$ and drugs as indicated. Western blots probed for ATM and phosphorylated Chk2. All glucocorticoids except dexamethasone rescued Chk2 phosphorylation associated with ATM deficiency in the cell model. Mometasone further displayed a dose-dependent rescue of Chk2 phosphorylation in primary patient-derived cells. The lower plots represent quantification of phosphorylated Chk2 from the Western Blot, n=3. H=Healthy; *denotes p<0.05, two-sided paired ratio t-test.

To identify drug candidates for A-T, a strong Cell Painting™ (Bray et al. 2016) phenotype associated with ATM deficiency in A549 cells was detected (e.g., square-shaped 'disease' samples versus diamond shaped 'healthy control' samples as illustrated in FIG. 9A). Small molecule compounds were then tested on the A-T disease model using the screening methods described herein. In one example embodiment, from approximately 2,000 compounds, including FDA-approved compounds and other highly translatable molecules, strong class effects were identified among several drugs. In particular, glucocorticoids showed strong enrichment when selected for efficacy in the screen, with all candidates rescuing high-dimensional disease phenotypes with minimal increase in side effects (FIG. 9A). Among glucocorticoids, the screen revealed two distinct groups that were distinguishable based on their side effect profiles. The group with greater side effects included betamethasone and other glucocorticoids, while the second group included the glucocorticoid mometasone among others (FIG. 9A). Notably, in addition to steroids, a second compound class was identified with a strong efficacy signal and decreased side-effect profile in the screen (FIG. 9A, Compound 1). Evaluation of the impact of glucocorticoids on the A-T phenotype revealed a strong reduction in the features contributing to the cellular phenotype (FIG. 9B).

To further validate these compounds, disease-specific studies were performed. In response to DNA damage, ATM stimulates phosphorylation of a host of target proteins, including the checkpoint kinase Chk2. As expected, it was observed that siRNA-mediated knockdown of ATM mRNA in the A549 model cell-line suppressed phosphorylation of Chk2 after $H_2O_2$ treatment. Moreover, most glucocorticoids tested restored Chk2 phosphorylation to nearly 50% of control levels, with betamethasone and dexamethasone showing the least rescue (FIG. 9C). Given the attractive phenotypic (side effect and disease score) profile of Mometasone in the screen and superior P-Chk2 rescue in the model cell line, we further validated the effect of Mometasone on phosphorylation of Chk2 in primary fibroblasts derived from a patient with A-T. A dose-dependent increase in Chk2 phosphorylation was also observed in these studies (FIG. 9D), suggesting that the screening platform can identify and differentiate hits that are highly translatable.

In summary, the screening method described herein identified significant class effects among glucocorticoids for A-T, and further highlighted the ability of the best-in-screen molecule to rescue a disease-relevant biomarker in patient-derived cells. Notably, the least efficacious compounds identified on the platform have already shown efficacy in trials of patients with A-T. These results highlight the approach described herein to rapidly discover clinically relevant therapies, and further enable sensitive differentiation of potential best-in-class molecules.

Example 2—Identification of Therapies for Spinal Muscular Atrophy

Spinal muscular atrophy (SMA) is a devastating genetic disease characterized by progressive muscle weakness and paralysis resulting from degeneration of lower motor neurons in the spinal cord and brainstem nuclei. Onset ranges from prenatal through young adulthood. SMA is one of the most common genetic causes of mortality in children and its incidence and carrier frequency are estimated to be 1 in 10,000 and 1 in 50, respectively.

Mutations in the gene SMN1 (survival motor neuron 1) cause SMA. Humans carry a second survival motor neuron gene, SMN2, and increases in the copy number of SMN2 are known to reduce the clinical severity of SMA. Thus, an important therapeutic strategy has focused on agents that increase transcription of SMN2 or increase the functionality of the gene product through modulation of the splicing machinery. The gene products of SMN genes appear to be involved in small nuclear ribonucleoprotein (snRNP) biogenesis and function (Fischer et al. (1997), Liu et al. (1997), Pellizzoni et al. (1998)) and in U2-dependent splicing events in motor neurons (Huo et al 2014). There are currently no FDA-approved small molecules for the treatment of SMA, and an antisense oligonucleotide based therapy has only recently been approved (FDA).

Among small molecules, HDAC inhibitors have been extensively studied in spinal muscular atrophy (reviewed in Mohseni et al. (2013)). Valproic acid (VPA) was among the first HDAC inhibitors to show clinical promise for SMA. The drug increases full length SMN protein in cell-based assays and in patients, and showed a modest clinical improvement in some clinical trials (Darbar et al. (2011), Swoboda et al. (2010), and Piepers et al. (2011)). Studies have demonstrated that many compounds in this class increase production of SMN protein, though only VPA and phenyl butyric acid (PBA) have been evaluated in clinical studies to date (Mohseni et al. (2013)). Given the therapeutic potential demonstrated by these studies, the identification of selective, potent, and CNS active drugs in this class remains an important goal.

Figure 10A:
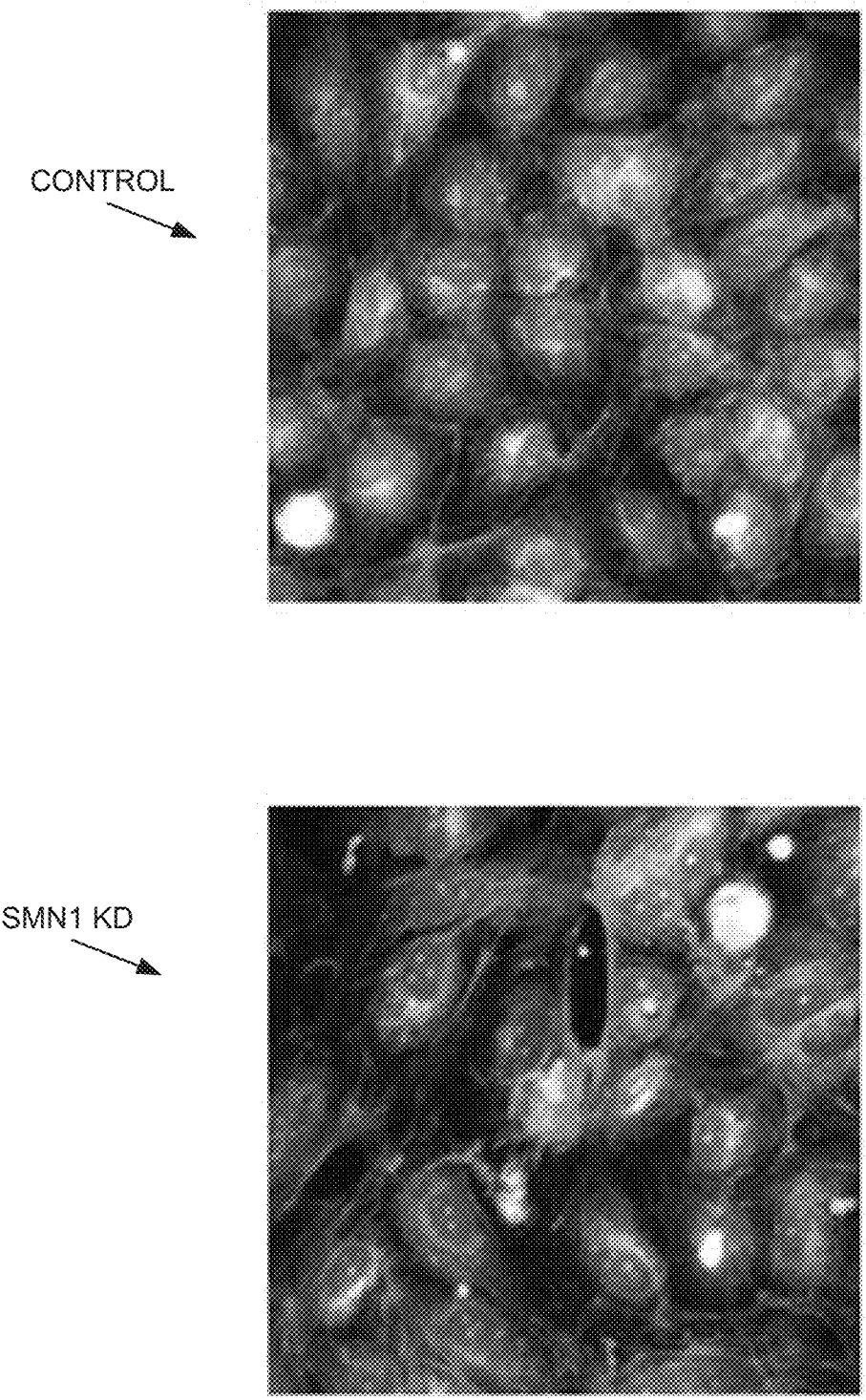
FIGS. 10A, 10B, 10C and 10D show examples of de novo identification of compounds that rescue a high-dimensional phenotype associated with SMA deficiency, in accordance with various embodiments of the present disclosure.
Figure 10B:
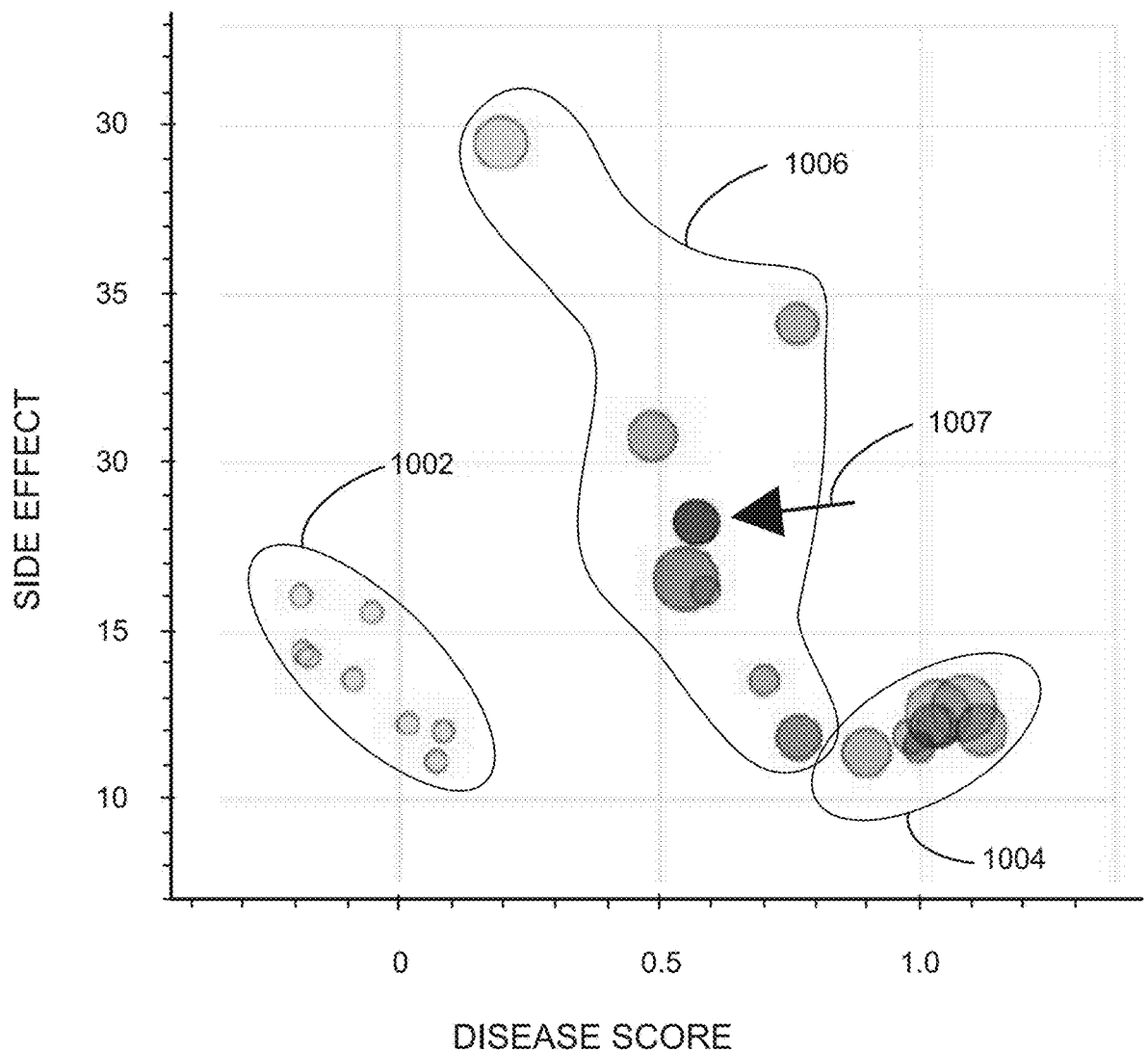
Figure 10C:
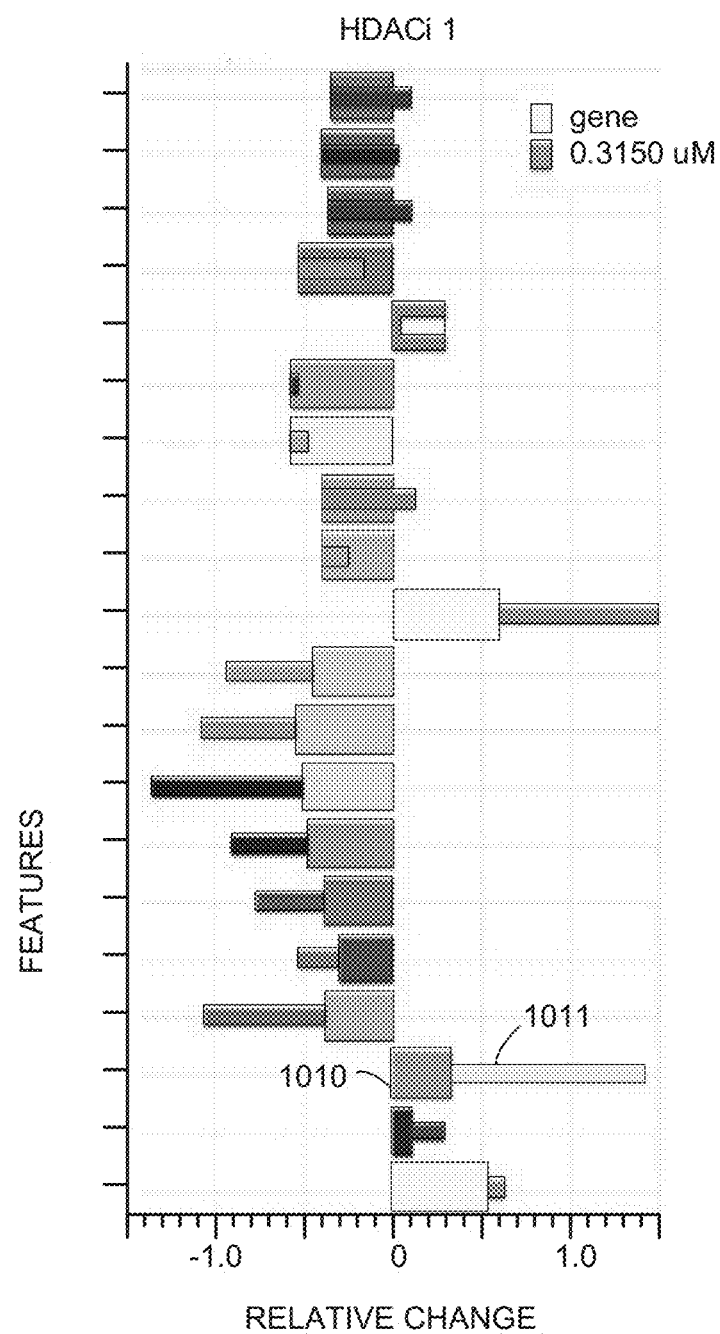
Figure 10D:
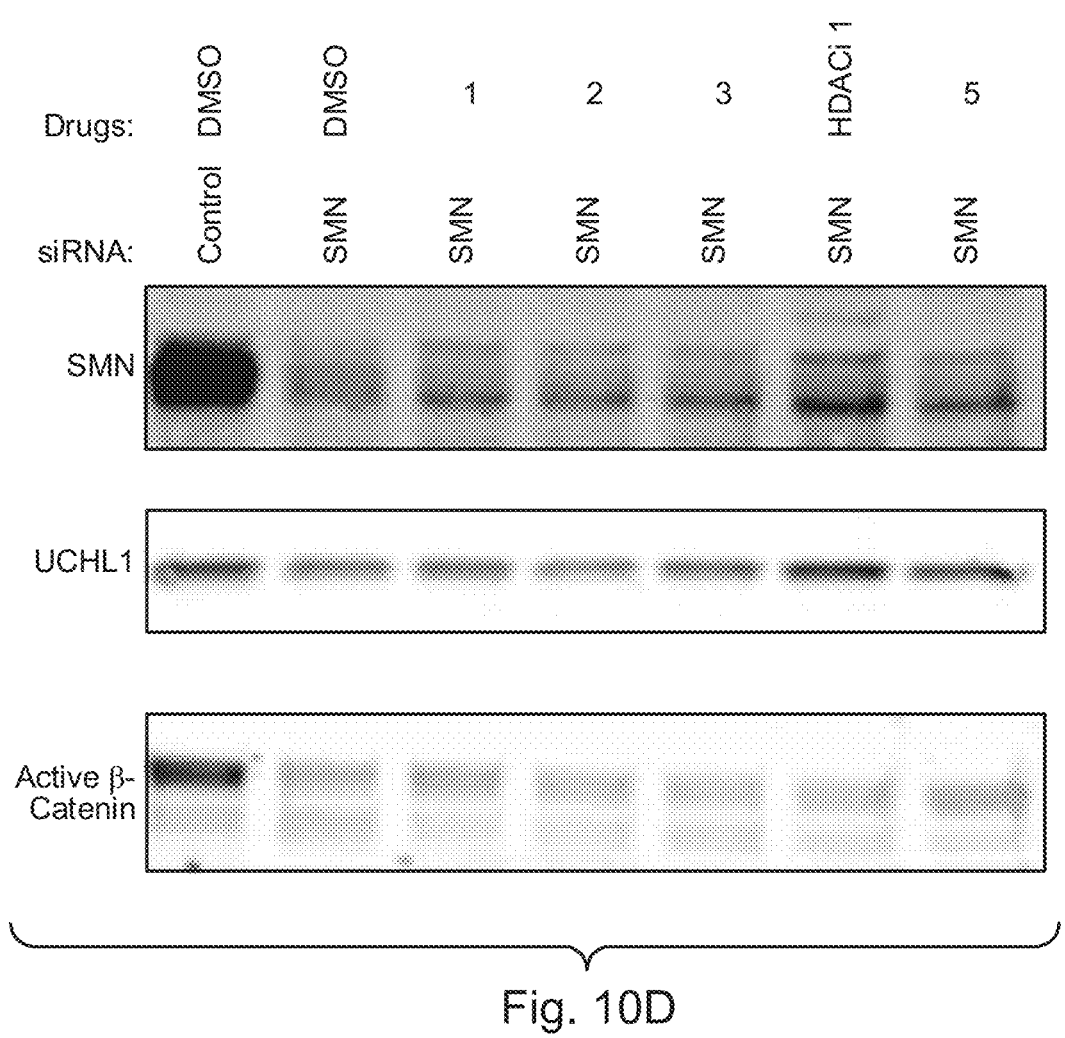

FIGS. 10A, 10B, 10C and 10D show de novo identification of compounds that rescue a high-dimensional phenotype associated with SMA deficiency. These figures illustrate results from screens to identify drug candidates for SMA. FIG. 10A shows representative images from a cellular imaging assay, as described herein, after SMN1/2 knockdown in HUVEC cells. FIG. 10B is a plot of on-target and on-target effects from several compounds identified based on their ability to rescue the SMN1/2 deficiency phenotype. 'Healthy' wells, SMN1 siRNA-treated 'sick' wells, and drug-treated sick wells are represented in groupings of dots 1002, 1004, and 1006, respectively. Two target classes were enriched from this screen, including HDAC inhibitors indicated by a representative drug (pointed to by arrow 1007). FIG. 10C illustrates rescue of SMN1/2 phenotypic features by HDAC inhibitor identified in FIG. 10B, with the relative fold-change in the gene expression represented as the wider outer boxes such as box 1010 and the effect of the inhibitor on the fold-change in expression represented by the overlaid narrower inner boxes such as box 1011. In FIG. 10C, colors and shading of colors of the boxes 1010 and 1011 may be used to illustrate variance in feature measurements. FIG. 10D shows that the HDAC inhibitors rescue SMN1/2 deficiency by increasing production of SMN1/2 protein.

A robust phenotype associated with SMN1/2 deficiency in HUVEC was identified (FIG. 10A) and small molecule screens were performed as described herein for compounds that rescue this phenotype. Several promising hits were recovered from these screens, including HDAC inhibitors, a drug class which has been under intense evaluation for the treatment of SMA. HDAC inhibition is thought to function by directly increasing transcription of the SMN2 gene by sustained acetylation of the SMN2 promoter. While no compound completely rescued the SMA phenotype, among the most efficacious hits in the model is a clinical stage HDAC inhibitor (FIG. 10B) and this drug rescued the 5 cellular features that are most contributory to the disease signature (FIG. 10C). Follow-up studies demonstrated that this compound rescues SMN1/2 deficiency by increasing production of SMN1/2 protein, likely through action on SMN2.

In summary, significant class effects were identified among multiple target classes, including HDACs, as potential treatments for SMA. This finding further demonstrates the ability of the screening method described herein to detect distinct classes of therapeutic effects, and rapidly uncover favorable treatments that may act directly on the target.

Example 3—Identification of Therapies for Neurofibromatosis Type 2

Spinal muscular atrophy (SMA) is a devastating genetic disease characterized by progressive muscle weakness and paralysis resulting from degeneration of lower motor neurons in the spinal cord and brainstem nuclei. Onset ranges from prenatal through young adulthood. SMA is one of the most common genetic causes of mortality in children and its incidence and carrier frequency are estimated to be 1 in 10,000 and 1 in 50, respectively.

Neurofibromatosis type 2 is an autosomal dominant cancer syndrome characterized by a predisposition to recurrent tumors in the central nervous system. Most commonly, patients with NF2 develop bilateral schwannomas (a clinical hallmark), meningiomas, and ependymomas which, while benign, can lead to hearing loss, paralysis, and early death (Martuza et al. 1988). While studies are ongoing to evaluate novel medical treatments for NF2, currently the standard of care is limited to surgical removal or radio ablation of tumors and supportive care for symptoms that arise from the disease. The disease affects an estimated 1 in 25,000 live births and exhibits near complete penetrance by 60 years of age (Asthagiri et al. (2009)).

NF2 is caused by loss of function mutations in the NF2 gene, which encodes the NF2 tumor suppressor protein. In addition to its role in neurofibromatosis, somatic inactivation of NF2 has been detected in 60% of sporadic meningiomas, a tumor that accounts for approximately 30% of intracranial neoplasms (Perry et al. (2004), Ruttledge et al. (1994)). An important challenge in therapeutic development for NF2 has been the characterization of complex biochemical pathways through which the protein exerts its functions. While recent results have identified multiple putative targets for medical intervention along disease relevant signaling pathways, an important challenge for the field remains understanding the most appropriate molecular target for therapeutic intervention (Evans et al. 2009).

To identify novel and effective treatments for NF2, a loss-of-function model of the disease in a primary human cells and screened for molecules that rescue the disease-specific phenotype. For example, consider an embodiment where 2000 small molecules screened, and the screening method described herein revealed 6 target classes with rescue activity, including novel targets yet to be described in the literature.

Figure 11C:
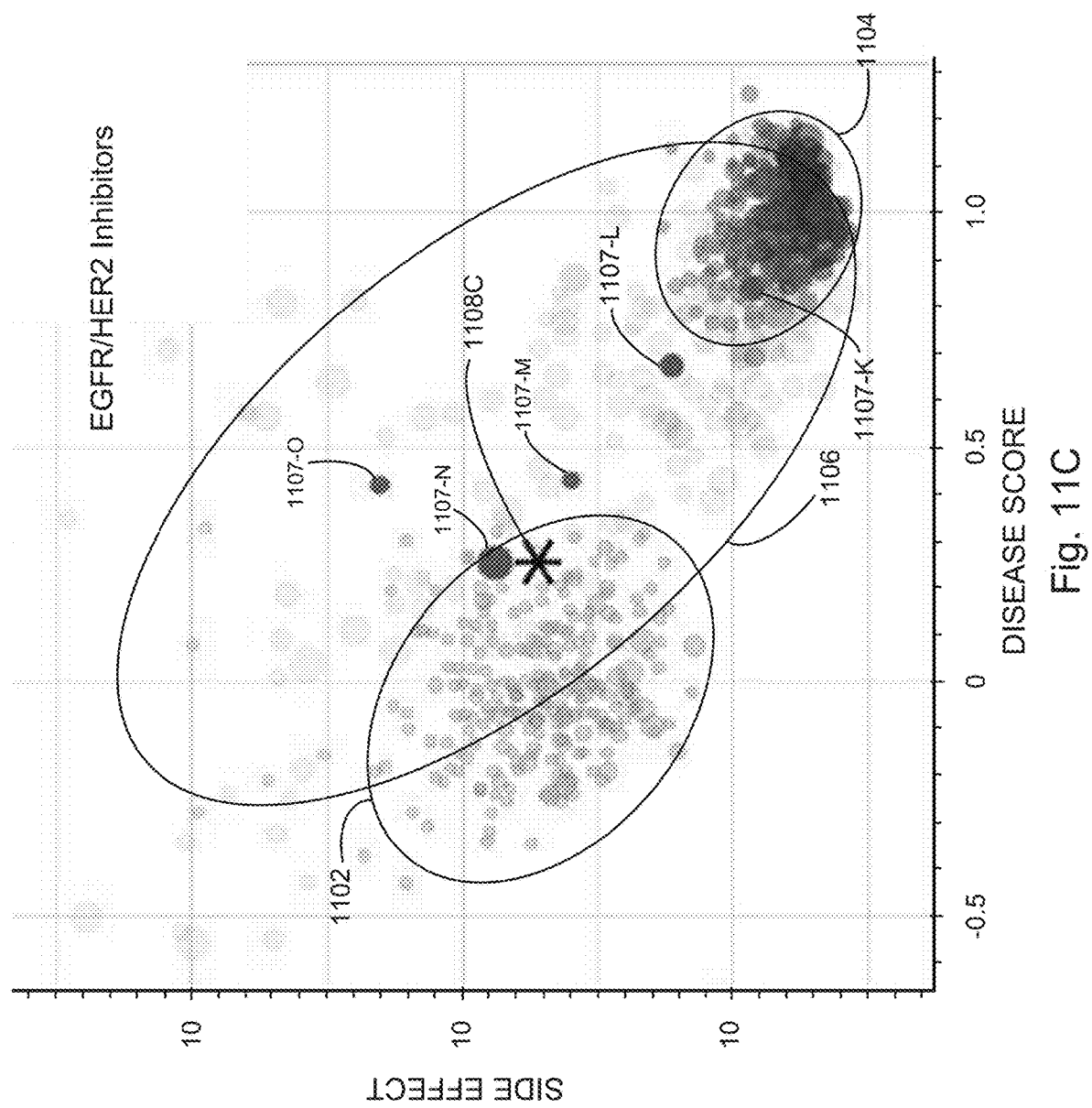

FIGS. 11A, 11B, and 11C show that inhibitors of mTOR, VEGF, and EGFR/Her2 rescue a high-dimensional phenotype associated with NF2 deficiency. These figures illustrate results from a series of primary drug screens to identify drug candidates for NF2 from a library of approximately 2000 small molecules. Scores for control perturbations (largely clustered in region 1102), test perturbations (largely clustered in region 1104), and query perturbations (largely clustered in region 1106), are shown in the plots. A small number of hits were algorithmically selected based on their effects in the assay and used for further screening. Compound classes 1107 (1107-A through 1107-O in FIGS. 11A-11C) with known efficacy are identified in the panels to demonstrate detection of phenotypic rescue on the platform: FIG. 11A=mTOR inhibitors (asterisk 1108-A identifies an alternative potential best in class molecule); FIG. 11B=VEGF inhibitors (arrow 1109 indicates sunitinib, asterisk 1108-B identifies an alternative potential best-in-class molecule); FIG. 11C=EGFR/Her2 inhibitors (asterisk 1108-C identifies a potential best in class molecule).

To date, three major target classes are in clinical development for NF2: mTOR inhibitors, VEGF inhibitors, and EGFR/Her2 inhibitors. Loss of NF2 leads to constitutive activation of mTOR complex 1 (mTORC1) signaling and thus, the mTORC1 inhibitor, everolimus, has been evaluated for clinical efficacy in the disease. While a Phase 2 study of Everolimus failed to demonstrate efficacy (Allen et al. (2014)), a Phase 2 study with a novel, highly selective mTOR inhibitor AZD2014 is currently underway (NCT02831257). Notably, in the screening methods described here, everolimus showed minimal efficacy and was not advanced to secondary screens. However, AZD2014 demonstrated strong rescue albeit with an elevated side-effect profile compared to another highly selective mTOR inhibitor (FIG. 11A, asterisk).

Blockade of vascular endothelial growth factor (VEGF) signaling has also been evaluated as a therapeutic approach for NF2. The VEGF receptor tyrosine kinase inhibitor sunitinib recently demonstrated activity in a Phase 2 study of recurrent, refractory meningioma, including patients with NF2 loss-of-function mutations (Omuro et al. (2015)). A second VEGF inhibitor, axitinib, is currently in Phase 2 for NF2 (NCT02129647). In the primary screening described herein, axitinib did not show sufficient efficacy to be advanced to follow-on assays. However, Sunitinib demonstrated a moderate rescue of NF2 loss-of-function phenotypes with minimal increase in side-effect profile (FIG. 11B, arrowhead). As with mTOR inhibitors, the screening methods described herein were able to identify a compound with a more striking efficacy profile that produced a complete rescue of the disease phenotype with minimal side effects (FIG. 11B, asterisk 1108-B).

The role of endothelial growth factor (EGFR) and Her2/ErbB2 signaling in NF2 is well documented in the literature and blockade of this signaling pathway with EGFR/Her2 inhibitors reduces proliferation of NF2-deficient glial cells (Houshmandi et al. (2009)). A Phase 2 study of the EGFR/ErbB2 inhibitor lapatinib was recently carried out in patients with NF2. The study found that lapatinib was well tolerated and produced antitumor activity in a subset of patients with NF2 (Allen et al. 2012). While lapatinib was not specifically evaluated in the primary screens described herein, several EGFR/ErbB2 inhibitors rescued NF2 loss-of-function phenotypes, with one drug in this class producing a robust rescue (FIG. 11C), further demonstrating that the screening method described herein can rapidly and sensitively identify clinically relevant drug classes.

Example 4—Identification of Therapies for Hereditary Hemorrhagic Telangiectasia

Hereditary hemorrhagic telangiectasia (HHT), is an autosomal dominant genetic disorder characterized by recurrent epistaxis (nosebleeds) and increased rick of arteriovenous malformations (AVMs). The disease causes abnormal blood vessel formation in the skin, mucous membranes, and often in organs such as the lungs, liver, and brain. Normally, capillaries connect high pressure arteries to low pressure veins. However, in HHT, malformation in capillary beds creates direct connection between the high pressure arteries and fragile veins, which can cause the veins to rupture resulting in internal bleeding.

Figure 12B:
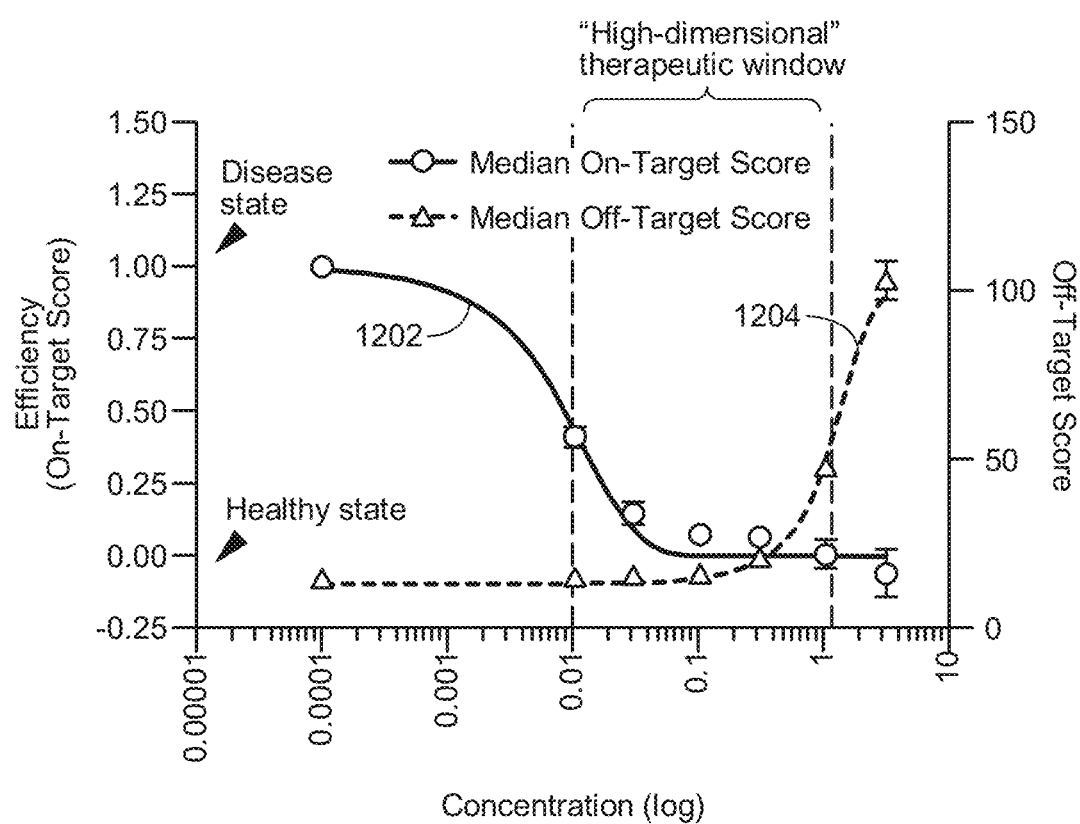
Figure 12C:
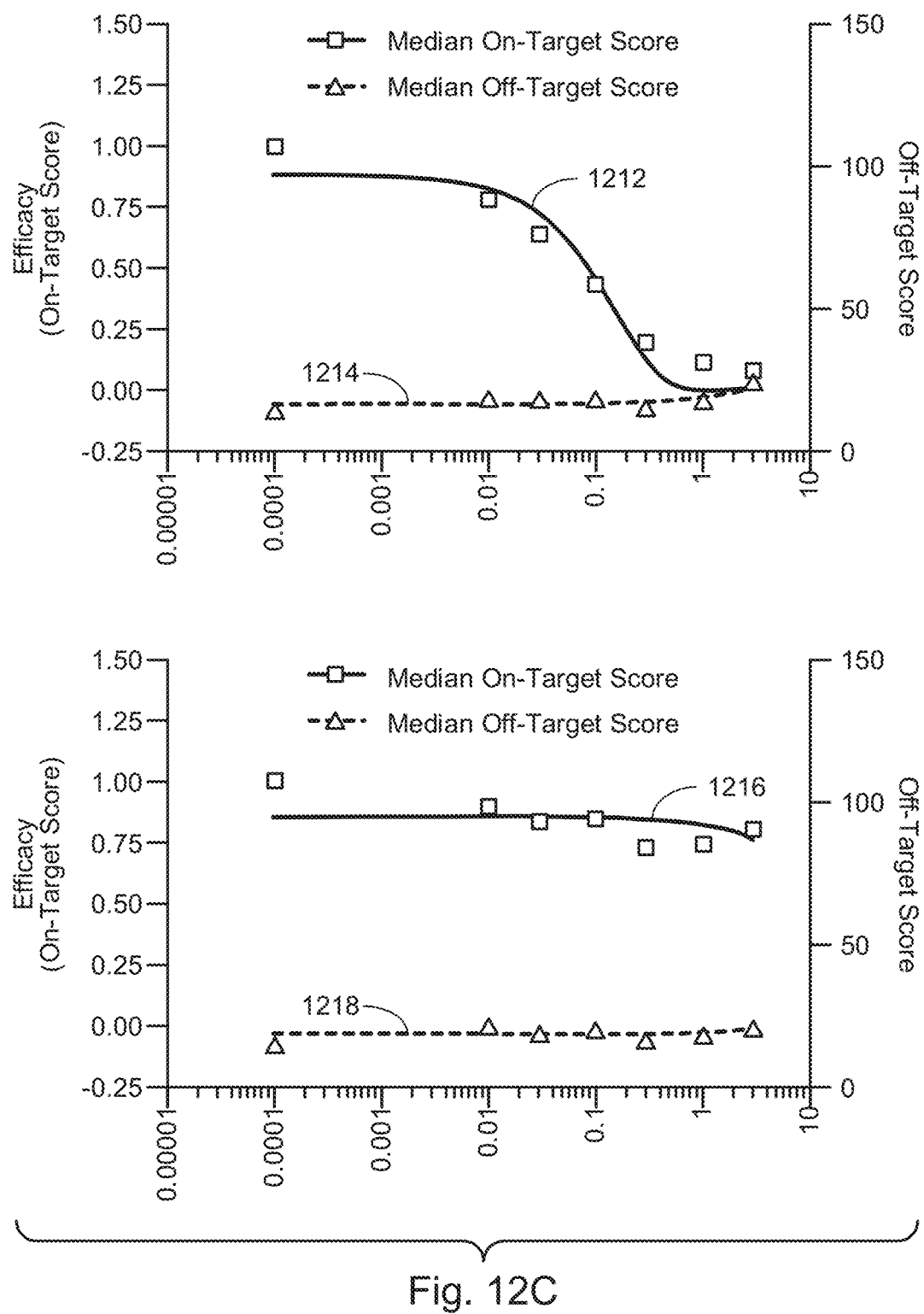
Figure 12D:
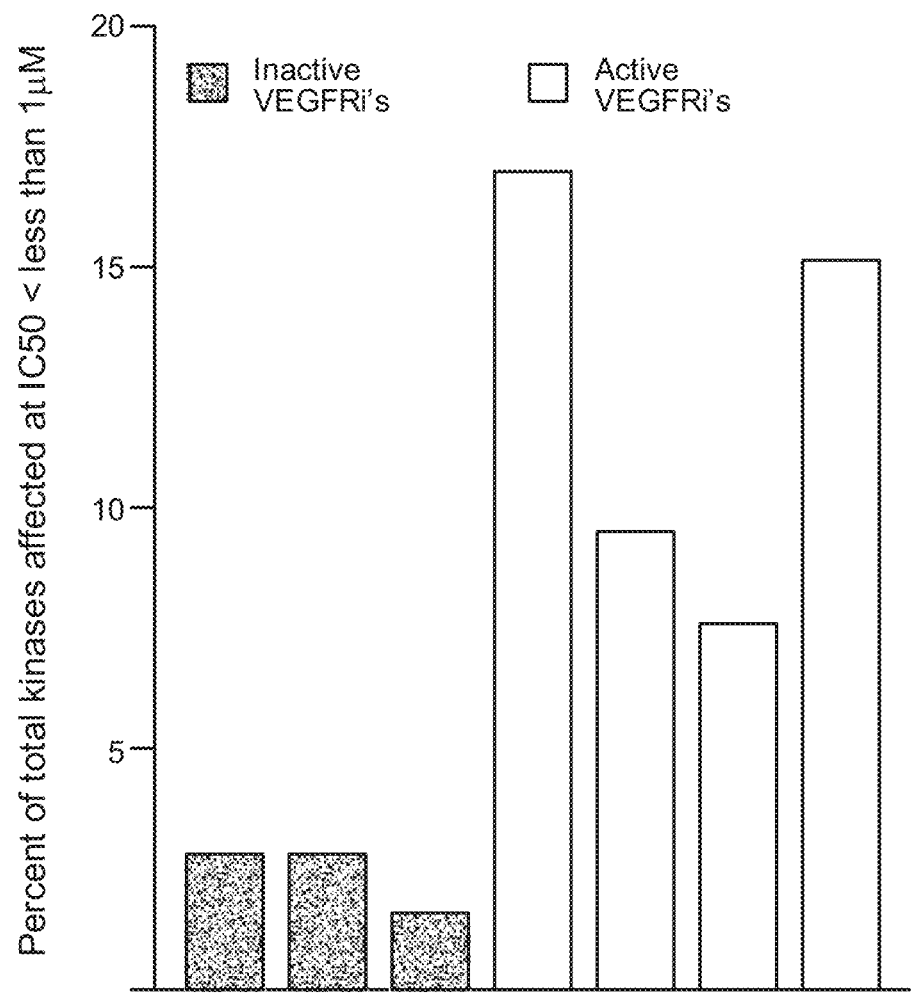
Figure 12E:
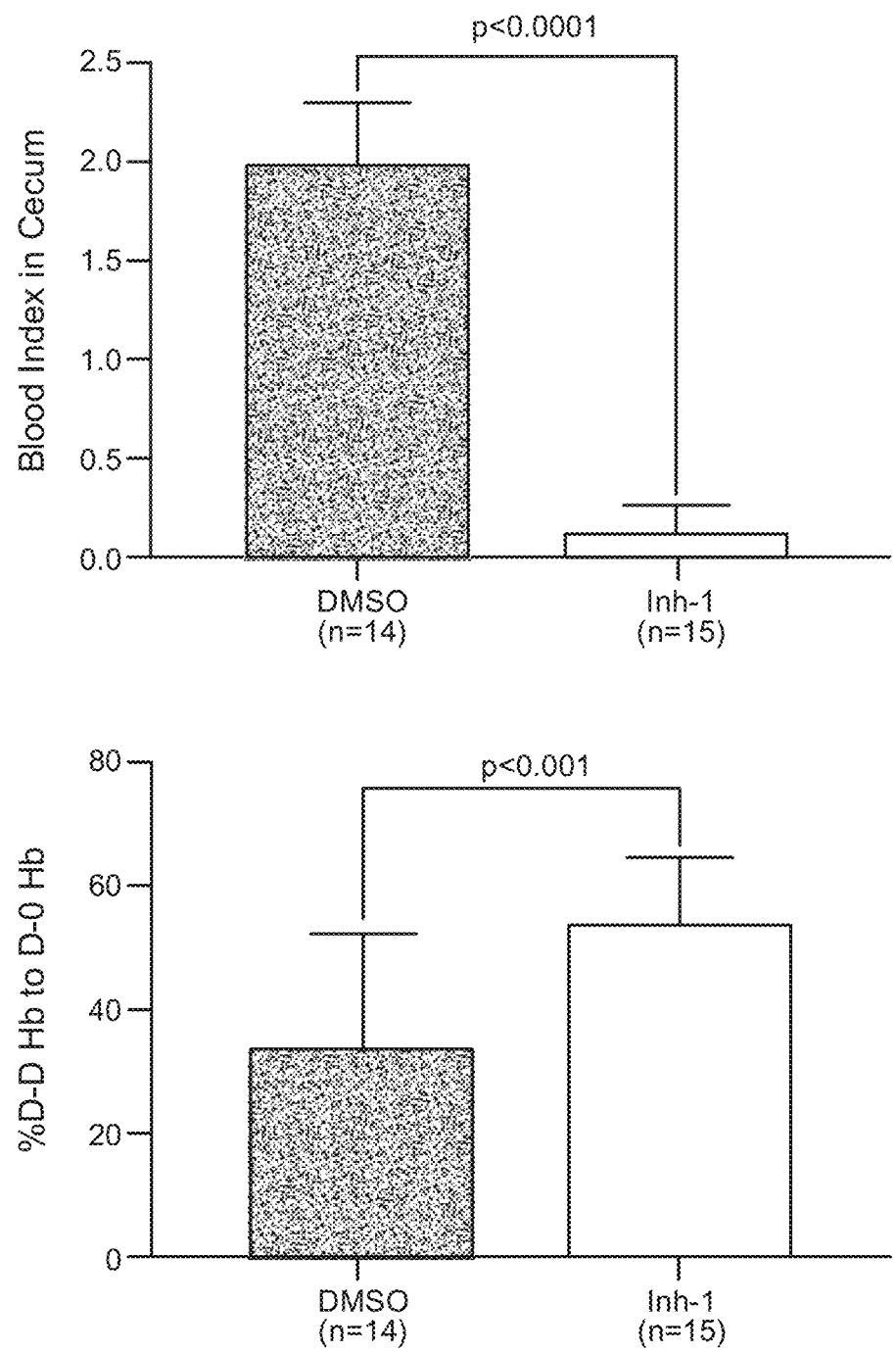

FIGS. 12A, 12B, 12C, 12D, and 12E illustrate results from screens of VEGFR inhibitors to identify drug candidates for the treatment of HHT, using an ACVRL1 knock down model. FIG. 12A shows cells in the test state (1220) versus the control state (1230), and query perturbations 1240, 1250, and 1260 incorporating increasing amounts of an Inh-1 drug candidate (bottom panels, left-to-right). FIG. 12B illustrates on-target and off-target model curves for a range of Inh-1 concentrations. FIG. 12C illustrates median on-target and off-target model curves for VEGFR inhibitors that were effective in the screen (top panel) and VEGFR inhibitors that were ineffective in the screen (bottom panel). FIG. 12D illustrates the percentage of total kinases that were affected by VEGFR inhibitors that were ineffective in the screen (left three) and effective in the screen (right four). Finally, FIG. 12E illustrates the reduction of bleeding caused by Inh-1 administration to ACVRL1-GI bleeding mice models.

One strategy being investigated for the treatment of HHT is administration of anti-angiogenic agents, such as vascular endothelial growth factor receptor (VEGFR) tyrosine kinase inhibitors. To identify novel and effective treatments for HHT, a loss-of-function model of the disease, based on knock-down of ACVRL1 translation, was screened for VEGFR inhibitors that rescue disease-specific phenotype in cell culture, using the image-based methods described herein. As shown in FIG. 12A, the ACVRL1 knock down model causes an elongated cellular phenotype (upper left panel), as compared to the round cell phenotype of healthy control cells (upper right panel). Increasing concentrations of Inh-1 (bottom panels, increasing left to right) rescue the elongated disease phenotype.

On-target and off-target scores for Inh-1 were then determined across a $1 \times 10^6$-fold titration of the drug, calculated as described herein. As shown in FIG. 12B, there is a 100-fold therapeutic window, at which Inh-1 rescues the disease phenotype in the cellular assays (as represented by curve 1202) without causing substantial off-target effects (as represented by curve 1204). As shown in FIG. 12C, the ability of Inh-1 to rescue the ACVRL1 knock down phenotype is not simply a VEGFR inhibitor effect, as only a subset of VEFR inhibitors are active in this model. Specifically, on-target (1212 and 1216) and off-target (1214 and 1218) effects for various VEGFR inhibitors were determined across a $5 \times 10^4$-fold concentration range. The top panel of FIG. 12C illustrates the median values determined for VEGFR inhibitors that were active in the model, while the bottom panel illustrates the median values determined for VEGFR inhibitors that were inactive in the model. Further experimentation, as shown in FIG. 12D, revealed that polyphamacology may be necessary to rescue the ACVRL1 knock down phenotype, as the VEGFR inhibitors that were active in the model inhibited multiple kinases at an IC50<1 μM. In contrast, the VEGFR inhibitors that were inactive in the model inhibited significantly fewer kinase inhibitors. The results for Inh-1 are indicated by the dashed box.

The in vivo effect of Inh-1 was tested by administration of the compound to an ACVRL1-GI bleeding mouse model. As shown in FIG. 12E, dissection and visualization of GI tissues in these mice reveals statistically significant reduction in bleeding ($p<0.0001$ (top graph); $p<0.001$ (bottom graph)) for the animals treated with Inh-1, as compared to DMSO treated control mice.

Succinct Descriptions of Various Aspects and Embodiments

Some of the aspects and embodiments described herein are summarized in the following non-inclusive succinct description of various aspects and embodiments:

1. A computer system embodiment for evaluating a query perturbation, in a cell based assay representing a test state, the cell based assay comprising a plurality of wells across one or more plates, the computer system comprising:

one or more processors;

a memory; and one or more programs, wherein the one or more programs are stored in the memory and are configured to be executed by the one or more processors, the one or more programs including instructions for:

(A) obtaining, for each respective control perturbation in a set of control perturbations, a corresponding control data point, thereby obtaining a plurality of control data points, wherein each corresponding control data point comprises a plurality of dimensions, each dimension in the plurality of dimensions representing a measure of central tendency of a different feature, in the plurality of features, determined across a corresponding plurality of control aliquots of cells in corresponding wells, in the plurality of wells, representing the respective control perturbation;

(B) obtaining, for each respective test perturbation in a set of one or more test perturbations, a corresponding test data point, thereby obtaining a plurality of test data points, wherein each corresponding test data point comprises the plurality of dimensions, each dimension in the plurality of dimensions comprising a measurement of central tendency of a different feature, in the plurality of features, determined across a corresponding plurality of test aliquots of the cells representing the respective test perturbation in corresponding wells in the plurality of wells;

(C) computing a composite test vector, the composite test vector between (i) a first point defined by a respective measure of central tendency across the plurality of control data points for each dimension in the plurality of dimensions and (ii) a second point defined by a respective measure of central tendency across the plurality of test data points for each dimension in the plurality of dimensions;

(D) obtaining a plurality of query perturbation data points, wherein each corresponding query perturbation data point comprises the plurality of dimensions, each dimension in the plurality of dimensions comprising a measure of central tendency of a different feature, in the plurality of features, determined across a plurality of instances of query perturbation aliquots of the cells representing a respective test perturbation, in the plurality of test perturbations, and a first amount of the query perturbation in a corresponding subset of the plurality of wells;

(E) computing a query perturbation vector, between (i) the first point and (ii) a respective measure of central tendency across the plurality of query perturbation data points for each dimension in the plurality of dimensions;

(F) computing an on-target score for the query perturbation as a projection of the query perturbation vector onto the composite test vector;

(G) computing an off-target score for the query perturbation as a rejection of the query perturbation vector against the composite test vector; and (H) evaluating the off-target score for the query perturbation thereby evaluating the query perturbation.

2. The computer system of embodiment 1, the one or more programs further including instructions for repeating the obtaining (D), computing (E), computing (F), and computing (G) for each query perturbation in a plurality of query perturbations and wherein the evaluating (H) comprises plotting each respective query perturbation in the plurality of query perturbations on a two-dimensional plot using the on-target score for the respective query perturbation as a coordinate in a first dimension of the two-dimensional plot and the off-target score for the respective query perturbation as a coordinate in a second dimension of the two-dimensional plot.

3. The computer system of embodiment 2, the one or more programs further including instructions for:

computing, for each respective control perturbation in the plurality of control perturbations, a corresponding control vector between (i) the first point and (ii) a second point defined by a measure of central tendency across the control data points associated with the respective control perturbation, for each dimension in the plurality of dimensions, thereby computing a plurality of control vectors; and computing an on-target score for each control perturbation as a projection of the corresponding control vector, in the plurality of control vectors, onto the composite test vector;

computing an off-target score for each control perturbation as a rejection of the corresponding control vector against the composite test vector; and wherein the evaluating (H) further comprises plotting each control perturbation in the plurality of control perturbations on the two-dimensional plot using the on-target score for the respective control perturbation as a coordinate in the first dimension and the off-target score for the respective control perturbation as a coordinate in the second dimension of the two-dimensional plot.

4. The computer system of embodiment 2, the one or more programs further including instructions for:

computing, for each respective well in the plurality of wells representing a control perturbation in the plurality of control perturbations, a corresponding control vector between (i) the first point for each dimension in the plurality of dimensions and (ii) a second point defined by a value of the corresponding feature, in the plurality of features, determined from the respective well, thereby computing a plurality of control vectors; and (F)(1) computing an on-target score for each respective control vector in the plurality of control vectors as a projection of the corresponding control vector onto the composite test vector;

(G)(1) computing an off-target score for each respective control vector in the plurality of control vectors as a rejection of the respective control vector against the composite test vector; and wherein the evaluating (H) further comprises plotting each respective control vector in the plurality of control vectors on the two-dimensional plot using the on-target score for the respective control vector as a coordinate in the first dimension and the off-target score for the respective control vector as a coordinate in the second dimension of the two-dimensional plot.

5. The computer system of any one of embodiments 2-4, the one or more programs further including instructions for:

computing, for each respective test perturbation in the plurality of test perturbations, a corresponding test vector between (i) the first point for each dimension in the plurality of dimensions and (ii) a second point defined by a measure of central tendency across the test data points associated with the respective test perturbation, thereby computing a plurality of test vectors;

computing an on-target score for each test perturbation as a projection of the corresponding test vector, in the plurality of test vectors, onto the composite test vector; and computing an off-target score for each test perturbation as a rejection of the corresponding test vector against the composite test vector; and wherein the evaluating (H) further comprises plotting each test perturbation in the plurality of test perturbations on the two-dimensional plot using the on-target score for the respective test perturbation as a coordinate in the first dimension and the off-target score for the respective test perturbation as a coordinate in the second dimension of the two-dimensional plot.

6. The computer system of any one of embodiments 2-4, the one or more programs further including instructions for:

computing, for each respective well in the plurality of wells representing a test perturbation in the plurality of test perturbations, a corresponding test vector between (i) the first point for each dimension in the plurality of dimensions and (ii) a second point defined by a measurement of the corresponding feature, in the plurality of features, in the respective well, thereby computing a plurality of test vectors; and (F)(2) computing an on-target score for each respective test vector in the plurality of test vectors as a projection of the corresponding test vector onto the composite test vector;

(G)(2) computing an off-target score for each respective test vector in the plurality of test vectors as a rejection of the respective test vector against the composite test vector; and wherein the evaluating (H) further comprises plotting each respective test vector in the plurality of test vectors on the two-dimensional plot using the on-target score for the respective test vector as a coordinate in the first dimension and the off-target score for the test vector as a coordinate in the second dimension of the two-dimensional plot.

7. The computer system of embodiment 5 or 6, the one or more programs further including instructions for:

coloring the plot of each respective test vector in the plurality of test vectors in the two-dimensional plot with a first color;

coloring the plot of each respective control vector in the plurality of control vectors in the two-dimensional plot with a second color; and coloring the plot of each query perturbation in the plurality of query perturbations in the two-dimensional plot with a third color.

8. The computer system of embodiment 5, the one or more programs further including instructions for sizing the plot of each respective test vector in the plurality of test vectors in the two-dimensional plot as a function of a variance of the measure of central tendency of the second point used to construct the respective test vector.

9. The computer system of embodiment 3, the one or more programs further including instructions for sizing the plot of each respective control vector in the plurality of control vectors in the two-dimensional plot as a function of a variance of the measure of central tendency of the second point used to construct the respective control vector.

10. The computer system of any one of embodiments 2-9, the one or more programs further including instructions for sizing the plot of each respective query perturbation in the plurality of query perturbations in the two-dimensional plot as a function of a variance of the respective measure of central tendency of the plurality of query perturbation data points for each dimension in the plurality of dimensions for the respective query perturbation.

11. The computer system of any one of embodiments 1-10, wherein the set of control perturbations consists of a plurality of control siRNA that do not directly affect expression of a gene associated with the test state.

12. The computer system of embodiment 11, wherein the plurality of control siRNA consists of between 10 and 50 different control siRNA.

13. The computer system of any one of embodiments 1-12, wherein the set of test perturbations consists of a plurality of target siRNA that directly affect expression of a gene associated with the test state.

14. The computer system of embodiment 13, wherein the plurality of target siRNA consists of between 4 and 12 different target siRNA.

15. The computer system of any one of embodiments 1-14, wherein the measure of central tendency of the different feature determined across the corresponding plurality of control aliquots of the cells representing the respective control perturbation is an arithmetic mean, weighted mean, midrange, midhinge, trimean, geometric mean, geometric median, Winsorized mean, median, or mode of the different feature across between two and twenty control aliquots of the cells representing the respective control perturbation in between two and twenty corresponding wells in the plurality of wells.

16. The computer system of any one of embodiments 1-15, wherein the measure of central tendency of the different feature across the corresponding plurality of test aliquots of the cells representing the respective test perturbation is an arithmetic mean, weighted mean, midrange, midhinge, trimean, geometric mean, geometric median, Winsorized mean, median, or mode of the different feature across between two and twenty test aliquots of the cells upon exposure representing the respective test perturbation in between two and twenty corresponding wells in the plurality of wells.

17. The computer system of any one of embodiments 1-16, wherein the measure of central tendency of the different feature across the corresponding plurality of query perturbation aliquots of the cells jointly representing the respective test perturbation and the query perturbation is an arithmetic mean, weighted mean, midrange, midhinge, trimean, geometric mean, geometric median, Winsorized mean, median, or mode of the different feature across between two and twenty query perturbation aliquots of the cells jointly representing the respective test perturbation and the query perturbation in between two and twenty corresponding wells in the plurality of wells.

18. The computer system of any one of embodiments 1-17, wherein each feature is derived from a combination of measurable characteristics selected from a color, a texture, and a size of the cell context, or an enumerated portion of the cell context.

19. The computer system of any one of embodiments 1-18, wherein the obtaining (A) comprises imaging a corresponding well in the plurality of wells to form a corresponding two-dimensional pixelated image having a corresponding plurality of native pixel values and wherein a different feature in the plurality of features of the obtaining (A) arises as a result of a convolution or a series convolutions and pooling operators run against native pixel values in the corresponding plurality of native pixel values of the corresponding two-dimensional pixelated image.

20. The computer system of any one of embodiments 1-19, wherein the respective plurality of control aliquots of the cells is exposed to the respective control perturbation for at least one hour prior to obtaining measurement of characteristics used to derive each feature in the plurality of features across the plurality of control aliquots.

21. The computer system of any one of embodiments 1-20, wherein the plurality of test aliquots of the cells is exposed to the respective test perturbation or at least one hour, two hours, three hours, one day, two days, three days, four days, or five days prior to obtaining measurement of characteristics used to derive each feature in the plurality of features across the plurality of test aliquots.

22. The computer system of any one of embodiments 1-21, wherein the plurality of query perturbation aliquots of the cells is exposed to the respective test perturbation and the query perturbation for at least one hour, two hours, three hours, one day, two days, three days, four days, or five days prior to obtaining measurement of characteristics used to derive each feature in the plurality of features across the plurality of query perturbation aliquots.

23. The computer system of any one of embodiments 1-22, wherein the plurality of dimensions consists of between 5 dimensions and 100,000 dimensions.

24. The computer system of any one of embodiments 1-23, wherein:
the plurality of features comprises a plurality of dimension reduction components; and each dimension reduction component in the plurality of dimension reduction components is a principal component derived by principal component analysis.

25. The computer system of any one of embodiments 1-24, wherein each feature in the plurality of features is determined from a characteristic that is optically measured.

26. The computer system of any one of embodiments 1-25, wherein
a first subset of the plurality of features are determined from characteristics that are optically measured; and
a second subset of the plurality of features are determined from characteristics that are non-optically measured.

27. The computer system of any one of embodiments 1-24, wherein each feature in the plurality of features is a feature is determined from a characteristic that is non-optically measured.

28. The computer system of embodiment 1, wherein:
the corresponding plurality of control aliquots of the cells of the obtaining (A) consists of cells of a single cell type,
the corresponding plurality of test aliquots of the cells of the obtaining (B) consists of cells of the single cell type, and
the plurality of instances of query perturbation aliquots of the cells jointly representing the respective test perturbation and the query perturbation of the obtaining (D) consists of cells of the single cell type.

29. The computer system of embodiments 2-27, wherein:
the corresponding plurality of control aliquots of the cells of each instance of the obtaining (A) consists of cells of a single cell type,
the corresponding plurality of test aliquots of the cells of each instance of the obtaining (B) consists of cells of the single cell type, and
the plurality of instances of query perturbation aliquots of the cells jointly representing the respective test perturbation and the query perturbation of each instance of the obtaining (D) consists of cells of the single cell type.

30. The computer system of any one of embodiments 1-29, wherein the obtaining (D), computing (E), computing (F), and computing (G) is repeated for each cell type in a plurality of cell types.

31. The computer system of embodiment 30, wherein the plurality of cell types comprises three cell types.

32. The computer system of embodiment 30, wherein the plurality of cell types comprises a first cell type and a second cell type that is the first cell type upon incurring a genetic modification.

33. The computer system of embodiment 32, wherein the genetic modification comprises at least one genetic deletion or insertion.

34. The computer system of any one of embodiment 1-33, wherein
the corresponding wells in the plurality of wells for the plurality of control aliquots of the cells of the obtaining (A) includes a first plurality of wells, wherein each well in the first plurality of wells comprises an aliquot of a different type of cells in a corresponding plurality of cell types,
the corresponding wells in the plurality of wells for the plurality of test aliquots of the cells of the obtaining (B) includes a second plurality of wells, wherein each well in the second plurality of wells comprises an aliquot of a different type of cells in the corresponding plurality of cell types, and
the corresponding wells in the plurality of wells for the plurality of query perturbation aliquots of the cells of the obtaining (D) includes a third plurality of wells, wherein each well in the third plurality of wells comprises an aliquot of a different type of cells in the corresponding plurality of cell types.

35. The computer system of embodiment 34, wherein the plurality of cell types comprises three cell types.

36. The computer system of any one of embodiments 2-33, wherein the corresponding wells in the plurality of wells for the plurality of control aliquots of the cells in each instance of the obtaining (A) includes a corresponding first plurality of wells, wherein each well in the corresponding first plurality of wells comprises an aliquot of a different type of cells in a corresponding plurality of cell types, the corresponding wells in the plurality of wells for the plurality of test aliquots of the cells of each instance of the obtaining (B) includes a corresponding second plurality of wells, wherein each well in the corresponding second plurality of wells comprises an aliquot of a different type of cells in the corresponding plurality of cell types, and the corresponding wells in the plurality of wells for the plurality of query perturbation aliquots of the cells of each instance of the obtaining (D) includes a corresponding third plurality of wells, wherein each well in the corresponding third plurality of wells comprises an aliquot of a different type of cells in the corresponding plurality of cell types.

37. The computer system of embodiment 36, wherein the plurality of cell types comprises three cell types.

38. The computer system of any one of embodiments 1-37, wherein:

the plurality of features comprises a plurality of dimension reduction components; and each dimension reduction component in the plurality of dimension reduction components is derived by a subset selection method or a discrete method.

39. The computer system of any one of embodiments 1-38, wherein a control perturbation in the set of control perturbations is a predetermined naive cell line, a cell line exposed to a non-acting siRNA, a cell line that has a modifying agent added to ensure that it is in a predetermined state, or cells that have been filtered using a sorting technology for one or more predetermined biomarkers before plating.

40. The computer system of any one of embodiments 1-39, wherein the set of control perturbations comprises ten control perturbations.

41. The computer system of any one of embodiments 1-40, wherein the set of test perturbations comprises ten test perturbations.

42. The computer system of any one of embodiments 1-41, wherein the set of control perturbations comprises a toxin, a CRISPR reagent, a signaling molecule, a cytokine, a predetermined drug, a siRNA, an sgRNA, a cell culture condition, or a genetic modification.

43. The computer system of embodiment 42, wherein the set test perturbations comprises a toxin, a CRISPR reagent, a signaling molecule, a cytokine, a predetermined drug, a siRNA, an sgRNA, a cell culture condition, or a genetic modification other than a control perturbation.

44. The computer system of any one of embodiments 1-43, wherein the corresponding plurality of query perturbation aliquots of the cells is jointly exposed to the respective test perturbation and the query perturbation for at least one hour prior, two hours, three hours, one day, two days, three days, four days, or five days prior to obtaining the measurement of the plurality of features in the obtaining (D).

45. The computer system of any one of embodiments 1-44, the one or more programs further including instructions for repeating the obtaining (D), computing (E), computing (F), and computing (G) for each respective amount of the query perturbation in a plurality of respective amounts of the query perturbation, wherein each respective amount of the query perturbation in the plurality of respective amounts of the query perturbation is expressed as a corresponding concentration of the query perturbation in the corresponding subset of the plurality of wells, thereby obtaining an on-target score and an off-target score at each concentration in a plurality of concentrations for the query perturbation and wherein the evaluating (H) comprises plotting the query perturbation at each respective concentration in the plurality of concentrations on a two-dimensional plot using the on-target score for the query perturbation at the respective concentration as a coordinate in a first dimension of the two-dimensional plot and the off-target score for the query perturbation at the respective concentration as a coordinate in a second dimension of the two-dimensional plot.

46. The computer system of any one of embodiments 1-44, the one or more programs further including instructions for repeating the obtaining (D), computing (E), computing (F), and computing (G) for each respective amount of the query perturbation in a plurality of respective amounts of the query perturbation, wherein:

each respective amount of the query perturbation in the plurality of respective amounts of the query perturbation is expressed as a corresponding concentration of the query perturbation in the corresponding subset of the plurality of wells, thereby obtaining an on-target score and an off-target score at each concentration in a plurality of concentrations for the query perturbation, the evaluating (H) comprises plotting the query perturbation at each respective concentration in the plurality of concentrations on a two-dimensional plot using the on-target score for the query perturbation at the respective concentration as a coordinate in a first dimension of the two-dimensional plot and the respective concentration as a coordinate in a second dimension of the two-dimensional plot thereby obtaining an on-target curve for the query perturbation, and the evaluating (H) further comprises plotting the query perturbation at each respective concentration in the plurality of concentrations on the two-dimensional plot using the off-target score for the query perturbation at the respective concentration as a coordinate in the first dimension of the two-dimensional plot and the respective concentration as a coordinate in the second dimension of the two-dimensional plot thereby obtaining an off-target curve for the query perturbation.

47. The computer system of embodiment 46, the one or more programs further including instructions for using the on-target curve and the off-target curve to quantify a therapeutic window for the query perturbation, wherein the therapeutic window is determined by an area of a closed two-dimensional shape bounded by (i) an amplitude of the on-target curve between a first position on the on-target curve that represents a maximum on-target score in the on-target curve and a second position that represents an intersection of the on-target curve and the off-target curve, (ii) an amplitude of the off-target curve between the second point and a third position on the off-target curve that represents a maximum off-target score in the off-target curve, and (iii) a line drawn between the first position and the third position.

48. The computer system of embodiment 47, wherein the area is weighted by a closest distance between the second position and the line drawn between the first position and the third position.

49. The computer system of embodiment 47, wherein the area is weighted by the concentration of the query perturbation at the second position.

50. The computer system of embodiment 46, the one or more programs further including instructions for using the on-target curve and the off-target curve to quantify a rescue quality for the query perturbation, wherein the rescue quality is determined by integrating a difference between (a) the amplitude of the first position and (b) the maximum on-target score at each respective concentration in the plurality of concentrations, wherein the maximum on-target score at each respective concentration in the plurality of concentrations is the largest on-target score from among the on-target curve and the off-target curve at the respective concentration.

51. The computer system of embodiment 46, the one or more programs further including instructions for using the on-target curve and the off-target curve to quantify a rescue quality for the query perturbation, wherein the rescue quality is calculated as:

$$\int_{i=[a]}^{[b]} \max(\text{phenotype}(c_i), \text{side}(c_i)) * \frac{\log(c_i * \text{weight})}{c_i} * dc$$

wherein,
$c_i$ is an $i^{th}$ concentration of the compound in the plurality of concentrations for the compound,
i is an index to each concentration of the compound in the plurality of concentrations,
[a] is one of a lowest and a highest concentration of the compound in the plurality of concentrations,
[b] is the other of the lowest and the highest concentration of the compound in the plurality of concentrations,
phenotype ($c_i$) is the on-target score for the compound at concentration c; in the phenotype curve,
side ($c_i$) is the on-target score for the compound at concentration $c_i$ in the side effect curve, and
weight is a numerical weight.

52. The computer system of any one of embodiments 1-51, wherein the one or more programs further include instructions for:
(I) computing a plurality of test vectors, wherein each respective test vector in the plurality of test vectors is between (i) the first point and (ii) a second point defined by a respective test data point in the set of test data points for each dimension in the plurality of dimensions;
(J) computing a plurality of control state vectors, wherein each respective control state vector in the plurality of control state vectors is between (i) the first point and (ii) a third point defined by a respective control data point in the set of control data points for each dimension in the plurality of dimensions;
(K) computing an on-target score for each respective test vector in the plurality of test vectors as a projection of the respective test vector onto the composite test vector;
(L) computing an off-target score for each respective test vector in the plurality of test vectors as a rejection of the respective test vector against the composite test vector;
(M) computing an on-target score for each respective control vector in the plurality of control vectors as a projection of the respective control vector onto the composite test vector;
(N) computing an off-target score for each respective control vector in the plurality of control vectors as a rejection of the respective control vector against the composite test vector;
(O) plotting each respective test vector in the plurality of test vector on a two-dimensional plot using the on-target score for the respective test vector as a coordinate in a first dimension of the two-dimensional plot and the off-target score for the respective test vector as a coordinate in a second dimension of the two-dimensional plot, thereby obtaining a plurality of test state data points;
(P) plotting each respective control vector in the plurality of control vector on the two-dimensional plot using the on-target score for the respective control vector as a coordinate in the first dimension and the off-target score for the respective control vector as a coordinate in the second dimension, thereby obtaining a plurality of control data points; and
(Q) computing a normalized distance between the plurality of test state data points and the plurality of control data points.

53. The computer system of 52, wherein the one or more programs further include instructions for:
(R) computing a normalized tightness of the plurality of test state data points.

54. The computer system of 53, wherein the normalized tightness is computed by a procedure that comprises:
for each respective test vector in the plurality of test vectors, computing a test state similarly metric between (i) the respective test vector and (ii) a distribution metric of the plurality of test vectors with the respective test vector removed from the plurality of test vectors, thereby obtaining a plurality of test state similarity metrics for the plurality of test vectors, each test state similarity metric in the plurality of test state similarity metrics uniquely corresponding to a test perturbation in the set of test perturbations, and
computing a complementary distribution, by a process comprising:
(a) for each respective control state vector in the plurality of control state vectors, computing a respective control similarity metric between (i) the respective control vector and (ii) a distribution metric of the plurality of control vectors with the respective control vector removed from the plurality of control vectors, thereby obtaining the plurality of control similarity metrics, each control similarity metric in the plurality of control similarity metrics uniquely corresponding to a control perturbation in the set of control perturbations, and
(b) computing the complementary distribution as a distribution metric of the plurality of control similarity metrics; and
determining a first measure of central tendency of the angle between (i) each respective test state similarity metric in the plurality of test state similarity metrics to (ii) the complementary distribution across the plurality of test state similarity metrics, and
normalizing the first measure of central tendency of the angle by a second measure of central tendency of the angle between (i) each control similarity metric in the plurality of control similarity metrics to (ii) the complementary distribution across the plurality of control similarity metrics, wherein the normalized first measure of central tendency represents the normalized tightness of the plurality of test state data points.

55. The computer system of embodiment 54, wherein the distribution metric of the plurality of test vectors with the respective test vector removed from the plurality of test vectors is a measure of central tendency of each corresponding dimension in the plurality of dimensions across the plurality of test vectors other than the respective test vector.

56. The computer system of embodiment 55, wherein the measure of central tendency of each corresponding dimension in the plurality of dimensions across the plurality of test vectors other than the respective test vector is an arithmetic mean, weighted mean, midrange, midhinge, trimean, geometric mean, geometric median, Winsorized mean, median, or mode of the corresponding dimension across the plurality of test vectors.

57. The computer system of embodiment 56, wherein the respective test state similarly metric between (i) the respective test vector and (ii) the distribution metric of the plurality of test vectors with the respective test vector removed from the plurality of test vectors is computed as a distance between corresponding dimensions of the test vector and the distribution metric of the plurality of test vectors with the respective test vector removed from the plurality of test vectors.

58. The computer system of embodiment 57, wherein the distance is an angular distance computed as:

$$\frac{\sum_{i}^{n} A_i B_i}{\sqrt{\sum_{i=1}^{n} A_i^2} \sqrt{\sum_{i=1}^{n} B_i^2}}$$

and wherein,
$A_i$ is a dimension i in the respective test vector,
$B_i$ is the distribution metric of corresponding dimension i in the plurality of dimensions across the plurality of test vectors other than the respective test vector, and
n is the number of dimensions in respective test vector.

59. The computer system of embodiment 54, wherein the distribution metric of the plurality of control vectors with the respective control vector removed from the plurality of control vectors is a measure of central tendency of each corresponding dimension in the plurality of dimensions across the plurality of control vectors other than the respective control vector.

60. The computer system of embodiment 59, wherein the measure of central tendency of each corresponding dimension in the plurality of dimensions across the plurality of control vectors other than the respective control vector is an arithmetic mean, weighted mean, midrange, midhinge, trimean, geometric mean, geometric median, Winsorized mean, median, or mode of the corresponding dimension across the plurality of control vectors.

61. The computer system of embodiment 60, wherein:
the respective control similarly metric between (i) the respective control vector and (ii) the distribution metric of the plurality of control vectors with the respective control vector removed from the plurality of control vectors is computed as a distance between corresponding dimensions of the control vector and the distribution metric of the plurality of control vectors with the respective control vector removed from the plurality of control vectors.

62. The computer system of embodiment 61, wherein the distance is an angular distance computed as:

$$\frac{\sum_{i}^{n} A_i B_i}{\sqrt{\sum_{i=1}^{n} A_i^2} \sqrt{\sum_{i=1}^{n} B_i^2}}$$

and wherein,
$A_i$ is a dimension i in the respective control vector,
$B_i$ is the distribution metric of corresponding dimension i in the plurality of dimensions across the plurality of control vectors other than the respective control vector, and
n is the number of dimensions in respective control vector.

63. The computer system of embodiment 50 or 51, the one or more programs further including instructions for:
determining an assay quality by a first procedure that comprises:
(a) computing a plurality of test vectors, wherein each respective test vector in the plurality of test vectors is between (i) the first point and (ii) a second point defined by a respective test data point in the set of test data points for each dimension in the plurality of dimensions;
(b) computing a plurality of control vectors, wherein each respective control vector in the plurality of control vectors is between (i) the first point and (ii) a third point defined by a respective control data point in the set of control data points for each dimension in the plurality of dimensions;
(c) computing an on-target score for each respective test vector in the plurality of test vectors as a projection of the respective test vector onto the composite test vector;
(d) computing an off-target score for each respective test vector in the plurality of test vectors as a rejection of the respective test vector against the composite test vector;
(e) computing an on-target score for each respective control vector in the plurality of control vectors as a projection of the respective control vector onto the composite test vector;
(f) computing an off-target score for each respective control vector in the plurality of control vectors as a rejection of the respective control vector against the composite test vector;
(g) plotting each respective test vector in the plurality of test vector on a two-dimensional plot using the on-target score for the respective test vector as a coordinate in a first dimension of the two-dimensional plot and the off-target score for the respective test vector as a coordinate in a second dimension of the two-dimensional plot, thereby obtaining a plurality of test state data points,
(h) plotting each respective control vector in the plurality of control vector on the two-dimensional plot using the on-target score for the respective control vector as a coordinate in the first dimension and the off-target score for the respective control vector as a coordinate in the second dimension, thereby obtaining a plurality of control data points; and
(i) computing the assay quality as a normalized distance between the plurality of test state data points and the plurality of control data points;
determining a test state quality by computing a normalized tightness of the plurality of test state data points;
using the rescue quality for the query perturbation, the assay quality, and the test state quality to calculate an overall quality.

64. The computer system of embodiment 63, wherein the overall quality is computed as:

$$(\text{rescue quality for the compound}) * \exp^{(assay\ quality - 1)} * \frac{1}{1 + \exp^{(1 - phenotype\ quality)}}.$$

65. The computer system of embodiment 63, wherein the normalized tightness is computed by a procedure that comprises:

for each respective test vector in the plurality of test vectors, computing a test state similarly metric between (i) the respective test vector and (ii) a distribution metric of the plurality of test vectors with the respective test vector removed from the plurality of test vectors, thereby obtaining a plurality of test state similarity metrics for the plurality of test vectors, each test state similarity metric in the plurality of test state similarity metrics uniquely corresponding to a test perturbation in the set of test perturbations, and computing a null distribution, by a process comprising:
(a) for each respective control vector in the plurality of control vectors, computing a respective control similarity metric between (i) the respective control vector and (ii) a distribution metric of the plurality of control vectors with the respective control vector removed from the plurality of control vectors, thereby obtaining the plurality of control similarity metrics, each control similarity metric in the plurality of control similarity metrics uniquely corresponding to a control perturbation in the set of control perturbations, and
(b) computing the null distribution as a distribution metric of the plurality of control similarity metrics; and determining a first measure of central tendency of the angle between (i) each respective test state similarity metric in the plurality of test state similarity metrics to (ii) the null distribution across the plurality of test state similarity metrics, and normalizing the first measure of central tendency of the angle by a second measure of central tendency of the angle between (i) each control similarity metric in the plurality of control similarity metrics to (ii) the null distribution across the plurality of control similarity metrics, wherein the normalize first measure of central tendency represents the normalized tightness of the plurality of test state data points.

66. The computer system of any one of embodiments 1-65, wherein the plurality of query perturbations comprises 1000 query perturbations.

67. The computer system of any one of embodiments 2-66, the one or more programs further including instructions for eliminating one or more query perturbations from the plurality of query perturbations using an elimination criterion that is based, at least in part, on the on-target score of each query perturbation in the plurality of query perturbations.

68. The computer system of embodiment 67, wherein the elimination criterion is $E = uudx - K^* uuudx$, wherein,
each respective query perturbation in the plurality of query perturbations that has an on-target score of less than E is eliminated from the plurality of query perturbations,
uudx=is a measure of central tendency of the on-target score across the plurality of query perturbations,
uuudx=is a standard deviation of the on-target score across the plurality of query perturbations,
K=is a weight, and
for each respective query perturbation remaining in the plurality of query perturbations, the obtaining (D), computing (E), computing (F), and computing (G) is repeated for each respective amount of the respective query perturbation in a plurality of respective amounts of the respective query perturbation, wherein each respective amount of the respective query perturbation is expressed as a corresponding concentration of the respective query perturbation in the corresponding subset of the plurality of wells, thereby obtaining an on-target score and an off-target score at each concentration in a plurality of concentrations for the respective query perturbation.

69. The computer system of embodiment 46, the one or more programs further including instructions for:
fitting the on-target curve to a first sigmoidal function; and
fitting the off-target curve to a second sigmoidal function.

70. The computer system of embodiment 69, wherein the first sigmoidal function has the form:

$$\left(c + \frac{(d-c)}{\left(1 + \left(\left(\frac{x}{EC_{50}}\right)\right)^b\right)}\right) + \left(c + \frac{(d-c)}{\left(1 + \left(\left(\frac{x}{EC_{50}}\right)\right)^b\right)}\right),$$

wherein
c=a minimum on-target score computed for the query perturbation,
d=a maximum on-target score computed for the query perturbation,
$EC_{50}$=a concentration of the query perturbation that represents half of its maximum on-target effect,
x=a concentration of the query perturbation in the plurality of concentrations, and
b=a hill slope of the on-target curve.

71. The computer system of embodiment 69 or 70, wherein the second sigmoidal function has the form:

$$\left(c' + \frac{(d'-c')}{\left(1 + \left(\left(\frac{x}{EC_{50'}}\right)\right)^{b'}\right)}\right) + \left(c' + \frac{(d'-c')}{\left(1 + \left(\left(\frac{x}{EC_{50'}}\right)\right)^{b'}\right)}\right),$$

wherein
c'=a minimum off-target score computed for the query perturbation,
d'=a maximum off-target score computed for the query perturbation,
$EC_{50}'$=a concentration of the query perturbation that represents half of its off-target effect,
x=a concentration of the query perturbation in the plurality of concentrations, and
b'=a hill slope of the off-target curve.

72. A method for evaluating a query perturbation in a cell based assay representing a test state, the cell based assay comprising a plurality of wells across one or more plates, the method comprising:

(A) obtaining, for each respective control perturbation in a set of control perturbations, a corresponding control data point, thereby obtaining a plurality of control data points, wherein each corresponding control data point comprises a plurality of dimensions, each dimension in the plurality of dimensions representing a measure of central tendency of a different feature, in a plurality of features, determined across a corresponding plurality of control aliquots of cells in corresponding wells, in the plurality of wells, representing the respective control perturbation;

(B) obtaining, for each respective test perturbation in a set of one or more test perturbations, a corresponding test data point, thereby obtaining a plurality of test data points, wherein each corresponding test data point comprises the plurality of dimensions, each dimension in the plurality of dimensions comprising a measurement of central tendency of a different feature, in the plurality of features, determined across a corresponding plurality of test aliquots of the cells representing the respective test perturbation in corresponding wells in the plurality of wells;

(C) computing a composite test vector, the composite test vector between (i) a first point defined by a respective measure of central tendency across the plurality of control data points for each dimension in the plurality of dimensions and (ii) a second point defined by a respective measure of central tendency across the plurality of test data points for each dimension in the plurality of dimensions;

(D) obtaining a plurality of query perturbation data points, wherein each corresponding query perturbation data point comprises the plurality of dimensions, each dimension in the plurality of dimensions comprising a measure of central tendency of a different feature, in the plurality of features, determined across a plurality of instances of query perturbation aliquots of the cells representing a respective test perturbation, in the plurality of test perturbations, and a first amount of the query perturbation in a corresponding subset of the plurality of wells;

(E) computing a query perturbation vector, between (i) the first point and (ii) a respective measure of central tendency across the plurality of query perturbation data points for each dimension in the plurality of dimensions;

(F) computing an on-target score for the query perturbation as a projection of the query perturbation vector onto the composite test;

(G) computing an off-target score for the query perturbation as a rejection of the query perturbation vector against the composite test vector; and (H) evaluating the off-target score for the query perturbation thereby evaluating the query perturbation.

73. A non-transitory computer readable storage medium and one or more computer programs embedded therein for evaluating a query perturbation in a cell based assay representing a test state, the cell based assay comprising a plurality of wells across one or more plates, the one or more computer programs comprising instructions which, when executed by a computer system, cause the computer system to perform a method comprising:

(A) obtaining, for each respective control perturbation in a set of control perturbations, a corresponding control data point, thereby obtaining a plurality of control data points, wherein each corresponding control data point comprises a plurality of dimensions, each dimension in the plurality of dimensions representing (i) a measure of central tendency of a different feature, in a plurality of features, determined across a corresponding plurality of control aliquots of cells in corresponding wells, in the plurality of wells, representing the respective control perturbation;

(B) obtaining, for each respective test perturbation in a set of one or more test perturbations, a corresponding test data point, thereby obtaining a plurality of test data points, wherein each corresponding test data point comprises the plurality of dimensions, each dimension in the plurality of dimensions comprising a measurement of central tendency of a different feature, in the plurality of features, determined across a corresponding plurality of test aliquots of the cells representing the respective test perturbation in corresponding wells in the plurality of wells:

(C) computing a composite test vector, the composite test vector between (i) a first point defined by a respective measure of central tendency across the plurality of control data points for each dimension in the plurality of dimensions and (ii) a second point defined by a respective measure of central tendency across the plurality of test data points for each dimension in the plurality of dimensions;

(D) obtaining a plurality of query perturbation data points, wherein each corresponding query perturbation data point comprises the plurality of dimensions, each dimension in the plurality of dimensions comprising a measure of central tendency of a different feature, in the plurality of features, determined across a plurality of instances of query perturbation aliquots of the cells representing a respective test perturbation, in the plurality of test perturbations, and a first amount of the query perturbation in a corresponding subset of the plurality of wells;

(E) computing a query perturbation vector, between (i) the first point and (ii) a respective measure of central tendency across the plurality of query perturbation data points for each dimension in the plurality of dimensions;

(F) computing an on-target score for the query perturbation as a projection of the query perturbation vector onto the composite test;

(G) computing an off-target score for the query perturbation as a rejection of the query perturbation vector against the composite test vector; and (H) evaluating the off-target score for the query perturbation thereby evaluating the query perturbation.

74. A computer system embodiment for evaluating a query perturbation, in a cell based assay representing a test state, the cell based assay comprising a plurality of wells across one or more plates, the computer system comprising:

one or more processors;

a memory; and one or more programs, wherein the one or more programs are stored in the memory and are configured to be executed by the one or more processors, the one or more programs including instructions for:

(A) obtaining, for each respective control perturbation in a set of control perturbations, a corresponding control data point, thereby obtaining a plurality of control data points, wherein each corresponding control data point comprises a plurality of dimensions, each dimension in the plurality of dimensions representing a measure of central tendency of a different feature, in a plurality of features, determined across a corresponding plurality of control aliquots of cells in corresponding wells, in the plurality of wells, representing the respective control perturbation;

(B) obtaining, for each respective test perturbation in a set of one or more test perturbations, a corresponding test data point, thereby obtaining a plurality of test data points, wherein each corresponding test data point comprises the plurality of dimensions, each dimension in the plurality of dimensions comprising a measurement of central tendency of a different feature, in the plurality of features, determined across a corresponding plurality of test aliquots of the cells representing the respective test perturbation in corresponding wells in the plurality of wells;

(C) computing a composite test vector, the composite test vector between (i) a first point defined by a respective measure of central tendency across the plurality of control data points for each dimension in the plurality of dimensions and (ii) a second point defined by a respective measure of central tendency across the plurality of test data points for each dimension in the plurality of dimensions;

(D) obtaining a plurality of query perturbation data points, wherein each corresponding query perturbation data point comprises the plurality of dimensions, each dimension in the plurality of dimensions comprising a measure of central tendency of a different feature, in the plurality of features, determined across a plurality of instances of query perturbation aliquots of the cells representing a respective test perturbation, in the plurality of test perturbations, and a first amount of the query perturbation in a corresponding subset of the plurality of wells; and (E) computing a query perturbation vector, between (i) the first point and (ii) a respective measure of central tendency across the plurality of query perturbation data points for each dimension in the plurality of dimensions.

75. The computer system of embodiment 74, wherein the one or more programs further include instructions for:
outputting the query perturbation vector in a human visible format.

76. The computer system of embodiment 74, wherein the one or more programs further include instructions for:
computing an on-target score for the query perturbation as a projection of the query perturbation vector onto the composite test vector.

77. The computer system of embodiment 76, wherein the one or more programs further include instructions for:
outputting the on-target score in a human visible format.

78. The computer system of embodiment 74, wherein the one or more programs further include instructions for:
computing an off-target score for the query perturbation as a rejection of the query perturbation vector against the composite test vector.

79. The computer system of embodiment 78, wherein the one or more programs further include instructions for:
evaluating the off-target score for the query perturbation thereby evaluating the query perturbation.

80. The computer system of embodiment 79, wherein the one or more programs further include instructions for:
outputting one or more of the off-target score and results of the evaluation of the off-target score in a human visible format.

81. The computer system of embodiment 74, wherein the one or more programs further include instructions for:
(F) computing an on-target score for the query perturbation as a projection of the query perturbation vector onto the composite test vector;
(G) computing an off-target score for the query perturbation as a rejection of the query perturbation vector against the composite test vector; and
(H) evaluating the off-target score for the query perturbation thereby evaluating the query perturbation.

82. The computer system of embodiment 81, wherein the one or more programs further include instructions for:
repeating the obtaining the plurality of query perturbation data points, the computing a query perturbation vector, computing the on-target score, and the computing the off-target score for each query perturbation in a plurality of query perturbations; and wherein the evaluating the off-target score comprises plotting each respective query perturbation in the plurality of query perturbations on a two-dimensional plot using the on-target score for the respective query perturbation as a coordinate in a first dimension of the two-dimensional plot and the off-target score for the respective query perturbation as a coordinate in a second dimension of the two-dimensional plot, wherein the two-dimensional plot is human visible.

83. The computer system of embodiment 74, wherein the one or more programs further include instructions for:
computing, for each respective control perturbation in the set of control perturbations, a corresponding control vector between the first point and a second point defined by a measure of central tendency across the control data points associated with the respective control perturbation, for each dimension in the plurality of dimensions, thereby computing a plurality of control vectors;
computing an on-target score for each control perturbation as a projection of the corresponding control vector, in the plurality of control vectors, onto the composite test vector;
computing an off-target score for each control perturbation as a rejection of the corresponding control vector against the composite test vector; and
wherein the evaluating further comprises:
plotting each control perturbation in the set of control perturbations on a two-dimensional plot using the on-target score for the respective control perturbation as a coordinate in a first dimension and the off-target score for the respective control perturbation as a coordinate in a second dimension of the two-dimensional plot.

84. The computer system of embodiment 74, the one or more programs further including instructions for:
computing, for each respective well in the plurality of wells representing a control perturbation in the set of control perturbations, a corresponding control vector between the first point for each dimension in the plurality of dimensions and a second point defined by a value of a corresponding feature, in the plurality of features, determined from the respective well, thereby computing a plurality of control vectors; and
computing an on-target score for each respective control vector in the plurality of control vectors as a projection of the corresponding control vector onto the composite test vector;
computing an off-target score for each respective control vector in the plurality of control vectors as a rejection of the respective control vector against the composite test vector; and
wherein the evaluating further comprises:
plotting each respective control vector in the plurality of control vectors on a two-dimensional plot using the on-target score for the respective control vector as a coordinate in a first dimension and the off-target score for the respective control vector as a coordinate in a second dimension of the two-dimensional plot.

85. The computer system of embodiment 74, wherein the one or more programs further include instructions for:
computing, for each respective test perturbation in the set of test perturbations, a corresponding test vector between the first point for each dimension in the plurality of dimensions and a second point defined by a measure of central tendency across the test data points associated with the respective test perturbation, thereby computing a plurality of test vectors;
computing an on-target score for each test perturbation as a projection of the corresponding test vector, in the plurality of test vectors, onto the composite test vector;
computing an off-target score for each test perturbation as a rejection of the corresponding test vector against the composite test vector; and
wherein the evaluating further comprises:
plotting each test perturbation in the set of test perturbations on a two-dimensional plot using the on-target score for the respective test perturbation as a coordinate in a first dimension and the off-target score for the respective test perturbation as a coordinate in a second dimension of the two-dimensional plot.

86. The computer system of embodiment 74, wherein the one or more programs further include instructions for:

computing, for each respective well in the plurality of wells representing a test perturbation in the set of test perturbations, a corresponding test vector between the first point for each dimension in the plurality of dimensions and a second point defined by a measurement of a corresponding feature, in the plurality of features, in the respective well, thereby computing a plurality of test vectors; and computing an on-target score for each respective test vector in the plurality of test vectors as a projection of the corresponding test vector onto the composite test vector;

computing an off-target score for each respective test vector in the plurality of test vectors as a rejection of the respective test vector against the composite test vector; and wherein the evaluating further comprises:

plotting each respective test vector in the plurality of test vectors on a two-dimensional plot using the on-target score for the respective test vector as a coordinate in a first dimension and the off-target score for the test vector as a coordinate in a second dimension of the two-dimensional plot.

87. The computer system of embodiment 74, wherein the set of control perturbations consists of a plurality of control siRNA that do not directly affect expression of a gene associated with the test state.

88. The computer system of embodiment 74, wherein the set of test perturbations consists of a plurality of target siRNA that directly affect expression of a gene associated with the test state.

89. The computer system of embodiment 74, wherein each feature is derived from a combination of measurable characteristics selected from a color, a texture, and a size of a cell context, or an enumerated portion of the cell context.

90. The computer system of embodiment 74, wherein the obtaining of control data points comprises:

imaging a corresponding well in the plurality of wells to form a corresponding two-dimensional pixelated image having a corresponding plurality of native pixel values and wherein a different feature in the plurality of features of the obtaining of control data points arises as a result of a convolution or a series convolutions and pooling operators run against native pixel values in a corresponding plurality of native pixel values of the corresponding two-dimensional pixelated image.

91. The computer system of embodiment 74, wherein each feature in the plurality of features is determined from a characteristic that is optically measured.

92. The computer system of embodiment 74, wherein:

a first subset of the plurality of features are determined from characteristics that are optically measured; and a second subset of the plurality of features are determined from characteristics that are non-optically measured.

93. The computer system of embodiment 74, wherein each feature in the plurality of features is a determined from a characteristic that is non-optically measured.

94. A method for evaluating a query perturbation in a cell based assay representing a test state, the cell based assay comprising a plurality of wells across one or more multiwell plates, the method comprising:

obtaining, for each respective control perturbation in a set of control perturbations, a corresponding control data point, thereby obtaining a plurality of control data points, wherein each corresponding control data point comprises a plurality of dimensions, each dimension in the plurality of dimensions representing a measure of central tendency of a different feature, in a plurality of features, determined across a corresponding plurality of control aliquots of cells in corresponding wells, in the plurality of wells, representing the respective control perturbation;

obtaining, for each respective test perturbation in a set of one or more test perturbations, a corresponding test data point, thereby obtaining a plurality of test data points, wherein each corresponding test data point comprises the plurality of dimensions, each dimension in the plurality of dimensions comprising a measurement of central tendency of a different feature, in the plurality of features, determined across a corresponding plurality of test aliquots of the cells representing the respective test perturbation in corresponding wells in the plurality of wells:

computing a composite test vector, the composite test vector between (i) a first point defined by a respective measure of central tendency across the plurality of control data points for each dimension in the plurality of dimensions and (ii) a second point defined by a respective measure of central tendency across the plurality of test data points for each dimension in the plurality of dimensions;

obtaining a plurality of query perturbation data points, wherein each corresponding query perturbation data point comprises the plurality of dimensions, each dimension in the plurality of dimensions comprising a measure of central tendency of a different feature, in the plurality of features, determined across a plurality of instances of query perturbation aliquots of the cells representing a respective test perturbation, in the set of test perturbations, and a first amount of the query perturbation in a corresponding subset of the plurality of wells; and computing a query perturbation vector, between the first point and a respective measure of central tendency across the plurality of query perturbation data points for each dimension in the plurality of dimensions.

95. A non-transitory computer readable storage medium and one or more computer programs embedded therein for evaluating a query perturbation in a cell based assay representing a test state, the cell based assay comprising a plurality of wells across one or more multiwell plates, the one or more computer programs comprising instructions which, when executed by a computer system, cause the computer system to perform a method comprising:

obtaining, for each respective control perturbation in a set of control perturbations, a corresponding control data point, thereby obtaining a plurality of control data points, wherein each corresponding control data point comprises a plurality of dimensions, each dimension in the plurality of dimensions representing a measure of central tendency of a different feature, in a plurality of features, determined across a corresponding plurality of control aliquots of cells in corresponding wells, in the plurality of wells, representing the respective control perturbation;

obtaining, for each respective test perturbation in a set of one or more test perturbations, a corresponding test data point, thereby obtaining a plurality of test data points, wherein each corresponding test data point comprises the plurality of dimensions, each dimension in the plurality of dimensions comprising a measurement of central tendency of a different feature, in the plurality of features, determined across a corresponding plurality of test aliquots of the cells representing the respective test perturbation in corresponding wells in the plurality of wells;

computing a composite test vector, the composite test vector between (i) a first point defined by a respective measure of central tendency across the plurality of control data points for each dimension in the plurality of dimensions and (ii) a second point defined by a respective measure of central tendency across the plurality of test data points for each dimension in the plurality of dimensions;

obtaining a plurality of query perturbation data points, wherein each corresponding query perturbation data point comprises the plurality of dimensions, each dimension in the plurality of dimensions comprising a measure of central tendency of a different feature, in the plurality of features, determined across a plurality of instances of query perturbation aliquots of the cells representing a respective test perturbation, in the set of test perturbations, and a first amount of the query perturbation in a corresponding subset of the plurality of wells; and computing a query perturbation vector, between the first point and a respective measure of central tendency across the plurality of query perturbation data points for each dimension in the plurality of dimensions.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

Various embodiments described herein can be implemented as a computer program product that comprises a computer program mechanism embedded in a non-transitory computer readable storage medium. For instance, the computer program product could contain the program modules shown and/or described in any combination of FIGS. 1, 2A-2D, 3, and 4A-4AD. These program modules can be stored on a CD-ROM, DVD, magnetic disk storage product, USB key, or any other non-transitory computer readable data or program storage product.

Many modifications and variations of the embodiments described herein can be made without departing from its spirit and scope, as will be apparent to those skilled in the art. The specific embodiments described herein are offered by way of example only. The embodiments were chosen and described in order to best explain the principles of the described technology and its practical applications, to thereby enable others skilled in the art to best utilize the described technology and various embodiments with various modifications as are suited to the particular use contemplated. The embodiments described are only to be limited by the terms of the appended claims, along with the full scope of equivalents to which such claims are entitled.

What is claimed is:

1. A computer system for evaluating a query perturbation, in a cell based assay representing a test state, the cell based assay comprising a plurality of wells across one or more multiwell plates, the computer system comprising:
   one or more processors;
   a memory; and
   one or more programs, wherein the one or more programs are stored in the memory and are configured to be executed by the one or more processors, the one or more programs including instructions for:
      obtaining, for each respective control perturbation in a set of control perturbations, a corresponding control data point by imaging a corresponding well in the plurality of wells to form a corresponding two-dimensional pixelated image having a corresponding plurality of native pixel values, thereby obtaining a plurality of control data points, wherein each corresponding control data point comprises a plurality of dimensions, each dimension in the plurality of dimensions representing a measure of central tendency of a different feature, in a plurality of features, determined across a corresponding plurality of control aliquots of cells in corresponding wells, in the plurality of wells, representing the respective control perturbation, and wherein a different feature in the plurality of features of the obtaining of the control data points arises as a result of a convolution or a series convolutions and pooling operators run against native pixel values in a corresponding plurality of native pixel values of the corresponding two-dimensional pixelated image;
      obtaining, for each respective test perturbation in a set of one or more test perturbations, a corresponding test data point, thereby obtaining a plurality of test data points, wherein each corresponding test data point comprises the plurality of dimensions, each dimension in the plurality of dimensions comprising a measurement of central tendency of a different feature, in the plurality of features, determined across a corresponding plurality of test aliquots of the cells representing the respective test perturbation in corresponding wells in the plurality of wells;
      computing a composite test vector, the composite test vector between a first point defined by a respective measure of central tendency across the plurality of control data points for each dimension in the plurality of dimensions and a second point defined by a respective measure of central tendency across the plurality of test data points for each dimension in the plurality of dimensions;
      obtaining a plurality of query perturbation data points, wherein each corresponding query perturbation data point comprises the plurality of dimensions, each dimension in the plurality of dimensions comprising a measure of central tendency of a different feature, in the plurality of features, determined across a plurality of instances of query perturbation aliquots of the cells representing a respective test perturbation, in the set of test perturbations, and a first amount of the query perturbation in a corresponding subset of the plurality of wells; and
      computing a query perturbation vector, between the first point and a respective measure of central tendency across the plurality of query perturbation data points for each dimension in the plurality of dimensions.

2. The computer system of claim 1, wherein the one or more programs further include instructions for:
   outputting the query perturbation vector in a human visible format.

3. The computer system of claim 1, wherein the one or more programs further include instructions for:
   computing an on-target score for the query perturbation as a projection of the query perturbation vector onto the composite test vector.

4. The computer system of claim 3, wherein the one or more programs further include instructions for:
   outputting the on-target score in a human visible format.

5. The computer system of claim 1, wherein the one or more programs further include instructions for:
   computing an off-target score for the query perturbation as a rejection of the query perturbation vector against the composite test vector.

6. The computer system of claim 5, wherein the one or more programs further include instructions for:
evaluating the off-target score for the query perturbation thereby evaluating the query perturbation.

7. The computer system of claim 6, wherein the one or more programs further include instructions for:
outputting one or more of the off-target score and results of an evaluation of the off-target score in a human visible format.

8. The computer system of claim 1, wherein the one or more programs further include instructions for:
computing an on-target score for the query perturbation as a projection of the query perturbation vector onto the composite test vector;
computing an off-target score for the query perturbation as a rejection of the query perturbation vector against the composite test vector; and
evaluating the off-target score for the query perturbation thereby evaluating the query perturbation.

9. The computer system of claim 8, wherein the one or more programs further include instructions for:
repeating the obtaining the plurality of query perturbation data points, the computing a query perturbation vector, computing the on-target score, and the computing the off-target score for each query perturbation in a plurality of query perturbations; and
wherein the evaluating the off-target score comprises plotting each respective query perturbation in the plurality of query perturbations on a two-dimensional plot using the on-target score for the respective query perturbation as a coordinate in a first dimension of the two-dimensional plot and the off-target score for the respective query perturbation as a coordinate in a second dimension of the two-dimensional plot, wherein the two-dimensional plot is human visible.

10. The computer system of claim 1, wherein the one or more programs further include instructions for:
computing, for each respective control perturbation in the set of control perturbations, a corresponding control vector between the first point and a second point defined by a measure of central tendency across the control data points associated with the respective control perturbation, for each dimension in the plurality of dimensions, thereby computing a plurality of control vectors;
computing an on-target score for each control perturbation as a projection of the corresponding control vector, in the plurality of control vectors, onto the composite test vector;
computing an off-target score for each control perturbation as a rejection of the corresponding control vector against the composite test vector; and
wherein the evaluating further comprises:
plotting each control perturbation in the set of control perturbations on a two-dimensional plot using the on-target score for the respective control perturbation as a coordinate in a first dimension and the off-target score for the respective control perturbation as a coordinate in a second dimension of the two-dimensional plot.

11. The computer system of claim 1, the one or more programs further including instructions for:
computing, for each respective well in the plurality of wells representing a control perturbation in the set of control perturbations, a corresponding control vector between the first point for each dimension in the plurality of dimensions and a second point defined by a value of a corresponding feature, in the plurality of features, determined from the respective well, thereby computing a plurality of control vectors; and
computing an on-target score for each respective control vector in the plurality of control vectors as a projection of the corresponding control vector onto the composite test vector;
computing an off-target score for each respective control vector in the plurality of control vectors as a rejection of the respective control vector against the composite test vector; and
wherein the evaluating further comprises:
plotting each respective control vector in the plurality of control vectors on a two-dimensional plot using the on-target score for the respective control vector as a coordinate in a first dimension and the off-target score for the respective control vector as a coordinate in a second dimension of the two-dimensional plot.

12. The computer system of claim 1, wherein the one or more programs further include instructions for:
computing, for each respective test perturbation in the set of test perturbations, a corresponding test vector between the first point for each dimension in the plurality of dimensions and a second point defined by a measure of central tendency across the test data points associated with the respective test perturbation, thereby computing a plurality of test vectors;
computing an on-target score for each test perturbation as a projection of the corresponding test vector, in the plurality of test vectors, onto the composite test vector;
computing an off-target score for each test perturbation as a rejection of the corresponding test vector against the composite test vector; and
wherein the evaluating further comprises:
plotting each test perturbation in the set of test perturbations on a two-dimensional plot using the on-target score for the respective test perturbation as a coordinate in a first dimension and the off-target score for the respective test perturbation as a coordinate in a second dimension of the two-dimensional plot.

13. The computer system of claim 1, wherein the one or more programs further include instructions for:
computing, for each respective well in the plurality of wells representing a test perturbation in the set of test perturbations, a corresponding test vector between the first point for each dimension in the plurality of dimensions and a second point defined by a measurement of a corresponding feature, in the plurality of features, in the respective well, thereby computing a plurality of test vectors; and
computing an on-target score for each respective test vector in the plurality of test vectors as a projection of the corresponding test vector onto the composite test vector;
computing an off-target score for each respective test vector in the plurality of test vectors as a rejection of the respective test vector against the composite test vector; and wherein the evaluating further comprises:
plotting each respective test vector in the plurality of test vectors on a two-dimensional plot using the on-target score for the respective test vector as a coordinate in a first dimension and the off-target score for the test vector as a coordinate in a second dimension of the two-dimensional plot.

14. The computer system of claim 1, wherein the set of control perturbations consists of a plurality of control siRNA that do not directly affect expression of a gene associated with the test state.

15. The computer system of claim 1, wherein the set of test perturbations consists of a plurality of target siRNA that directly affect expression of a gene associated with the test state.

16. The computer system of claim 1, wherein each feature is derived from a combination of measurable characteristics selected from a color, a texture, and a size of a cell context, or an enumerated portion of the cell context.

17. The computer system of claim 1, wherein each feature in the plurality of features is determined from a characteristic that is optically measured.

18. The computer system of claim 1, wherein:
a first subset of the plurality of features are determined from characteristics that are optically measured; and
a second subset of the plurality of features are determined from characteristics that are non-optically measured.

19. The computer system of claim 1, wherein each feature in the plurality of features is a determined from a characteristic that is non-optically measured.

20. A method for evaluating a query perturbation in a cell based assay representing a test state, the cell based assay comprising a plurality of wells across one or more multiwell plates, the method comprising:
obtaining, by one or more processors for each respective control perturbation in a set of control perturbations, a corresponding control data point by imaging a corresponding well in the plurality of wells to form a corresponding two-dimensional pixelated image having a corresponding plurality of native pixel values, thereby obtaining a plurality of control data points, wherein each corresponding control data point comprises a plurality of dimensions, each dimension in the plurality of dimensions representing a measure of central tendency of a different feature, in a plurality of features, determined across a corresponding plurality of control aliquots of cells in corresponding wells, in the plurality of wells, representing the respective control perturbation, and wherein a different feature in the plurality of features of the obtaining of the control data points arises as a result of a convolution or a series convolutions and pooling operators run against native pixel values in a corresponding plurality of native pixel values of the corresponding two-dimensional pixelated image;
obtaining, by the one or more processors for each respective test perturbation in a set of one or more test perturbations, a corresponding test data point, thereby obtaining a plurality of test data points, wherein each corresponding test data point comprises the plurality of dimensions, each dimension in the plurality of dimensions comprising a measurement of central tendency of a different feature, in the plurality of features, determined across a corresponding plurality of test aliquots of the cells representing the respective test perturbation in corresponding wells in the plurality of wells;
computing, by the one or more processors, a composite test vector, the composite test vector between (i) a first point defined by a respective measure of central tendency across the plurality of control data points for each dimension in the plurality of dimensions and (ii) a second point defined by a respective measure of central tendency across the plurality of test data points for each dimension in the plurality of dimensions;
obtaining, by the one or more processors, a plurality of query perturbation data points, wherein each corresponding query perturbation data point comprises the plurality of dimensions, each dimension in the plurality of dimensions comprising a measure of central tendency of a different feature, in the plurality of features, determined across a plurality of instances of query perturbation aliquots of the cells representing a respective test perturbation, in the set of test perturbations, and a first amount of the query perturbation in a corresponding subset of the plurality of wells; and
computing, by the one or more processors, a query perturbation vector, between the first point and a respective measure of central tendency across the plurality of query perturbation data points for each dimension in the plurality of dimensions.

21. A non-transitory computer readable storage medium and one or more computer programs embedded therein for evaluating a query perturbation in a cell based assay representing a test state, the cell based assay comprising a plurality of wells across one or more multiwell plates, the one or more computer programs comprising instructions which, when executed by a computer system, cause the computer system to perform a method comprising:
obtaining, by one or more processors for each respective control perturbation in a set of control perturbations, a corresponding control data point by imaging a corresponding well in the plurality of wells to form a corresponding two-dimensional pixelated image having a corresponding plurality of native pixel values, thereby obtaining a plurality of control data points, wherein each corresponding control data point comprises a plurality of dimensions, each dimension in the plurality of dimensions representing a measure of central tendency of a different feature, in a plurality of features, determined across a corresponding plurality of control aliquots of cells in corresponding wells, in the plurality of wells, representing the respective control perturbation, and wherein a different feature in the plurality of features of the obtaining of the control data points arises as a result of a convolution or a series convolutions and pooling operators run against native pixel values in a corresponding plurality of native pixel values of the corresponding two-dimensional pixelated image;
obtaining, by the one or more processors for each respective test perturbation in a set of one or more test perturbations, a corresponding test data point, thereby obtaining a plurality of test data points, wherein each corresponding test data point comprises the plurality of dimensions, each dimension in the plurality of dimensions comprising a measurement of central tendency of a different feature, in the plurality of features, determined across a corresponding plurality of test aliquots of the cells representing the respective test perturbation in corresponding wells in the plurality of wells;
computing, by the one or more processors, a composite test vector, the composite test vector between (i) a first point defined by a respective measure of central tendency across the plurality of control data points for each dimension in the plurality of dimensions and (ii) a second point defined by a respective measure of central tendency across the plurality of test data points for each dimension in the plurality of dimensions;
obtaining, by the one or more processors, a plurality of query perturbation data points, wherein each corresponding query perturbation data point comprises the plurality of dimensions, each dimension in the plurality of dimensions comprising a measure of central tendency of a different feature, in the plurality of features, determined across a plurality of instances of query perturbation aliquots of the cells representing a respective test perturbation, in the set of test perturbations, and a first amount of the query perturbation in a corresponding subset of the plurality of wells; and computing, by the one or more processors, a query perturbation vector, between the first point and a respective measure of central tendency across the plurality of query perturbation data points for each dimension in the plurality of dimensions.

\* \* \* \* \*